United States Patent [19]

Lok et al.

[11] Patent Number: 4,973,785

[45] Date of Patent: * Nov. 27, 1990

[54] MOLECULAR SIEVE COMPOSITIONS

[75] Inventors: Brent M. T. Lok, New City; Bonita K. Marcus, Rye; Lawrence D. Vail, New Rochelle; Edith M. Flanigen, White Plains; Robert L. Patton, Katonah; Stephen T. Wilson, Shrub Oak, all of N.Y.

[73] Assignee: UOP, Des Plaines

[ * ] Notice: The portion of the term of this patent subsequent to Apr. 26, 2005 has been disclaimed.

[21] Appl. No.: 182,738

[22] Filed: Apr. 18, 1988

Related U.S. Application Data

[62] Division of Ser. No. 600,312, May 13, 1984, Pat. No. 4,793,984.

[51] Int. Cl.$^5$ ................................................ C07C 5/27
[52] U.S. Cl. .................................. 585/481; 208/111; 208/120; 208/136; 585/266; 585/275; 585/415; 585/475; 585/514; 585/527; 585/533; 585/667; 585/666; 585/731; 585/740
[58] Field of Search .................. 585/481, 670, 666

[56] References Cited

U.S. PATENT DOCUMENTS

| | | | |
|---|---|---|---|
| 3,941,871 | 3/1976 | Dwyer et al. | 423/326 |
| 4,061,724 | 12/1977 | Grose et al. | 423/335 |
| 4,310,440 | 1/1982 | Wilson et al. | 252/435 |
| 4,420,467 | 12/1983 | Whittam | 423/328 |
| 4,440,871 | 4/1984 | Lok et al. | 502/214 |
| 4,486,397 | 12/1984 | Eshraghi et al. | 423/306 |
| 4,500,651 | 2/1985 | Lok et al. | 502/208 |
| 4,554,143 | 11/1985 | Messina et al. | 423/306 |
| 4,567,029 | 1/1986 | Wilson et al. | 423/306 |
| 4,740,650 | 4/1988 | Pellet et al. | 585/481 |
| 4,793,984 | 12/1988 | Lok et al. | 423/306 |

FOREIGN PATENT DOCUMENTS

| | | | |
|---|---|---|---|
| 0054364 | 6/1982 | European Pat. Off. | |
| 0055046 | 6/1982 | European Pat. Off. | |
| 0055529 | 7/1982 | European Pat. Off. | |
| 0059059 | 9/1982 | European Pat. Off. | |
| 249914 | 12/1987 | European Pat. Off. | 585/481 |
| 8387189 | 5/1983 | Japan . | |
| 2047790 | 6/1982 | United Kingdom . | |

OTHER PUBLICATIONS

"Aluminophosphates Broaden Shape Selective Catalyst Types", Haggin, Chemical and Engineering News, Jun. 20, 1983, pp. 36-37.

Primary Examiner—Asok Pal

[57] ABSTRACT

Crystalline molecular sieves having three-dimensional microporous framework structures of $ELO_2$, $AlO_2$, $SiO_2$ and $PO_2$ framework oxide units are disclosed. The molecular sieves have an empirical chemical composition on an anhydrous basis expressed by the formula:

mR: $(EL_wAl_xP_ySi_z)O_2$ wherein "R" represents at least one organic templating agent present in the intracrystalline pore system; "m" represents the molar amount of "R" present per mole of $(EL_wAl_xP_ySi_z)O_2$; "EL" represents at least one element capable of forming a framework oxide unit; and "w", "x", "y" and "z" represent the mole fractions of element(s) "EL", aluminum, phosphorus and silicon, respectively, present as framework oxides. Their use as adsorbents, catalysts, etc. is also disclosed.

6 Claims, 3 Drawing Sheets

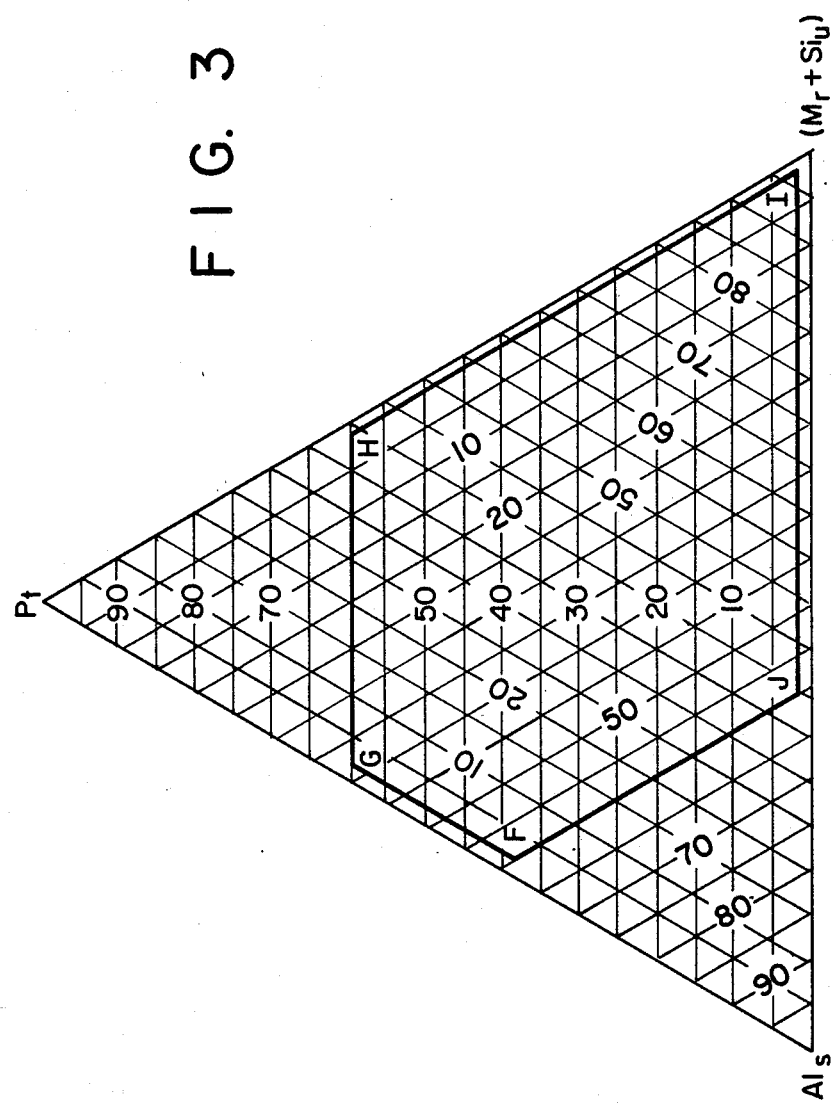

MOLECULAR SIEVE COMPOSITIONS

This is a division of our copending application Ser. No. 600,312, filed Apr. 13, 1984, now U.S. Pat. No. 4,793,984.

FIELD OF THE INVENTION

The instant invention relates to a novel class of three-dimensional microporous crystalline molecular sieves, to the method of their preparation and to their use as adsorbents and catalysts. The invention relates to novel molecular sieves having at least one element capable of forming a framework oxide units, e.g., "ELO$_2$", with tetrahedral oxide units of aluminum (AlO$_2$−), phosphorous (PO$_2$+) and silicon (SiO$_2$). These compositions may be prepared hydrothermally from gels containing reactive compounds of silicon, aluminum and phosphorus and at least one additional element capable of forming a framework oxide unit, and preferably at least one organic templating agent which may function in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing AlO$_2$ and SiO$_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain AlO$_2$ tetrahedra as essential framework constituents, but which exhibit the ion-exchange and/or adsorption characteristics of the zeolite are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral frame work containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,319,440 issued Jan. 12, 1982 to Wilson et al. These materials are formed from AlO$_2$ and PO$_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982 (now U.S. Pat. No. 4,440,871), there is described a novel class of silicon-substituted aluminophosphates which are both microporous and crystalline. The materials have a three dimensionally crystal framework of PO$_2$+, exclusive of any alkali metal or calcium which may optionally be present, an as-synthesized empirical chemical composition on an anhydrous basis of:

mR: (Si$_x$Al$_y$P$_z$)O$_2$ 

wherein "R" represents at least one organic templating agent present in the intracrystalline pore system; "m" represents the moles of "R" present per mole of (Si$_x$Al$_y$P$_z$)O$_2$ and has a value of per zero to 0.3; the maximum value of each case depending upon the molecular dimensions of the templating agent and the available void volume of the pore system of the particular silicoaluminophosphate species involved; and "x", "y", and "z" represents the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983 (now U.S. Pat. No. 4,500,651) there is described a novel class of titanium-containing molecular sieves whose chemical composition in the as-synthesized and anhydrous form is represented by the unit empirical formula:

mR:(Ti$_x$Al$_y$P$_z$)O$_2$ 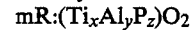

wherein "R" represents at least one organic templating agent present in the intracrystalline pore system; "m" represents the moles of "R" present per mole of (Ti$_x$Al$_y$P$_z$)O$_2$ and has a value of between zero and about 5.0; and "x", "y" "z" represent the mole fractions of titanium, aluminum and phosphorus, respectively, present as tetrahedral oxides.

In copending and commonly assigned application Ser. No. 514,334, filed July 15, 1983 (now U.S. Pat. No. 4,567,029), there is described a novel class of crystalline metal aluminophosphates having three-dimensional microporous framework structures of MO$_2$, AlO$_2$ and PO$_2$ tetrahedral units and having an empirical chemical compositions on an anhydrous basis expressed by the formula:

mR:(M$_x$Al$_y$P$_z$)O$_2$ 

wherein "R" represents at least one organic templating agent present in the intracrystalline pore system; "m" represents the moles of "R" present per mole of (M$_x$Al$_y$P$_z$)O$_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983 (now U.S. Pat. No. 4,683,217), there is described a novel class of crystalline ferroaluminophosphates having a three-dimensional microporous framework structure of FeO$_2$, AlO$_2$ and PO$_2$ tetrahedral units and having an empirical chemical composition on an anhydrous basis expressed by the formula mR:(Fe$_x$Al$_y$P$_z$)O$_2$ 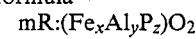

wherein "R" represents at least one organic templating agent present in the intracrystalline pore system; "m" represents the moles of "R" present per mole of (Fe$_x$Al$_y$P$_z$)O$_2$ and has a value of from zero to 0.3; and "x", "y" and "z" represent the mole fraction of the iron, aluminum and phosphorus, respectively, present as tetrahedral oxides. The instant molecular sieve compositions are characterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

The instant invention relates to new molecular sieve compositions having at least one element other than silicon, aluminum and phosphorus where such element is capable of forming a framework oxide unit with $AlO_2^-$, $PO_2^+$, and $SiO_2$ tetrahedral oxide units.

DESCRIPTION OF THE FIGURES

FIG. 3 is a ternary diagram wherein parameters relating to the reaction mixtures employed in the preparation of the compositions of this invention are set forth as mole fractions.

SUMMARY OF THE INVENTION

Figure 1:
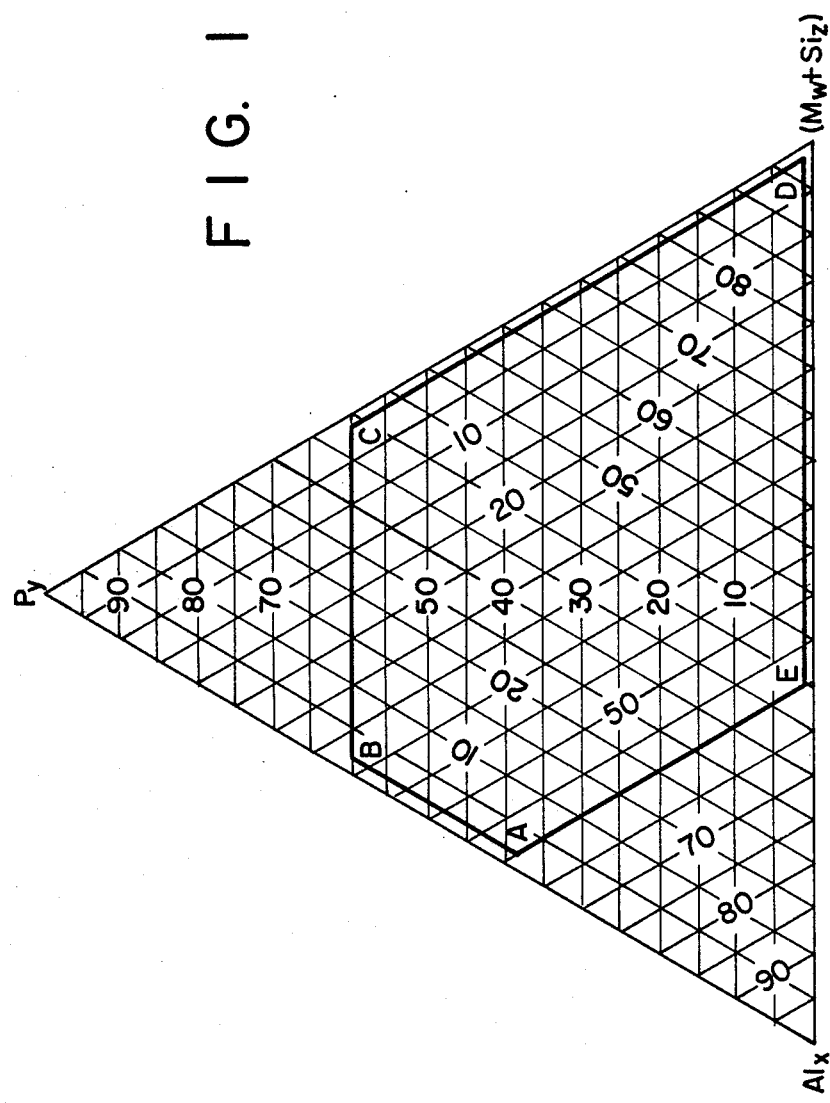
FIG. 1 is a ternary diagram wherein parameters relating to the insant compositions are set forth as mole fractions.

The instant invention relates to a new class of molecular sieves in which at least one element capable of forming a framework oxide unit is provided to form crystal framework structures of $SiO_2$, $AlO_2^-$ and $ELO_2^n$ units wherein "EL" represents at least one element present as a framework oxide unit "$ELO_2^n$" with charge "n" where "n" may be $-3$, $-2$, 0 or $+1$. These new molecular sieves exhibit ion-exchange, adsorption and catalytic properties and, accordingly, find wide use of adsorbents and catalysts.

The members of this novel class of compositions have crystal framework structures of $SiO_2$, $AlO_2$, $PO_2^+$ and $ELO_2^n$ framework oxides units, where "n" is $-3$, $-2$, $-1$, 0 or $+1$, and have an empirical chemical composition on an anhydrous basis expressed by the formula:

mR: $(EL_wAl_xP_ySi_z)O_2$ wherein "R" represents at least one organic templating agent present in the intracrystalline pore system; "m" represents the molar amount of "R" present per mole of $(EL_wAl_xP_ySi_z)O_2$ and has a value from zero to about 0.3; "EL" represents at least one element capable of forming a framework oxide unit as hereinafter described; and "w", "x", "y" and "z" represent the mole fractions of "EL", aluminum, phosphorus and silicon, respectively, present as framework oxide units. "EL" denominates the elements present in addition to aluminum, phosphorus and silicon and may be a single element or may be two or more elements such that the molecular sieves contain one or more framework oxide units "$ELO_2^n$" in addition to framework tetrahedral oxide units $SiO_2$, $AlO_2^-$ and $PO_2^+$.

The molecular sieves of the instant invention will be generally referred to by the acronym "ELAPSO" to designate element(s) "EL" in an oxide framework of $SiO_2$, $AlO_2^-$, $PO_2^+$ and $ELO_2^n$ oxide units. Actual class members will be identified by replacing the "EL" of the acronym with the element(s) present as a $ELO_2^n$ oxide unit(s). For example "CoAPSO" designates a molecular sieve comprised of $SiO_2$, $AlO_2^-$, $PO_2^+$ and $CoO_2^{-2}$ (and/or $CoO_2^{-1}$) framework oxide units, and "CoZnAPSO" designates a molecular sieve having $SiO_2$, $AlO_2^-$, $PO_2^+$, $CoO_2^{-2}$ (and/or $COO_2^{-1}$) and $ZnO_2^{-2}$ framework oxide units to identify various structural species which make up each of the subgeneric classes, each species is assigned a number and is identified as "ELAPSO-i" wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of three-dimensional microporous crystalline molecular sieves in which at least one element capable of forming a framework oxide unit is provided to form crystal framework structures of $SiO_2$, $SiO_2^-$, $PO_2^+$ and $ELO_2^n$ framework oxide units wherein "EL" represents at least one element capable of forming a framework oxide unit "$ELO_2^n$" with charge "n" where "n" is $-3$, $-2$, $-1$, 0 or $+1$. These molecular sieves exhibit ion-exchange, adsorption and catalytic properties and accordingly find wide use as adsorbents and catalysts.

The ELAPSO compositions are formed with elements capable of forming framework oxide units in the presence of $SiO_2$, $SIO_2^-$ and $PO_2^+$ tetrahedral oxide units where element "EL" is at least one element capable of forming a three dimensional oxide framework in the presence of aluminum, phosphorus and silicon oxide units, and has a mean "T-O" distance in tetrahedral oxide structures of between about 1.51 Angstroms and about 2.06 angstroms, has a cation electronegativity between about 125 kcal/g-atom and about 310 kcal/g-atom and is capable of forming stable M-O-P, M-O-Al or M-O-M bonds in crystalline three dimensional oxide structures where the "M-O" bond dissociation energy, D°, is greater than about 59 kcal/mole at 298° K. The use of "M" in the aforementioned discussion on bond energies is one of convenience since the prior art has heretofore employed "M" to designate the element (EL) bonded to oxygen. For the purposes of discussion herein any reference to M-O-P, M-O-Al, M-O-M or M-O refers to the substitution of element(s) "EL" for the "M" designation. The "T-O" distance denominates the bond length of the "T-O" bond where "T" is element(s) "EL" occupying the tetrahedral cation site and is related to the Shannon/Prewitt crystal to ionic radii. Elements known to occur in tetrahedral coordination with oxygen are discussed in: Joseph V. Smith, "Feldspar Minerals", Springer-Verlag, Berlin, N.Y., Vol. I, pp. 55–65 and 106–113 (1974); R. D. Shannon, *Acta. Cryst.*, A32, p. 751 (1976); R. D. Shannon, C. T. Prewitt, *Acta. Cryst.*, B25, p. 925 (1969); and F. Donald Bloss, "Crystallography and Crystal Chemistry", Holt, Rinehart and Winston, Inc., N.Y., pp. 278–279 (1971). The "T-O" distance is calculated according to the procedures heretofore employed and as discussed in, R. D. Shannon, *Acta Cryst.*, A32, p. 751 (1976) and R. D. Shannon, C. T. Prewitt, *Acta Cryst.*, B25, p. 925 (1969), based, respectively, on the ionic and crystal radius of oxide ion, $O^{2-}$, of 1.40 Angstroms and 1.26 Angstroms. The cation electronegativity of element(s) "EL" is determined consistent with the procedure set forth in A. S. Povarennykh, "Crystal Chemical Classification of Minerals", Vol. I, translation from Russian by J. E. S.

Bradley, Plenum Press, New York-London, p. 32 (1972). The bond dissociation energy of "M-O" is determined according to the procedures discussed in: V. I. Vedeneyve, L. V. Gurvich, V. N. Kondrat'Yev, V. A. Medvedev and Ye. L. Frankevich, "Bond Energies, Ionization Potentials and Electron Affinities," New York, ST. Martins Press, English Translation, p. 29ff (1966); "The Oxide Handbook", 2nd Ed., G. V. Samsonov, ED., translation from Russian by R. K. Johnston, IFI/Plenum Data Company, pp. 86-90 (1982); and "Bond Dissociation Energies in Simple Molecules", B. deB. Darwent, NSRSSONBS 31, U.S. Dept. Of Commerce, National Bureau of Standards, pp. 9-47 (1970).

Further embodiments of the instant invention relates to the molecular sieves as above defined being characterized by element(s) "EL" characterized by at least one of the following criteria:

(1) "EL" is characterized by an electronic orbital configuration selected from the group consisting of $d^0$, $d^1$, $d^2$, $d^5$, $d^6$, $d^7$, or $d^{10}$ where the small crystal field stabilization energy of the metal ligand "-OM" favors tetrahedral coordination of element EL ("EL" denominated here also as "M") with $O^{2-}$, as discussed in "Inorganic Chemistry" J. E. Huheey, Harper Row, p. 348 (1978):

(2) "EL" is characterized as capable of forming stable oxo or hydroxo species in aqueous solution as evidenced by a first hydrolysis constant, $K_{11}$, greater than $10^{-14}$, as discussed in "The Hydrolysis of Cations", C. F. Baes and R. E. Mesmer, John Wiley & Sons (1976);

(3) "EL" is selected from the group of elements known to occur in crystal structure type geometrically related to the different silica modifications, quarts, cristobalite or tridymite, as discussed in E. Parthe, "Crystal Chemistry of Tetrahedral Structures", Gordon and Breach, New York, London, pp. 66-68 (1964); and (4) "EL" is an element which in its cation form is classified by Pearson, (J. E. Huheey, "Inorganic Chemistry", Harper & Row, p. 276 (1978)) as "hard or borderline" acids which interact with the "hard" base $O^{2-}$ to form more stable bonds than the cations classified as "soft" acids.

In one embodiment of the invention element "EL" is preferably at least one element selected from the group consisting of arsenic, beryllium, boron, chromium, cobalt, gallium, germanium, iron, lithium, magnesium, manganese, titanium, vanadium and zinc.

The relative amounts of silicon, aluminum phosphorus and element(s) "EL" are expressed by the empirical chemical formula (anhydrous):

mR: $(El_wAl_xP_ySi_z)O_2$ where "w", "x", "y" and "z" represents the mole fractions of said element(s) "EL", aluminum, phosphorus, and silicon, respectively. When "EL" comprises two or more elements, "w" represents the mole fractions of said elements ($EL_1$, $EL_2$, $EL_3$, $EL_4$, etc.) and "w" equals the sum of "$w_1$", "$w_2$", "$w_3$", "$w_4$", etc., wherein "$w_1$", "$w_2$", "$w_3$", "$w_4$" and etc. represents the individual mole fractions of elements $EL_1$, $EL_2$, $EL_3$, $EL_4$ and etc. and each has a value of at least 0.01.

The molecular sieves of the instant invention have three-dimensional microporous crystalline framework structures of $ELO_2^n$, $AlO_2^-$, $PO_2^+$ and $SiO_2$ framework oxide units having an empirical chemical composition on an anhydrous basis expressed by the formula:

mR: $(EL_wAl_xP_ySi_z)O_2$ wherein "R" represents an organic templating agent present in the intracrystalline pore system; "m" represents the molar amount of "R" present per mole of $(EL_wAl_xP_ySi_z)O_2$ and has a value of zero to about 0.3;

"EL" represents at least one element capable of forming a three dimensional oxide framework has a mean "T-O" distance in tetrahedral oxide structures of between about 1.51 Angstroms and about 2.06 Angstroms, has a certain electronegativity between about 124 kcal/g-atom to 310 kcal/g-atom and is capable of forming stable M-O-P, M-O-Al or M-O-M bonds in crystalline three dimensional oxide structures where the "M-O" bond dissociation energy, $D°$, is greater than about 59 kcal/mole at 298° K.; and "w", "x", "y" and "z" represent the mole fractions of element(s) "EL", aluminum, phosphorus and silicon, respectively, present as framework oxide units. The use of "M" in the aforementioned discussion on bond energies is one of convenience since the prior art has heretofore employed "M" to dominate the element (EL) bonded to oxygen. For the purpose of discussion herein any reference to M-O-P, M-O-Al, M-O-M or M-O refers to the substitution of element(s) "EL" for the "M" designation. The mole fractions "w", "x", "y" and "z" are generally defined as being within the pentagonal compositional area defined by points A, B, C, D and E of the ternary diagram of FIG. 1, said points A, B, C, D and E of FIG. 1 having the following values for "w", "x", "y", and "z":

| Point | Mole Fraction | | |
|---|---|---|---|
| | x | y | (z + w) |
| A | 0.60 | 0.39–(0.01)p | 0.01(p + 1) |
| B | 0.39–(0.01 p) | 0.60 | 0.01(p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "EL" in the $(EL_wAl_xP_ySi_z)O_2$ constituent and is preferably an integer from one (1) to fourteen (14).

Figure 2:
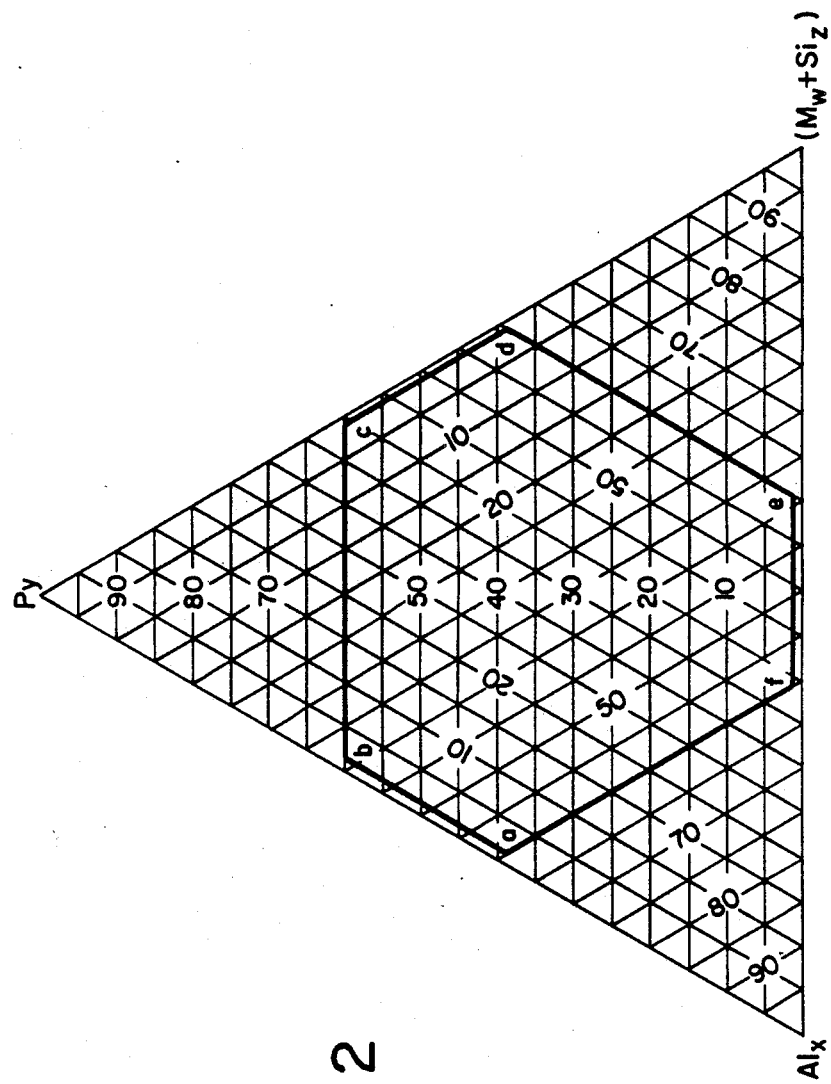
FIG. 2 is a ternary diagram wherein parameters relating to preferred compositions are set forth as mole fractions.

In a preferred subclass of the ELAPSO molecular sieves the values of "w", "x", "y" and "z", where "w" is as above defined, in the above formula are within the tetragonal compositional area defined by points, a, b, c and d of the ternary diagram which is FIG. 2, said points a, b, c and d representing the following values for "w", "x", "y" and "z";

| Point | Mole Fraction | | |
|---|---|---|---|
| | x | y | (z + w) |
| a | 0.60 | 0.39–(0.01)p | 0.01(p + 1) |
| b | 0.39–(0.01 p) | 0.60 | 0.01(p + 1) |
| c | 0.10 | 0.55 | 0.35 |
| d | 0.55 | 0.10 | 0.35 | where "p" is as above defined.

While it is believed that the elements "EL", aluminum, phosphorus and silicon in the framework constituents are present in tetrahedral coordination with oxygen, i.e. as tetrahedral oxide units, it is theoretically possible that some fraction of these framework constituents are present in coordination with five or six oxygen atoms. The convenient reference herein to the framework oxide units are represented by formulae which indicate tetrahedral oxide units, although as above noted other tetrahedral coordination may exist. It is not, moreover, necessarily the case that all the elements "EL" of any given synthesized product be part of the framework in the aforementioned types of coordination with oxygen. Some of each constituent may be in some as yet undetermined form.

The ELAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

ELAPSO compositions are generally synthesized by hydrothermal crystallization from a reaction mixture containing active sources of element(s) "EL", silicon, aluminum and phosphorus, preferably an organic templating, i.e., structure-directing, agent which is preferably a compound of an element of Group VA of the Periodic Table, and/or optionally an alkali of other metal. The reaction mixture is generally placed in a sealed pressure vessel, preferably lined with an inert plastic material such as polytetrafluoroethylene and heated, preferably under autogeneous pressure at an effective temperature which is preferably between about 50° C. and about 250° C., more preferably between 100° C. and 200° C., until crystals of the ELAPSO product are obtained, usually an effective crystallization line of from several hours to several weeks. Generally, effective crystallization times of from about 2 hours to about 30 days are employed with typically from 4 hours to about 20 days being employed to obtain ELAPSO product. The product is recovered by any convenient method such as centrifugation or filtration.

In synthesizing the ELAPSO compositions of the instant invention, it is preferred to employ a reaction mixture composition expressed in terms of molar ratios as follows:

AR: $(EL_yAl_sP_tSi_u)O_2$; $BH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; "EL" represents at least one element, as herein before described, capable of forming a framework oxide unit, $ELO_2^n$, with $SiO_2$, $AlO_2^-$ and $PO_2^+$ tetrahedral oxide units; "n" has a value of $-3$, $-2$, $-1$, 0 or $+1$; and "r", "s", "EL", aluminum, phosphorus, and silicon respectively, and each has a value of at least 0.01. In a preferred embodiment the reaction mixture is selected such that the mole fractions "r", "s", "t", and "u" are generally defined as being within the pentagonal compositional area defined by points E, F, G, H, and I of the ternary diagram of FIG. 3. Points E, F, G, H, and I of FIG. 3 have the following values for "r", "s", "t", and "u":

| Point | Mole Fraction | | |
|---|---|---|---|
| | s | t | (u + r) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "r", "s", "t", and "u" such that $(r+s+t+u)=1.00$ mole, whereas in the examples the reaction mixtures may be expressed in terms of molar oxide ratios normalized to the moles of $P_2O_5$. This latter form is readily converted to the former form by routine calculations by dividing the number of moles of each component (including the template and water) by the total number of moles of elements "EL", aluminum, phosphorus and silicon which results in normalized mole fractions based on total moles of the aforementioned components.

In forming reaction mixtures from which the EAPSO molecular sieves are formed an organic templating agent is preferably employed and may be any of those heretofore proposed for use in the synthesis of conventional zeolite aluminosulicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use of templating agents are the amines, quarterly phosphonium and quaternary ammonium compounds, the latter two being represented generally by the formulae $R_4X^+$ wherein "X" is nitrogen or phosphorous and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents may either produce mixtures of the desired ELAPSOs or the more strongly directing templating species may control the course of the reaction with the other templating species serving primarily to establish the pH conditions of the reaction gel. Representative templating agents includes: tetramethylammonium; tetraethylammonium; tetrapropylammonium; tetrabutylammonium ions; tetrapentylammonium ions; di-n-propylamine; tripropylamine; triethylamine; triethanolamine; piperidine; cyclohexylaminel; 2-methylpyridine; N,N-diemthylbenzylamine; N,N-dimethylethanolamine; chline; N,N'-dimethylpiperazine; 1,4-diazabicyclo (2,2,2,) octaine; N-methyldiethanolamine, M-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; ci-n-pentylamine; isopropylamine; t-butylamine; ethylenediamine; pyrrolidine; and 2-imidazolidone. Not every templating agent will direct the formation of every species of ELAPSO, i.e., a single templating agent may, with proper manipulation of the reaction conditions, direct the formation of several ELAPSO compositions, and a given ELAPSO composition can be produced using several different templating agents.

The source of silicon may be silica, either as a silica sol or as fumed silica, a reactive solid amorphous precipitated silica, silica gel, alkoxides of silicon, silica containing clays silicic acid or alkali metal silicate and mixtures thereof.

The most suitable phosphorus source yet found for the present process is phosphoric acid, but organic phosphats such as triethyl phosphate have been found satisfactory, and so also have crystalline or amorphous aluminophosphates such as the $AlPO_4$ compositions of U.S. Pat. No. 4,310,440. Organo-phosphorus compounds, such as tetrabutylphosphonium bromide do not, apparently, serve as reactive sources of phosphorus, but these compounds do functions as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, aluminum-containing clays, sodium sluminate and aluminum trichloride, can be employed but are not preferred.

The element(s) "EL" can be introduced into the reaction system in any form which permits the formation in situ a of a reactive form of the element, i.e., reactive to form a framework oxide unit of element "EL". Compounds of element(s) "EL" which may be employed include oxides, hydroxides, alkoxides, nitrates, sulfates, halides, carboxylates and mixtures thereof. Representative compounds which may be employed include: carboxylates of arsenic and beryllium; cobalt chloride hexahydrate, alpha cobaltous iodide; cobaltous sulfate; cobalt acetate; cobaltous bromide; cobaltous chloride; boron alkoxides; chromium acetate; gallium alkoxides; zinc acetate; zinc bromide; zinc formate; zinc iodide; zinc sulfate heptahydrate; germanium dioxide; iron (II) acetate; lithium acetate; magnesium acetate; magnesium bromide; magnesium chloride; magnesium iodide; magnesium nitrate; magnesium sulfate; manganese acetate; maganese bromide; manganese sulfate; titanium tetrachloride; titanium carboxylates; titanium acetate; zinc acetate; and the like.

While not essential to the synthesis of ELAPSO compositions, stirring or other moderate agitation of the reaction mixture and/or seeding the reaction mixture with seed crystals of either the ELAPSO species to be produced or a topologically similar aluminophosphate, aluminosilicate or molecular sieve composition, facilitates the crystallization procedure.

After crystallization of ELAPSO product may be isolated and advantageously washed with water and dried in air. The as-synthesized ELAPSO generally contains within its internal pore system at least one form of any templating agent employed in its formation. Most commonly this organic moiety, derived from any organic template, is present, at least in part, as a charge-balancing cation as is generally the case with as-synthesized aluminosilicate zeolites prepared from organic-containing reaction systems. It is possible, however, that some or all of the organic moiety may be an occuled molecular species in a particular ELAPSO species. As a general rule the templating agent, and hence the occluded organic species, is too large to move freely through the pore system of the ELAPSO product and must be removed by calcining the ELAPSO at temperatures of 200° C. to 700° C. to thermally degrade the organic species. In some instances the pores of the ELAPSO compositions are sufficiently large to permit transport of the templating agent, particularly if the latter is a small molecule, and accordingly complete or partial removal thereof may be accomplished by conventional desorption procedures such as carried out in the case of zeolites. It will be understood that the term "as-synthesized" as used herein does not include the condition of ELAPSO species wherein any organic moiety occupying the intracrystalline pore system as a result of the hydrothermal crystallization process has been reduced by post-synthesis treatment such that the value of "m" in the composition formula:

mR: $(M_wAl_xP_ySi_z)O_2$ has a value of less than 0.02. The other symbols of the formula are as defined hereinabove. In those preparations in which an alkoxide is employed as the source of element(s) "EL", aluminum, phosphorous and/or silicon, the corresponding alcohol is necessarily present in the reaction mixture since it is a hydrolysis product of the alkoxide. It has not been determined whether this alcohol participates in the syntheses process as a templating agent. For the purpose of this application, however, this alcohol is arbitrarily omitted from the class of templating agents, even if it is present in the as-synthesized ELAPSO material.

Since the present ELAPSO compositions are formed from $AlO_2^-$, $PO_2^+$, $SiO_2$ and $ELO_2^n$ framework oxide units which, respectively, have a net charge of $-1$, $+1$, 0 and "n", where "n" is $-3$, $-2$, $-1$, 0 or $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^-$ tetrahedron or a simple cation such as an alkali metal cation, a cation of the element "EL" present in the reaction mixture, or an organic cation derived from the templating agent. Similarly, an $ELO_2^n$ oxide unit can be balanced electrically by association with $PO_2^{30}$ tetrahedra, a simple cation such as an alkali metal cation, a cation of the metal "EL", organic cations derived from the templating agent, or other divalent or polyvalent metal cions introduced from an extraneous source. It has also been postulated that non-adjacent $AlO_2^-$ and $PO_2^+$ tetrahedral pairs ca be balanced by $Na^+$ and $OH^-$ respectively [Flanigen and Grose, Molecular Sieve Zeolites-I, ACS, Washington, DC. (1971)].

The ELAPSO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of ELAPSO compositions will ordinarily be possible only after the organic moiety present as a result of synthesis has been removed from the pore system. Dehydration to remove water present in the as-synthesized ELAPSO compositions can usually be accomplished, to some degree at least, in the usual manner without removal of the organic moiety, but the absence of the organic species greatly facilitates adsorption and desorption procedures. The ELAPSO materials will have various degrees of hydrothermal and thermal stability, some being quite remarkable in this regard, and will function as molecular sieve adsorbents and hydrocarbon conversion catalysts or catalyst bases.

In the examples a stainless steel reaction vessel is utilized which is lined with an inert plastic material, polytetrafluoroethylene, to avoid contamination of the reaction mixture. In general, the final reaction mixture from which each ELAPSO composition is crystallized is prepared by forming mixtures of less than all of the reagents and thereafter incorporating into these mixtures additional reagents either singly or in the form of other intermediate mixtures of two or more reagents. In some instances the admixed reagents retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray patterns of reaction products are obtained by X-ray analysis using standard X-ray powder diffraction techniques. The radiation source is a highly-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed at 2θ where θ is the Bragg angle as observed on the strip chart. Intensities are determined from the heights of diffraction peaks after subtracting background, "$I_o$" being the intensity of the strongest line or peak, and "I" being the intensity of each of the other peaks.

Alternatively, the X-ray patterns are obtained from the copper K-alpha radiation by use of computer based techniques using Siemens D-500 X-ray powder diffractometers, Siemens Type K-805 X-ray source, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° (denotes plus or minus 0.4) on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak, and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through W, wherein said x-ray patterns are for both the as-synthesized and calcined forms unless otherwise noted:

TABLE A

| 2θ | (ELAPSO-5) d(Å) | Relative Intensity |
|---|---|---|
| 7.2–7.7 | 12.28–11.48 | m–vs |
| 19.4–19.9 | 4.58–4.46 | w–m |
| 20.85–21.3 | 4.26–4.17 | w–vs |
| 22.1–22.6 | 4.02–3.93 | m–vs |

TABLE A-continued

| 2θ | (ELAPSO-5) d(Å) | Relative Intensity |
|---|---|---|
| 25.6–26.1 | 3.480–3.414 | vw–m |

TABLE B

| 2θ | (ELAPSO-11) d(Å) | Relative Intensity |
|---|---|---|
| 7.8–8.2 | 11.19–10.85 | m–s |
| 9.0–9.8 | 9.83–9.03 | vw–vs |
| 12.8–13.6 | 6.92–6.51 | vw–m |
| 19.9–20.5 | 4.46–4.33 | m–s |
| 20.8–21.8 | 4 27–4.08 | m–vs |
| 22.0–22.6 | 4.04–3.93 | m–vs |
| 22.6–23.1 | 3.93–3.85 | vw–vs |
| 23.1–23.5 | 3.85–3.79 | w–vs |

TABLE C

| 2θ | (ELAPSO-14) d(Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 30.1 | w |

TABLE D

| 2θ | (ELAPSO-16) d(Å) | Relative Intensity |
|---|---|---|
| 11.3–11.6 | 7.83–7.63 | w–vs |
| 18.55–18.9 | 4.78–4.70 | vw |
| 21.85–22.2 | 4.07–4.00 | m–vs |
| 22.8–23.3 | 3.900–3.818 | w–m |
| 26.4–27.3 | 3.370–3.267 | w–m |
| 29.6–29.9 | 3.018–2.988 | w–m |

TABLE E

| 2θ | (ELAPSO-17) d(Å) | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2θ | (ELAPSO-18) d(Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2θ | (ELAPSO-20) d(Å) | Relative Intensity |
|---|---|---|
| 13.8–14.2 | 6.42–6.23 | m–vs |
| 19.6–20.15 | 4.53–4.41 | m |
| 24.1–24.7 | 3.695–3.603 | m–vs |
| 27.9–28.6 | 3.198–3.121 | w |
| 31.3–32.05 | 2.861–2.791 | w |

TABLE G-continued

(ELAPSO-20)

| 2θ | d(Å) | Relative Intensity |
|---|---|---|
| 34.35–35.0 | 2.610–2.601 | w–m |

TABLE H

(ELAPSO-31)

| 2θ | d(Å) | Relative Intensity |
|---|---|---|
| 8.4–9.5 | 10.53–9.31 | w–s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w–m |

TABLE J*

(ELAPSO-33)

| 2θ | d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

(ELAPSO-33)

| 2θ | d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

(ELAPSO-34)

| 2θ | d(Å) | Relative Intensity |
|---|---|---|
| 9.3–9.8 | 9.51–9.03 | m–vs |
| 12.6–13.2 | 7.03–6.71 | w–m |
| 15.8–16.3 | 5.61–5.44 | vw–m |
| 20.25–21.2 | 4.39–4.19 | w–vs |
| 24.8–25.4 | 3.59–3.507 | vw–m |
| 30.0–30.9 | 2.979–2.894 | vw–m |

TABLE M

(ELAPSO-35)

| 2θ | d(Å) | Relative Intensity |
|---|---|---|
| 10.6–11.1 | 8.35–7.97 | vw–vs |
| 13.1–13.7 | 6.76–6.46 | vw–vs |
| 17.0–17.6 | 5.22–5.04 | w–s |
| 20.6–21.25 | 4.31–4.18 | vw–m |
| 21.6–22.3 | 4.11–3.99 | m–vs |
| 28.1–28.8 | 3.175–3.100 | vw–m |

TABLE N

(ELAPSO-36)

| 2θ | d(Å) | Relative Intensity |
|---|---|---|
| 7.45–8.0 | 11.14–11.05 | vs |
| 8.1–8.3 | 10.91–10.65 | w–m |
| 16.3–16.6 | 5.44–5.34 | w–m |
| 18.9–19.4 | 4.70–4.57 | w–m |
| 20.7–21.0 | 4.29–4.23 | w–m |

TABLE O

(ELAPSO-37)

| 2θ | d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

(ELAPSO-39)

| 2θ | d(Å) | Relative Intensity |
|---|---|---|
| 9.2–9.6 | 9.61–9.21 | m |
| 13.1–13.5 | 6.76–6.56 | m |
| 17.8–18.4 | 4.98–4.82 | w–m |
| 20.8–21.3 | 4.27–4.17 | m–vs |
| 22.2–22.85 | 4.00–3.892 | m–vs |
| 26.4–27.05 | 3.376–3.296 | w–m |

TABLE Q

(ELAPSO-40)

| 2θ | d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

(ELAPSO-41)

| 2θ | d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

TABLE S

(ELAPSO-42)

| 2θ | d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.060 | m–s |
| 24.1–24.25 | 3.69–3.67 | vs |
| 27.25–27.4 | 3.273–3.255 | s |
| 30.05–30.25 | 2.974–2.955 | m–s |

TABLE T

(ELAPSO-43)

| 2θ | d(Å) | Relative Intensity |
|---|---|---|
| 12.3–12.95 | 7.20–6.83 | m–vs |
| 16.8–17.45 | 5.28–5.09 | vw–w |
| 21.45–21.85 | 4.145–4.071 | m–vs |
| 27.1–27.85 | 3.291–3.232 | w–vs |
| 32.4–33.2 | 2.763–2.699 | vw–m |

TABLE U

(ELAPSO-44)

| 2θ | d(Å) | Relative Intensity |
|---|---|---|
| 9.2–9.6 | 9.61–9.21 | m–vs |
| 15.9–16.3 | 5.57–5.44 | vw–m |
| 20.5–21.0 | 4.33–4.23 | m–vs |
| 24.3–25.1 | 3.66–3.548 | w–m |

TABLE U-continued

| 2θ | (ELAPSO-44) d(Å) | Relative Intensity |
|---|---|---|
| 30.5–31.1 | 2.931–2.876 | vw–m |

TABLE V

| 2θ | (ELAPSO-46) d(Å) | Relative Intensity |
|---|---|---|
| 7.2–8.1 | 12.28–10.92 | vs |
| 12.9–13.6 | 6.86–6.51 | vw |
| 21.2–22.2 | 4.19–4.501 | vw–m |
| 22.5–23.45 | 3.95–3.793 | vw–m |
| 26.6–27.9 | 3.351–3.198 | vw–m |

TABLE W

| 2θ | (ELAPSO-47) d(Å) | Relative Intensity |
|---|---|---|
| 9.4–9.6 | 9.41–9.21 | vs |
| 12.8–13.1 | 6.92–6.76 | vw–m |
| 16.0–16.3 | 5.54–5.44 | vw–m |
| 20.5–21.0 | 4.31–4.23 | m–vs |
| 24.6–25.3 | 3.613–3.526 | vw |
| 30.6–31.1 | 2.921–2.876 | vw–m |

The following examples are provided to further illustrate the invention and are not intended to be limiting thereof:

ELAPSO MOLECULAR SIEVE COMPOSITIONS

The ELAPSO molecular sieves of the invention may be prepared having one or more elements present as framework oxide units such that the ELAPSO molecular sieves contain framework oxide units "$ELO_2$", $AlO_2^-$, $PO_2^+$ and $SiO_2$ where "EL" denominates at least one element capable of forming a framework oxide unit with $AlO_2^-$, $PO_2^+$ and $SiO_2$ tetrahedral oxide units. The following ELAPSO molecular sieves are representative of molecular sieves prepared according to the instant invention:

A. COBALT-ALUMINUM-PHOSPHORUS-SILICON-OXIDE MOLECULAR SIEVES

Molecular sieves containing cobalt, aluminum, phosphorus and silicon as framework tetrahedral oxide units are prepared as follows:

Preparative Reagents

In the following examples the CoAPSO compositions were prepared using numerous reagents. The reagents employed and abbreviations employed herein, if any, for such reagents are as follows:

(a) Alipro: aluminum isoproproxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) Co(Ac)$_2$: cobalt acetate Co(C$_2$H$_3$O$_2$)$_2$.4H$_2$O;
(e) CoSO$_4$: cobalt sulfate (CoSO$_4$.7H$_2$O);
(f) H$_3$PO$_4$: 85 weight percent phosphoric acid in water;
(g) TBAOH: tetrabutylammonium hydroxide (25 wt % in methanol);
(h) Pr$_2$NH: di-n-propylamine, (C$_3$H$_7$)$_2$NH;
(i) Pr$_3$N: tri-n-propylamine, (C$_3$H$_7$)$_3$N;
(j) Quin: Quinuclidine (C$_7$H$_{13}$N);
(k) MQuin: Methyl Quinuclidine hydroxide, (C$_7$H$_{13}$NCH$_3$OH);
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water)

Preparative Procedure

The CoAPSO compositions were prepared by preparing reaction mixtures having a molar composition expressed as:

eR:fCoO:hAl$_2$O$_3$:iP$_2$O$_5$:gSiO$_2$:jH$_2$O

wherein e, f, h, i, g and j represent the moles of template R, cobalt (expressed as the oxide), Al$_2$O$_3$, P$_2$O$_5$ (H$_3$PO$_4$ expressed as P$_2$O$_5$), SiO$_2$ and H$_2$O, respectively. The values for e, f, h, i, g and j were as set forth in the hereafter discussed preparative examples.

The reaction mixtures were prepared by forming a starting reaction mixture comprising the H$_3$PO$_4$ and one half of the water. This mixture was stirred and the aluminum source (Alipro or CATAPAL) added. The resulting mixture was blended until a homogeneous mixture was observed. The LUDOX-LS was then added to the resulting mixture and the new mixture blended until a homogeneous mixture was observed. The cobalt source (Co(Ac)$_2$, Co(SO$_4$) or mixtures thereof) was dissolved in the remaining water and combined with the first mixture. The combined mixture was blended until a homogenous mixture was observed. The organic templating agent was added to this mixture and blended for about two to four minutes until a homogenous mixture was observed. The resulting mixture (final reaction mixture) as placed in a lined (polytetrafluoroethylene) stainless stell pressure vessel and digested at a temperature (150° C., 200° C. or 225° C.) for a time. Alternatively, if the digestion temperature was 100° C. the final reaction mixture was placed in a lined (polytetrafluoroethylene) screw top bottle for a time. All digestions were carried out at the autogeneous pressure. The products were removed from the reaction vessel cooled and evaluated as set forth hereinafter.

The following examples are provided to further illustrate the invention and are not intended to be limiting thereof:

EXAMPLES 1A TO 31A

CoAPSO molecular sieves were prepared according to the above described procedure and the coAPSO products determined by x-ray analysis. The results of examples 1A to 31A are set forth in Tables I-A and II-A. Tables I-A and II-A also contain examples AA to EA wherein X-ray analysis of the reaction mixture product did not show CoAPSO products.

In the Tables I-A and II-A, the reaction mixtures are described as the ratio of molar oxides:

eR:fCoO:0.9Al$_2$O$_3$:0.9P$_2$O$_5$:gSiO$_2$:5OH$_2$O

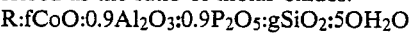

where "e", "R", "f" and "e" are as above defined. Examples were prepared using this reaction mixture unless otherwise noted in Tables I-A to II-A. The values for "e", "f" and "g" are given in Tables I-A and II-A.

TABLE I-A

| Example | Template | e | f | g | Temp (°C.) | Time (days) | CoAPSO Product(s)[1] |
|---|---|---|---|---|---|---|---|
| 1A | Quin | 1 | 0.2 | 0.2 | 150 | 4 | CoAPSO-16; CoAPSO-35 |
| 2A | Quin | 1 | 0.2 | 0.2 | 150 | 10 | CoAPSO-16; CoAPSO-35 |
| 3A | Quin | 1 | 0.2 | 0.2 | 200 | 4 | CoAPSO-16; CoAPSO-35 |
| 4A | Quin | 1 | 0.2 | 0.2 | 200 | 10 | CoAPSO-16; CoAPSO-35 |
| 5A | Quin | 1 | 0.2 | 0.2 | 100 | 4 | CoAPSO-35; CoAPSO-16 |
| 6A | Quin | 1 | 0.2 | 0.2 | 100 | 10 | CoAPSO-16; CoAPSO-35 |
| 7A | MQuin | 1 | 0.2 | 0.2 | 150 | 2 | CoAPSO-35; CoAPSO-17 |
| 8A | MQuin | 1 | 0.2 | 0.2 | 150 | 7 | CoAPSO-35 |
| 9A | MQuin | 1 | 0.2 | 0.2 | 200 | 2 | CoAPSO-35 |
| 10A | MQiun | 1 | 0.2 | 0.2 | 200 | 7 | CoAPSO-35 |
| 11A 2,3 | TBAOH | 2 | 0.4 | 0.4 | 200 | 4 | CoAPSO-36; CoAPSO-5 |
| 12A 2,3 | TBAOH | 2 | 0.4 | 0.4 | 200 | 10 | CoAPSO-36; CoAPSO-5 |

[1] Major species as indentified by x-ray powder diffraction pattern of product, except that when two or more species were identified the species are listed in the order of their predominence in the product.
2 The molar amount of $Al_2O_3$ was 0.8 instead of 0.9.
3 Send crystals of CoAPO-36 were employed in this examples, as disclosed in U.S. Ser. No. 514,334, filed July 15, 1983.

TABLE II-A

| Example | Template | e | f | g | Temp (°C.) | Time (days) | CoAPSO Product(s)[1] |
|---|---|---|---|---|---|---|---|
| 13A | C-hex | 1.0 | 0.2 | 0.6 | 150 | 4 | CoAPSO-44; CoAPSO-5 CoAPSO-13 |
| 14A | C-hex | 1.0 | 0.2 | 0.6 | 150 | 10 | CoAPSO-44; CoAPSO-5 CoAPSO-13 |
| 15A | C-hex | 1.0 | 0.2 | 0.6 | 200 | 4 | CoAPSO-44 |
| 16A | C-hex | 2.0 | 0.2 | 0.6 | 150 | 4 | CoAPSO-44; CoAPSO-13 |
| 17A | C-hex | 2.0 | 0.2 | 0.6 | 150 | 10 | CoAPSO-44; CoAPSO-13 |
| 18A | C-hex | 2.0 | 0.2 | 0.6 | 200 | 4 | CoAPSO-44 |
| 19A | C-hex | 2.0 | 0.2 | 0.6 | 200 | 10 | CoAPSO-44 |
| 20A | $Pr_3N$ | 1.0 | 0.2 | 0.2 | 150 | 4 | CoAPSO-5 |
| 21A | $Pr_3N$ | 1.0 | 0.2 | 0.2 | 150 | 11 | CoAPSO-5 |
| 22A | $Pr_3N$ | 1.0 | 0.2 | 0.2 | 200 | 4 | CoAPSO-5 |
| 23A | $Pr_3N$ | 1.0 | 0.2 | 0.2 | 200 | 11 | CoAPSO-5 |
| 24A | $Pr_3N$ | 1.0 | 0.2 | 0.2 | 150 | 2 | CoAPSO-5 |
| 25A | $Pr_3N$ | 1.0 | 0.2 | 0.2 | 150 | 15 | CoAPSO-5 |
| 26A | $Pr_3N$ | 1.0 | 0.2 | 0.2 | 200 | 2 | CoAPSO-5 |
| 27A | $Pr_3N$ | 1.0 | 0.2 | 0.2 | 200 | 15 | CoAPSO-5 |
| 28A | $Pr_3N$ | 1.0 | 0.2 | 0.2 | 150 | 21 | CoAPSO-5 |
| 29A | $Pr_3N$ | 1.5 | 0.2 | 0.2 | 150 | 3 | CoAPSO-5; CoAPSO-36 |
| 30A | $Pr_3N$ | 1.5 | 0.2 | 0.2 | 150 | 10 | CoAPSO-5; CoAPSO-36 |
| 31A | $Pr_3N$ | 1.5 | 0.2 | 0.2 | 200 | 3 | CoAPSO-5; CoAPSO-36 |
| AA* | TBAOH | 2.0 | 0.4 | 0.4 | 150 | 4 | — |
| BA* | TBAOH | 2.0 | 0.4 | 0.4 | 150 | 10 | — |
| CA | $Pr_3N$ | 1.0 | 0.2 | 0.2 | 100 | 4 | — |
| DA | $Pr_3N$ | 1.0 | 0.2 | 0.2 | 100 | 11 | — |
| EA | $Pr_3N$ | 1.0 | 0.2 | 0.2 | 200 | 21 | — |

[1] Major species as identified by x-ray powder diffraction pattern of product, except that when two or more species were identified the species are listed in the order of their predominence in the product. A "—" indicates that X-ray analysis failed to show CoAPSO products.
*The molar amount of $Al_2O_3$ was 0.8 instead of 0.9.

EXAMPLES 32A TO 61A

Examples 32A to 61A were carried out using di-n-propylamine as the organic templating agent. The preparative procedure was as above described except that in examples 39A to 45A and 53A to 61A the preparative procedure was modified such that the cobalt acetate was added to the phosphoric acid and water, followed by addition of the aluminum source, silicon source and then the organic templating agent. The aluminum source in examples 32A to 45A, 60A and 61A was aluminum isoproproxide and in examples 46A to 59A the aluminum source was CATAPAL. The reaction mixtures for examples 32A to 61A are described in terms of the molar oxide ratios: $ePr_2NH:0.2CoO:0.9Al_2O_3:0.9-P_2O_5:0.2SiO_2:5OH_2O$ where "e" is the moles of template $Pr_2NH$ and where "e" was one (1) for examples 32A to 35A, 42A to 45A, 49A to 52A, 56A to 61A and "e" was two (2) for examples 36A to 41A, 46A to 48A, 53A to 55A. Examples FA, GA, HA and IA are reaction mixtures where X-ray analysis of the reaction products did not show CoAPSO products. Examples 32 to 61 and F, G, H, and I are set forth in Table III.

TABLE III-A

| Example | Temp (°C.) | Time (days) | CoAPSO Products(s)[1] |
|---|---|---|---|
| 32A | 150 | 4 | CoAPSO-11; CoAPSO-39 |
| 33A | 150 | 11 | CoAPSO-11; CoAPSO-46; CoAPSO-39 |
| 34A | 200 | 4 | CoAPSO-11; CoAPSO-39; CoAPSO-46 |
| 35A | 200 | 11 | CoAPSO-11; CoAPSO-39; CoAPSO-5 |
| 36A | 150 | 10 | CoAPSO-46 |
| 37A | 200 | 4 | CoAPSO-11; CoAPSO-5; CoAPSO-39 |
| 38A | 200 | 10 | CoAPSO-11; CoAPSO-5 |
| 39A | 150 | 10 | CoAPSO-46 |
| 40A | 200 | 4 | CoAPSO-11; CoAPSO-5; CoAPSO-39; CoAPSO-46 |
| 41A | 200 | 10 | CoAPSO-11; CoAPSO-5; CoAPSO-39; CoAPSO-46 |

TABLE III-A-continued

| Example | Temp (°C.) | Time (days) | CoAPSO Products(s)[1] |
|---|---|---|---|
| 42A | 150 | 4 | CoAPSO-11 |
| 43A | 150 | 11 | CoAPSO-11; CoAPSO-46 |
| 44A | 200 | 4 | CoAPSO-11; CoAPSO-39 |
| 45A | 200 | 11 | CoAPSO-11; CoAPSO-39 |
| 46A | 150 | 4 | CoAPSO-46 |
| 47A | 150 | 10 | CoAPSO-46; CoAPSO-11 |
| 48A | 200 | 4 | CoAPSO-46; CoAPSO-11 |
| 49A | 150 | 10 | CoAPSO-11 |
| 50A | 150 | 4 | CoAPSO-11 |
| 51A | 200 | 10 | CoAPSO-11 |
| 52A | 200 | 4 | CoAPSO-11 |
| 53A | 150 | 10 | CoAPSO-11; CoAPSO-46 |
| 54A | 200 | 4 | CoAPSO-46; CoAPSO-11; CoAPSO-20 |
| 55A | 200 | 10 | CoAPSO-46; CoAPSO-11; CoAPSO-20 |
| 56A | 150 | 4 | CoAPSO-11 |
| 57A | 150 | 10 | CoAPSO-11 |
| 58A | 200 | 4 | CoAPSO-11 |
| 59A | 200 | 10 | CoAPSO-11 |
| 60A | 150 | 4 | CoAPSO-11 |
| 61A | 150 | 4 | CoAPSO-11 |
| FA | 100 | 4 | — |
| GA | 100 | 11 | — |
| HA | 150 | 4 | — |
| IA | 150 | 4 | — |

[1]Major species as identified by x-ray powder diffraction pattern of product, except that when two or more species were identified the species are listed in the order of their predominence in the product. A "—" indicates that X-ray analysis failed to show CoAPSO products.

EXAMPLES 62A TO 83A

Examples 62A to 83A were carried out according to the preparative procedure employed in examples 1A to 31A except that the organic templating agent was the TEAOH (tetraethylammonium hydroxide). The reaction mixtures for examples 62A to 83A were:

1.0TEAOH:fCoO:0.9Al$_2$O$_3$:0.9P$_2$O$_5$:gSiO$_2$:50H$_2$O wherein "f" was 0.2 except that "f" was 0.1 for examples 78A to 79A and was 0.05 for examples 80A to 83A; and g was 0.2 for examples 62A to 70A and was 0.6 for examples 71A to 83A. The reactive cobalt source was cobalt (II) sulfate for examples 62A to 70A and cobalt (II) acetate for examples 71A to 83A.

The results of examples 62A to 83A are set forth in Table IV-A.

TABLE IV-A

| Example | Temp (°C.) | Time (days) | CoAPSO Product(s)[1] |
|---|---|---|---|
| 62A | 150 | 4 | CoAPSO-34; CoAPSO-5 |
| 63A | 150 | 12 | CoAPSO-34; CoAPSO-5 |
| 64A | 150 | 12 | CoAPSO-34 |
| 65A | 200 | 4 | CoAPSO-34; CoAPSO-5 |
| 66A | 200 | 12 | CoAPSO-5; CoAPSO-34 |
| 67A | 200 | 12 | CoAPSO-34 |
| 68A | 100 | 4 | CoAPSO-34 |
| 69A | 100 | 12 | CoAPSO-34 |
| 70A | 100 | 12 | CoAPSO-34 |
| 71A | 100 | 2 | CoAPSO-34 |
| 72A | 100 | 7 | CoAPSO-34 |
| 73A | 150 | 2 | CoAPSO-34; CoAPSO-5 |
| 74A | 150 | 13 | CoAPSO-34; CoAPSO-5 |
| 75A | 200 | 2 | CoAPSO-5; CoAPSO-34 |
| 76A | 200 | 7 | CoAPSO-5; CoAPSO-34 |
| 77A | 100 | 14 | CoAPSO-34 |
| 78A | 100 | 14 | CoAPSO-34 |
| 79A | 100 | 28 | CoAPSO-34 |
| 80A | 100 | 10 | CoAPSO-34 |
| 81A | 100 | 20 | CoAPSO-34 |
| 82A | 100 | 2 | CoAPSO-34 |
| 83A | 100 | 4 | CoAPSO-34 |

[1]Major species as identified by x-ray powder diffraction pattern of product, except that when two or more species were identified the species are listed in the order of their predominence in the product.

EXAMPLES 84A TO 106A

Examples 84A to 106A were carried out according to the preparative procedure employed in examples 1A to 31A except that the organic template was as is shown in Table V-A. The reaction mixture was:

eR:f5CoO:0.9 Al$_2$O$_3$:0.9 P$_2$O$_5$:0.6 SiO$_2$:50 H$_2$O where "e" was one (1) except that "e" was 1.5 for examples 94A to 97A and "e" was 2.0 for example 140A. The results of examples 84A to 106A are set forth in Table V-A.

TABLE V-A

| Example | Template | e | f | Temp (°C.) | Time (days) | CoAPSO Product(s)[1] |
|---|---|---|---|---|---|---|
| 84A | TEAOH | 1.0 | 0.025 | 125 | 3 | CoAPSO-34; CoAPSO-18; |
| 85A | TEAOH | 1.0 | 0.025 | 125 | 5 | CoAPSO-34; CoAPSO-5; |
| 86A | TEAOH | 1.0 | 0.025 | 100 | 5 | CoAPSO-34; CoAPSO-5; |
| 87A | TEAOH | 1.0 | 0.025 | 100 | 5 | CoAPSO-34; |
| 88A | TEAOH | 1.0 | 0.025 | 100 | 3 | CoAPSO-34; |
| 89A | TEAOH | 1.0 | 0.025 | 100 | 5 | CioAPSO-34; |
| 90A | TEAOH | 1.0 | 0.025 | 100 | 7 | CoAPSO-34; |
| 91A | Quin | 1.0 | 0.2 | 225 | 5 | CoAPSO-35; CoAPSO-16 |
| 92A | C-hex | 1.0 | 0.2 | 225 | 5 | CoAPSO-5; CoAPSO-44 |
| 93A[2] | Pr$_3$N | 1.5 | 0.2 | 150 | 2 | CoAPSO-36; |
| 94A[2] | Pr$_3$N | 1.5 | 0.2 | 150 | 7 | CoAPSO-36; |
| 95A[2] | Pr$_3$N | 1.5 | 0.2 | 200 | 2 | CoAPSO-36; CoAPSO-5 |
| 96A[2] | Pr$_3$N | 1.5 | 0.2 | 200 | 7 | CoAPSO-36; CoAPSO-5 |
| 97A[3] | Pr$_2$NH | 1.0 | 0.2 | 150 | 4 | CoAPSO-31; CoAPSO-11 |
| 98A[3] | Pr$_2$NH | 1.0 | 0.2 | 150 | 10 | CoAPSO-46; CoAPSO-31 |

TABLE V-A-continued

| Example | Template | e | f | Temp (°C.) | Time (days) | CoAPSO Product(s)[1] |
|---|---|---|---|---|---|---|
| 99A[3] | Pr$_2$NH | 1.0 | 0.2 | 200 | 4 | CoAPSO-31; CoAPSO-11 |
| 100A[3] | Pr$_2$NH | 1.0 | 0.2 | 200 | 10 | CoAPSO-31; CoAPSO-11; CoAPSO-5; CoAPSO-46 |
| 101A[3] | Pr$_2$NH | 1.0 | 0.2 | 150 | 2 | CoAPSO-31 |
| 102A[3] | Pr$_2$NH | 1.0 | 0.2 | 150 | 3 | CoAPSO-31 |
| 103A[3] | Pr$_2$NH | 1.0 | 0.2 | 200 | 2 | CoAPSO-31; CoAPSO-46 |
| 104A | DEEA | 2.0 | 0.2 | 150 | 2 | CoAPSO-47 |
| 105A | TMAOH | 1.0 | 0.2 | 150 | 4 | CoAPSO-20 |
| 106A | TMAOH | 1.0 | 0.2 | 200 | 4 | CoAPSO-20 |

[1] Major species as identified by x-ray powder diffraction pattern of product, except that when two or more species were identified the spaces are listed in the order of their predominance in the product.
[2] Seed crystals of CoAPO-36 were employed (copending U.S. Ser. No. 514,334, filed July 15, 1983).
[3] Seed crystals of AlPO$_4$-31 (U.S. Pat. No. 4,310,440) were employed.

EXAMPLE 107A

Samples of the products were subjected to chemical analysis. The chemical analysis for each product is given hereinafter with the example in which the CoAPSO was prepared being given in parenthesis after the designation of the CoAPSO species.

(a) The chemical analysis for CoAPSO-11 (example 35A) was:

| Component | Weight Percent |
|---|---|
| Al$_2$O$_3$ | 31.1 |
| P$_2$O$_5$ | 46.1 |
| CoO | 6.4 |
| SiO$_2$ | 3.5 |
| Carbon | 5.2 |
| LOI* | 11.7 |

*LOI = Loss on Ignition

The above chemical analysis give an overall product composition in molar oxide ratios (anhydrous basis) of: 0.085 CoO; 0.305 Al$_2$O$_3$:0.325 P$_2$O$_5$:0.058 SiO$_2$: and a formula (anhydrous basis) of:

0.07R(Co$_{0.06}$Al$_{0.47}$P$_{0.46}$Si$_{0.04}$)O$_2$ (b) The chemical analysis for CoAPSO-11 (example 42A) was:

| Component | Weight Percent |
|---|---|
| Al$_2$O$_3$ | 32.5 |
| P$_2$O$_5$ | 44.7 |
| CoO | 4.4 |
| SiO$_2$ | 1.4 |
| Carbon | 3.9 |
| LOI* | 15.7 |

*LOI = Loss on Ignition

The above chemical analysis gives an overall product composition in molar oxide ratios (anhydrous basis) of: 0.059 CoO; 0.319 Al$_2$O$_3$:0.315 P$_2$O$_5$:0.023 SiO$_2$; and a formula (anhydrous basis) of:

0.05R(Co$_{0.04}$Al$_{0.47}$P$_{0.47}$Si$_{0.02}$)O$_2$ (c) The chemical analysis for CoAPSO-20 (example 106A) was:

| Component | Weight Percent |
|---|---|
| Al$_2$O$_3$ | 27.7 |
| P$_2$O$_5$ | 37.8 |
| CoO | 4.6 |
| SiO$_2$ | 10.0 |
| Carbon | 9.4 |
| LOI* | 18.4 |

*LOI = Loss on Ignition

The above chemical analysis gives an overall product composition in molar oxide ratios (anhydrous basis) of: 0.061 CoO; 0.272 Al$_2$O$_3$:0.266 P$_2$O$_5$:0.166 SiO$_2$; and a formula (anhydrous basis) of:

0.20R(Co$_{0.05}$Al$_{0.42}$P$_{0.41}$Si$_{0.13}$)O$_2$ (d) The chemical analysis for CoAPSO-31 (example 101A) was:

| Component | Weight Percent |
|---|---|
| Al$_2$O$_3$ | 32.3 |
| P$_2$O$_5$ | 42.4 |
| CoO | 4.3 |
| SiO$_2$ | 3.8 |
| Carbon | 2.8 |
| LOI* | 16.6 |

*LOI = Loss on Ignition

The above chemical analysis gives an overall product composition in molar oxide ratios (anhydrous basis) of: 0.057 CoO; 0.317 Al$_2$O$_3$:0.299 P$_2$O$_5$:0.063 SiO$_2$; and a formula (anhydrous basis) of:

0.04R(Co$_{0.04}$Al$_{0.47}$P$_{0.44}$Si$_{0.05}$)O$_2$ (e) The chemical analysis for CoAPSO-34 (example 69A) was:

| Component | Weight Percent |
|---|---|
| Al$_2$O$_3$ | 28.2 |
| P$_2$O$_5$ | 41.7 |
| CoO | 4.7 |
| SiO$_2$ | 1.1 |
| Carbon | 5.9 |
| LOI* | 23.6 |

*LOI = Loss on Ignition

The above chemical analysis gives an overall product composition in molar oxide ratios (anhydrous basis) of: 0.063 CoO; 0.277 Al$_2$O$_3$:0.294 P$_2$O$_5$:0.018 SiO$_2$; and a formula (anhydrous basis) of:

0.06R(Co$_{0.05}$Al$_{0.45}$P$_{0.48}$Si$_{0.02}$)O$_2$ (f) The chemical analysis for CoAPSO-34 (example 72A) was:

| Component | Weight Percent |
|---|---|
| Al$_2$O$_3$ | 28.4 |
| P$_2$O$_5$ | 40.6 |
| CoO | 4.6 |
| SiO$_2$ | 2.2 |
| Carbon | 7.8 |
| LOI* | 23.3 |

*LOI = Loss on Ignition

The above chemical analysis gives an overall product composition in molar oxide ratios of: 0.061 CoO; 0.279

Al$_2$O$_3$:0.282 P$_2$O$_5$:0.037 SiO$_2$; and a formula (anhydrous basis) of:

0.08R(Co$_{0.05}$Al$_{0.46}$P$_{0.46}$Si$_{0.03}$)O$_2$ (g) The chemical analysis for CoAPSO-34 (example 79A) was:

| Component | Weight Percent |
|---|---|
| Al$_2$O$_3$ | 31.7 |
| P$_2$O$_5$ | 40.5 |
| CoO | 2.5 |
| SiO$_2$ | 3.4 |
| Carbon | 8.4 |
| LOI* | 20.8 |

*LOI = Loss on Ignition

The above chemical analysis gives an overall product composition in molar oxide ratios of: 0.033CoO:0.311 Al$_2$O$_3$:0.285 P$_2$O$_5$:0.057SiO$_2$; and a formula (anhydrous basis) of:

0.09R(Co$_{0.03}$Al$_{0.49}$P$_{0.45}$Si$_{0.05}$)O$_2$ (h) The chemical analysis for CoAPSO-34 (example 106A) was:

| Component | Weight Percent |
|---|---|
| Al$_2$O$_3$ | 32.0 |
| P$_2$O$_5$ | 39.6 |
| CoO | 1.2 |
| SiO$_2$ | 2.7 |
| Carbon | 6.4 |
| LOI* | 22.8 |

*LOI = Loss on Ignition

The above chemical analysis gives an overall product composition in molar oxide ratios of: 0.016 CoO; 0.314 Al$_2$O$_3$:0.279 P$_2$O$_5$:0.045 SiO$_2$; and a formula (anhydrous basis) of:

0.07R(Co$_{0.01}$Al$_{0.50}$P$_{0.45}$Si$_{0.04}$)O$_2$ (i) The chemical analysis for CoAPSO-34 (example 83A) was:

| Component | Weight Percent |
|---|---|
| Al$_2$O$_3$ | 33.8 |
| P$_2$O$_5$ | 40.6 |
| CoO | 1.6 |
| SiO$_2$ | 2.1 |
| Carbon | 6.6 |
| LOI* | 21.7 |

*LOI = Loss on Ignition

The above chemical analysis gives an overall product composition in molar oxide ratios (anhydrous basis) of: 0.021 CoO; 0.332Al$_2$O$_3$:0.286 P$_2$O$_5$:0.035SiO$_2$; and a formula (anhydrous basis) of:

0.07R(Co$_{0.02}$Al$_{0.53}$P$_{0.46}$Si$_{0.03}$)O$_2$ (j) The chemical analysis for CoAPSO-34 (example 77A) was:

| Component | Weight Percent |
|---|---|
| Al$_2$O$_3$ | 30.1 |
| P$_2$O$_5$ | 41.7 |
| CoO | 4.8 |
| SiO$_2$ | 2.6 |
| Carbon | 9.0 |
| LOI* | 19.5 |

*LOI = Loss on Ignition

The above chemical analysis gives an overall product composition in molar oxide ratios (anhydrous basis) of: 0.064 CoO; 0.295 Al$_2$O$_3$: 0.294 P$_2$O$_5$:0.043 SiO$_2$; and a formula (anhydrous basis) of:

0.09R(Co$_{0.05}$Al$_{0.46}$P$_{0.46}$Si$_{0.03}$)O$_2$ (k) The chemical analysis of CoAPSO-34 (example 89A) was:

| Component | Weight Percent |
|---|---|
| Al$_2$O$_3$ | 31.8 |
| P$_2$O$_5$ | 38.8 |
| CoO | 0.71 |
| SiO$_2$ | 2.2 |
| Carbon | 6.6 |
| LOI* | 24.1 |

*LOI = Loss on Ignition

The above chemical analysis gives an overall product composition in molar oxide ratios (anhydrous basis) of: 0.01 CoO; 0.312 Al$_2$O$_3$:0.273 P$_2$O$_5$: 0.037 SiO$_2$; and a formula (anhydrous basis) of:

0.07R(Co$_{0.01}$Al$_{0.51}$P$_{0.45}$Si$_{0.03}$)O$_2$ where the value for cobalt is rounded off from 0.008.

(l) The chemical analysis of CoAPSO-34 (example 90A) was:

| Component | Weight Percent |
|---|---|
| Al$_2$O$_3$ | 32.4 |
| P$_2$O$_5$ | 39.3 |
| CoO | 0.66 |
| SiO$_2$ | 3.5 |
| Carbon | 7.2 |
| LOI* | 23.5 |

*LOI = Loss on Ignition

The above chemical analysis gives an overall product composition in molar oxide ratios (anhydrous basis) of: 0.009 CoO; 0.318 Al$_2$O$_3$:0.277 P$_2$O$_5$:0.058 SiO$_2$; and a formula (anhydrous basis) of:

0.08R(Co$_{0.01}$Al$_{0.51}$P$_{0.44}$Si$_{0.05}$)O$_2$ where the value for cobalt is rounded off from 0.007.

(m) The chemical analysis of CoAPSO-35 (example 10A) was:

| Component | Weight Percent |
|---|---|
| Al$_2$O$_3$ | 27.0 |
| P$_2$O$_5$ | 41.6 |
| CoO | 4.3 |
| SiO$_2$ | 4.3 |
| Carbon | 13.0 |
| LOI* | 22.1 |

*LOI = Loss on Ignition

The above chemical analysis gives an overall product composition in molar oxide ratios (anhydrous basis) of: 0.057 CoO; 0.265 Al$_2$O$_3$:0.290 P$_2$O$_5$:0.054 SiO$_2$; and a formula (anhydrous basis) of:

0.14R(Co$_{0.05}$Al$_{0.43}$P$_{0.48}$Si$_{0.04}$)O$_2$ (n) The chemical analysis of CoAPSO-36 (example 93A) was:

| Component | Weight Percent |
|---|---|
| Al$_2$O$_3$ | 29.5 |
| P$_2$O$_5$ | 39.6 |
| CoO | 5.2 |
| SiO$_2$ | 6.6 |
| Carbon | 3.3 |

| Component | Weight Percent |
|---|---|
| LOI* | 18.5 |

*LOI = Loss on Ignition

The above chemical analysis gives an overall product composition in molar oxide ratios (anhydrous basis) of: 0.069 CoO; 0.289 $Al_2O_3$:0.279 $P_2O_5$:0.110 $SiO_2$; and a formula (anhydrous basis) of:

0.03R($Co_{0.05}Al_{0.44}P_{0.42}Si_{0.08}$)$O_2$ (o) The chemical analysis of CoAPSO-44 (example 19A) was:

| Component | Weight Percent |
|---|---|
| $Al_2O_3$ | 26.3 |
| $P_2O_5$ | 36.3 |
| CoO | 4.5 |
| $SiO_2$ | 10.0 |
| Carbon | 13.2 |
| LOI* | 22.6 |

*LOI = Loss on Ignition

The above chemical analysis gives an overall product composition in molar oxide ratios (anhydrous basis) of: 0.06 CoO; 0.258 $Al_2O_3$:0.256 $P_2O_5$:0.166 $SiO_2$; and a formula (anhydrous basis) of:

0.18R($Co_{0.05}Al_{0.41}P_{0.41}Si_{0.13}$)$O_2$ (p) The chemical analysis of CoAPSO-46 (example 36A) was:

| Component | Weight Percent |
|---|---|
| $Al_2O_3$ | 31.4 |
| $P_2O_5$ | 31.5 |
| CoO | 6.2 |
| $SiO_2$ | 2.9 |
| Carbon | 4.2 |
| LOI* | 27.5 |

*LOI = Loss on Ignition

The above chemical analysis gives an overall product composition in molar oxide ratios (anhydrous basis) of: 0.08 CoO; 0.31 $Al_2O_3$:0.22 $P_2O_5$:0.05 $SiO_2$; and a formula (anhydrous basis) of:

0.06R($Co_{0.07}Al_{0.52}P_{0.37}Si_{0.04}$)$O_2$ (q) The chemical analysis of CoAPSO-47 (example 104A) was:

| Component | Weight Percent |
|---|---|
| $Al_2O_3$ | 22.7 |
| $P_2O_5$ | 39.8 |
| CoO | 8.2 |
| $SiO_2$ | 2.9 |
| Carbon | 11.4 |
| LOI* | 25.2 |

*LOI = Loss on Ignition

The above chemical analysis gives an overall product composition in molar oxide ratios of: 0.109 CoO; 0.223 $Al_2O_3$:0.280 $P_2O_5$:0.048 $SiO_2$; and a formula (anhydrous basis) of:

0.16R($Co_{0.09}Al_{0.38}P_{0.48}Si_{0.04}$)$O_2$

EXAMPLE 108A

EDAX (energy dispersive analysis by x-ray) microprobe analysis in conjunction with SEM (scanning electron microscope) was carried out on clean crystals of CoAPSO products. Analysis of crystals having a morphology characteristic of the CoAPSO compositions noted hereinafter gave the following analysis based on relative peak heights:

| Average of Spot Probes | |
|---|---|
| (a) CoAPSO-11 (example 42A): | |
| Co | 1.0 |
| Al | 8.0 |
| P | 10.0 |
| Si | 1.0 |
| (b) CoAPSO-20 (example 106A): | |
| Co | 0.5 |
| Al | 8.0 |
| P | 7.5 |
| Si | 3.4 |
| (c) CoAPSO-34 (example 69A): | |
| Co | 0.5 |
| Al | 8.0 |
| P | 10.0 |
| Si | 1.0 |
| (d) CoAPSO-35 (example 10A): | |
| Co | 0.5 |
| Al | 9.0 |
| P | 7.5 |
| Si | 1.0 |
| (e) CoAPSO-36 (example 95A): | |
| Co | 0.6 |
| Al | 9.1 |
| P | 9.4 |
| Si | 2.2 |
| (f) CoAPSO-44 (example 16A): | |
| Co | 1.0 |
| Al | 8.0 |
| P | 8.0 |
| Si | 0.6 |
| (g) CoAPSO-47 (example 104A): | |
| Co | 0.7 |
| Al | 8.4 |
| P | 9.2 |
| Si | 2.8 |

EXAMPLE 109A

Samples of the CoAPSO products were tested for adsorption capacities. The CoAPSO products were evaluated either in the as-synthesized form or were calcined in air or nitrogen, to remove at least part of the organic templating agent, as hereinafter set forth. The adsorption capacities of each calcined sample were measured using a standard McBain-Bakr gravimetric adsorption apparatus. The samples were activated in a vacuum at 350° C. prior to measurement. The McBain-Bakr data for the aforementioned calcined CoAPSO products were:

(a) CoAPSO-11 (example 61A):

| Adsorbate | Kinetic Diameter, Å | Pressure (Torr) | Temp (°C.) | Wt. % Adsorbed* |
|---|---|---|---|---|
| $O_2$ | 3.46 | 106 | −183 | 6.9 |
| $O_2$ | 3.46 | 744 | −183 | 12.1 |
| isobutane | 5.0 | 740 | 24.2 | 3.9 |
| cyclo-hexane | 6.0 | 82 | 23.9 | 13.5 |
| neopentane | 6.2 | 741 | 25.3 | 3.6 |
| $H_2O$ | 2.65 | 4.6 | 24.9 | 7.1 |
| $H_2O$ | 2.65 | 19 | 24.8 | 21.0 |

*calcined in air at 600° C. for 1 hour prior to activation

The above data demonstrate that the pore size of the calcined product is about 6.0 Å.

(b) CoAPSO-20 (example 106A):

| Adsorbate | Kinetic Diameter, Å | Pressure (Torr) | Temp (°C.) | Wt. % Adsorbed* |
|---|---|---|---|---|
| O$_2$ | 3.46 | 102 | −183 | 5 |
| O$_2$ | 3.46 | 744 | −183 | 6.4 |
| H$_2$O | 2.65 | 4.6 | 23.3 | 10 |
| H$_2$O | 2.65 | 19 | 23.2 | 14 |

The above data demonstrate that the pore size of the calcined products is about 3.0 Å.

(c) CoAPSO-31 (example 102A):

| Adsorbate | Kinetic Diameter, Å | Pressure (Torr) | Temp (°C.) | Wt. % Adsorbed* |
|---|---|---|---|---|
| O$_2$ | 3.46 | 105 | −183 | 6.9 |
| O$_2$ | 3.46 | 741 | −183 | 12.8 |
| neopentane | 6.2 | 739 | 23.5 | 5.8 |
| H$_2$O | 2.65 | 4.6 | 23.5 | 5.8 |
| H$_2$O | 2.65 | 20 | 24.0 | 15.9 |

The above data demonstrate that the pore size of the calcined product is greater than about 6.2 Å.

(d) CoAPSO-34 (example 78A):

| Adsorbate | Kinetic Diameter, Å | Pressure (Torr) | Temp (°C.) | Wt. % Adsorbed* |
|---|---|---|---|---|
| O$_2$ | 3.46 | 103 | −183 | 15.9 |
| O$_2$ | 3.46 | 731 | −183 | 28.2 |
| n-hexane | 4.3 | 103 | 23.9 | 9.8 |
| isobutane | 5.0 | 741 | 23.3 | 1.8 |
| H$_2$O | 2.65 | 4.6 | 23.8 | 11.3 |
| H$_2$O | 2.65 | 18.5 | 24.0 | 28.9 |

The above data demonstrate that the pore size of the calcined products is about 4.3 Å.

(e) CoAPSO-34 (example 89A):

| Adsorbate | Kinetic Diameter, Å | Pressure (Torr) | Temp (°C.) | Wt. % Adsorbed* |
|---|---|---|---|---|
| O$_2$ | 3.46 | 105 | −183 | 18.6 |
| O$_2$ | 3.46 | 741 | −183 | 28.8 |
| isobutane | 5.0 | 108 | 23.9 | 9.9 |
| n-hexane | 4.3 | 742 | 23.3 | 1.2 |
| H$_2$O | 2.65 | 4.6 | 23.8 | 10.7 |
| H$_2$O | 2.65 | 20.0 | 24.0 | 30.1 |

*calcined in air at 600° C. for one hour prior to activation.

(f) CoAPSO-35 (example 8A):

| Adsorbate | Kinetic Diameter, Å | Pressure (Torr) | Temp (°C.) | Wt. % Adsorbed* |
|---|---|---|---|---|
| O$_2$ | 3.46 | 103 | −183 | 11.7 |
| O$_2$ | 3.46 | 731 | −183 | 15.5 |
| iso-butane | 5.0 | 741 | 24.5 | 0.6 |
| n-hexane | 4.3 | 103 | 24.4 | 3.5 |
| H$_2$O | 2.65 | 4.6 | 24.4 | 14.3 |
| H$_2$O | 2.65 | 18.5 | 23.9 | 22.7 |

*calcined in nitrogen at 500° C. for 2.0 hours prior to acivation.

The above data demonstrate that the pore size of the calcined products is about 4.3 Å.

(g) CoAPSO-44 (example 19A):

| Adsorbate | Kinetic Diameter, Å | Pressure (Torr) | Temp (°C.) | Wt. % Adsorbed* |
|---|---|---|---|---|
| O$_2$ | 3.46 | 103 | −183 | 24.8 |
| O$_2$ | 3.46 | 731 | −183 | 31.4 |
| n-hexane | 4.3 | 103 | 24.4 | 7.4 |
| isobutane | 5.0 | 741 | 24.5 | 0.3 |
| H$_2$O | 2.65 | 4.6 | 24.4 | 27.8 |
| H$_2$O | 2.65 | 18.5 | 23.9 | 35.1 |

*calcined in air at 500° C. for 1.25 hrs. prior to activaton.

The above data demonstrate that the pore size of the calcined products is about 4.3 Å.

(h) CoAPSO-47 (example 104A):

| Adsorbate | Kinetic Diameter, Å | Pressure (Torr) | Temp (°C.) | Wt. % Adsorbed* |
|---|---|---|---|---|
| O$_2$ | 3.46 | 102 | −183 | 4.1 |
| O$_2$ | 3.46 | 744 | −183 | 4.9 |
| isobutane | 5.0 | 746 | 24.1 | 0.6 |
| n-hexane | 4.3 | 95 | 23.6 | 1.3 |
| H$_2$O | 2.65 | 4.6 | 23.3 | 9.6 |
| H$_2$O | 2.65 | 19 | 23.2 | 14.3 |

*calcined in air at 500° C. for 1.5 hrs. prior to activation.

The above data demonstrate that the pore size of the calcined products is about 4.3 Å.

EXAMPLE 110A (a) The as-synthesized CoAPSO-5 of example 76A was subjected to analysis by x-ray. The CoAPSO-5 product was characterized by the x-ray powder diffraction pattern of Table VII-A below:

TABLE VII-A

| 2θ | d, (Å) | 100 × I/Io |
|---|---|---|
| 7.4 | 11.95 | 100 |
| 9.6* | 9.21 | 65 |
| 12.9** | 6.86 | 19 |
| 14.1* | 6.28 | 10 |
| 14.9 | 5.95 | 26 |
| 16.0* | 5.54 | 32 |
| 17.8* | 4.98 | 13 |
| 19.8 | 4.48 | 61 |
| 20.5* | 4.33 | 55 |
| 21.1 | 4.21 | 74 |
| 22.4** | 3.97 | 94 |
| 23.0* | 3.87 | 10 |
| 24.8 | 3.59 | 16 |
| 25.2 | 3.53 | 16 |
| 26.0** | 3.427 | 42 |
| 27.4** | 3.255 | 13 |
| 28.2* | 3.164 | 10 |
| 29.1 | 3.069 | 19 |
| 29.5* | 3.028 | 10 |
| 30.1 | 2.969 | 29 |
| 30.6* | 2.921 | 23 |
| 31.1* | 2.876 | 19 |
| 33.7** | 2.660 | 10 |
| 34.5** | 2.600 | 19 |
| 37.0 | 2.430 | 7 |
| 37.7 | 2.386 | 16 |
| 41.5 | 2.176 | 7 |
| 42.2 | 2.141 | 8 |
| 43.7 | 2.071 | 7 |
| 44.9** | 2.019 | 7 |
| 47.8** | 1.903 | 10 |
| 48.9* | 1.863 | 10 |
| 55.8 | 1.647 | 10 |

*peak resulting from CoAPSO-34
**peak resulting from CoAPSO-34 and CoAPSO-5

(b) CoAPSO-5, of example 21A was calcined in air at 600° for four hours. The calcined product was characterized by the x-ray powder diffraction pattern of Table VIII-A below:

TABLE VIII-A

| 2θ | d, (Å) | 100 × I/Io |
|---|---|---|
| 7.4 | 11.95 | 100 |
| 12.9 | 6.86 | 22 |
| 14.8 | 5.99 | 13 |
| 19.7 | 4.51 | 39 |
| 20.3* | 4.37 | 83 |
| 21.0 | 4.23 | 74 |
| 21.4* | 4.15 | 99 |
| 22.4 | 3.97 | 74 |
| 22.9* | 3.88 | 35 |
| 24.4 | 3.65 | 13 |
| 25.9 | 3.440 | 30 |
| 27.1** | 3.290 | 17 |
| 28.1* | 3.175 | 26 |
| 29.0 | 3.079 | 26 |
| 30.1 | 2.969 | 30 |
| 33.7 | 2.660 | 13 |
| 34.6 | 2.592 | 22 |
| 35.6* | 2.522 | 26 |
| 37.0 | 2.430 | 13 |
| 37.8 | 2.380 | 13 |
| 42.8 | 2.113 | 13 |
| 43.8 | 2.067 | 9 |
| 47.8 | 1.903 | 9 |
| 55.8 | 1.647 | 9 |

*peak from tridynite
**impurity peak (c) The species denominated herein as CoAPSO-5 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" are the mole fractions as above defined with reference to FIG. 1 or FIG. 2; and having in the as-synthesized or calcined form a characteristic x-ray powder diffraction pattern which contains at least the d-spacings set forth in Table IX-A:

TABLE IX-A

| 2θ | d, (Å) | Relative Intensity |
|---|---|---|
| 7.3–7.5 | 12.11–11.79 | m–vs |
| 14.7–14.9 | 6.03–5.95 | w–m |
| 19.6–19.8 | 4.53–4.48 | w–m |
| 20.9–21.2 | 4.25–4.19 | w–vs |
| 22.3–22.4 | 3.99–3.97 | m–vs |
| 25.8–26.0 | 3.453–3.427 | vw–m |

(d) The CoAPSO-5 compositions for which x-ray powder diffraction patterns have been obtained to date have patterns which are characterized by the x-ray pattern of Table X-A:

TABLE X-A

| 2θ | d, (Å) | 100 × I/Io |
|---|---|---|
| 7.3–7.5 | 12.11–11.79 | 32–100 |
| 12.7–12.9 | 6.97–6.86 | 2–22 |
| 14.7–14.9 | 6.03–5.95 | 10–26 |
| 19.6–19.8 | 4.53–4.48 | 7–39 |
| 20.9–21.2 | 4.25–4.19 | 19–100 |
| 22.3–22.4 | 3.99–3.97 | 25–94 |
| 24.4–24.8 | 3.65–3.59 | 2–16 |
| 25.8–26.0 | 3.453–3.427 | 6–41 |
| 29.0–29.1 | 3.079–3.069 | 3–26 |
| 29.9–30.1 | 2.988–2.969 | 3–30 |
| 33.5–33.7 | 2.667–2.660 | 2–13 |
| 34.4–34.6 | 2.607–2.592 | 4–22 |
| 36.8–37.0 | 2.442–2.430 | 2–13 |
| 37.5–37.8 | 2.398–2.380 | 3–16 |

TABLE X-A-continued

| 2θ | d, (Å) | 100 × I/Io |
|---|---|---|
| 41.4–41.5 | 2.181–2.176 | 1–7 |
| 42.2–42.8 | 2.141–2.113 | 1–13 |
| 43.7–43.8 | 2.071–2.067 | 0–9 |
| 44.9–45.0 | 2.019–2.014 | 1–7 |
| 47.5–47.8 | 1.914–1.903 | 3–10 |
| 55.6–55.8 | 1.653–1.647 | 1–10 |

EXAMPLE 111A (a) The as-synthesized CoAPSO-11 of example 42A was subjected to analysis by x-ray. The CoAPSO-11 product was characterized by the x-ray powder diffraction pattern of Table XI-A below:

TABLE XI-A

| 2θ | d, (Å) | 100 × I/Io |
|---|---|---|
| 7.9 | 11.19 | 32 |
| 9.3 | 9.51 | 72 |
| 12.3* | 7.20 | 16 |
| 13.1 | 6.76 | 24 |
| 15.6 | 5.68 | 32 |
| 16.2 | 5.47 | 12 |
| 18.2 | 4.87 | 16 |
| 18.9 | 4.70 | 12 |
| 20.3 | 4.37 | 40 |
| 21.0 | 4.23 | 100 |
| 22.1 | 4.02 | 56 |
| 22.5 | 3.95 | 60 |
| 22.7 | 3.92 | 72 |
| 23.1 | 3.85 | 68 |
| 24.6 | 3.62 | 20 |
| 26.3 | 3.389 | 28 |
| 28.2 | 3.164 | 16 |
| 28.5 | 3.132 | 24 |
| 29.4 | 3.038 | 20 |
| 29.6 | 3.018 | 16 |
| 29.9 | 2.988 | 16 |
| 31.3 | 2.858 | 16 |
| 32.6 | 2.747 | 24 |
| 34.0 | 2.637 | 16 |
| 36.3 | 2.475 | 12 |
| 37.6 | 2.392 | 20 |
| 39.3 | 2.292 | 12 |
| 42.8 | 2.113 | 8 |
| 44.8 | 2.023 | 8 |
| 50.5 | 1.807 | 12 |
| 54.4 | 1.687 | 12 |

*peak may contain impurity (b) CoAPSO-11, of example 42A was calcined in air at 600° for 1.5 hours. The calcined product was characterized by the x-ray powder diffraction pattern of Table XII-A below:

TABLE XII-A

| 2θ | d, (Å) | 100 × I/Io |
|---|---|---|
| 8.1 | 10.92 | 70 |
| 9.5 | 9.31 | 83 |
| 13.1 | 6.76 | 26 |
| 13.5 | 6.56 | 30 |
| 15.8 | 5.61 | 56 |
| 18.5* | 4.80 | 17 |
| 19.2 | 4.62 | 13 |
| 20.2 | 4.40 | sh |
| 20.3 | 4.37 | 35 |
| 21.3 | 4.17 | 100 |
| 22.3 | 3.99 | 61 |
| 22.5 | 3.95 | sh |
| 23.0 | 3.87 | 65 |
| 23.4 | 3.80 | 52 |
| 24.3 | 3.66 | 17 |
| 25.1 | 3.548 | 17 |
| 26.5 | 3.363 | 30 |
| 26.6 | 3.351 | sh |
| 28.2 | 3.164 | 13 |

TABLE XII-A-continued

| 2θ | d, (Å) | 100 × I/Io |
|---|---|---|
| 28.9 | 3.089 | 26 |
| 29.5 | 3.028 | 17 |
| 30.1 | 2.969 | 13 |
| 30.5 | 2.931 | 17 |
| 31.8 | 2.814 | 17 |
| 32.9 | 2.722 | 22 |
| 34.7 | 2.585 | 13 |
| 36.2 | 2.481 | 13 |
| 37.9 | 2.374 | 17 |
| 38.3 | 2.350 | 17 |
| 39.5 | 2.281 | 9 |

*peak may contain impurity (c) The species denominated herein as CoAPSO-11 has a three-dimensional microporous crystal framework structure of $CoO_2$, $AlO_2$, $PO_2$ and $SiO_2$ tetrahedral units and has an empirical chemical composition on an anhydrous basis expressed by the formula:

$mR:(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XIII-A:

TABLE XIII-A

| 2θ | d, (Å) | Relative Intensity |
|---|---|---|
| 7.9–8.1 | 11.19–10.92 | m |
| 9.3–9.5 | 9.51–9.31 | m–s |
| 21.0–21.3 | 4.23–4.17 | vs |
| 22.1–22.3 | 4.02–3.99 | m |
| 22.7–23.1 | 3.92–3.85 | m |
| 23.2–23.4 | 3.83–3.80 | m |

(d) The CoAPSO-11 compositions for which x-ray powder diffraction patterns have been obtained to date have patterns which are characterized by the x-ray pattern of Table XIV-A:

TABLE XIV-A

| 2θ | d, (Å) | 100 × I/Io |
|---|---|---|
| 7.9–8.1 | 11.19–10.92 | 32–70 |
| 9.3–9.5 | 9.51–9.31 | 72–83 |
| 12.3* | 7.20 | 16 |
| 13.1–13.2 | 6.76–6.71 | 16–26 |
| 13.5–13.6 | 6.56–6.51 | 30 |
| 15.6–15.8 | 5.68–5.61 | 32–56 |
| 16.2–16.3 | 5.47–5.44 | 8–12 |
| 18.2–18.5 | 4.87–4.80 | 16–17 |
| 18.9–19.2 | 4.70–4.62 | 12–13 |
| 19.7–20.2 | 4.51–4.40 | sh |
| 20.3 | 4.37 | 35–40 |
| 21.0–21.3 | 4.23–4.17 | 100 |
| 22.1–22.3 | 4.02–3.99 | 56–61 |
| 22.4–22.6 | 3.97–3.93 | sh–60 |
| 22.7–23.1 | 3.92–3.85 | 65–72 |
| 23.2–23.4 | 3.83–3.80 | 52–68 |
| 24.3–24.6 | 3.66–3.62 | 17–20 |
| 25.1 | 3.548 | 17 |
| 26.3–26.5 | 3.389–3.363 | 28–30 |
| 26.6 | 3.351 | sh |
| 28.1–28.2 | 3.175–3.164 | 13–16 |
| 28.5–28.9 | 3.132–3.089 | 24–26 |
| 29.4–29.5 | 3.038–3.028 | 17–20 |
| 29.6–30.5 | 3.018–2.931 | 13–17 |
| 31.3–31.8 | 2.858–2.814 | 16–17 |
| 32.6–32.9 | 2.747–2.722 | 22–24 |
| 34.0–34.7 | 2.637–2.585 | 13–16 |
| 36.2–36.3 | 2.481–2.475 | 12–13 |
| 36.7–37.9 | 2.392–2.374 | 17–20 |
| 38.3–38.4 | 2.350–2.344 | 17–18 |
| 39.3–39.5 | 2.292–2.281 | 9–12 |
| 42.8–42.9 | 2.113–2.108 | 8–9 |
| 44.7–44.8 | 2.027–2.023 | 8–9 |
| 50.5–50.6 | 1.807–1.804 | 9–12 |
| 54.4–54.6 | 1.687–1.681 | 9–12 |

*peak may contain impurity

EXAMPLE 112-A (a) The as-synthesized CoAPSO-16 of example 4A was subjected to analysis by x-ray. The CoAPSO-16 product was characterized by the x-ray powder diffraction pattern of Table XV-A below:

TABLE XV-A

| 2θ | d, (Å) | 100 × I/Io |
|---|---|---|
| 8.7* | 10.16 | 17 |
| 11.0* | 8.04 | 40 |
| 11.5 | 7.69 | 32 |
| 13.0* | 6.81 | 15 |
| 15.9* | 5.57 | 13 |
| 17.3* | 5.13 | 55 |
| 17.9* | 4.96 | 13 |
| 18.8 | 4.72 | 23 |
| 20.8* | 4.27 | (sh) |
| 21.2* | 4.19 | 40 |
| 22.0** | 4.04 | 100 |
| 23.2** | 3.83 | 21 |
| 23.8* | 3.74 | 11 |
| 25.1* | 3.548 | 9 |
| 26.9** | 3.314 | 23 |
| 28.6* | 3.121 | 26 |
| 28.8* | 3.100 | 26 |
| 29.0 | 3.079 | 15 |
| 29.6 | 3.018 | 11 |
| 29.9 | 2.988 | 15 |
| 32.2* | 2.780 | 34 |
| 32.8 | 2.730 | 9 |
| 34.6** | 2.592 | 13 |
| 35.8* | 2.508 | 11 |
| 37.9 | 2.374 | 9 |
| 40.1 | 2.249 | 9 |
| 42.2* | 2.141 | 11 |
| 43.0* | 2.103 | 9 |
| 44.5 | 2.036 | 9 |
| 48.6** | 1.873 | 13 |
| 49.6 | 1.838 | 11 |
| 51.6 | 1.771 | 11 |
| 52.6 | 1.740 | 6 |
| 55.0 | 1.670 | 6 |
| 55.4* | 1.658 | 11 |

*peak resulting from CoAPSO-35
**peak resulting from CoAPSO-16 and CoAPSO-35

(b) The species denominated herein as CoAPSO-16 has a three-dimensional microporous crystal framework structure of $CoO_2$, $AlO_2$, $PO_2$ and $SiO_2$ tetrahedral units and has an empirical chemical composition on an anhydrous basis expressed by the formula:

$mR:(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XVI-A:

TABLE XVI-A

| 2θ | d, (Å) | Relative Intensity |
|---|---|---|
| 11.4–11.6 | 7.76–7.63 | w–s |
| 17.2–17.4 | 5.16–5.10 | m |
| 18.7–18.9 | 4.75–4.70 | vw–m |
| 21.9–22.1 | 4.06–4.02 | vs |
| 23.1–23.3 | 3.85–3.82 | m |
| 26.8–27.0 | 3.326–3.302 | m |
| 29.8–29.9 | 2.998–2.988 | w–m |

(c) The CoAPSO-16 compositions for which x-ray powder diffraction patterns have been obtained to date have patterns which are characterized by the x-ray pattern of Table XVII-A:

TABLE XVII-A

| 2θ | d, (Å) | 100 × I/Io |
|---|---|---|
| 11.4–11.6 | 7.76–7.63 | 11–79 |
| 17.2–17.4 | 5.16–5.10 | 66–80 |
| 18.7–18.9 | 4.75–4.70 | 7–53 |
| 21.9–22.1 | 4.06–4.02 | 100 |
| 23.1–23.3 | 3.85–3.82 | 21–24 |
| 26.8–27.0 | 3.326–3.302 | 23–28 |
| 29.0 | 3.079 | 14–18 |
| 29.5–29.7 | 3.028–3.008 | 4–15 |
| 29.8–29.9 | 2.998–2.988 | 15–29 |
| 32.7–32.9 | 2.739–2.722 | 3–9 |
| 34.5–34.7 | 2.600–2.585 | 9–13 |
| 37.8–38.0 | 2.380–2.368 | 6–9 |
| 40.0–40.2 | 2.534–2.243 | 1–9 |
| 44.3–44.6 | 2.045–2.032 | 2–9 |
| 48.5–48.7 | 1.877–1.870 | 8–13 |
| 49.5–49.7 | 1.841–1.834 | 8–11 |
| 51.5–51.7 | 1.774–1.768 | 6–11 |
| 52.5–52.7 | 1.743–1.737 | 6–7 |
| 54.9–55.1 | 1.672–1.667 | 1–6 |

EXAMPLE 113A (a) The as-synthesized CoAPSO-16 of example 106A was subjected to analysis by x-ray. The CoAPSO-20 product was characterized by the x-ray powder diffraction pattern of Table XVIII-A below:

TABLE XVIII-A

| 2θ | d, (Å) | 100 × I/Io |
|---|---|---|
| 10.293 | 8.5942 | 7 |
| 12.078 | 7.3278 | 1 |
| 13.925 | 6.3595 | 46 |
| 14.376 | 6.1609 | 2 |
| 18.773 | 4.7268 | 2 |
| 19.738 | 4.4977 | 42 |
| 20.507 | 4.3307 | 3 |
| 22.093 | 4.0233 | 3 |
| 24.227 | 3.6735 | 100 |
| 26.363 | 3.3806 | 3 |
| 26.941 | 3.3094 | 3 |
| 28.052 | 3.1808 | 11 |
| 31.442 | 2.8451 | 11 |
| 31.759 | 2.8175 | 2 |
| 31.980 | 2.7985 | 2 |
| 34.523 | 2.5980 | 16 |
| 37.426 | 2.4029 | 1 |
| 40.075 | 2.2499 | 4 |
| 42.614 | 2.1215 | 4 |
| 47.3 | 1.922 | 4 |
| 51.8 | 1.765 | 8 |

(b) CoAPSO-20, of example 106A was calcined in air at 500° for one hour. The calcined product was characterized by the x-ray powder diffraction pattern of Table XIX-A below:

TABLE XIX-A

| 2θ | d, (Å) | 100 × I/Io |
|---|---|---|
| 10.6* | 8.39 | 7 |
| 21.1* | 7.30 | 3 |
| 12.2* | 7.24 | 2 |
| 14.0 | 6.33 | 75 |
| 14.8* | 6.01 | 3 |
| 16.1* | 5.51 | 2 |
| 19.8 | 4.48 | 38 |
| 22.2 | 4.01 | 4 |
| 24.3 | 3.66 | 100 |
| 26.7* | 3.344 | 3 |
| 27.6* | 3.227 | 2 |
| 28.1 | 3.173 | 14 |
| 31.5 | 2.839 | 13 |
| 32.2* | 2.781 | 2 |
| 32.4* | 2.764 | 2 |
| 34.6 | 2.593 | 18 |
| 40.2 | 2.244 | 3 |
| 42.5 | 2.127 | 4 |
| 47.3 | 1.922 | 4 |
| 51.8 | 1.765 | 8 |

(c) The species denominated herein as CoAPSO-20 has a three-dimensional microporous crystal framework structure of $CoO_2$, $AlO_2$, $PO_2$ and $SiO_2$ tetrahedral units and has an empirical chemical composition on an anhydrous basis expressed by the formula:

$mR:(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XX-A:

TABLE XX-A

| 2θ | d, (Å) | Relative Intensity |
|---|---|---|
| 13.9–14.0 | 6.37–6.33 | m |
| 19.7–19.8 | 4.51–4.48 | m |
| 24.2–24.3 | 3.68–3.66 | vs |
| 28.0–28.1 | 3.187–3.175 | w |
| 31.4–31.5 | 2.849–2.840 | w |
| 34.5–34.6 | 2.600–2.592 | w |

(d) The CoAPSO-20 compositions for which x-ray powder diffraction patterns have been obtained to date have patterns which are characterized by the x-ray pattern of Table XXI-A:

TABLE XXI-A

| 2θ | d, (Å) | 100 × I/Io |
|---|---|---|
| 13.9–14.0 | 6.37–6.33 | 44–75 |
| 19.7–19.8 | 4.51–4.48 | 38–42 |
| 22.1–22.2 | 4.02–4.00 | 3–4 |
| 24.2–24.3 | 3.68–3.66 | 100 |

TABLE XXI-A(continued)

| 2θ | d, (Å) | 100 × I/Io |
|---|---|---|
| 28.0–28.1 | 3.187–3.175 | 11–14 |
| 31.4–31.5 | 2.849–2.840 | 11–12 |
| 34.5–34.6 | 2.600–2.592 | 16–18 |
| 40.1–40.2 | 2.249–2.243 | 3–4 |
| 42.5–42.6 | 2.127–2.122 | 3–4 |
| 47.3–47.4 | 1.922–1.918 | 4–5 |
| 51.8–51.9 | 1.765–1.762 | 8–9 |

EXAMPLE 114A (a) The as-synthesized CoAPSO-31 of example 101A was subjected to analysis by x-ray. The CoAPSO-31 product was characterized by the x-ray powder diffraction pattern of Table XXII-A below:

TABLE XXII-A

| $2\theta$ | d, (Å) | 100 × I/Io |
|---|---|---|
| 8.5 | 10.35 | 58 |
| 17.1 | 5.19 | 5 |
| 18.4 | 4.82 | 2 |
| 20.3 | 4.38 | 42 |
| 21.1 | 4.20 | 4 |
| 22.1 | 4.03 | 28 |
| 22.7 | 3.93 | 100 |
| 23.2 | 3.83 | 2 |
| 25.2 | 3.537 | 4 |
| 25.7 | 3.464 | 3 |
| 28.0 | 3.187 | 12 |
| 29.8 | 3.000 | 6 |
| 31.8 | 2.816 | 20 |
| 35.2 | 2.549 | 9 |
| 36.2 | 2.482 | 2 |
| 37.2 | 2.417 | 2 |
| 37.7 | 2.386 | 2 |
| 38.3 | 2.352 | 2 |
| 39.4 | 2.288 | 3 |
| 39.7 | 2.271 | 2 |
| 40.3 | 2.239 | 2 |
| 45.3 | 2.002 | 2 |
| 46.8 | 1.943 | 2 |
| 48.7 | 1.869 | 2 |
| 51.7 | 1.768 | 4 |

(b) CoAPSO-31, of part (a) was calcined in air at 500° for 1.5 hours. The calcined product was characterized by the x-ray powder diffraction pattern of Table XXIII-A below:

TABLE XXIII-A

| $2\theta$ | d, (Å) | 100 × I/Io |
|---|---|---|
| 8.5 | 10.36 | 73 |
| 14.8 | 5.99 | 4 |
| 17.1 | 5.19 | 10 |
| 18.4 | 4.81 | 4 |
| 20.3 | 4.37 | 56 |
| 21.4 | 4.15 | 3 |
| 22.1 | 4.03 | 47 |
| 22.7 | 3.93 | 100 |
| 23.4 | 3.80 | 3 |
| 25.2 | 3.530 | 6 |
| 25.7 | 3.464 | 7 |
| 28.0 | 3.184 | 15 |
| 29.8 | 2.300 | 10 |
| 31.0 | 2.885 | 2 |
| 31.8 | 2.813 | 31 |
| 35.2 | 2.548 | 10 |
| 36.3 | 2.476 | 5 |
| 37.3 | 2.409 | 3 |
| 37.7 | 2.385 | 3 |
| 38.3 | 2.348 | 3 |
| 39.4 | 2.287 | 4 |
| 39.7 | 2.270 | 3 |
| 40.3 | 2.237 | 3 |
| 46.7 | 1.944 | 5 |
| 47.6 | 1.910 | 3 |
| 48.7 | 1.868 | 3 |
| 49.3 | 1.849 | 2 |
| 51.7 | 1.768 | 6 |

(c) The species denominated herein as CoAPSO-31 has a three-dimensional microporous crystal framework structure of $CoO_2$, $AlO_2$, $PO_2$ and $SiO_2$ tetrahedral units and has an empirical chemical composition on an anhydrous basis expressed by the formula:

mR:(Co$_w$Al$_x$P$_y$Si$_z$)O$_2$ where "R" represents at least one organic templating agent present in the intracrystalline pore system; "m" represents the molar amount of "R" per mole of (Co$_w$Al$_x$P$_y$Si$_z$)O$_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXIV-A:

TABLE XXIV-A

| $2\theta$ | d, (Å) | Relative Intensity |
|---|---|---|
| 8.5–8.6 | 10.40–10.28 | m |
| 20.2–20.3 | 4.40–4.37 | m |
| 22.0–22.1 | 4.04–4.02 | m |
| 22.6–22.7 | 3.93–3.92 | vs |
| 28.0–28.1 | 3.187–3.175 | w |
| 31.7–31.8 | 2.823–2.814 | m |

(d) The CoAPSO-31 compositions for which x-ray powder diffraction patterns have been obtained to date have patterns which are characterized by the x-ray pattern of Table XXV-A:

TABLE XXV-A

| $2\theta$ | d, (Å) | 100 × I/Io |
|---|---|---|
| 8.5–8.6 | 10.40–10.28 | 58–73 |
| 14.7–14.8 | 6.03–5.99 | 2–4 |
| 17.0–17.2 | 5.22–5.16 | 5–10 |
| 18.4–18.5 | 4.82–4.80 | 2–4 |
| 20.2–20.3 | 4.40–4.37 | 42–56 |
| 21.1–21.4 | 4.21–4.15 | 3–4 |
| 22.0–22.1 | 4.04–4.02 | 28–47 |
| 22.6–22.7 | 3.93–3.92 | 100 |
| 23.2–23.4 | 3.83–3.80 | 2–3 |
| 25.1–25.2 | 3.548–3.534 | 4–6 |
| 25.7–25.8 | 3.466–3.453 | 3–7 |
| 28.0–28.1 | 3.187–3.175 | 12–15 |
| 29.7–29.8 | 3.008–2.998 | 6–10 |
| 31.0–31.1 | 2.885–2.876 | 2–4 |
| 31.7–31.8 | 2.823–2.814 | 20–31 |
| 35.2–35.3 | 2.550–2.543 | 9–10 |
| 36.2–36.3 | 2.481–2.475 | 2–5 |
| 37.2–37.3 | 2.417–2.411 | 2–3 |
| 37.7–37.8 | 2.386–2.380 | 2–3 |
| 38.2–38.4 | 2.356–2.344 | 2–3 |
| 39.3–39.4 | 2.292–2.287 | 3–4 |
| 39.6–39.7 | 2.276–2.270 | 2–3 |
| 40.2–40.3 | 2.243–2.238 | 2–3 |
| 45.2–45.3 | 2.006–2.002 | 1–2 |
| 46.7–46.8 | 1.945–1.941 | 2–5 |
| 47.5–47.6 | 1.914–1.910 | 2–3 |
| 48.7–48.8 | 1.870–1.866 | 2–3 |
| 49.2–49.3 | 1.852–1.848 | 1–2 |
| 51.6–51.7 | 1.771–1.768 | 4–6 |

EXAMPLE 115A (a) The as-synthesized CoAPSO-34 of example 90A was subjected to analysis by x-ray. The CoAPSO-34 product was characterized by the x-ray powder diffraction pattern of Table XXVI-A below:

TABLE XXVI-A

| $2\theta$ | d, (Å) | 100 × I/Io |
|---|---|---|
| 9.6 | 9.22 | 100 |
| 12.9 | 6.84 | 11 |
| 14.2 | 6.26 | 10 |
| 16.1 | 5.51 | 35 |
| 18.1 | 4.92 | 15 |
| 20.7 | 4.29 | 62 |
| 22.3 | 3.98 | 3 |
| 23.2 | 3.84 | 4 |
| 25.3 | 3.522 | 17 |
| 26.0 | 3.430 | 14 |
| 27.7 | 3.217 | 2 |

TABLE XXVI-A-continued

| 2θ | d, (Å) | 100 × I/Io |
|---|---|---|
| 28.5 | 3.136 | 3 |
| 29.7 | 3.010 | 4 |
| 30.7 | 2.914 | 25 |
| 31.3 | 2.855 | 16 |
| 31.8 | 2.817 | 3 |
| 34.5 | 2.597 | 6 |
| 36.3 | 2.473 | 3 |
| 39.8 | 2.263 | 3 |
| 43.3 | 2.090 | 3 |
| 43.6 | 2.075 | 3 |
| 47.6 | 1.911 | 2 |
| 47.8 | 1.904 | 3 |
| 49.2 | 1.853 | 5 |
| 51.1 | 1.786 | 3 |
| 53.4 | 1.716 | 3 |
| 54.7 | 1.678 | 2 |

(b) CoAPSO-34, of part (a) was calcined in air at 600° for one hour. The calcined product was characterized by the x-ray powder diffraction pattern of Table XXVII-A below:

TABLE XXVII-A

| 2θ | d, (Å) | 100 × I/Io |
|---|---|---|
| 9.6 | 9.20 | 100 |
| 10.1 | 8.77 | 6 |
| 13.0 | 6.80 | 14 |
| 16.2 | 5.46 | 8 |
| 17.9 | 4.97 | 4 |
| 18.0 | 4.94 | 3 |
| 19.3 | 4.60 | 4 |
| 20.5 | 4.34 | 3 |
| 20.8 | 4.27 | 14 |
| 21.4 | 4.15 | 4 |
| 23.3 | 3.82 | 2 |
| 24.3 | 3.67 | 3 |
| 25.1 | 3.543 | 3 |
| 25.3 | 3.524 | 3 |
| 25.7 | 3.464 | 2 |
| 26.2 | 3.402 | 5 |
| 31.0 | 2.831 | 10 |
| 31.6 | 2.835 | 5 |
| 31.8 | 2.815 | 3 |

(c) The species denominated herein as CoAPSO-34 has a three-dimensional microporous crystal framework structure of $CoO_2$, $AlO_2$, $PO_2$ and $SiO_2$ tetrahedral units and has an empirical chemical composition on an anhydrous basis expressed by the formula:

$mR:(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions, being as above defined with reference to FIG. 1 or FIG. 2; and having in the as-synthesized or calcined form a characteristic x-ray powder diffraction pattern which contains at least the d-spacings set forth in Table XXVIII-A:

TABLE XXVIII-A

| 2θ | d, (Å) | Relative Intensity |
|---|---|---|
| 9.4–9.8 | 9.41–9.03 | s–vs |
| 12.86–13.06 | 6.86–6.76 | w |
| 14.08–14.30 | 6.28–6.19 | w–m |
| 15.90–16.20 | 5.57–5.47 | vw–m |
| 20.60–20 83 | 4.31–4.26 | w–vs |
| 30.50–30 80 | 2.931–2.903 | w–m |

(d) The CoAPSO-34 compositions for which x-ray powder diffraction patterns have been obtained to date have patterns which are characterized by the x-ray pattern of Table XXIX-A:

TABLE XXIX-A

| 2θ | d, (Å) | 100 × I/Io |
|---|---|---|
| 9.4–9.8 | 9.41–9.03 | 87–100 |
| 10.09–10.14 | 8.77–8.72 | 1–6 |
| 12.86–13.06 | 6.86–6.76 | 11–18 |
| 14.08–14.30 | 6.28–6.19 | 10–24 |
| 15.90–16.24 | 5.57–5.47 | 8–35 |
| 17.85–18.05 | 4.97–4.92 | 3–15 |
| 19.13–19.48 | 4.65–4.55 | 1–4 |
| 20.48–20.56 | 4.34–4.33 | sh-3 |
| 20.60–20.83 | 4.31–4.26 | 14–100 |
| 21.41–22.35 | 4.15–3.98 | 3–4 |
| 23.18–23.31 | 3.84–3.82 | 2–3 |
| 24.25–24.53 | 3.67–3.63 | 0–3 |
| 25.13–25.29 | 3.543–3.520 | 3–17 |
| 25.72–25.98 | 3.464–3.430 | 3–14 |
| 26.06–26.19 | 3.414–3.402 | 5–9 |
| 27.73–27.80 | 3.217–3.209 | 2–16 |
| 28.30–28.46 | 3.153–3.136 | 3–9 |
| 29.50–29.68 | 3.028–3.010 | 4–14 |
| 30.50–30.80 | 2.931–2.903 | 12–25 |
| 31.04–31.33 | 2.881–2.855 | 7–16 |
| 31.60–31.79 | 2.831–2.815 | 3–5 |
| 34.40–34.53 | 2.607–2.597 | 5–6 |
| 36.20–36.32 | 2.481–2.473 | 3–8 |
| 38.40–38.60 | 2.344–2.332 | 3–5 |
| 39.70–39.83 | 2.270–2.263 | 3–4 |
| 43.10–43.28 | 2.099–2.090 | sh-6 |
| 43.40–43.61 | 2.045–2.075 | 3–10 |
| 47.40–47.59 | 1.918–1.911 | sh-2 |
| 47.77–47.80 | 1.904–1.903 | 3–10 |
| 49.17–49.20 | 1.853–1.852 | 5–10 |
| 49.90–50.40 | 1.828–1.809 | 0–11 |
| 51.13–51.20 | 1.786–1.784 | 3–10 |
| 53.20–53.39 | 1.722–1.716 | 3–10 |
| 54.60–54.70 | 1.681–1.678 | 2–7 |
| 55 80–55.90 | 1.647–1.645 | 2–10 |

EXAMPLE 116A (a) The As-synthesized CoAPSO-35 of example 10A was subjected to analysis by x-ray. The CoAPSO-35 product was characterized by the x-ray powder diffraction pattern of Table XXX-A below;

TABLE XXX-A

| 2θ | d, (Å) | 100 × I/Io |
|---|---|---|
| 7.9* | 11.19 | 8 |
| 8.6 | 10.28 | 18 |
| 10.9 | 8.12 | 45 |
| 11.6 | 7.63 | 8 |
| 13.4 | 6.61 | 30 |
| 15.9 | 5.57 | 15 |
| 17.3 | 5.13 | 83 |
| 17.8 | 4.98 | 20 |
| 20.9 | 4.25 | 58 |
| 21.9 | 4.06 | 100 |
| 22.7 | 3.92 | 13 |
| 23.3 | 3.82 | 38 |
| 24.9 | 3.58 | 13 |
| 25.6 | 3.480 | 8 |
| 26.9 | 3.314 | 28 |
| 28.3 | 3.153 | 45 |
| 29.1 | 3.069 | 13 |
| 31.4* | 2.849 | 10 |
| 32.2 | 2.780 | 40 |
| 34.3 | 2.614 | 10 |
| 35.2* | 2.550 | 8 |
| 35.9 | 2.501 | 8 |
| 37.8 | 2.380 | 5 |
| 39.4 | 2.287 | 5 |
| 41.9 | 2.156 | 8 |
| 42.6 | 2.122 | 10 |
| 44.6 | 2.032 | 8 |
| 47.8 | 1.903 | 8 |
| 48.6 | 1.873 | 8 |
| 49.8 | 1.831 | 10 |

TABLE XXX-A-continued

| 2θ | d, (Å) | 100 × I/Io |
|---|---|---|
| 51.2 | 1.784 | 10 |
| 55.7 | 1.650 | 8 |

*impurity peak (b) CoAPSO-35, of example 10A was calcined in air at 500° C., for two hours. The calcined product was characterized by the x-ray powder diffraction pattern of Table XXXI-A below:

TABLE XXXI-A

| 2θ | d, (Å) | 100 × I/Io |
|---|---|---|
| 8.7 | 10.16 | 26 |
| 11.0 | 8.04 | 90 |
| 11.8 | 7.50 | 21 |
| 13.7 | 6.46 | 100 |
| 16.2 | 5.47 | 16 |
| 17.4 | 5.10 | 26 |
| 17.6 | 5.04 | 37 |
| 21.2 | 4.19 | 42 |
| 22.3 | 3.99 | 58 |
| 23.2 | 3.83 | 26 |
| 23.7 | 3.75 | 37 |
| 25.1 | 3.548 | 26 |
| 25.3 | 3.520 | 32 |
| 26.3 | 3.389 | 26 |
| 27.5 | 3.243 | 42 |
| 28.6 | 3.121 | 53 |
| 28.8 | 3.100 | 53 |
| 29.6 | 3.018 | 32 |
| 31.9* | 2.805 | 26 |
| 32.8 | 2.730 | 42 |
| 34.5 | 2.600 | 21 |
| 35.0 | 2.564 | 21 |
| 35.8 | 2.508 | 16 |

*impurity peak (c)( The species denominated herein as CoAPSO-35 has a three-dimensional microporous crystal framework structure of $CoO_2$, $AlO_2$, $PO_2$ and $SiO_2$ tetrahedral units and has an empirical chemical composition on an anhydrous basis expressed by the formula:

mR:$(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXII-A:

TABLE XXXII-A

| 2θ | d, (Å) | Relative Intensity |
|---|---|---|
| 10.9–11.0 | 8.12–8.04 | m–vs |
| 13.4–13.7 | 6.61–6.46 | m–vs |
| 17.3–17.4 | 5.13–5.10 | m–s |
| 20.9–21.2 | 4.25–4.19 | m |
| 21.9–22.3 | 4.06–3.99 | m–vs |
| 28.3–28.6 | 3.153–3.121 | m |

(d) The CoAPSO-35 compositions for which x-ray powder diffraction patterns have been obtained to date have patterns which are characterized by the x-ray pattern of Table XXXIII-A:

TABLE XXXIII-A

| 2θ | d, (Å) | 100 × I/Io |
|---|---|---|
| 7.9* | 11.19 | 8 |
| 8.6–8.7 | 10.28–10.16 | 18–26 |
| 10.9–11.0 | 8.12–8.04 | 45–90 |

TABLE XXXIII-A-continued

| 2θ | d, (Å) | 100 × I/Io |
|---|---|---|
| 11.6–11.8 | 7.63–7.50 | 8–21 |
| 13.4–13.7 | 6.61–6.46 | 30–100 |
| 15.9–16.2 | 5.57–5.47 | 15–16 |
| 17.3–17.4 | 5.13–5.10 | 26–83 |
| 17.6–17.8 | 5.04–5.98 | 20–37 |
| 20.9–21.2 | 4.25–4.19 | 42–58 |
| 21.9–22.3 | 4.06–3.99 | 58–100 |
| 22.7–23.2 | 3.92–3.83 | 13–26 |
| 23.3–23.7 | 3.83–3.75 | 37–38 |
| 24.9–25.1 | 3.58–3.548 | 13–26 |
| 25.3 | 3.520 | 32 |
| 25.6–26.3 | 3.480–3.389 | 8–26 |
| 26.9–27.5 | 3.314–3.243 | 28–42 |
| 28.3–28.6 | 3.153–3.121 | 45–53 |
| 28.8–29.6 | 3.100–3.018 | 13–53 |
| 31.4–31.9 | 2.849–2.805 | 10–26 |
| 32.2–32.8 | 2.780–2.730 | 40–42 |
| 34.3–34.5 | 2.614–2.600 | 10–21 |
| 35.0–35.2* | 2.564–2.550 | 8–21 |
| 35.8–35.9 | 2.508–2.501 | 8–16 |
| 37.8–37.9 | 2.380–2.374 | 5 |
| 39.4–39.5 | 2.287–2.281 | 5 |
| 41.9–42.0 | 2.156–2.151 | 8 |
| 42.6–42.7 | 2.122–2.118 | 10 |
| 44.6–44.7 | 2.032–2.027 | 8 |
| 47.8–47.9 | 1.903–1.900 | 8 |
| 48.6–48.7 | 1.873–1.870 | 8 |
| 49.8–49.9 | 1.831–1.828 | 10 |
| 51.2–51.3 | 1.784–1.781 | 10 |
| 55.6–55.7 | 1.653–1.650 | 8 |

EXAMPLE 117A (a) The as-synthesized CoAPSO-36 of example 93A was subjected to analysis by x-ray. The CoAPSO-36 product was characterized by the x-ray powder diffraction pattern of Table XXXIV-A below:

TABLE XXXIV-A

| 2θ | d, (Å) | 100 × I/Io |
|---|---|---|
| 7.3 | 12.11 | 7 |
| 8.0 | 11.12 | 100 |
| 8.2 | 10.74 | 29 |
| 9.2 | 9.65 | 4 |
| 12.9 | 6.86 | 5 |
| 13.6 | 6.52 | 8 |
| 13.7 | 6.48 | 8 |
| 15.9 | 5.57 | 14 |
| 16.5 | 5.38 | 42 |
| 18.4 | 4.83 | 6 |
| 19.1 | 4.64 | 37 |
| 20.8 | 4.27 | 49 |
| 21.6 | 4.12 | 7 |
| 21.8 | 4.09 | 22 |
| 22.1 | 4.03 | 28 |
| 22.6 | 3.94 | 29 |
| 23.0 | 3.86 | 9 |
| 24.0 | 3.71 | 9 |
| 27.3 | 3.267 | 20 |
| 27.7 | 3.226 | 7 |
| 28.4 | 3.148 | 13 |
| 28.7 | 3.116 | 5 |
| 29.2 | 3.063 | 12 |
| 30.4 | 2.940 | 7 |
| 32.1 | 2.792 | 12 |
| 34.9 | 2.571 | 12 |

(b) CoAPSO-36, of example 93A was calcined in air at 500° for one hour. The calcined product was characterized by the x-ray powder diffraction pattern of Table XXXV-A below:

TABLE XXXV-A

| 2θ | d, (Å) | 100 × I/Io |
|---|---|---|
| 7.4 | 12.00 | 8 |

TABLE XXXV-A-continued

| 2θ | d, (Å) | 100 × I/Io |
|---|---|---|
| 8.0 | 11.10 | 100 |
| 8.3 | 10.69 | 33 |
| 13.6 | 6.52 | 13 |
| 15.9 | 5.58 | 8 |
| 16.6 | 5.36 | 32 |
| 19.3 | 4.59 | 29 |
| 20.8 | 4.27 | 26 |
| 21.5 | 4.14 | 8 |
| 21.8 | 4.07 | 11 |
| 22.3 | 3.98 | 19 |
| 22.7 | 3.92 | 17 |
| 24.0 | 3.71 | 7 |
| 27.3 | 3.266 | 19 |
| 27.8 | 3.215 | 10 |
| 28.3 | 3.154 | 12 |
| 28.4 | 3.145 | 13 |
| 28.5 | 3.131 | 10 |
| 29.2 | 3.062 | 13 |
| 32.0 | 2.797 | 10 |

(c) The species denominated herein as CoAPSO-36 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXVI-A:

TABLE XXXVI-A

| 2θ | d, (Å) | Relative Intensity |
|---|---|---|
| 7.8–8.0 | 11.33–11.05 | vs |
| 8.2–8.3 | 10.78–10.65 | m |
| 16.4–16.6 | 5.40–5.34 | m |
| 19.0–19.3 | 4.67–4.60 | m |
| 20.7–21.0 | 4.29–4.23 | m |
| 22.3–22.6 | 3.99–3.93 | w-m |

(d) The CoAPSO-36 compositions for which x-ray powder diffraction patterns have been obtained to date have patterns which are characterized by the x-ray pattern of Table XXXVII-A:

TABLE XXXVII-A

| 2θ | d, (Å) | 100 × I/Io |
|---|---|---|
| 7.3–7.5 | 12.11–11.79 | 7–8 |
| 7.8–8.0 | 11.33–11.05 | 100 |
| 8.2–8.3 | 10.78–10.65 | 29–33 |
| 9.2–9.3 | 9.61–9.51 | 4–5 |
| 12.9–13.0 | 6.86–6.81 | 4–5 |
| 13.5–13.6 | 6.56–6.51 | 8–13 |
| 13.7 | 6.46 | 7–8 |
| 15.8–16.0 | 5.61–5.54 | 8–14 |
| 16.4–16.6 | 5.40–5.34 | 32–42 |
| 18.4 | 4.82 | 4–6 |
| 19.0–19.3 | 4.67–4.60 | 29–36 |
| 20.7–21.0 | 4.29–4.23 | 26–49 |
| 21.5–21.7 | 4.13–4.10 | 7–8 |
| 21.8–22.0 | 4.08–4.04 | 11–22 |
| 22.3–22.6 | 3.99–3.93 | 17–29 |
| 22.9–23.0 | 3.88–3.87 | 5–9 |
| 23.9–24.0 | 3.72–3.71 | 7–9 |
| 27.2–27.3 | 3.278–3.267 | 19–20 |
| 27.6–27.8 | 3.232–3.209 | 7–10 |
| 28.3–28.4 | 3.153–3.143 | 12–13 |
| 28.5–28.7 | 3.132–3.110 | 5–10 |
| 29.0–29.2 | 3.079–3.058 | 12–13 |
| 30.3–30.4 | 2.950–2.940 | 5–7 |
| 32.0–32.1 | 2.797–2.788 | 10–12 |
| 34.7–34.9 | 2.585–2.571 | 10–12 |

EXAMPLE 118A (a) The as-synthesized CoAPSO-39 of example 45A was subjected to analysis by x-ray. The CoAPSO-39 product was characterized by the x-ray powder diffraction pattern of Table XXXVIII-A below:

TABLE XXXVIII-A

| 2θ | d, (Å) | 100 × I/Io |
|---|---|---|
| 8.0* | 11.05 | 31 |
| 9.4** | 9.41 | 47 |
| 13.1* | 6.76 | 22 |
| 13.3 | 6.66 | 16 |
| 14.8* | 5.99 | 9 |
| 15.6* | 5.68 | 31 |
| 16.2* | 5.47 | 6 |
| 18.1 | 4.90 | 16 |
| 19.0* | 4.67 | 9 |
| 20.2* | 4.40 | 41 |
| 21.0** | 4.23 | 100 |
| 22.1* | 4.02 | 53 |
| 22.4** | 3.97 | 53 |
| 22.6* | 3.93 | 69 |
| 23.1* | 3.85 | 66 |
| 24.7* | 3.60 | 13 |
| 26.4** | 3.376 | 28 |
| 26.9 | 3.314 | 13 |
| 27.7* | 3.220 | 13 |
| 28.1 | 3.175 | 13 |
| 28.6** | 3.121 | 25 |
| 29.4 | 3.038 | 13 |
| 30.2 | 2.959 | 13 |
| 31.4* | 2.849 | 13 |
| 32.7** | 2.739 | 22 |
| 34.2** | 2.622 | 16 |
| 34.6 | 2.592 | 6 |
| 36.2 | 2.481 | 6 |
| 37.6 | 2.392 | 16 |
| 37.8** | 2.380 | 16 |
| 39.4** | 2.287 | 9 |
| 42.9** | 2.108 | 9 |
| 44.6** | 2.032 | 9 |
| 48.6 | 1.873 | 6 |
| 50.6* | 1.804 | 6 |
| 51.4 | 1.778 | 6 |
| 54.5** | 1.684 | 9 |
| 55.6** | 1.653 | 6 |

*peak resulting from CoAPSO-11
**peak resulting from CoAPSO-11 and CoAPSO 39

(b) The species denominated herein as CoAPSO-39 has a three-dimensional microporous crystal framework structure of $CoO_2$, $AlO_2$, $PO_2$ and $SiO_2$ tetrahedral units and has an empirical chemical composition on any anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXIX-A:

TABLE XXXIX-A

| 2θ | d, (Å) | Relative Intensity |
|---|---|---|
| 9.4–9.5 | 9.41–9.31 | m |
| 13.3–13.4 | 6.66–6.61 | m |
| 18.1–18.2 | 4.90–4.87 | w-m |
| 21.0–21.2 | 4.23–4.19 | vs |
| 22.4–22.5 | 3.97–3.95 | m-s |
| 26.4–26.5 | 3.376–3.363 | m |

(c) The CoAPSO-39 compositions for which x-ray powder diffraction patterns have been obtained to date have patterns which are characterized by the x-ray pattern of Table XXXX-A:

TABLE XXXX-A

| 2θ | d, (Å) | 100 × I/Io |
|---|---|---|
| 9.4–9.5 | 9.41–9.31 | 31–43 |
| 13.3–13.4 | 6.66–6.61 | 22–30 |
| 18.1–18.2 | 4.90–4.87 | 16–31 |
| 21.0–21.2 | 4.23–4.19 | 100 |
| 22.4–22.5 | 3.97–3.95 | 53–80 |
| 26.4–26.5 | 3.376–3.363 | 28–29 |
| 26.9–27.0 | 3.314–3.302 | 6–13 |
| 28.1–28.2 | 3.175–3.164 | 13–15 |
| 28.6–28.7 | 3.121–3.11 | 10–25 |
| 29.4–29.5 | 3.038–3.028 | 13–18 |
| 30.2 | 2.959 | 13–15 |
| 32.7–32.8 | 2.739–2.730 | 17–22 |
| 34.2–34.3 | 2.622–2.614 | 12–16 |
| 34.5–34.6 | 2.617–2.592 | 6–10 |
| 36.2–36.3 | 2.481–2.475 | 6–8 |
| 37.6–37.9 | 2.392–2.374 | 16–17 |
| 39.4–39.5 | 2.287–2.281 | 9–11 |
| 42.9–43.0 | 2.108–2.103 | 8–9 |
| 44.6–44.8 | 2.032–2.023 | 6–9 |
| 48.5–48.6 | 1.877–1.873 | 5–6 |
| 51.4–51.6 | 1.778–1.771 | 5–6 |
| 54.5–54.6 | 1.684–1.681 | 9–10 |
| 55.4–55.6 | 1.658–1.653 | 5–6 |

EXAMPLE 119A (a) The as-synthesized CoAPSO-44 of example 19A was subjected to analysis by x-ray. The CoAPSO-44 product was characterized by the x-ray powder diffraction pattern of Table XXXXI-A below:

TABLE XXXXI-A

| 2θ | d, (Å) | 100 × I/Io |
|---|---|---|
| 4.8* | 18.41 | 8 |
| 9.4 | 9.41 | 100 |
| 13.1 | 6.76 | 22 |
| 13.9 | 6.37 | 5 |
| 15.9 | 5.57 | (sh) |
| 16.2 | 5.47 | 37 |
| 17.4 | 5.10 | 5 |
| 19.0 | 4.67 | 9 |
| 20.8 | 4.27 | 72 |
| 21.8 | 4.08 | 17 |
| 22.7 | 3.92 | 9 |
| 23.1 | 3.85 | 9 |
| 24.4 | 3.65 | 49 |
| 26.2 | 3.401 | 31 |
| 27.8 | 3.209 | 11 |
| 29.0 | 3.079 | sh |
| 29.7 | 3.008 | 8 |
| 30.1 | 2.969 | 20 |
| 30.8 | 2.903 | 49 |
| 31.6 | 2.831 | 3 |
| 32.5 | 2.755 | 6 |
| 32.9 | 2.722 | 6 |
| 34.8 | 2.578 | 5 |
| 35.5 | 2.529 | 9 |
| 38.6 | 2.332 | 5 |
| 39.3 | 2.292 | 3 |
| 39.8 | 2.265 | sh |
| 40.0 | 2.254 | 6 |
| 42.2 | 2.141 | 5 |
| 42.6 | 2.122 | 5 |
| 43.7 | 2.071 | 3 |
| 44.4 | 2.040 | 3 |
| 46.2 | 1.965 | 3 |
| 47.3 | 1.922 | 3 |
| 48.2 | 1.888 | 12 |
| 48.7 | 1.870 | 8 |
| 50.3 | 1.814 | 15 |
| 52.0 | 1.759 | 5 |
| 53.8 | 1.704 | 9 |
| 54.8 | 1.675 | 3 |

(b) CoAPSO-44 of example 19A was calcined in air at 500° C. for 1.25 hours. The calcined product was characterized by the x-ray powder diffraction pattern of Table XXXXII-A below:

TABLE XXXXII-A

| 2θ | d, (Å) | 100 × I/Io |
|---|---|---|
| 8.9 | 9.94 | 20 |
| 9.3 | 9.51 | 100 |
| 12.9 | 6.86 | 24 |
| 14.0 | 6.33 | 5 |
| 15.8 | 5.61 | sh |
| 16.0 | 5.54 | 14 |
| 17.8 | 4.98 | 18 |
| 19.1 | 4.65 | 4 |
| 20.5 | 4.33 | 40 |
| 22.1 | 4.02 | 4 |
| 22.3 | 3.99 | 4 |
| 23.0 | 3.87 | 7 |
| 25.1 | 3.548 | 12 |
| 25.8 | 3.453 | 13 |
| 27.6 | 3.232 | 3 |
| 28.2 | 3.164 | 4 |
| 29.5 | 3.028 | 3 |
| 30.6 | 2.921 | 21 |
| 31.1 | 2.876 | 14 |
| 31.7 | 2.823 | 4 |
| 32.2 | 2.780 | 2 |
| 33.4 | 2.683 | 3 |
| 33.7 | 2.660 | 4 |
| 34.5 | 2.600 | 8 |
| 36.2 | 2.481 | 5 |
| 38.2 | 2.356 | 2 |
| 38.7 | 2.327 | 2 |
| 39.2 | 2.298 | 2 |
| 39.8 | 2.265 | 3 |
| 42.9 | 2.108 | 3 |
| 43.4 | 2.085 | 4 |
| 47.6 | 1.910 | 3 |
| 49.0 | 1.859 | 5 |
| 49.8 | 1.831 | 3 |
| 50.6 | 1.804 | 4 |
| 51.0 | 1.791 | 4 |
| 53.2 | 1.722 | 3 |
| 54.7 | 1.678 | 2 |

(c) The species denominated herein as CoAPSO-44 has a three-dimensional microporous crystal framework structure of $CoO_2$, $AlO_2$, $PO_2$ and $SiO_2$ tetrahedral units and has an empirical chemical composition on an anhydrous basis expressed by the formula:

mR:$(Co_wAl_xP_ySi_z)O_2$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXXIII-A:

TABLE XXXXIII-A

| 2θ | d, (Å) | Relative Intensity |
|---|---|---|
| 9.3–9.5 | 9.51–9.31 | vs |
| 16.0–16.3 | 5.54–5.44 | w–m |
| 20.5–20.8 | 4.33–4.27 | m |
| 24.3–25.1 | 3.66–3.548 | w–m |
| 25.8–26.2 | 3.453–3.401 | vw–m |
| 30.7–31.1 | 2.912–2.876 | vw–m |

(d) The CoAPSO-44 compositions for which x-ray powder diffraction patterns have been obtained to date have patterns which are characterized by the x-ray pattern of Table XXXXIV-A:

TABLE XXXXIV-A

| 2θ | d, (Å) | 100 × I/Io |
|---|---|---|
| 4.8* | 18.41 | 8 |
| 8.9 | 9.94 | 20 |
| 9.3–9.5 | 9.51–9.31 | 100 |
| 12.9–13.1 | 6.86–6.76 | 22–24 |
| 13.7–14.0 | 6.46–6.33 | 5–6 |
| 15.8–15.9 | 5.61–5.57 | sh |
| 16.0–16.3 | 5.54–5.44 | 14–37 |
| 17.4–17.8 | 5.10–4.98 | 5–18 |
| 18.9–19.1 | 4.70–4.65 | 4–9 |
| 20.5–20.8 | 4.33–4.27 | 40–72 |
| 21.8–22.1 | 4.08–4.02 | 4–17 |
| 22.3–22.7 | 3.99–3.92 | 4–9 |
| 23.0–23.1 | 3.87–3.85 | 7–9 |
| 24.3–25.1 | 3.66–3.548 | 12–49 |
| 25.8–26.2 | 3.453–3.401 | 13–31 |
| 27.6–27.8 | 3.232–3.209 | 3–11 |
| 28.2 | 3.164 | 4 |
| 29.0–29.5 | 3.079–3.028 | sh–3 |
| 29.7–30.6 | 3.008–2.921 | 8–21 |
| 30.7–31.1 | 2.912–2.876 | 4–49 |
| 31.6–31.7 | 2.831–3.823 | 3–4 |
| 32.2 | 2.780 | 2 |
| 32.5–33.7 | 2.755–2.660 | 3–6 |
| 34.5–34.8 | 2.600–2.578 | 5–8 |
| 35.4–36.2 | 2.536–2.481 | 5–9 |
| 38.2–38.6 | 2.356–2.332 | 2–5 |
| 38.7–39.3 | 2.327–2.292 | 2–3 |
| 39.8–40.0 | 2.265–2.254 | sh–3 |
| 42.2–42.9 | 2.141–2.108 | 3–5 |
| 43.4–43.7 | 2.085–2.071 | 3–4 |
| 44.4–46.2 | 2.040–1.965 | 3 |
| 47.3–47.6 | 1.922–1.910 | 3 |
| 48.1–49.0 | 1.892–1.859 | 5–12 |
| 49.8–50.3 | 1.831–1.814 | 3–15 |
| 50.6 | 1.804 | 3 |
| 51.0–52.0 | 1.791–1.759 | 4–5 |
| 53.2–53.8 | 1.722–1.704 | 3–9 |
| 54.7–54.8 | 1.678–1.675 | 2–3 |

EXAMPLE 120A (a) The as-synthesized CoAPSO-46 of example 36 was subjected to analysis by x-ray. The CoAPSO-46 product was characterized by the x-ray powder diffraction pattern of Table XXXXV-A below:

TABLE XXXXV-A

| 2θ | d, (Å) | 100 × I/Io |
|---|---|---|
| 6.6 | 13.39 | 11 |
| 6.9 | 12.81 | 7 |
| 7.2 | 12.28 | 12 |
| 7.7 | 11.48 | 100 |
| 12.5 | 7.08 | 7 |
| 13.1 | 6.76 | 5 |
| 13.3 | 6.66 | 6 |
| 13.5 | 6.56 | 4 |
| 15.0 | 5.91 | 4 |
| 15.4 | 5.75 | 5 |
| 16.1 | 5.51 | 3 |
| 16.8 | 5.28 | 6 |
| 17.4 | 5.10 | 4 |
| 17.5 | 5.07 | 5 |
| 19.9 | 4.46 | 5 |
| 20.6 | 4.31 | 5 |
| 21.0 | 4.23 | 4 |
| 21.4 | 4.15 | sh |
| 21.7 | 4.10 | 13 |
| 22.2 | 4.00 | 3 |
| 22.9 | 3.88 | 7 |
| 23.8 | 3.74 | 4 |
| 24.3 | 3.66 | 5 |
| 26.3 | 3.389 | 3 |
| 26.9 | 3.314 | 7 |
| 27.8 | 3.209 | 10 |
| 28.3 | 3.153 | 5 |
| 28.8 | 3.010 | 6 |
| 29.9 | 2.988 | 4 |
| 30.2 | 2.959 | 4 |
| 30.7 | 2.912 | 4 |
| 30.9 | 2.894 | 4 |
| 31.2 | 2.867 | 5 |
| 31.8 | 2.814 | 3 |
| 33.0 | 2.714 | 4 |
| 34.2 | 2.622 | 3 |
| 36.0 | 2.495 | 5 |
| 36.6 | 2.455 | 3 |
| 44.0 | 2.058 | 3 |

(b) The species denominated herein is CoAPSO-46 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXXVI-A:

TABLE XXXXVI-A

| 2θ | d, (Å) | Relative Intensity |
|---|---|---|
| 6.5–6.7 | 13.60–13.19 | w |
| 7.2–7.4 | 12.28–11.95 | w |
| 7.6–7.8 | 11.63–11.33 | vs |
| 21.6–21.7 | 4.11–4.10 | w |
| 27.8–27.9 | 3.209–3.198 | w |

(c) The CoAPSO-46 compositions for which x-ray powder diffraction patterns have been obtained to date have patterns which are characterized by the x-ray pattern of Table XXXXVII-A:

TABLE XXXXVII-A

| 2θ | d, (Å) | 100 × I/Io |
|---|---|---|
| 6.5–6.7 | 13.60–13.19 | 11 |
| 6.9–7.0 | 12.81–12.63 | 7 |
| 7.2–7.4 | 12.28–11.95 | 12 |
| 7.6–7.8 | 11.63–11.33 | 100 |
| 12.5–12.6 | 7.08–7.03 | 7 |
| 13.1–13.3 | 6.76–6.66 | 5 |
| 13.5–13.9 | 6.56–6.37 | 4 |
| 15.0–15.1 | 5.91–5.87 | 4 |
| 15.4 | 5.75 | 5 |
| 16.1 | 5.51 | 3 |
| 16.7–16.8 | 5.31–5.28 | 6 |
| 17.4–17.5 | 5.10–5.07 | 4 |
| 19.9–20.0 | 4.46–4.44 | 5 |
| 20.5–20.6 | 4.33–4.31 | 5 |
| 21.0 | 4.23 | 4 |

TABLE XXXXVII-A-continued

| 2θ | d, (Å) | 100 × I/Io |
|---|---|---|
| 21.4 | 4.15 | sh |
| 21.6–21.7 | 4.11–4.10 | 13 |
| 22.1–22.2 | 4.02–4.00 | 3 |
| 22.8–22.9 | 3.90–3.88 | 7 |
| 23.8 | 3.74 | 4 |
| 24.2–24.3 | 3.68–3.66 | 5 |
| 26.3–26.4 | 3.389–3.376 | 3 |
| 26.8–26.9 | 3.326–3.314 | 7 |
| 27.8–27.9 | 3.209–3.198 | 10 |
| 28.3–28.4 | 3.153–3.143 | 5 |
| 28.8–28.9 | 3.010–3.089 | 6 |
| 29.8–29.9 | 2.998–2.988 | 4 |
| 30.2 | 2.959 | 4 |
| 30.7 | 2.912 | 4 |
| 30.9–31.0 | 2.894–2.885 | 4 |
| 31.2–31.3 | 2.867–2.858 | 5 |
| 31.8–31.9 | 2.814–2.805 | 3 |
| 32.8–33.0 | 2.730–2.714 | 4 |
| 34.2–34.3 | 2.622–2.614 | 3 |
| 35.9–36.0 | 2.510–2.495 | 5 |
| 36.5–36.6 | 2.462–2.455 | 3 |
| 44.0–44.1 | 2.058–2.053 | 3 |

EXAMPLE 121A (a) The as-synthesized CoAPSO-47 of example 104A was subjected to analysis by x-ray. The CoAPSO-47 was characterized by the x-ray powder diffraction pattern of Table XXXXVIII-A below:

TABLE XXXXVIII-A

| 2θ | d, (Å) | 100 × I/Io |
|---|---|---|
| 9.4 | 9.37 | 94 |
| 12.9 | 6.88 | 16 |
| 13.8 | 6.40 | 9 |
| 16.0 | 5.55 | 40 |
| 17.5 | 5.06 | 14 |
| 18.9 | 4.69 | 6 |
| 20.6 | 4.32 | 100 |
| 21.8 | 4.08 | 11 |
| 22.4 | 3.97 | 4 |
| 23.0 | 3.87 | 12 |
| 24.6 | 3.62 | 38 |
| 25.9 | 3.443 | 22 |
| 27.6 | 3.230 | 11 |
| 29.5 | 3.030 | 6 |
| 30.6 | 2.926 | 42 |
| 31.5 | 2.844 | 3 |
| 33.1 | 2.707 | 3 |
| 34.5 | 2.602 | 9 |
| 35.7 | 2.518 | 7 |
| 38.4 | 2.345 | 4 |
| 39.6 | 2.275 | 4 |
| 42.5 | 2.128 | 4 |
| 47.6 | 1.910 | 4 |
| 48.5 | 1.877 | 11 |
| 50.3 | 1.815 | 7 |
| 52.3 | 1.749 | 2 |
| 53.2 | 1.721 | 5 |
| 53.9 | 1.700 | 3 |
| 54.3 | 1.690 | 3 |

(b) CoAPSO-47, of example 104A was calcined in air at 500° for 1.5 hours. The calcined product was characterized by the x-ray powder diffraction pattern of Table XXXXIX-A below:

TABLE XXXXIX-A

| 2θ | d, (Å) | 100 × I/Io |
|---|---|---|
| 9.6 | 9.18 | 100 |
| 3.1 | 6.77 | 26 |
| 14.2 | 6.23 | 3 |
| 16.3 | 5.44 | 10 |
| 18.1 | 4.90 | 16 |
| 19.4 | 4.58 | 3 |
| 21.0 | 4.24 | 26 |
| 22.5 | 3.96 | 3 |
| 23.5 | 3.79 | 3 |
| 25.5 | 3.499 | 11 |
| 26.4 | 3.381 | 9 |
| 28.7 | 3.113 | 4 |
| 31.2 | 2.868 | 14 |
| 31.7 | 2.824 | 6 |

(c) The species denominated herein as CoAPSO-47 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table LI-A:

TABLE LI-A

| 2θ | d, (Å) | Relative Intensity |
|---|---|---|
| 9.4–9.6 | 9.41–9.21 | vs |
| 12.8–13.1 | 6.92–6.76 | w–m |
| 16.0–16.3 | 5.54–5.44 | w–m |
| 20.6–21.0 | 4.31–4.23 | m–vs |
| 25.5–25.9 | 3.493–3.440 | w–m |
| 30.6–31.1 | 2.921–2.876 | w–m |

(d) The CoAPSO-47 compositions for which x-ray powder diffraction patterns have been obtained to date have patterns which are characterized by the x-ray pattern of Table LII-A:

TABLE LII-A

| 2θ | d, (Å) | 100 × I/Io |
|---|---|---|
| 9.4–9.6 | 9.41–9.21 | 94–100 |
| 12.8–13.1 | 6.92–6.76 | 16–26 |
| 13.8–14.2 | 6.42–6.24 | 3–9 |
| 16.0–16.3 | 5.54–5.44 | 10–40 |
| 17.5–18.1 | 5.07–4.90 | 14–16 |
| 18.9–19.4 | 4.70–4.58 | 3–6 |
| 20.6–21.0 | 4.31–4.23 | 26–100 |
| 21.8 | 4.08 | 11 |
| 22.4–22.5 | 3.97–3.95 | 3–4 |
| 23.0–23.5 | 3.87–3.79 | 3–12 |
| 24.6 | 3.62 | 38 |
| 25.5–25.9 | 3.493–3.440 | 11–22 |
| 26.4 | 3.376 | 9 |
| 27.6 | 3.232 | 11 |
| 28.7 | 3.110 | 4 |
| 29.5 | 3.028 | 6 |
| 30.6–31.1 | 2.921–2.876 | 13–42 |
| 31.5–31.7 | 2.840–2.823 | 3–6 |
| 33.1 | 2.706 | 3 |
| 34.5 | 2.600 | 9 |
| 35.7 | 2.515 | 7 |
| 38.4 | 2.344 | 4 |
| 39.6 | 2.276 | 4 |
| 42.5 | 2.127 | 4 |
| 47.6 | 1.910 | 4 |
| 48.5 | 1.877 | 11 |
| 50.3 | 1.814 | 7 |
| 52.3 | 1.749 | 2 |
| 53.2 | 1.722 | 5 |
| 53.9 | 1.701 | 3 |
| 54.3 | 1.689 | 3 |

EXAMPLE 122A

In order to demonstrate the catalytic activity of the CoAPSO compositions, calcined samples of the CoAPSO products were tested for catalytic cracking by n-butane cracking.

The n-butane cracking was carried out using a bench scale rector. The reactor was a cylindrical quartz tube 254 mm. in length and 10.3 mm. I.D. In each test the reactor was loaded with particles of the test CoAPSO's which were 20–40 mesh (U.S. std.) in size and in an amount of from 0.5 to 5 grams, the quantity being selected so that the conversion of n-butane was at least 5% and not more than 90% under the test conditions. Most of the CoAPSO had been previously calcined in air to remove organic materials from the pore system, and were activated in situ in the reactor in a flowing stream of helium at 500° C., for one hour. In some instances, samples were calcined in situ. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the CoAPSO compositions. The $k_A$ value (cm$^3$/g min) obtained for the CoAPSO compositions are set forth, below.

| CoAPSO of Example No: | Rate Constant ($k_A$) |
|---|---|
| CoAPSO-11 (Ex. 50A) | 1.0 |
| CoAPSO-11 (Ex. 42A)* | 2.0 |
| CoAPSO-11 (Ex. 42A) | 1.9 |
| CoAPSO-11 (Ex. 61A) | 1.4 |
| CoAPSO-31 (Ex. 102A) | 2.1 |
| CoAPSO-34 (Ex. 89A)* | 1.5 |
| CoAPSO-34 (Ex. 89A) | 8.7 |
| CoAPSO-34 (Ex. 90A) | 11.8 |
| CoAPSO-34 (Ex. 83A) | 28.1 |
| CoAPSO-34 (Ex. 77A)* | 11.1 |
| CoAPSO-35 (Ex. 10A)* | 1.0 |
| CoAPSO-44 (Ex. 19A) | 18.1 |
| CoAPSO-46 (Ex. 36A) | 2.4 |
| CoAPSO-47 (Ex. 104A) | 2.3 |
| CoAPSO-44 (Ex. 19A)* | 2.7 |
| CoAPSO-36 (Ex. 93A)* | 1.0 |
| CoAPSO-34 (Ex. 83A)* | 4.1 |
| CoAPSO-34 (Ex. 69A)* | 9.4 |
| CoAPSO-34 (Ex. 79A)* | 5.2 |
| CoAPSO-34 (Ex. 78A)* | 4.6 |
| CoAPSO-34 (Ex. 81A)* | 3.3 |

*calcined in situ at 500° C. in helium for 2 hours prior to activation.

B. MAGNESIUM-ALUMINUM-PHOSPHORUS-SILICON OXIDE MOLECULAR SIEVES

Molecular sieves containing magnesium, aluminum, phosphorus and silicon as framework tetrahedral oxide units are prepared as follows:

Preparative Reagents

In the following examples the MgAPSO compositions were prepared using numerous reagents. The reagents employed and abbreviations employed herein, if any, for such reagents are as follows:

(a) Alipro: aluminum isoproxide;

(b) CATAPAL: Trademark of Condea for hydrated pseudo-boehmite;

(c) LUDOX LS: Trademark of DuPont for an aqueous solution of 30 weight percent SiO$_2$ and 0.1 weight percent Na$_2$O;

(d) Mg(Ac)$_2$: magnesium acetate tetrahydrate, Mg(C$_2$H$_3$O$_2$)$_2$.4H$_2$O;

(e) H$_3$PO$_4$: 85 weight percent phosphoric acid in water;

(f) TBAOH: tetrabutylammonium hydroxide (40 wt. % in water);

(g) Pr$_2$NH: di-n-propylamine;

(h) Pr$_3$N: tri-n-propylamine;

(i) Quin: Quinuclidine;

(j) MQuin: Methyl Quinuclidine hydroxide (17.9% in water);

(k) C-hex; cyclohexylamine;

(l) TEAOH; tetraethylammonium hydroxide (40 wt. % in water).

(m) DEEA: diethylethanolamine;

(n) i-Pr$_2$NH: di-isopropylamine;

(o) TEABr: tetraethylammonium bromide; and (p) TPAOH: tetrapropylammonium hydroxide (40 wt. % in water).

PREPARATIVE PROCEDURE

The MgAPSO compositions were prepared by preparing reaction mixtures having a molar composition expressed as:

eR:fMgO:hAl$_2$O$_3$:iP$_2$O$_5$:gSiO$_2$:jH$_2$O wherein e, f, g, h, i and j represent the moles of template R, magnesium (expressed as the oxide, SiO$_2$, Al$_2$O$_3$, P$_2$O$_5$ (H$_3$PO$_4$ expressed as P$_2$O$_5$) and H$_2$O, respectively. The values for 3, f, g, h, i and j were as set forth in the hereinafter discussed preparative examples.

The reaction mixtures were prepared by three procedures, designated hereinafter as Methods A, B and C, unless otherwise noted in the preparative examples.

Method A was employed for examples 1B to 25B, 27B-30B, 39B-46B, 55B-57B, 61B, 63B-71B, 77B-85B and 87B-106B. Method B was employed for examples 31B-38B and 47B-54B. Method C was employed for examples 26B, 62B and 72-76B. The aluminum source was aluminum iso-propoxide except that CATAPAL was the aluminum source in examples 39B-55B and 58B-61B.

Method A

The reaction mixture was prepared by mixing the ground aluminum source (Al-ipro or CATAPAL) with the H$_3$PO$_4$ and water on a gradual basis with occasional cooling with an ice bath. The resulting mixture was blended until a homogeneous mixture was observed. When the aluminum source was CATAPAL the water and H$_3$PO$_4$ were first mixed and the CATAPAL added thereto. The magnesium actate was dissolved in portion of the water and was then added followed by addition of the LUDOX-LS. The combined mixture was blended until a homogeneous mixture was observed. The organic templating agent was added to this mixture and blended until a homogeneous mixture was observed. The resulting mixture (final reaction mixture) was placed in a lined (polytetrafluoroethylene) stainless steel pressure vessel and digested at a temperature (150° C. or 200° C.) for an effective time. Alternatively, if the digestion temperature was 100° C., the final reaction mixture was placed in a lined (polytetrafluoroethylene) screw top bottle for a time. All digestions were carried out at the autogeneous pressure. The products were removed from the reaction vessel cooled and evaluated as set forth hereinafter.

Method B

When method B was employed the organic templating agent was di-n-propylamine. The aluminum source, silicon source and one-half of the water were first mixed and blended until a homogeneous mixture was observed. A second solution was prepared by mixing the remaining water, the H3P4 and the magnesium acetate. This solution was then added to the above mixture. The magnesium acetate and H3PO4 solution was then added to the above mixture and blended until a homogeneous mixture was observed. The organic templating agent(s) was then added and the resulting reaction mixture digested and product recovered as was done in Method A.

Method C

Method C was carried out by mixing aluminum iso-propoxide, LUDOX LS and water in a blender or by mixing water and aluminum iso-propoxide in a blender followed by addition of the LUDOX LS. H3PO4 and magnesium acetate were then added to this mixture. The organic templating agent was then added to the resulting mixture and digested and product recovered as was done in Method A.

The following examples are provided to further illustrate the invention and are not intended to be limiting thereof.

EXAMPLES 1B TO 90B and AB to QB

MgAPSO molecular sieves were prepared according to the above described Methods A, B and C by preparing reaction mixtures expressed as eR:fMgO:hAl$_2$O$_3$:iP$_2$O$_5$:gSiO$_2$:jH$_2$O wherein, e, f, h, i, g and j represent the moles of template R, magnesium (expressed as the oxide), Al$_2$O$_3$, SiO$_2$, P$_2$O$_5$ (H$_3$PO$_3$ expressed as P$_2$O$_5$), and H$_2$O respectively. The values for e, f, g, h and i for examples 1B to 90B are set forth in Table I-B to VI-B. The value of "j" was 50 in examples 1B to 84B and 87B-90B and was 75B in example 85B and was 7B in example 86B. Tables IB to VI-B also shows the temperature (°C.) and time (hours) employed for digestion and indicates the final MgAPSO(s) formed.

Examples AA to QB represent reaction mixtures wherein crystalline MgAPSO products were not observed when the reaction products were subjected to X-ray analysis. The results of Examples AB to QB are set forth in Table VII-B.

TABLE I-B

| Example | Template | e | f | h | i | g | Temp(°C.) | Time(hrs) | MgAPSO Product(s)[2] |
|---|---|---|---|---|---|---|---|---|---|
| 1B | Pr$_3$N | 1.0 | 0.2 | 0.9 | 0.9 | 0.2 | 150 | 48 | MgAPSO-5; MgAPSO-36 |
| 2B | Pr$_3$N | 1.0 | 0.2 | 0.9 | 0.9 | 0.2 | 150 | 166 | MgAPSO-5; MgAPSO-36 |
| 3B | Pr$_3$N | 1.0 | 0.2 | 0.9 | 0.9 | 0.2 | 200 | 48 | MgAPSO-5; MgAPSO-36 |
| 4B | Pr$_3$N | 1.0 | 0.2 | 0.9 | 0.9 | 0.6 | 200 | 166 | MgAPSO-5; MgAPSO-36 |
| 5B[1,3] | Pr$_3$N | 1.0 | 0.2 | 0.9 | 0.9 | 0.6 | 150 | 88 | MgAPSO-36; MgAPSO-5 |
| 6B[1,3] | Pr$_3$N | 1.0 | 0.2 | 0.9 | 0.9 | 0.6 | 200 | 88 | MgAPSO-36; MgAPSO-5 |
| 7B[3] | Pr$_3$N | 1.5 | 0.2 | 0.9 | 0.9 | 0.6 | 150 | 48 | MgAPSO-5; MgAPSO-36 |
| 8B[3] | Pr$_3$N | 1.5 | 0.2 | 0.9 | 0.9 | 0.6 | 150 | 160 | MgAPSO-5; MgAPSO-36 |
| 9B[3] | Pr$_3$N | 1.5 | 0.9 | 0.9 | 0.9 | 0.6 | 200 | 48 | MgAPSO-5; MgAPSO-36 |
| 10B[3] | Pr$_3$N | 1.5 | 0.2 | 0.9 | 0.9 | 0.6 | 200 | 160 | MgAPSO-5; MgAPSO-36 |
| 11B[3] | TPAOH | 1.0 | 0.2 | 0.9 | 0.9 | 0.6 | 150 | 48 | MgAPSO-5; |
| 12B[3] | TPAOH | 1.0 | 0.2 | 0.9 | 0.9 | 0.6 | 150 | 112 | MgAPSO-5; |
| 13B[3] | TPAOH | 1.0 | 0.2 | 0.9 | 0.9 | 0.6 | 200 | 48 | MgAPSO-5; MgAPSO-36 |
| 14B[3] | TPAOH | 1.0 | 0.2 | 0.9 | 0.9 | 0.6 | 200 | 112 | MgAPSO-5; MgAPSO-36 |

[1]Seed crystal of MAPO-36 employed, as disclosed in copending U.S. Ser. No. 514,334.
[2]Major species as identified by x-ray diffraction pattern of product, except that when two or more species were identified the species are listed in the order of their predominance in the MgAPSO products.
[3]LUDOX-LS was added before the magnesium acetate in these example.

TABLE II-B

| Example | Template | e | f | h | i | g | Temp(°C.) | Time(hrs) | MgAPSO Product(s)[1] |
|---|---|---|---|---|---|---|---|---|---|
| 15B[2] | DEEA | 1.0 | 0.2 | 0.9 | 0.9 | 0.6 | 150 | 88 | MgAPSO-5; MgAPSO-47 |
| 16B[2] | DEEA | 1.0 | 0.2 | 0.9 | 0.9 | 0.6 | 200 | 88 | MgAPSO-5; MgAPSO-47 |
| 17B | Pr$_2$NH | 1.0 | 0.2 | 0.9 | 0.9 | 0.2 | 150 | 48 | MgAPSO-11; MgAPSO-5; |
| 18B | Pr$_2$NH | 1.0 | 0.2 | 0.9 | 0.9 | 0.2 | 150 | 166 | MgAPSO-11; MgAPSO-5; MgAPSO-39; MgAPSO-46 |
| 19B | Pr$_2$NH | 1.0 | 0.2 | 0.9 | 0.9 | 0.2 | 200 | 48 | MgAPSO-5; MgAPSO-11; MgAPSO-39 |
| 20B | Pr$_2$NH | 1.0 | 0.2 | 0.9 | 0.9 | 0.2 | 200 | 166 | MgAPSO-11; MgAPSO-39; MgAPSO-5 |
| 21B | Pr$_2$NH | 1.0 | 0.1 | 0.95 | 0.8 | 0.4 | 125 | 300 | MgAPSO-11 |
| 22B | Pr$_2$NH | 1.0 | 0.1 | 0.95 | 0.8 | 0.4 | 150 | 47 | MgAPSO-39; MgAPSO-11; MgAPSO-46; MgAPSO-31 |
| 23B | Pr$_2$NH | 1.0 | 0.1 | 0.95 | 0.8 | 0.4 | 150 | 165 | MgAPSO-39; MgAPSO-46; MgAPSO-11; MgAPSO-31 |
| 24B | Pr$_2$NH | 1.0 | 0.1 | 0.95 | 0.8 | 0.4 | 200 | 47 | MgAPSO-11; MgAPSO-5; MgAPSO-39; MgAPSO-31 |
| 25B | Pr$_2$NH | 1.0 | 0.1 | 0.95 | 0.8 | 0.4 | 200 | 165 | MgAPSO-11; MgAPSO-5; MgAPSO-46 |
| 26B | Pr$_2$NH | 1.0 | 0.4 | 1.0 | 1.0 | 0.4 | 150 | 182 | MgAPSO-46 |
| 27B[2] | Pr$_2$NH | 2.0 | 0.9 | 0.9 | 0.2 | 0.2 | 150 | 96 | MgAPSO-46 |
| 28B[2] | Pr$_2$NH | 2.0 | 0.9 | 0.9 | 0.2 | 0.2 | 150 | 238 | MgAPSO-46; MgAPSO-11 |
| 29B[2] | Pr$_2$NH | 2.0 | 0.9 | 0.9 | 0.2 | 0.2 | 200 | 96 | MgAPSO-11; MgAPSO-46; MgAPSO-39 |

[1] Major species as identified by x-ray diffraction pattern of product, except that when two or more species were identified the species are listed in the order of their predominance in the MgAPSO products.
[2]LUDOX-LS was added before magnesium acetate in these examples.

TABLE III-B

| Example | Template | e | f | h | i | g | Temp(°C.) | Time(hrs) | MgAPSO Product(s)[1] |
|---|---|---|---|---|---|---|---|---|---|
| 30B[2] | Pr$_2$NH | 2.0 | 0.9 | 0.9 | 0.2 | 0.2 | 200 | 238 | MgAPSO-11; MgAPSO-46; MgAPSO-39; MgAPSO-33 |
| 31B | Pr$_2$NH | 1.5 | 0.2 | 0.9 | 0.9 | 0.2 | 150 | 144 | MgAPSO-39; MgAPSO-11; MgAPSO-46 |
| 32B | Pr$_2$NH | 1.5 | 0.2 | 0.9 | 0.9 | 0.2 | 200 | 144 | MgAPSO-39; MgAPSO-11; MgAPSO-46 |
| 33B | Pr$_2$NH | 1.5 | 0.2 | 0.9 | 0.9 | 0.2 | 150 | 144 | MgAPSO-39; MgAPSO-11; MgAPSO-46 |
| 34B | Pr$_2$NH | 1.5 | 0.2 | 0.9 | 0.9 | 0.2 | 200 | 144 | MgAPSO-39; MgAPSO-11; MgAPSO-46 |
| 35B | Pr$_2$NH | 1.0 | 0.2 | 2.7 | 0.9 | 0.2 | 150 | 142 | MgAPSO-39; MgAPSO-11 |
| 36B | Pr$_2$NH | 1.0 | 0.2 | 2.7 | 0.9 | 0.2 | 200 | 142 | MgAPSO-11; MgAPSO-39; MgAPSO-46 |
| 37B | Pr$_2$NH | 2.0 | 0.2 | 2.7 | 0.9 | 0.2 | 150 | 142 | MgAPSO-46 |
| 38B | Pr$_2$NH | 2.0 | 0.2 | 2.7 | 0.9 | 0.2 | 200 | 142 | MgAPSO-46 |
| 39B[2] | Pr$_2$NH | 1.0 | 0.2 | 0.9 | 0.9 | 0.2 | 150 | 96 | MgAPSO-11; MgAPSO-39; MgAPSO-46 |
| 40B[2] | Pr$_2$NH | 1.0 | 0.2 | 0.9 | 0.9 | 0.2 | 150 | 190 | MgAPSO-11; MgAPSO-39; MgAPSO-46 |
| 41B[2] | Pr$_2$NH | 1.0 | 0.2 | 0.9 | 0.9 | 0.2 | 200 | 96 | MgAPSO-11; MgAPSO-39; MgAPSO-46 |
| 42B[2] | Pr$_2$NH | 1.0 | 0.2 | 0.9 | 0.9 | 0.2 | 200 | 190 | MgAPSO-11; MgAPSO-39; MgAPSO-46 |
| 43B[2] | Pr$_2$NH | 2.0 | 0.2 | 0.9 | 0.9 | 0.2 | 150 | 96 | MgAPSO-46; MgAPSO-20 |
| 44B[2] | Pr$_2$NH | 2.0 | 0.2 | 0.9 | 0.9 | 0.2 | 150 | 190 | MgAPSO-46 |
| 45B[2] | Pr$_2$NH | 2.0 | 0.2 | 0.9 | 0.9 | 0.2 | 200 | 96 | MgAPSO-39; MgAPSO-46 |
| 46B[2] | Pr$_2$NH | 2.0 | 0.2 | 0.9 | 0.9 | 0.2 | 200 | 190 | MgAPSO-39; MgAPSO-46 |

[1]Major species as identified by x-ray diffraction pattern of product, except that when two or more species were identified the species are listed in the order of their predominaze in the MgAPSO products.
[2]LUDOX-LS was added before the magnesium acetate in this example.

TABLE IV-B

| Example | Template | e | f | h | i | g | Temp(°C.) | Time(hrs) | MgAPSO Product(s)[4] |
|---|---|---|---|---|---|---|---|---|---|
| 47B | Pr$_2$NH | 1.0 | 0.2 | 0.9 | 0.9 | 0.2 | 150 | 94 | MgAPSO0-11; MgAPSO-39; MgAPSO-5 |
| 48B | Pr$_2$NH | 1.0 | 0.2 | 0.9 | 0.9 | 0.2 | 150 | 238 | MgAPSO-11; MgAPSO-39; MgAPSO-5 |
| 49B | Pr$_2$NH | 1.0 | 0.2 | 0.9 | 0.9 | 0.2 | 200 | 94 | MgAPSO-11; MgAPSO-39; MgAPSO-5 |
| 50B | Pr$_2$NH | 1.0 | 0.2 | 0.9 | 0.9 | 0.2 | 200 | 238 | MgAPSO-11; MgAPSO-5; MgAPSO-39; MgAPSO-46 |
| 51B | Pr$_2$NH | 2.0 | 0.2 | 0.9 | 0.9 | 0.2 | 150 | 94 | MgAPSO-46; MgAPSO-39; MgAPSO-5 |
| 52B | Pr$_2$NH | 2.0 | 0.2 | 0.9 | 0.9 | 0.2 | 150 | 238 | MgAPSO-46; MgAPSO-11; MgAPSO-39 |
| 53B | Pr$_2$NH | 2.0 | 0.2 | 0.9 | 0.9 | 0.2 | 200 | 94 | MgAPSO-46; |
| 54B | Pr$_2$NH | 2.0 | 0.2 | 0.9 | 0.9 | 0.2 | 200 | 238 | MgAPSO-46; MgAPSO-39 |
| 55B[1,2] | Pr$_2$NH | 2.0 | 0.2 | 0.9 | 0.9 | 0.2 | 150,200 | 113 | MgAPSO-39; MgAPSO-31; MgAPSO-11 |
| 56B | i-Pr$_2$NH | 1.0 | 0.2 | 0.9 | 0.9 | 0.2 | 150 | 88 | MgAPSO-5; MgAPSO-11; MgAPSO-34 |
| 57B | i-Pr$_2$NH | 1.0 | 0.2 | 0.9 | 0.9 | 0.2 | 200 | 88 | MgAPSO-5; MgAPSO-11; MgAPSO-34 |
| 58B[3,5] | i-Pr$_2$NH | 1.0 | 0.2 | 0.9 | 0.9 | 0.2 | 150 | 96 | MgAPSO-5; MgAPSO-11; MgAPSO-39 |
| 59B[3,5] | i-Pr$_2$NH | 1.0 | 0.2 | 0.9 | 0.9 | 0.2 | 200 | 96 | MgAPSO-5; MgAPSO-11; MgAPSO-39 |
| 60B[5] | i-Pr$_2$NH | 1.0 | 0.17 | 0.92 | 0.95 | 0.1 | 150 | 93 | MgAPSO-5; MgAPSO-11 |
| 61B[5] | i-Pr$_2$NH | 1.0 | 0.17 | 0.92 | 0.95 | 0.1 | 200 | 93 | MgAPSO-5; MgAPSO-39; MgAPSO-11 |
| 62B | i-Pr$_2$NH | 1.0 | 0.4 | 1.0 | 1.0 | 0.4 | 150 | 231 | MgAPSO-5; MgAPSO-11 |

[1]AlPO$_4$-31 seed crystal
[2]Two mixtures were digested with one at 150° C. and one at 200° C.
[3]SAPO-11 seed crystal as disclosed in U.S. Ser. No. 400,438
[4]Major species as identified by x-ray diffraction pattern of product, except that when two or more species were identified the species are listed in the order of their predominance in the MgAPSO products.
[5]LUDOX-LS was added before magnesium acetate in this example.

TABLE V-B

| Example | Template | e | f | h | i | g | Temp(°C.) | Time(hrs) | MgAPSO Product(s)[1] |
|---|---|---|---|---|---|---|---|---|---|
| 63B | TEAOH | 1.0 | 0.2 | 0.9 | 0.9 | 0.2 | 150 | 48 | MgAPSO-34 |
| 64B | TEAOH | 1.0 | 0.2 | 0.9 | 0.9 | 0.2 | 150 | 166 | MgAPSO-34 |
| 65B | TEAOH | 1.0 | 0.2 | 0.9 | 0.9 | 0.2 | 200 | 48 | MgAPSO-34; MgAPSO-5 |
| 66B | TEAOH | 1.0 | 0.2 | 0.9 | 0.9 | 0.2 | 200 | 166 | MgAPSO-34 |
| 67B | TEAOH | 1.0 | 0.2 | 0.9 | 0.9 | 0.6 | 150 | 40 | MgAPSO-34; MgAPSO-5 |
| 68B | TEAOH | 1.0 | 0.2 | 0.9 | 0.9 | 0.6 | 150 | 121 | MgAPSO-34 |
| 69B | TEAOH | 1.0 | 0.2 | 0.9 | 0.9 | 0.6 | 200 | 40 | MgAPSO-5; MgAPSO-34 |
| 70B | TEAOH | 1.0 | 0.2 | 0.9 | 0.9 | 0.6 | 200 | 121 | MgAPSO-5; MgAPSO-34 |
| 71B | TEAOH | 1.0 | 0.2 | 0.9 | 0.9 | 0.6 | 150 | 114 | MgAPSO-34; MgAPSO-5 |
| 72B | TEAOH | 1.0 | 0.4 | 1.0 | 1.0 | 0.4 | 100 | 111 | MgAPSO-34 |
| 73B | TEAOH | 1.0 | 0.4 | 1.0 | 1.0 | 0.4 | 100 | 182 | MgAPSO-34 |
| 74B | TEAOH | 1.0 | 0.4 | 1.0 | 1.0 | 0.4 | 150 | 111 | MgAPSO-34 |
| 75B | TEAOH | 1.0 | 0.4 | 1.0 | 1.0 | 0.4 | 150 | 182 | MgAPSO-34 |
| 76B | TEAOH | 1.0 | 0.4 | 1.0 | 1.0 | 0.4 | 150 | 231 | MgAPSO-34; MgAPSO-5 |

[1]Major species as identified by x-ray diffraction pattern of product, except that when two or more species were identified the species are listed in the order of their predominance in the MgAPSO products.

TABLE VI-B

| Example | Template | e | f | h | i | g | Temp(°C.) | Time(hrs) | MgAPSO Product(s)[1] |
|---|---|---|---|---|---|---|---|---|---|
| 77B | Quin | 1.0 | 0.2 | 0.9 | 0.9 | 0.2 | 150 | 48 | MgAPSO-35; MgAPSO-16 |
| 78B | Quin | 1.0 | 0.2 | 0.9 | 0.9 | 0.2 | 150 | 166 | MgAPSO-35; MgAPSO-16 |

TABLE VI-B-continued

| Example | Template | e | f | h | i | g | Temp(°C.) | Time(hrs) | MgAPSO Product(s)[1] |
|---|---|---|---|---|---|---|---|---|---|
| 79B | Quin | 1.0 | 0.2 | 0.9 | 0.9 | 0.2 | 200 | 48 | MgAPSO-35; MgAPSO-16 |
| 80B | Quin | 1.0 | 0.2 | 0.9 | 0.9 | 0.2 | 200 | 166 | MgAPSO-35; MgAPSO-16 |
| 81B | MQuin | 1.0 | 0.2 | 0.9 | 0.9 | 0.2 | 150 | 40 | MgAPSO-35 |
| 82B | MQuin | 1.0 | 0.2 | 0.9 | 0.9 | 0.2 | 150 | 121 | MgAPSO-35 |
| 83B | MQuin | 1.0 | 0.2 | 0.9 | 0.9 | 0.2 | 200 | 40 | MgAPSO-35 |
| 84B | MQuin | 1.0 | 0.2 | 0.9 | 0.9 | 0.2 | 200 | 121 | MgAPSO-35 |
| 85B | MQuin | 1.0 | 0.2 | 0.9 | 0.9 | 0.6 | 150 | 114 | MgAPSO-35; MgAPSO-16 |
| 86B[2] | TBAOH | 2.0 | 0.4 | 0.8 | 1.0 | 0.4 | 200 | 48 | MgAPSO-5 |
| 87B[3] | C-hex | 1.0 | 0.2 | 0.9 | 0.9 | 0.6 | 150 | 40 | MgAPSO-44; MgAPSO-5 |
| 88B[3] | C-hex | 1.0 | 0.2 | 0.9 | 0.9 | 0.6 | 200 | 107 | MgAPSO-44; MgAPSO-5 |
| 89B[3] | C-hex | 1.0 | 0.2 | 0.9 | 0.9 | 0.6 | 150 | 40 | MgAPSO-5; MgAPSO-44 |
| 90B[3] | C-hex | 1.0 | 0.2 | 0.9 | 0.9 | 0.6 | 200 | 107 | MgAPSO-5; MgAPSO-44 |

[1] Major species as identified by x-ray diffraction pattern of product, except that when two or more species were identified the species are listed in the order of their predominance in the MgAPSO products.
[2] The mixing order in this example was in the order of the aluminum source, magnesium source, silicon source and the phosphorus source.
[3] LUDOX-LS was added before magnesium acetate in this example.

TABLE VII-B[1]

| Example | Template | e | f | h | i | g | j | Temp(°C.) | Time(hrs) | Method |
|---|---|---|---|---|---|---|---|---|---|---|
| AB | TPABr | 1.0 | 0.4 | 1.0 | 1.0 | 0.4 | 50 | 150 | 231 | C |
| BB | Pr$_2$NH | 1.0 | 0.1 | 0.95 | 0.8 | 0.4 | 50 | 125 | 47 | A |
| CB | Pr$_2$NH | 1.0 | 0.1 | 0.95 | 0.8 | 0.4 | 50 | 125 | 165 | A |
| DB | Pr$_2$NH | 1.0 | 0.4 | 1.0 | 1.0 | 0.4 | 50 | 100 | 111 | C |
| EB | Pr$_2$NH | 1.0 | 0.4 | 1.0 | 1.0 | 0.4 | 50 | 100 | 182 | C |
| FB | Pr$_2$NH | 1.0 | 0.4 | 1.0 | 1.0 | 0.4 | 50 | 150 | 111 | C |
| GB | Pr$_2$NH | 1.0 | 0.2 | 0.9 | 0.9 | 0.2 | 50 | 150 | 96 | B |
| HB | Pr$_2$NH | 1.0 | 0.2 | 0.9 | 0.9 | 0.2 | 50 | 150 | 235 | B |
| IB | Pr$_2$NH | 1.0 | 0.2 | 0.9 | 0.9 | 0.2 | 50 | 200 | 96 | B |
| JB | Pr$_2$NH | 1.0 | 0.2 | 0.9 | 0.9 | 0.2 | 50 | 200 | 235 | B |
| KB | Pr$_2$NH | 2.0 | 0.2 | 0.9 | 0.9 | 0.2 | 50 | 150 | 96 | B |
| LB | Pr$_2$NH | 2.0 | 0.2 | 0.9 | 0.9 | 0.2 | 50 | 150 | 235 | B |
| MB | Pr$_2$NH | 2.0 | 0.2 | 0.9 | 0.9 | 0.2 | 50 | 200 | 96 | B |
| NB | Pr$_2$NH | 2.0 | 0.2 | 0.9 | 0.9 | 0.2 | 50 | 200 | 235 | B |
| OB | TBAOH | 2.0 | 0.4 | 0.8 | 1.0 | 0.4 | 71 | 150 | 48 | 2 |
| PB | TBAOH | 2.0 | 0.4 | 0.8 | 1.0 | 0.4 | 71 | 150 | 160 | 2 |
| QB | TBAOH | 2.0 | 0.4 | 0.8 | 1.0 | 0.4 | 71 | 200 | 160 | 2 |

[1] Reaction mixtures from which crystalline MgAPSO products were not identified by x-ray analysis of the products.
[2] The mixing order in this example was in the order of the aluminum source, the magnesium source, the silicon source and the phosphorus source.

EXAMPLES 91B to 106B

MgAPSO molecular sieves were prepared according to the procedures employed in examples 1 B to 90B. The aluminum source was CATAPAL in examples 96B and 97B.

The results of preparative examples 91B to 106B are set forth in Table VIII-B.

EXAMPLE 107B

Samples of the MgAPSO products were subjected to chemical analysis. The chemical analysis for each of the analyzed products is given hereinafter:

(a) The chemical analysis for the MgAPSO-5 of example 4B was:

TABLE VIII-B

| Example[2] | Template | e | f | h | i | g | Temp(°C.) | Time(hrs) | MgAPSO Product(s)[1] |
|---|---|---|---|---|---|---|---|---|---|
| 91B | MQuin | 1.0 | 0.1 | 0.9 | 0.9 | 0.6 | 150 | 450 | MgAPSO-35 |
| 92B | TEAOH | 1.0 | 0.1 | 0.9 | 0.9 | 0.6 | 150 | 44 | MgAPSO-5; MgAPSO-34 |
| 93B | TEAOH | 1.0 | 0.1 | 0.9 | 0.9 | 0.6 | 150 | 44 | MgAPSO-5; MgAPSO-34 |
| 94B | TEAOH | 1.0 | 0.05 | 1.0 | 1.0 | 0.4 | 100 | 280 | MgAPSO-34 |
| 95B | TEAOH | 1.0 | 0.1 | 1.0 | 1.0 | 0.4 | 100 | 280 | MgAPSO-34 |
| 96B | Pr$_2$NH | 2.0 | 0.1 | 0.9 | 0.9 | 0.6 | 150 | 122 | MgAPSO-43; MgAPSO-46 |
| 97B | Pr$_2$NH | 2.0 | 0.1 | 0.9 | 0.9 | 0.6 | 150 | 122 | MgAPSO-43; MgAPSO-46 |
| 98B | Quin | 1.0 | 0.2 | 0.9 | 0.9 | 0.6 | 220 | 114 | MgAPSO-16; MgAPSO-35 |
| 99B | C-hex | 1.0 | 0.2 | 0.9 | 0.9 | 0.6 | 220 | 114 | MgAPSO-44; MgAPSO-5 |
| 100B | TMAOH | 1.0 | 0.2 | 0.9 | 0.7 | 0.6 | 100 | 18 | MgAPSO-20 |
| 101B | TMAOH | 1.0 | 0.2 | 0.9 | 0.7 | 0.6 | 150 | 111 | MgAPSO-20 |
| 102B | TMAOH | 1.0 | 0.2 | 0.9 | 0.7 | 0.6 | 200 | 22 | MgAPSO-20 |
| 103B | TMAOH | 1.0 | 0.2 | 0.9 | 0.7 | 0.6 | 200 | 111 | MgAPSO-20 |
| 104B | DEEA | 2.0 | 0.2 | 0.9 | 0.7 | 0.6 | 100 | 111 | MgAPSO-47 |
| 105B | DEEA | 2.0 | 0.2 | 0.9 | 0.7 | 0.6 | 100 | 22 | MgAPSO-47; MgAPSO-5 |
| 106B | DEEA | 2.0 | 0.2 | 0.9 | 0.7 | 0.6 | 100 | 111 | MgAPSO-47 |

[1] Major species as identified by x-ray diffraction pattern of product, except that when two or more species were identified the species are listed in the order of their predominance in the MgAPSO products.
[2] LUDOX-LS was added before magnesium acetate in examples 91B to 106B.

| Component | Weight Percent |
|---|---|
| $Al_2O_3$ | 31.3 |
| $P_2O_5$ | 45.4 |
| MgO | 2.8 |
| $SiO_2$ | 3.9 |
| Carbon | 5.0 |
| LOI* | 13.7 |

*LOI = Loss on Ignition

The above chemical analysis gives an overall product composition in molar oxide ratios (anhydrous basis) of: 0.23 MgO: 1.00 $Al_2O_3$: 1.04 $P_2O_5$: 0.21 $SiO_2$; and a formula (anhydrous basis) of:

0.03R($Mg_{0.05}Al_{0.44}P_{0.46}Si_{0.05}$)$O_2$ (b) The chemical analysis for MgAPSO-36 of example 5B was:

| Component | Weight Percent |
|---|---|
| $Al_2O_3$ | 31.2 |
| $P_2O_5$ | 44.6 |
| MgO | 2.6 |
| $SiO_2$ | 8.6 |
| Carbon | 6.2 |
| LOI* | 13.9 |

*LOI = Loss on Ignition

The above chemical analysis gives an overall product composition in molar oxide ratios (anhydrous basis) of: 0.21 MgO; 1.00 $Al_2O_3$: 1.03 $P_2O_5$: 0.45 $SiO_2$; and a formula (anhydrous basis) of:

0.04R($Mg_{0.05}Al_{0.43}P_{0.44}Si_{0.10}$)$O_2$ (c) The chemical analysis for the MgAPSO-46 of example 44B was:

| Component | Weight Percent |
|---|---|
| $Al_2O_3$ | 30.1 |
| $P_2O_5$ | 38.4 |
| MgO | 4.1 |
| $SiO_2$ | 4.4 |
| Carbon | 10.6 |
| LOI* | 22.5 |

*LOI = Loss on Ignition

The above chemical analysis gives an overall product composition in molar oxide ratios (anhydrous basis) of: 0.34 MgO; 1.00 $Al_2O_3$: 0.92 $P_2O_5$: 0.25 $SiO_2$: and a formula (anhydrous basis) of:

0.11R($Mg_{0.08}Al_{0.45}P_{0.41}Si_{0.06}$)$O_2$ (d) The chemical analysis of the MgAPSO-34 of example 63B was:

| Component | Weight Percent |
|---|---|
| $Al_2O_3$ | 31.7 |
| $P_2O_5$ | 37.0 |
| MgO | 3.0 |
| $SiO_2$ | 2.9 |
| Carbon | 8.3 |
| LOI* | 21.6 |

*LOI = Loss on Ignition

The above chemical analysis gives an overall product composition in molar oxide ratios (anhydrous basis) of: 0.24 MgO; 1.00 $Al_2O_3$: 0.84 $P_2O_5$: 0.16 $SiO_2$; and a formula (anhydrous basis) of:

0.07R($Mg_{0.06}Al_{0.49}P_{0.41}Si_{0.04}$)$O_2$ (e) The chemical analysis for the MgAPSO-34 of example 63B was:

| Component | Weight Percent |
|---|---|
| $Al_2O_3$ | 29.8 |
| $P_2O_5$ | 40.4 |
| MgO | 2.3 |
| $SiO_2$ | 6.9 |
| Carbon | 10.4 |
| LOI* | 21.1 |

*LOI = Loss on Ignition

The above chemical analysis gives an overall product composition in molar oxide ratios (anhydrous basis) of: 0.20 MgO; 1.00 $Al_2O_3$: 0.97 $P_2O_5$: 0.39 $SiO_2$: and a formula (anhydrous basis of:

0.08R($Mg_{0.04}Al_{0.44}P_{0.43}Si_{0.09}$)$O_2$ (f) The chemical analysis of the MgAPSO-34 of example 74B was:

| Component | Weight Percent |
|---|---|
| $Al_2O_3$ | 28.6 |
| $P_2O_5$ | 33.9 |
| MgO | 4.9 |
| $SiO_2$ | 3.7 |
| Carbon | 9.0 |
| LOI* | 27.1 |

*LOI = Loss on Ignition

The above chemical analysis gives an overall product composition in molar oxide ratios (anhydrous basis) of: 0.43 MgO; 1.00 $Al_2O_3$: 0.85 $P_2O_5$: 0.22 $SiO_2$; and a formula (anhydrous basis) of:

0.08R($Mg_{0.10}Al_{0.46}P_{0.38}Si_{0.05}$)$O_2$ (g) The chemical analysis for the MgAPSO-35 of example 85B was:

| Component | Weight Percent |
|---|---|
| $Al_2O_3$ | 28.3 |
| $P_2O_5$ | 42.7 |
| MgO | 2.8 |
| $SiO_2$ | 4.0 |
| Carbon | 9.8 |
| LOI* | 19.6 |

*LOI = Loss on Ignition

The above chemical analysis gives an overall product composition in molar oxide ratios of: 0.37R;0.25 MgO; 1.0 $Al_2O_3$; 1.08 $P_2O_5$; 0.24 $SiO_2$; and a formula (anhydrous basis) of:

0.08($Mg_{0.05}Al_{0.43}P_{0.47}Si_{0.05}$)$O_2$ (h) The chemical analysis for the MgAPSO-20 of example 101B was:

| Component | Weight Percent |
|---|---|
| $Al_2O_3$ | 27.8 |
| $P_2O_5$ | 31.4 |
| MgO | 3.1 |
| $SiO_2$ | 15.2 |
| Carbon | 9.7 |
| LOI* | 21.2 |

*LOI = Loss on Ignition

The above chemical analysis gives an overall product composition in molar oxide ratios (anhydrous basis) of: 0.74R;0.28 MgO; 1.00 $Al_2O_3$: 0.81 $P_2O_5$: 0.93 $SiO_2$; and a formula (anhydrous basis) of:

0.15R($Mg_{0.06}Al_{0.41}P_{0.34}Si_{0.19}$)$O_2$ (i) The chemical analysis for the MgAPSO-43 of example 97B was:

| Component | Weight Percent |
|---|---|
| $Al_2O_3$ | 32.3 |
| $P_2O_5$ | 33.1 |
| MgO | 3.6 |
| $SiO_2$ | 8.2 |
| Carbon | 9.1 |
| LOI* | 21.1 |

LOI* = Loss on Ignition

The above chemical analysis gives an overall product composition in molar oxide ratios (anhydrous basis) of: 0.40R; 0.28 MgO; 1.00 $Al_2O_3$: 0.74 $P_2O_5$: 0.43 $SiO_2$; and a formula (anhydrous basis) of:
0.10R($Mg_{0.07}Al_{0.48}P_{0.35}Si_{0.10}$)$O_2$ (j) The chemical analysis for the MgAPSO-47 of example 104B was:

| Component | Weight Percent |
|---|---|
| $Al_2O_3$ | 33.1 |
| $P_2O_5$ | 29.3 |
| MgO | 2.8 |
| $SiO_2$ | 7.7 |
| Carbon | 5.7 |
| LOI* | 25.4 |

*LOI = Loss on Ignition

The above chemical analysis gives an overall product composition in molar oxide ratios (anhydrous basis) of: 0.24R; 0.21 MgO; 1.00 $Al_2O_3$: 0.64 $P_2O_5$: 0.39 $SiO_2$; and a formula (anhydrous basis) of:
0.06R($Mg_{0.06}Al_{0.51}P_{0.33}Si_{0.10}$)$O_2$

EXAMPLE 108B

EDAX (energy dispersive analysis by x-ray) microprobe analysis in conjunction with SEM (scanning electron microscope) was carried out on clear crystals from the products of examples. Analysis of crystals having a morphology characteristic of the MgAPSO products as prepared in the following referenced examples gave the following analysis based on relative peak heights:

| Average of Spot Probes | |
|---|---|
| (a) MgAPSO-5(Example 4B): | |
| Mg | 3 |
| Al | 46 |
| P | 48 |
| Si | 3 |
| (b) MgAPSO-36(Example 5B): | |
| Mg | 3 |
| Al | 40 |
| P | 48 |
| Si | 9 |
| (c) MgAPSO-46(Example 44B): | |
| Mg | 5 |
| Al | 39 |
| P | 49 |
| Si | 6 |
| (d) MgAPSO-34(Example 63B): | |
| Mg | 6 |
| Al | 44 |
| P | 45 |
| Si | 6 |
| (e) MgAPSO-34(Example 75B): | |
| Mg | 6 |
| Al | 42 |
| P | 44 |
| Si | 8 |
| (f) MgAPSO-35(Example 80B): | |
| Mg | 4 |
| Al | 41 |
| P | 51 |
| Si | 4 |
| (g) MgAPSO-47(Example 104B): | |
| Mg | 2 |
| Al | 42 |
| P | 43 |
| Si | 13 |

EXAMPLES 109B

Samples of the MgAPSO products were evaluated for adsorption capacities in the as-synthesized form or were calcined in air or nitrogen, to remove at least part of the organic templating agent, as hereinafter set forth. The adsorption capacities of each as-synthesized or calcined sample were measured using a standard McBain - Bakr gravimetric adsorption apparatus. The samples were activated in a vacuum at 350° C., prior to measurements. The McBain-Bakr data for the selected MgAPSO products were:

| (a) Example 4B (MgAPSO-5): | | | |
|---|---|---|---|
| Adsorbate | Kinetic Diameter, Å | Pressure (Torr) | Temp (°C.) | Wt. % Adsorbed* |
| $O_2$ | 3.46 | 99 | −183 | 13.2 |
| $O_2$ | 3.46 | 749 | −183 | 15.5 |
| Cyclohexane | 6.0 | 57 | 23.4 | 7.9 |
| neopentane | 6.2 | 100 | 23.4 | 5.0 |
| $H_2O$ | 2.65 | 4.6 | 23.2 | 16.0 |
| $H_2O$ | 2.65 | 16.8 | 23.5 | 21.3 |

*calcined in air at 600° C. for 2.25 hrs.

The above data demonstrate that the pore size of the calcined product is greater than about 6.2 Å.

| (b) Example 101B (MgAPSO-20): | | | |
|---|---|---|---|
| Adsorbate | Kinetic Diameter, Å | Pressure (Torr) | Temp (°C.) | Wt. % Adsorbed* |
| $O_2$ | 3.46 | 99 | −183 | 0.8 |
| $O_2$ | 3.46 | 750 | −183 | 2.7 |
| $H_2O$ | 2.65 | 4.6 | 23.2 | 16.5 |
| $H_2O$ | 2.65 | 16.8 | 23.5 | 19.9 |

*calcined in air at 600° C. for 1.5 hrs.

The above data demonstrate that the pore size of the calcined product is about 3.0 Å.

| (c) Example 63B (MgAPSO-34): | | | |
|---|---|---|---|
| Adsorbate | Kinetic Diameter, Å | Pressure (Torr) | Temp (°C.) | Wt. % Adsorbed* |
| $O_2$ | 3.46 | 100 | −183 | 21.7 |
| $O_2$ | 3.46 | 734 | −183 | 33.6 |
| isobutane | 5.0 | 300 | 23 | 1.3 |
| n-hexane | 4.3 | 51 | 24 | 10.4 |
| $H_2O$ | 2.65 | 4.6 | 23 | 27.1 |
| $H_2O$ | 2.65 | 18.5 | 24 | 32.9 |

*calcined in air at 600° C. for 1.5 hours.

The above data demonstrate that the pore size of the calcined product is about 4.3 Å.

| Adsorbate | Kinetic Diameter, Å | Pressure (Torr) | Temp (°C.) | Wt. % Adsorbed* |
|---|---|---|---|---|
| (d) Example 84B (MgAPSO-35): | | | | |
| O₂ | 3.46 | 100 | −183 | 6.7 |
| O₂ | 3.46 | 734 | −183 | 9.2 |
| isobutane | 5.0 | 100 | 24 | 0.3 |
| n-hexane | 4.3 | 51 | 24 | 1.1 |
| H₂O | 2.65 | 4.6 | 23 | 11.5 |
| H₂O | 2.65 | 19.5 | 23 | 17.7 |

*calcined in nitrogen at 500° C. for 2 hrs.

| Adsorbate | Kinetic Diameter, Å | Pressure (Torr) | Temp (°C.) | Wt. % Adsorbed* |
|---|---|---|---|---|
| (e) Example 91B (MgAPSO-35): | | | | |
| O₂ | 3.46 | 100 | −183 | 11.2 |
| O₂ | 3.46 | 744 | −183 | 14.0 |
| isobutane | 5.0 | 100 | 22.8 | 0.2 |
| n-hexane | 4.3 | 49 | 22.3 | 5.7 |
| H₂O | 2.65 | 4.6 | 23.1 | 16.1 |
| H₂O | 2.65 | 17.8 | 22.9 | 20.5 |

*calcined at 500° C. in air for 6.7 hours.

The above data demonstrate that the pore size of the calcined product is about 4.3 Å. In addition, the data demonstrate that in part (d) the template was not sufficiently removed by the calcination.

| Adsorbate | Kinetic Diameter, Å | Pressure (Torr) | Temp (°C.) | Wt. % Adsorbed* |
|---|---|---|---|---|
| (f) Example 5B (MgAPSO-36): | | | | |
| O₂ | 3.46 | 100 | −183 | 12.9 |
| O₂ | 3.46 | 734 | −183 | 15.4 |
| isobutane | 5.0 | 100 | 24 | 5.2 |
| cyclohexane | 6.0 | 59 | 23.7 | 9.0 |
| neopentane | 6.2 | 100 | 24.5 | 5.5 |
| H₂O | 2.65 | 4.6 | 23 | 16.8 |
| H₂O | 2.65 | 20 | 23.6 | 23.5 |

*calcined in air at 500° C. for 2.0 hrs. and in air at 600° C. for two additional hours.

The above data demonstrate that the pore size of the calcined product is greater than 6.2 Å.

| Adsorbate | Kinetic Diameter, Å | Pressure (Torr) | Temp (°C.) | Wt. % Adsorbed* |
|---|---|---|---|---|
| (g) Example 44B (MgAPSO-46): | | | | |
| O₂ | 3.46 | 100 | −183 | 20.7 |
| O₂ | 3.46 | 734 | −183 | 24.7 |
| neopentane | 6.2 | 100 | 24.5 | 8.4 |
| isobutane | 5.0 | 100 | 24 | 7.8 |
| cyclo-hexane | 6.0 | 59 | 23.7 | 11.9 |
| H₂O | 2.65 | 4.6 | 23 | 22.0 |
| H₂O | 2.65 | 20.0 | 23.6 | 27.4 |

*calcined in nitrogen at 500° C. for 1.75 hours.

The above data demonstrate that the pore size of the calcined product is greater than about 6.2 Å.

| Adsorbate | Kinetic Diameter, Å | Pressure (Torr) | Temp (°C.) | Wt. % Adsorbed* |
|---|---|---|---|---|
| (h) Example 104B (MgAPSO-47): | | | | |
| O₂ | 3.46 | 99 | −183 | 14.1 |
| O₂ | 3.46 | 725 | −183 | 29.2 |
| isobutane | 5.0 | 100 | 22.8 | 0.2 |
| n-hexane | 4.3 | 49 | 23.3 | 4.2 |
| H₂O | 2.65 | 4.6 | 23.1 | 18.5 |
| H₂O | 2.65 | 17.8 | 22.9 | 28.7 |

*calcined in air at 500° C. for 1.75 hrs.

The above data demonstrate that the pore size of the calcined product is about 4.3 Å.

EXAMPLE 110B (a) MgAPSO-5, as prepared to in example 4B, was subjected to X-ray analysis. MgAPSO-5 was determined to have a characteristic x-ray powder diffraction pattern which contains the d-spacings set forth below:

| 2θ | d, (Å) | 100 × I/Io |
|---|---|---|
| 7.35 | 11.71 | 83 |
| 7.9* | 11.19 | (sh) |
| 12.8 | 6.92 | 11 |
| 14.8 | 5.99 | 18 |
| 15.8* | 5.61 | 1 |
| 16.4* | 5.40 | 2 |
| 19.0* | 4.67 | (sh) |
| 19.65 | 4.52 | 48–52 |
| 21.0 | 4.23 | 54 |
| 22.2 | 4.004 | 100 |
| 23.6* | 3.770 | 1 |
| 24.7 | 3.604 | 4 |
| 25.75 | 3.460 | 31 |
| 27.2* | 3.278 | 3 |
| 28.9 | 3.089 | 20 |
| 29.8 | 2.998 | 18 |
| 31.8* | 2.814 | 1 |
| 33.5 | 2.675 | 5 |
| 34.4 | 2.607 | 17 |
| 36.8 | 2.442 | 4 |
| 37.6 | 2.392 | 11 |
| 40.7 | 2.217 | 1 |
| 41.3 | 2.186 | 3 |
| 42.05 | 2.149 | 4 |
| 42.85 | 2.110 | 3 |
| 43.4 | 2.085 | 2 |
| 44.8 | 2.023 | 2 |
| 45.4 | 1.998 | 2 |
| 47.4 | 1.918 | 6 |
| 51.1 | 1.787 | 2 |
| 51.7 | 1.768 | 2 |
| 52.4 | 1.746 | 1 |
| 55.2 | 1.664 | 4 |

*impurity peak (B) A portion of the as-synthesized MgAPSO-5 of part (a) was calcined in air at 600° C. for about 2.25 hours. The calcined product was characterized by the x-ray powder diffraction pattern below:

| 2θ | d, (Å) | 100 × I/Io |
|---|---|---|
| 7.4 | 11.95 | 94 |
| 7.9** | 11.19 | sh |
| 8.2** | 10.78 | sh |
| 12.9 | 6.86 | 20 |
| 14.9 | 5.95 | 8 |
| 16.4** | 5.40 | 2 |
| 19.3** | 4.60 | sh |
| 19.8 | 4.48 | 33 |
| 21.1 | 4.21 | 52 |
| 22.4 | 3.969 | 100 |
| 24.8 | 3.590 | 4 |
| 26.0 | 3.427 | 27 |
| 27.1** | 3.290 | 2 |
| 27.9** | 3.198 | 2 |
| 28.3* | 3.154 | 2 |
| 29.1 | 3.069 | 20 |
| 30.15 | 2.964 | 15 |
| 33.7 | 2.660 | 5 |
| 34.6 | 2.592 | 18 |
| 37.0 | 2.430 | 4 |
| 37.8 | 2.380 | 10 |
| 41.6 | 2.171 | 1 |
| 42.4 | 2.132 | 1 |
| 42.9 | 2.108 | 1 |
| 43.6 | 2.076 | 1 |
| 45.0 | 2.015 | 1 |
| 46.2 | 1.965 | 1 |
| 47.8 | 1.903 | 4 |
| 50.9 | 1.794 | 1 |

-continued

| 2θ | d, (Å) | 100 × I/Io |
|---|---|---|
| 51.6 | 1.771 | 1 |
| 55.8 | 1.648 | 2 |

*peak may contain impurity
**impurity peak (c) The MGAPSO-5 compositions are generally characterized by the data in Table IX-B below:

TABLE IX-B

| 2θ | d, (Å) | Relative Intensity |
|---|---|---|
| 7.2–7.4 | 12.28–11.95 | m–vs |
| 14.6–14.95 | 6.07–5.93 | w–m |
| 19.4–19.8 | 4.58–4.48 | m |
| 20.85–21.1 | 4.26–4.21 | vw–vs |
| 22.15–22.4 | 4.01–3.97 | m–vs |
| 25.6–25.95 | 3.480–3.434 | m |

(d) The MgAPSO-5 compositions for which x-ray powder diffraction data have been obtained to date have patterns which are characterized by the x-ray powder diffraction pattern below in Table X-B, below:

TABLE X-B

| 2θ | d, (Å) | 100 × I/Io |
|---|---|---|
| 7.2–7.4 | 12.28–11.95 | 69–100 |
| 12.65–12.9 | 7.00–6.86 | 8–12 |
| 14.6–14.95 | 6.07–5.93 | 15–35 |
| 19.4–19.8 | 4.58–4.48 | 38–73 |
| 20.85–21.1 | 4.26–4.21 | (sh)-100 |
| 22.15–22.4 | 4.013–3.969 | 48–100 |
| 24.4–24.85 | 3.648–3.583 | 0–14 |
| 25.6–25.95 | 3.480–3.434 | 23–44 |
| 28.7–29.1 | 3.110–3.069 | 12–20 |
| 29.65–30.15 | 3.013–2.964 | 15–21 |
| 33.4–33.75 | 2.683–2.656 | 2–11 |
| 34.2–34.65 | 2.622–2.589 | 11–19 |
| 36.6–37.0 | 2.455–2.430 | 0–4 |
| 37.4–37.8 | 2.405–2.380 | 5–11 |
| 40.6–40.7 | 2.222–2.217 | 0–1 |
| 41.1–41.6 | 2.196–2.171 | 0–3 |
| 41.85–42.4 | 2.159–2.132 | 3–4 |
| 42.6–43.05 | 2.122–2.101 | 0–3 |
| 43.2–43.5 | 2.094–2.080 | 0–2 |
| 44.6–45.0 | 2.032–2.015 | 0–2 |
| 45.3–45.6 | 2.002–1.989 | 0–1 |
| 46.1–46.35 | 1.969–1.959 | 0–1 |
| 47.2–47.75 | 1.926–1.905 | 4–6 |
| 50.4 | 1.811 | 0–1 |
| 50.9–51.1 | 1.794–1.787 | 0–3 |
| 51.6–51.9 | 1.771–1.762 | 0–4 |
| 52.2–52.4 | 1.752–1.746 | 0–1 |
| 55.2–55.8 | 1.664–1.648 | 0–4 |

EXAMPLE 111-B (a) MgAPSO-11, as prepared to in example 17B, was subjected to x-ray analysis. MgAPSO-11 was determined to have a characteristic x-ray powder diffraction pattern which contains the d-spacings set forth below:

| 2θ | d, (Å) | 100 × I/Io |
|---|---|---|
| 7.3** | 12.11 | 47 |
| 8.0 | 8.04 | 19 |
| 9.3 | 9.51 | 30 |
| 12.8** | 6.92 | (sh) |
| 13.1 | 6.76 | 13 |
| 14.75** | 6.01 | 6 |
| 15.6 | 5.68 | 20 |
| 16.1 | 5.51 | 3 |
| 18.8 | 4.72 | 3 |
| 19.6** | 4.53 | 15 |
| 20.25 | 4.39 | 32 |
| 21.0* | 4.23 | 100 |
| 22.0 | 4.040 | (sh) |
| 22.3** | 3.987 | 57 |
| 22.6 | 3.934 | (sh) |
| 23.0 | 3.867 | 46 |
| 24.4** | 3.648 | sh |
| 24.6 | 3.619 | 9 |
| 25.7** | 3.467 | 11 |
| 26.3 | 3.389 | 20 |
| 28.5** | 3.132 | 11 |
| 28.85 | 3.095 | 11 |
| 29.35* | 3.043 | 4 |
| 29.8 | 2.998 | 9 |
| 31.4 | 2.849 | 6 |
| 32.7 | 2.739 | 13 |
| 34.1 | 2.629 | 10 |
| 34.3** | 2.614 | sh |
| 36.2** | 2.481 | 4 |
| 37.6* | 2.392 | 12 |
| 39.3 | 2.293 | 3 |
| 40.6 | 2.222 | 1 |
| 41.9* | 2.156 | 2 |
| 42.9 | 2.108 | 4 |
| 44.6 | 2.032 | 3 |
| 54.4 | 1.687 | 1 |

*Peak may contain impurity
**Impurity peak (b) A portion of the as-synthesized MgAPSO-11 of part (a) was calcined in air at 600° C. for about 2 hours. The calcined product was characterized by the x-ray powder diffraction pattern below:

| 2θ | d, (Å) | 100 × I/Io |
|---|---|---|
| 7.4* | 11.95 | 30 |
| 8.1 | 10.92 | 35 |
| 9.6 | 9.21 | 35 |
| 13.0 | 6.81 | 19 |
| 15.8 | 5.61 | 30 |
| 18.2* | 4.87 | 4 |
| 19.7* | 4.51 | 9 |
| 20.15 | 4.41 | 22 |
| 21.2 | 4.19 | 100 |
| 22.3 | 3.987 | 74 |
| 22.9 | 3.883 | sh |
| 23.35 | 3.810 | 43 |
| 26.0* | 3.427 | sh |
| 26.3 | 3.389 | 17 |
| 26.7 | 3.339 | sh |
| 28.8 | 3.100 | sh |
| 29.0* | 3.079 | 17 |
| 29.5 | 3.028 | 9 |
| 30.0* | 2.979 | 4 |
| 31.0* | 2.885 | 3 |
| 31.7 | 2.823 | 15 |
| 32.6 | 2.747 | 15 |
| 33.8 | 2.652 | 3 |
| 34.1* | 2.629 | 15 |
| 36.2 | 2.481 | 12 |
| 37.9 | 2.374 | 15 |
| 43.2 | 2.094 | 4 |

*Impurity peak (c) The MgAPSO-11 compositions are generally characterized by the data of Table XI-B below:

TABLE XI-B

| 2θ | d, (Å) | Relative Intensity |
|---|---|---|
| 9.0–9.6 | 9.83–9.21 | vw–m |
| 20.8–21.2 | 4.27–4.19 | vs |
| 22.0–22.4 | 4.04–3.97 | vw–m |
| 22.4–22.8 | 3.97–3.90 | vw–vs |

TABLE XI-B-continued

| 2θ | d, (Å) | Relative Intensity |
|---|---|---|
| 22.8–23.1 | 3.90–3.85 | m |

(d) The MgAPSO-11 compositions for which x-ray powder diffraction data have been obtained to date have patterns which are characterized by the x-ray powder diffraction pattern shown in Table XII-B, below:

TABLE XII-B

| 2θ | d, (Å) | 100 × I/Io |
|---|---|---|
| 7.8–8.15 | 11.33–10.85 | sh-35 |
| 9.0–9.6 | 9.83–9.21 | 6–60 |
| 12.9–13.2 | 6.86–6.71 | sh-22 |
| 15.4–15.9 | 5.75–5.57 | sh-30 |
| 15.95–16.35 | 5.56–5.42 | sh-3 |
| 18.7–19.1 | 4.75–4.65 | 0–4 |
| 20.0–20.5 | 4.44–4.33 | sh-38 |
| 20.8–21.2 | 4.27–4.19 | 100 |
| 22.0–22.4 | 4.040–3.969 | sh-72 |
| 22.4–22.8 | 3.969–3.900 | sh-90 |
| 22.8–23.1 | 3.900–3.850 | 21–48 |
| 23.35 | 3.810 | 0–4 |
| 24.4–24.9 | 3.648–3.576 | 0–9 |
| 26.2–26.7 | 3.401–3.339 | 0–21 |
| 28.4–28.8 | 3.143–3.100 | sh-17 |
| 29.3–29.5 | 3.048–3.028 | 0–6 |
| 29.6–30.0 | 3.018–2.979 | 0–17 |
| 31.2–31.7 | 2.867–2.823 | 0–15 |
| 32.4–32.8 | 2.763–2.730 | 0–18 |
| 33.8–34.5 | 2.652–2.600 | 9–13 |
| 35.7 | 2.515 | 0–3 |
| 36.1–36.8 | 2.488–2.442 | 0–11 |
| 37.5–37.9 | 2.398–2.374 | 0–17 |
| 39.15–39.6 | 2.301–2.276 | 0–3 |
| 40.25–40.75 | 2.241–2.214 | 0–1 |
| 41.2–41.4 | 2.191–2.181 | 0–1 |
| 41.8–42.1 | 2.161–2.146 | 0–4 |
| 42.8–43.2 | 2.113–2.094 | 0–5 |
| 44.5–44.9 | 2.036–2.019 | 0–4 |
| 50.3–50.7 | 1.814–1.801 | 0–3 |
| 54.4–54.6 | 1.687–1.681 | 0–3 |

EXAMPLE 112B (a) MgAPSO-16, as prepared to in example 93B, was subjected to x-ray analysis. MgAPSO-16 was determined to have a characteristic x-ray powder diffraction pattern which contains the d-spacings set forth below:

| 2θ | d, (Å) | 100 × I/Io |
|---|---|---|
| 8.6** | 10.30 | 13 |
| 10.95** | 8.10 | 36 |
| 11.45 | 7.73 | 64 |
| 13.3** | 6.66 | 24 |
| 15.85** | 5.60 | 6 |
| 17.25** | 5.14 | 50 |
| 17.75** | 4.99 | 9 |
| 18.7 | 4.74 | 45 |
| 20.4** | 4.35 | 35 |
| 20.75** | 4.28 | 10 |
| 21.1** | 4.21 | 26 |
| 21.55** | 4.12 | sh |
| 21.85* | 4.07 | 100 |
| 23.05* | 3.858 | 26 |
| 26.3** | 3.391 | 5 |
| 26.75* | 3.332 | 25 |
| 28.45** | 3.135 | 17 |
| 28.65** | 3.116 | 18 |
| 29.0* | 3.079 | 17 |
| 29.9 | 2.987 | 20 |
| 32.0** | 2.796 | 30 |
| 32.85 | 2.727 | 3 |
| 34.6** | 2.592 | 6 |
| 34.85 | 2.573 | 4 |
| 35.65** | 2.519 | 12 |
| 37.9* | 2.373 | 8 |
| 39.95* | 2.256 | 5 |
| 42.0** | 2.152 | 4 |
| 42.9** | 2.108 | 4 |
| 44.3* | 2.044 | 4 |
| 48.55* | 1.876 | 10 |
| 49.35** | 1.846 | 5 |
| 51.4** | 1.778 | 5 |
| 52.2** | 1.752 | 2 |
| 52.5 | 1.743 | 2 |
| 55.0** | 1.670 | 5 |

*Peak may contain impurity
**Impurity peak (b) A portion of the as-synthesized MgAPSO-16 of part (a) was calcined in air at 600° C. for about 2 hours. The calcined product was characterized by the x-ray powder diffraction pattern below:

| 2θ | d, (Å) | 100 I/Io |
|---|---|---|
| 8.7** | 10.16 | 25 |
| 11.0** | 8.04 | 185 |
| 11.4 | 7.76 | sh |
| 13.6** | 6.51 | 200 |
| 17.5** | 5.07 | 50 |
| 18.7 | 4.75 | 10 |
| 21.2** | 4.23 | 45 |
| 22.2* | 4.004 | 100 |
| 22.8* | 3.900 | 15 |
| 23.7** | 3.754 | 30 |
| 25.1** | 3.548 | 15 |
| 26.4** | 3.376 | 15 |
| 27.3* | 3.267 | 40 |
| 28.7** | 3.110 | 65 |
| 29.0* | 3.079 | sh |
| 29.7 | 3.008 | 45 |
| 32.0** | 2.797 | 15 |
| 32.6** | 2.747 | 50 |
| 33.2 | 2.706 | sh |
| 34.6* | 2.592 | 10 |
| 35.6** | 2.522 | 5 |

*Peak may contain impurity
**Impurity peak (c) The MgAPSO-16 compositions are characterized by the data of Table XIII-B below:

TABLE XIII-B

| 2θ | d, (Å) | Relative Intensity |
|---|---|---|
| 11.4–11.5 | 7.76–7.69 | m |
| 18.7–18.8 | 4.75–4.72 | w–m |
| 21.85–22.2 | 4.07–4.00 | vs |
| 22.8–23.3 | 3.900–3.818 | w–m |
| 26.75–27.3 | 3.332–3.267 | w–m |
| 29.7–29.9 | 3.008–2.988 | w–m |

(d) The MgAPSO-16 compositions for which x-ray powder diffraction data have been obtained to date have patterns which are characterized by the x-ray powder diffraction pattern shown in Table XIV-B, below

TABLE XIV-B

| 2θ | d, (Å) | 100 × I/Io |
|---|---|---|
| 11.5–11.5 | 7.76–7.69 | sh–64 |
| 18.7–18.8 | 4.75–4.72 | 10–45 |
| 21.85–22.2 | 4.07–4.00 | 100 |
| 22.8–23.3 | 3.900–3.818 | 15–26 |
| 26.75–27.3 | 3.332–3.267 | 16–40 |
| 28.95–29.0 | 3.084–3.079 | sh–17 |
| 29.7–29.9 | 3.008–2.988 | 9–45 |

TABLE XIV-B-continued

| 2θ | d, (Å) | 100 × I/Io |
|---|---|---|
| 32.8–33.2 | 2.730–2.968 | sh–3 |
| 34.6–34.85 | 2.592–2.573 | 4–10 |
| 37.8–38.0 | 2.380–2.368 | 4–7 |
| 39.4–39.95 | 2.287–2.256 | 2–5 |
| 44.3–44.5 | 2.044–2.036 | 2–10 |
| 48.55–48.6 | 1.876–1.873 | 7–10 |
| 52.4–52.5 | 1.746–1.743 | 1–2 |

EXAMPLE 113B (a) MgAPSOP-20, as prepared in example 98B, was subjected to x-ray analysis. MgAPSO-20 was determined to have a characteristic x-ray powder diffraction pattern which contains the d-spacings set forth below:

| 2θ | d, (Å) | 100 × I/Io |
|---|---|---|
| 13.9 | 6.36 | 44 |
| 19.75 | 4.50 | 42 |
| 22.05 | 4.029 | 3 |
| 24.2 | 3.676 | 100 |
| 28.0 | 3.184 | 12 |
| 31.4 | 2.849 | 10 |
| 34.5 | 2.601 | 14 |
| 37.35 | 2.408 | 1 |
| 38.45* | 2.340 | 1 |
| 40.0 | 2.253 | 4 |
| 42.55 | 2.124 | 5 |
| 47.3 | 1.921 | 4 |
| 49.0* | 1.859 | 1 |
| 49.4* | 1.846 | 2 |
| 51.7 | 1.768 | 8 |

*impurity peak (b) A portion of the as-synthesized MgAPSO-20 of part (a) was calcined in air at 600° C. for about 1.5 hours. The calcined product was characterized by the x-ray powder diffraction pattern of below:

| 2θ | d, (Å) | 100 × I/Io |
|---|---|---|
| 14.15 | 7.27 | 100 |
| 20.05 | 4.43 | 20 |
| 22.45 | 3.964 | 4 |
| 24.6 | 3.616 | 54 |
| 28.5 | 3.132 | 15 |
| 32.0 | 2.799 | 10 |
| 35.0 | 2.564 | 10 |

(c) The MgAPSO-20 compositions are characterized by the data of Table XV-B below:

TABLE XV-B

| 2θ | d, (Å) | Relative Intensity |
|---|---|---|
| 13.8–14.2 | 6.42–6.23 | m–vs |
| 19.6–20.15 | 6.53–4.41 | m |
| 24.1–24.7 | 3.695–3.603 | m–vs |
| 27.9–28.6 | 3.198–3.121 | w |
| 31.3–32.05 | 2.861–2.791 | w |
| 34.35–35.0 | 2.610–2.601 | w |

(d) The MgAPSO-20 compositions for which x-ray powder diffraction data have been obtained to date have patterns which are characterized by the x-ray powder diffraction pattern shown in Table XVI-B, below:

TABLE XVI-B

| 2θ | d, (Å) | 100 × I/Io |
|---|---|---|
| 13.8–14.2 | 6.42–6.23 | 42–100 |
| 19.6–20.15 | 4.55–4.41 | 22–43 |

TABLE XVI-B-continued

| 2θ | d, (Å) | 100 × I/Io |
|---|---|---|
| 21.95–22.45 | 4.050–3.964 | 3–7 |
| 24.1–24.7 | 3.695–3.603 | 56–100 |
| 27.9–28.6 | 3.198–3.121 | 11–15 |
| 31.3–32.05 | 2.861–2.791 | 10–12 |
| 34.35–35.0 | 2.610–2.601 | 10–16 |
| 37.2–37.35 | 2.417–2.408 | 1–2 |
| 39.9–40.0 | 2.260–2.253 | 3–4 |
| 42.4–42.55 | 2.130–2.124 | 5 |
| 47.15–47.3 | 1.927–1.921 | 4–5 |
| 51.55–51.7 | 1.772–1.768 | 8 |

EXAMPLE 114B (a) MgAPSO-34, as prepared in example 68B, was subjected to x-ray analysis. MgAPSO-34 was determined to have a characteristic x-ray powder diffraction pattern which contains the d-spacings set forth below:

| 2θ | d, (Å) | 100 × I/Io |
|---|---|---|
| 9.5 | 9.32 | 100 |
| 12.8 | 6.91 | 15 |
| 14.1 | 6.30 | 15 |
| 16.0 | 5.55 | 52 |
| 17.95 | 4.94 | 21 |
| 20.5 | 4.32 | 92 |
| 22.2 | 4.002 | 4 |
| 23.0 | 3.864 | 5 |
| 25.15 | 3.540 | 23 |
| 25.8 | 3.455 | 18 |
| 27.5 | 3.243 | 3 |
| 28.3 | 3.151 | 4 |
| 29.5 | 3.029 | 4 |
| 30.5 | 2.932 | 33 |
| 31.2 | 2.866 | 22 |
| 31.6* | 2.833 | 5 |
| 32.25 | 2.775 | 3 |
| 34.35 | 2.611 | 7 |
| 38.6 | 2.332 | 2 |
| 36.2 | 2.480 | 8 |
| 39.6 | 2.277 | 4 |
| 43.1 | 2.100 | 3 |
| 47.5 | 1.915 | 4 |
| 48.9 | 1.862 | 6 |
| 50.9 | 6.795 | 4 |
| 53.0 | 1.727 | 4 |
| 54.5 | 1.684 | 2 |
| 55.75 | 1.649 | 4 |

*impurity peak (b) A portion of the as-synthesized MgAPSO-34 of part (a) was calcined in air at 550° C. for about 2 hours. The calcined product was characterized by the x-ray powder diffraction pattern below:

| 2θ | d, (Å) | 100 × I/Io |
|---|---|---|
| 9.7 | 9.12 | 100 |
| 13.1 | 6.76 | 22 |
| 14.2 | 6.24 | 1 |
| 16.3 | 5.44 | 15 |
| 18.1 | 4.90 | 10 |
| 19.3 | 4.60 | 3 |
| 20.95 | 4.24 | 31 |
| 21.6* | 4.11 | sh |
| 22.4 | 3.969 | 3 |
| 23.35 | 3.809 | 3 |
| 25.35 | 3.513 | 11 |
| 26.3 | 3.389 | 10 |
| 28.5 | 3.132 | 4 |
| 30.0 | 2.979 | sh |
| 31.0 | 2.885 | 23 |
| 33.8 | 2.652 | 2 |
| 35.0 | 2.564 | 3 |
| 36.6 | 2.455 | 1 |

-continued

| 2θ | d, (Å) | 100 × I/Io |
|---|---|---|
| 43.7 | 2.071 | 1 |
| 49.4 | 1.845 | 2 |
| 51.3 | 1.781 | 2 |
| 52.2 | 1.752 | 1 |
| 53.1 | 1.725 | 1 |
| 54.0 | 1.698 | 2 |

*impurity peak (c) The MgAPSO-34 compositions are characterized by the data of Table XVII-B below:

TABLE XVII-B

| 2θ | d, (Å) | Relative Intensity |
|---|---|---|
| 9.3–9.7 | 9.51–9.12 | vs |
| 15.8–16.3 | 5.61–5.44 | w–m |
| 20.25–21.0 | 4.39–4.23 | m–vs |
| 25.7–26.3 | 3.466–3.389 | vw–m |
| 30.0–30.8 | 2.979–2.903 | vw–m |
| 30.9–31.4 | 2.894–2.849 | w–m |

(d) The MgAPSO-34 compositions for which x-ray powder diffraction data have been obtained to date have patterns which are characterized by the x-ray powder diffraction pattern shown in Table XVIII-B below.

TABLE VIII-B

| 2θ | d, (Å) | 100 × I/Io |
|---|---|---|
| 9.3–9.7 | 9.51–9.12 | 99–100 |
| 12.6–13.1 | 7.03–6.76 | 11–25 |
| 13.8–14.3 | 6.42–6.19 | 0–24 |
| 15.8–16.3 | 5.61–5.44 | 13–56 |
| 17.8–18.2 | 4.98–4.87 | 5–28 |
| 19.1–19.4 | 4.65–4.58 | 0–3 |
| 20.25–21.0 | 4.39–4.23 | 22–100 |
| 22.2–22.5 | 4.004–3.952 | 0–6 |
| 22.8–23.4 | 3.900–3.802 | 0–6 |
| 24.9–25.4 | 3.576–3.507 | 6–27 |
| 25.7–26.3 | 3.466–3.389 | 6–29 |
| 27.4–28.0 | 3.255–3.187 | 0–4 |
| 28.2–28.8 | 3.164–3.100 | 0–4 |
| 29.0–29.6 | 3.079–3.018 | 0–6 |
| 30.0–30.8 | 2.979–2.903 | 0–34 |
| 30.9–31.4 | 2.894–2.849 | 16–30 |
| 32.2–32.4 | 2.780–2.763 | 0–4 |
| 33.8–34.5 | 2.401–2.600 | 0–15 |
| 34.6–35.0 | 2.592–2.564 | 0–4 |
| 36.0–36.6 | 2.495–2.456 | 0–4 |
| 38.4–39.0 | 2.344–2.309 | 0–2 |
| 43.0–43.7 | 2.103–2.071 | 0–3 |
| 44.6–45.0 | 2.032–2.015 | 0–1 |
| 47.2–47.6 | 1.926–1.910 | 0–4 |
| 48.3–49.4 | 1.884–1.845 | 0–6 |
| 50.2 | 1.817 | 0–2 |
| 50.7–51.4 | 1.801–1.778 | 0–4 |
| 51.3–51.5 | 1.781–1.774 | 0–2 |
| 52.9–53.1 | 1.731–1.725 | 0–4 |
| 54.1–54.6 | 1.695–1.681 | 0–4 |
| 55.5–55.9 | 1.656–1.645 | 0–4 |

EXAMPLE 115B (a) MgAPSO-35, as prepared in example 85B, was subjected to x-ray analysis. MgAPSO-35 was determined to have a characteristic x-ray powder diffraction pattern which contains the d-spacings set forth below:

| 2θ | d, (Å) | 100 × I/Io |
|---|---|---|
| 8.6 | 10.28 | 11 |
| 10.9 | 8.12 | 44 |
| 11.4** | 7.76 | 2 |
| 13.4 | 6.61 | 20 |
| 15.9 | 5.57 | 9 |
| 17.3 | 5.13 | 80 |
| 17.7 | 5.01 | sh |
| 18.7** | 4.75 | 1 |
| 20.9 | 4.25 | 54 |
| 21.9* | 4.06 | 100 |
| 22.7** | 3.917 | sh |
| 23.25 | 3.826 | 27 |
| 24.9 | 3.576 | 6 |
| 25.8 | 3.453 | 1 |
| 26.85* | 3.320 | 16 |
| 27.1 | 3.290 | sh |
| 28.3 | 3.153 | 44 |
| 29.0 | 3.079 | 10 |
| 31.45* | 2.844 | sh |
| 32.1 | 2.788 | 37 |
| 32.4* | 2.763 | sh |
| 34.3* | 2.614 | 7 |
| 35.2** | 2.550 | 1 |
| 35.8 | 2.508 | 2 |
| 37.6* | 2.392 | 2 |
| 39.4 | 2.287 | 1 |
| 40.9 | 2.206 | 1 |
| 41.8 | 2.161 | 4 |
| 42.5 | 2.127 | 5 |
| 44.5* | 2.036 | 4 |
| 47.5 | 1.914 | 2 |
| 48.3* | 1.884 | 4 |
| 48.8 | 1.866 | 4 |
| 49.4 | 1.845 | 5 |
| 51.0 | 1.791 | 7 |
| 55.2 | 1.664 | 4 |

*peak may contain impurity
**impurity (c) A portion of the as-synthesized MgAPSO-35 of part (a) was calcined in air at 500° C. for about 68 hours. The calcined product was characterized by the x-ray powder diffraction pattern below:

| 2θ | d, (Å) | 100 × I/Io |
|---|---|---|
| 8.5 | 10.40 | 21 |
| 10.8 | 8.19 | 100 |
| 11.3* | 7.83 | sh |
| 13.3 | 6.66 | 76 |
| 15.8 | 5.61 | 3 |
| 17.2 | 5.16 | 31 |
| 20.15* | 4.41 | 110 |
| 20.8 | 4.27 | sh |
| 21.25* | 4.18 | 97 |
| 21.85 | 4.07 | 40 |
| 22.8* | 3.900 | 43 |
| 23.1 | 3.850 | sh |
| 24.2* | 3.678 | 6 |
| 24.8 | 3.590 | 6 |
| 26.2* | 3.401 | 45 |
| 27.0 | 3.302 | 10 |
| 27.3 | 3.267 | 10 |
| 28.3 | 3.153 | 24 |
| 29.5 | 3.028 | 19 |
| 30.9* | 2.894 | 5 |
| 31.4 | 2.849 | 7 |
| 32.2 | 2.780 | 19 |
| 32.7 | 2.739 | sh |
| 33.8* | 2.652 | 4 |
| 34.4 | 2.607 | 5 |
| 35.3* | 2.543 | 21 |
| 36.0 | 2.495 | 4 |
| 37.2* | 2.417 | 4 |
| 38.4 | 2.344 | 6 |
| 39.8 | 2.265 | 4 |
| 40.9 | 2.206 | 2 |
| 41.9 | 2.156 | 5 |
| 42.6 | 2.122 | 6 |
| 43.5* | 2.085 | 3 |
| 44.8 | 2.023 | 2 |
| 45.1 | 2.010 | 4 |

-continued

| 2θ | d, (Å) | 100 × I/Io |
|---|---|---|
| 48.4 | 1.881 | 2 |
| 49.3 | 1.848 | 2 |
| 51.3 | 1.781 | 3 |
| 55.5 | 1.656 | 5 |

*impurity peak (c) The MgAPSO-35 compositions are generally characterized by the data of Table XIXB below:

TABLE XIXB

| 2θ | d, (Å) | Relative Intensity |
|---|---|---|
| 10.6–11.1 | 8.35–7.97 | m–vs |
| 13.1–13.7 | 6.76–6.46 | w–vs |
| 17.0–17.6 | 5.22–5.04 | m–s |
| 20.6–21.2 | 4.31–4.19 | vw–m |
| 21.6–22.2 | 4.11–4.00 | m–vs |
| 28.1–28.8 | 3.175–3.100 | m |

(d) The MgAPSO-35 compositions for which x-ray powder diffraction data have been obtained to date have patterns which are characterized by the x-ray powder diffraction pattern shown in Table XX-B, below:

TABLE XX-B

| 2θ | d, (Å) | 100 × I/Io |
|---|---|---|
| 8.3–8.8 | 10.65–10.05 | 10–21 |
| 10.6–11.1 | 8.35–7.97 | 36–100 |
| 13.1–13.7 | 6.76–6.46 | 17–100 |
| 15.7–16.0 | 5.64–5.54 | 0–9 |
| 17.0–17.6 | 5.22–5.04 | 25–80 |
| 17.7–17.8 | 5.01–4.98 | 0-sh |
| 20.6–21.2 | 4.31–4.19 | sh-54 |
| 21.6–22.2 | 4.11–4.00 | 40–100 |
| 23.0–23.7 | 3.867–3.754 | sh-27 |
| 24.6–25.2 | 3.619–3.534 | 5–8 |
| 25.8–26.4 | 3.453–3.376 | 0–8 |
| 26.6–27.3 | 3.351–3.267 | 10–16 |
| 27.1 | 3.290 | sh-10 |
| 28.1–28.8 | 3.175–3.100 | 24–44 |
| 28.9–29.7 | 3.089–3.008 | 5–23 |
| 31.45–31.5 | 2.844–2.840 | sh-7 |
| 31.9–32.4 | 2.805–2.763 | 19–37 |
| 32.4–32.7 | 2.763–2.739 | sh |
| 34.1–34.7 | 2.629–2.585 | 5–9 |
| 35.6–36.1 | 2.522–2.488 | 0–4 |
| 37.1–38.0 | 2.404–2.368 | 0–6 |
| 39.4–39.9 | 2.287–2.259 | 0–4 |
| 40.8–40.9 | 2.212–2.206 | 0–1 |
| 41.7–42.2 | 2.166–2.141 | 0–5 |
| 42.2–42.7 | 2.132–2.118 | 0–6 |
| 44.5–44.8 | 2.036–2.023 | 0–7 |
| 45.0–45.1 | 2.014–2.010 | 0–1 |
| 47.4–47.7 | 1.914–1.907 | 0–2 |
| 48.2–48.6 | 1.888–1.873 | 0–4 |
| 48.7–49.0 | 1.870–1.859 | 0–4 |
| 49.3–49.7 | 1.848–1.834 | 0–5 |
| 50.8–51.5 | 1.797–1.774 | 0–7 |
| 55.2–55.6 | 1.664–1.653 | 0–4 |

EXAMPLE 116B (a) The MgAPSO-36, as prepared in example 5B, was subjected to x-ray analysis. MgAPSO-36 was determined to have a characteristic x-ray powder diffraction pattern which contains the d-spacings set forth below:

| 2θ | d, (Å) | 100 × I/Io |
|---|---|---|
| 7.4** | 11.95 | sh |
| 7.9 | 11.19 | 100 |
| 8.1 | 10.92 | sh |
| 12.8** | 6.92 | 3 |
| 13.45 | 6.58 | 6 |
| 14.75** | 6.01 | 4 |
| 15.7 | 5.64 | (sh) |
| 16.3 | 5.44 | 31 |
| 18.9 | 4.70 | 41 |
| 19.5** | 4.55 | 7 |
| 20.7* | 4.29 | 49 |
| 21.55 | 4.12 | (sh) |
| 21.8 | 4.077 | (sh) |
| 22.35* | 3.978 | 42 |
| 22.8 | 3.900 | (sh) |
| 23.8 | 3.739 | 9 |
| 25.7** | 3.466 | 6 |
| 27.1 | 3.290 | 14 |
| 28.2 | 3.164 | 10 |
| 28.9* | 3.089 | 12 |
| 30.1 | 2.969 | 7 |
| 31.8 | 2.814 | 11 |
| 33.0* | 2.714 | 3 |
| 34.6* | 2.592 | 16 |
| 35.7 | 2.515 | 4 |
| 37.6* | 2.349 | 3 |
| 39.3 | 2.293 | 1 |
| 40.1 | 2.249 | 3 |
| 41.3 | 2.186 | 4 |
| 42.0** | 2.151 | 2 |
| 43.0 | 2.103 | 2 |
| 44.0 | 2.058 | 2 |
| 45.3 | 2.002 | 1 |
| 46.6 | 1.949 | 1 |
| 47.3 | 1.922 | 3 |
| 48.8 | 1.867 | 1 |
| 51.1 | 1.787 | 2 |
| 53.7 | 1.707 | 2 |
| 55.4 | 1.659 | 3 |

*peak may contain impurity
**impurity peak (b) A portion of the as-synthesized MgAPSO-36 of part (a) was calcined in air at 500° C. for about 2 hours and at 600° C. for an additional 2 hours. The calcined product was characterized by the x-ray powder diffraction pattern below:

| 2θ | d, (Å) | 100 × I/Io |
|---|---|---|
| 7.4** | 11.95 | sh |
| 7.9 | 11.19 | 100 |
| 8.2 | 10.78 | sh |
| 12.8** | 6.92 | 3 |
| 13.45 | 6.58 | 8 |
| 14.9** | 5.95 | 2 |
| 15.9 | 5.57 | sh |
| 16.5 | 5.37 | 24 |
| 19.3 | 4.60 | 38 |
| 19.75** | 4.50 | sh |
| 20.8 | 4.27 | 25 |
| 21.2** | 4.19 | sh |
| 21.8 | 4.08 | sh |
| 22.35 | 3.978 | 25 |
| 22.6** | 3.934 | sh |
| 23.0 | 3.867 | sh |
| 23.9 | 3.723 | 5 |
| 24.9** | 3.576 | 1 |
| 25.8** | 3.453 | 4 |
| 27.2 | 3.278 | 16 |
| 28.35 | 3.148 | 7 |
| 29.1* | 3.069 | 10 |
| 29.9 | 2.988 | 3 |
| 30.4* | 2.940 | 5 |
| 32.0 | 2.797 | 8 |
| 33.2 | 2.698 | 1 |
| 35.0* | 2.564 | 7 |
| 36.0 | 2.495 | 3 |
| 37.7* | 2.386 | 2 |
| 39.5 | 2.281 | 1 |
| 40.3 | 2.238 | 2 |
| 41.3 | 2.186 | 4 |

| 2θ | d, (Å) | 100 × I/Io |
|---|---|---|
| 42.0** | 2.151 | 2 |
| 43.5 | 2.080 | 1 |
| 44.3 | 2.045 | 1 |
| 45.4 | 1.998 | 1 |
| 47.6 | 1.910 | 3 |
| 51.2 | 1.784 | 1 |
| 55.5 | 1.656 | 1 |

*peak may contain impurity
**impurity peak (c) The MgAPSO-36 compositions are generally characterized by the data of Table XXI-B below:

TABLE XXI-B

| 2θ | d, (Å) | Relative Intensity |
|---|---|---|
| 7.8–8.0 | 11.33–11.05 | vs |
| 16.3–16.5 | 5.44–5.37 | m |
| 18.9–19.3 | 4.70–4.60 | m |
| 20.7–20.8 | 4.29–4.27 | m |
| 22.35 | 3.98 | m |

(d) The MgAPSO-36 compositions for which x-ray powder diffraction data have been obtained to date have patterns which are characterized by the x-ray powder diffraction pattern shown in Table XXII-B below:

TABLE XXII-B

| 2θ | d, (Å) | 100 × I/Io |
|---|---|---|
| 7.8–8.0 | 11.33–11.05 | 100 |
| 8.1–8.2 | 10.92–10.78 | 0-sh |
| 13.45 | 6.58 | 6–8 |
| 15.7–15.9 | 5.64–5.57 | sh |
| 16.3–16.5 | 5.44–5.37 | 24–31 |
| 18.9–19.3 | 4.70–4.60 | 38–41 |
| 20.7–20.8 | 4.29–4.27 | 25–49 |
| 21.0 | 4.23 | 0-sh |
| 21.55–21.8 | 4.12–4.08 | sh |
| 21.8–21.9 | 4.077–4.058 | sh |
| 22.35 | 3.978 | 25–42 |
| 22.8–23.0 | 3.900–3.867 | (sh) |
| 23.8–23.9 | 3.739–3.723 | 5–9 |
| 27.1–27.2 | 3.290–3.278 | 14–16 |
| 28.1–28.35 | 3.176–3.148 | 7–10 |
| 28.8–29.1 | 3.100–3.069 | 10–12 |
| 29.9–30.1 | 2.988–2.969 | 3–7 |
| 31.8–32.0 | 2.814–2.797 | 8–11 |
| 33.0–33.2 | 2.714–2.698 | 1–3 |
| 34.6–35.0 | 2.592–2.564 | 7–16 |
| 35.7–36.0 | 2.515–2.495 | 3–4 |
| 37.6–37.7 | 2.392–2.386 | 2–3 |
| 39.3–39.5 | 2.293–2.281 | 1 |
| 40.1–40.3 | 2.249–2.238 | 2–3 |
| 41.3 | 2.186 | 4 |
| 43.0–43.5 | 2.103–2.080 | 1–2 |
| 43.95–44.3 | 2.060–2.045 | 1–2 |
| 45.2–45.4 | 2.006–1.998 | 1 |
| 46.6 | 1.949 | 0–1 |
| 47.3–47.6 | 1.922–1.910 | 3 |
| 48.8 | 1.867 | 0–1 |
| 51.1–51.2 | 1.787–1.784 | 1–2 |
| 53.7 | 1.707 | 0–2 |
| 55.3–55.5 | 1.661–1.656 | 1–3 |

EXAMPLE 117B (a) MgAPSO-39, as prepared in example 55B, was subjected to x-ray analysis. MgAPSO-39 was determined to have a characteristic x-ray powder diffraction pattern which contains at least the d-spacings set forth below:

| 2θ | d, (Å) | 100 × I/Io |
|---|---|---|
| 8.1** | 10.92 | 6 |
| 8.5** | 10.40 | 15 |
| 8.9** | 9.98 | 1 |
| 9.45 | 9.34 | 30 |
| 12.4** | 7.13 | 2 |
| 13.4* | 6.60 | 48 |
| 14.2** | 6.22 | 2 |
| 14.4** | 6.15 | 2 |
| 14.6** | 6.06 | 2 |
| 15.65** | 5.66 | 4 |
| 18.15 | 4.89 | 33 |
| 20.3** | 4.38 | 17 |
| 21.3* | 4.18 | 70 |
| 22.1* | 4.027 | 13 |
| 22.6 | 3.929 | 100 |
| 23.15** | 3.844 | 10 |
| 26.4** | 3.375 | 3 |
| 27.0 | 3.301 | 4 |
| 27.8** | 3.208 | 3 |
| 28.0* | 3.191 | 4 |
| 28.7* | 3.113 | 9 |
| 29.7 | 3.007 | 13 |
| 30.3 | 2.953 | 25 |
| 31.7** | 2.823 | 5 |
| 32.7 | 2.736 | 12 |
| 34.1* | 2.632 | 7 |
| 35.1** | 2.555 | 2 |
| 36.7* | 2.448 | 2 |
| 38.1* | 2.361 | 9 |
| 39.25** | 2.295 | 2 |
| 41.0 | 2.200 | 2 |
| 43.3 | 2.089 | 2 |
| 43.8 | 2.067 | 1 |
| 45.0 | 2.015 | 1 |
| 46.2* | 1.966 | 2 |
| 47.2* | 1.926 | 1 |
| 48.8 | 1.867 | 4 |
| 49.4 | 1.845 | 3 |
| 51.45* | 1.776 | 4 |
| 52.3 | 1.749 | 2 |
| 54.55 | 1.683 | 2 |

*peak may contain impurity
**impurity peak (b) The MgAPSO-39 compositions are generally characterized by the data of Table XXIII-B below:

TABLE XXIII-B

| 2θ | d, (Å) | Relative Intensity |
|---|---|---|
| 9.2–9.6 | 9.61–9.21 | m |
| 13.1–13.5 | 6.76–6.56 | m |
| 17.8–18.3 | 4.98–4.85 | m |
| 20.8–21.3 | 4.27–4.17 | m–vs |
| 22.2–22.8 | 4.00–3.90 | vs |
| 30.0–30.3 | 2.979–2.950 | w–m |

(c) The MgAPSO-39 compositions for which x-ray powder diffraction data have been obtained to date have patterns which are characterized by the x-ray powder diffraction pattern shown in Table XXIV-B below.

TABLE XXIV-B

| 2θ | d, (Å) | 100 × I/Io |
|---|---|---|
| 9.2–9.6 | 9.61–9.21 | 20–53 |
| 13.1–13.5 | 6.76–6.56 | 25–53 |
| 17.8–18.3 | 4.98–4.85 | 23–34 |
| 20.8–21.3 | 4.27–4.17 | 70–100 |
| 22.2–22.8 | 4.004–3.900 | 97–100 |
| 26.8–27.05 | 3.326–3.296 | 3–4 |
| 28.0–28.2 | 3.191–3.175 | 0–4 |
| 28.6–28.8 | 3.121–3.100 | sh-17 |
| 29.4–29.8 | 3.038–2.998 | 13–20 |
| 30.0–30.3 | 2.979–2.950 | 17–29 |
| 32.4–32.8 | 2.763–2.730 | 10–16 |
| 33.9–34.2 | 2.644–2.622 | sh-11 |

TABLE XXIV-B-continued

| 2θ | d, (Å) | 100 × I/Io |
|---|---|---|
| 36.7–36.85 | 2.448–2.439 | 0–2 |
| 37.8–38.1 | 2.380–2.362 | 5–9 |
| 40.7–41.0 | 2.217–2.201 | 0–5 |
| 43.0–43.4 | 2.103–2.085 | 0–2 |
| 45.0 | 2.014 | 0–1 |
| 46.2–46.3 | 1.966–1.961 | 0–2 |
| 47.2–47.3 | 1.926–1.922 | 0–1 |
| 48.5–48.85 | 1.877–1.864 | 4–5 |
| 49.0–49.5 | 1.859–1.841 | 0–3 |
| 51.0–51.5 | 1.791–1.778 | 3–5 |
| 52.1–52.4 | 1.755–1.746 | 0–4 |
| 54.2–54.6 | 1.692–1.681 | 0–2 |

EXAMPLE 118B (a) MgAPSO-43, as prepared in example 92B, was subjected to x-ray analysis. MgAPSO-43 was determined to have a characteristic x-ray powder diffraction pattern which contains the d-spacings set forth below:

| 2θ | d, (Å) | 100 × I/Io |
|---|---|---|
| 6.5** | 13.63 | 8 |
| 7.6** | 11.66 | 35 |
| 12.3 | 7.20 | 100 |
| 13.05** | 6.77 | 4 |
| 14.45** | 6.14 | 4 |
| 15.15* | 5.85 | 2 |
| 16.5** | 5.37 | 3 |
| 17.3 | 5.13 | 12 |
| 19.7* | 4.51 | 3 |
| 20.35** | 4.37 | 2 |
| 21.45* | 4.14 | 49 |
| 22.65** | 3.928 | 6 |
| 23.9** | 3.726 | 3 |
| 24.0 | 3.701 | 3 |
| 24.35 | 3.653 | 2 |
| 26.7* | 3.336 | 7 |
| 27.6 | 3.232 | 39 |
| 28.05* | 3.182 | 18 |
| 28.55* | 3.126 | 5 |
| 29.65** | 2.013 | 1 |
| 30.95** | 2.889 | 2 |
| 32.8** | 2.729 | 7 |
| 33.05 | 2.710 | 8 |
| 35.8* | 2.510 | 3 |
| 38.3** | 2.350 | 2 |
| 39.55** | 2.278 | 1 |
| 43.75** | 2.070 | 2 |
| 44.05** | 2.055 | 1 |
| 45.4 | 1.997 | 3 |
| 45.65** | 1.998 | 3 |
| 49.0** | 1.859 | 3 |
| 51.1* | 1.788 | 4 |
| 52.0* | 1.759 | 1 |
| 53.0 | 1.728 | 3 |
| 53.7 | 1.707 | 2 |

*peak may contain impurity
**impurity peak (b) A portion of the as-synthesized MgAPSO-43 of part (a) was calcined in air at 500° C. for about 1 hour and at 600° C. for about 1.5 hours. The calcined product was characterized by the x-ray powder diffraction pattern below:

| 2θ | d, (Å) | 100 × I/Io |
|---|---|---|
| 6.95* | 12.73 | 30 |
| 8.15* | 10.87 | 47 |
| 12.95 | 6.83 | 35 |
| 17.4 | 5.10 | 10 |
| 21.45 | 4.14 | 100 |
| 23.2* | 3.832 | 44 |
| 28.15 | 3.167 | 25 |

*impurity peak (c) The MgAPSO-43 compositions are generally characterized by the data of Table XXV-B below:

TABLE XXV-B

| 2θ | d, (Å) | Relative Intensity |
|---|---|---|
| 12.3–12.95 | 7.20–6.83 | m–vs |
| 17.3–17.45 | 5.13–5.09 | w |
| 21.45–21.6 | 4.15–4.12 | m–vs |
| 27.6–27.75 | 3.232–3.215 | m |
| 33.05–33.2 | 2.710–2.699 | w |

(d) The MgAPSO-43 compositions for which x-ray powder diffraction data have been obtained to date have patterns which are characterized by the x-ray powder diffraction pattern shown in Table XXVI-B below:

TABLE XXVI-B

| 2θ | d, (Å) | 100 × I/Io |
|---|---|---|
| 12.3–12.95 | 7.20–6.83 | 35–100 |
| 15.15–15.5 | 5.85–5.37 | 2–4 |
| 17.3–17.45 | 5.13–5.09 | 12 |
| 19.7–19.85 | 4.51–4.47 | 3–5 |
| 21.45–21.6 | 4.15–4.12 | 49–100 |
| 24.35–24.5 | 3.653–3.635 | 2 |
| 26.7–26.85 | 3.336–3.319 | 7–9 |
| 27.6–27.75 | 3.232–3.215 | 39–50 |
| 28.05–28.2 | 3.182–3.165 | 18–25 |
| 28.55–28.75 | 3.126–3.107 | 5–6 |
| 33.05–33.2 | 2.710–2.699 | 8–12 |
| 35.8–35.9 | 2.510–2.502 | 3–4 |
| 45.4–45.55 | 1.997–1.991 | 3 |
| 51.1–51.2 | 1.788–1.785 | 4 |
| 52.0–52.25 | 1.759–1.750 | 1–2 |
| 53.0–53.1 | 1.728–1.725 | 3–4 |
| 53.7–53.95 | 1.707–1.700 | 2 |

EXAMPLE 119B (c) MgAPSO-44, as prepared in example 88B, was subjected to X-ray analysis. MgAPSO-44 was determined to have a characteristic X-ray powder diffraction pattern which contains the d-spacings set forth below:

| 2θ | d, (Å) | 100 × I/Io |
|---|---|---|
| 6.7** | 13.19 | 64 |
| 7.3** | 12.11 | 12 |
| 9.35 | 9.46 | 100 |
| 12.95* | 6.84 | 16 |
| 13.7 | 6.46 | 2 |
| 14.5 | 6.11 | 5 |
| 14.8** | 5.99 | 3 |
| 16.1 | 5.54 | 35 |
| 17.3 | 5.13 | 7 |
| 18.9 | 4.70 | 8 |
| 19.6** | 4.53 | 9 |
| 20.7 | 4.29 | 100 |
| 20.9** | 4.25 | sh |
| 21.7 | 4.10 | 13 |
| 22.3** | 3.986 | 28 |
| 22.5 | 3.952 | sh |
| 23.0 | 3.867 | 7 |
| 24.3 | 3.663 | 37 |
| 25.8** | 3.453 | sh |
| 26.1 | 3.414 | 7 |
| 27.5 | 3.243 | 10 |
| 28.8** | 3.998 | 4 |
| 29.6 | 3.018 | sh |
| 29.9* | 2.988 | 15 |

-continued

| 2θ | d, (Å) | 100 × I/Io |
|---|---|---|
| 30.7 | 2.912 | 48 |
| 31.4 | 2.849 | 1 |
| 32.4 | 2.763 | 4 |
| 32.7 | 2.739 | 3 |
| 33.4** | 2.683 | 1 |
| 34.3** | 2.614 | 3 |
| 34.8 | 2.578 | 4 |
| 35.4 | 2.536 | 6 |
| 36.8 | 2.442 | 1 |
| 37.5** | 2.398 | 3 |
| 38.4 | 2.344 | 1 |
| 39.1 | 2.304 | 1 |
| 39.8 | 2.265 | 1 |
| 42.0* | 2.146 | 6 |
| 43.4 | 2.085 | 2 |
| 46.5 | 1.957 | 1 |
| 47.1 | 1.929 | 3 |
| 48.0* | 1.895 | 8 |
| 48.5 | 1.877 | 5 |
| 50.1 | 1.821 | 10 |
| 51.8 | 1.768 | 1 |
| 53.6 | 1.710 | 10 |
| 54.6 | 1.681 | 1 |
| 55.3** | 1.661 | 1 |

*peak may contain impurity
**impurity peak (b) A portion of the as-synthesized MgAPSO-44 of part (a) was calcined in air for 2.5 hours at 500° C. and then for 0.25 hour at 600° C. The calcined product was characterized by the x-ray powder diffraction pattern below:

| 2θ | d, (Å) | 100 × I/Io |
|---|---|---|
| 2.9** | 30.46 | 8 |
| 7.35** | 12.03 | 64 |
| 8.9** | 9.94 | sh |
| 9.1** | 9.72 | sh |
| 9.5 | 9.31 | 100 |
| 12.8* | 6.92 | 35 |
| 13.9 | 6.37 | 4 |
| 14.7** | 6.07 | 3 |
| 16.0 | 5.54 | 20 |
| 17.8 | 4.98 | 53 |
| 19.6** | 4.53 | 14 |
| 20.6 | 4.31 | 82 |
| 21.1** | 4.21 | 16 |
| 22.3* | 3.986 | sh-28 |
| 23.0 | 3.867 | 7-8 |
| 25.0* | 3.562 | 18 |
| 25.8* | 3.453 | 17 |
| 27.6 | 3.232 | 1 |
| 28.2 | 3.164 | 3 |
| 28.9** | 3.089 | 4 |
| 29.8 | 2.998 | 4 |
| 30.5* | 2.931 | 24 |
| 31.0 | 2.885 | 16 |
| 31.6 | 2.831 | sh |
| 32.2 | 2.780 | 1 |
| 33.2 | 2.698 | sh |
| 33.5** | 2.675 | 3 |
| 34.3** | 2.614 | 8 |
| 34.8 | 2.578 | 1 |
| 36.0 | 2.494 | 3 |
| 37.7** | 2.386 | 2 |
| 38.5 | 2.338 | 1 |
| 39.0 | 2.309 | 1 |
| 39.6 | 2.276 | 3 |
| 42.0* | 2.151 | 1 |
| 42.9** | 2.108 | 2 |
| 43.3 | 2.090 | 1 |
| 47.5* | 1.918 | 4 |
| 48.8 | 1.866 | 3 |
| 50.8 | 1.797 | 4 |
| 51.6 | 1.771 | 1 |
| 53.0 | 1.728 | 4 |
| 54.3** | 1.689 | 1 |

-continued

| 2θ | d, (Å) | 100 × I/Io |
|---|---|---|
| 55.6 | 1.656 | 1 |

*peak may contain impurity
**impurity peak (c) The MgAPSO-44 compositions are generally characterized by the data of Table XXVII-B below:

TABLE XXVII-B

| 2θ | d, (Å) | 100 × I/Io |
|---|---|---|
| 9.2-9.45 | 9.61-9.37 | vs |
| 15.9-16.1 | 5.57-5.50 | m |
| 17.2-18.0 | 5.16-4.93 | vw-m |
| 20.5-20.75 | 4.33-4.28 | m-vs |
| 24.3-25.0 | 3.663-3.562 | w-m |
| 30.5-31.0 | 2.931-2.885 | w-m |

(d) The MgAPSO-44 compositions for which x-ray powder diffraction data have been obtained to date have patterns which are characterized by the x-ray powder diffraction shown in Table XXVIII-B below:

TABLE XXVIII-B

| 2θ | d, (Å) | 100 × I/Io |
|---|---|---|
| 9.2-9.45 | 9.61-9.37 | 100 |
| 12.8-13.0* | 6.92-6.81 | 11-35 |
| 13.6-14.0 | 6.51-6.33 | 2-4 |
| 14.5-14.6 | 6.11-6.07 | 0-5 |
| 15.9-16.1 | 5.57-5.50 | 20-36 |
| 17.2-18.0 | 5.16-4.93 | 7 |
| 18.8-19.0 | 4.72-4.67 | 7-53 |
| 20.5-20.75 | 4.33-4.28 | 58-100 |
| 21.7-21.8 | 4.10-4.08 | 0-18 |
| 22.3-22.6 | 3.986-3.934 | sh |
| 23.0-23.3 | 3.867-3.817 | 8 |
| 24.3-25.0* | 3.663-3.562 | 17-58 |
| 25.8-26.15* | 3.453-3.406 | 10-18 |
| 27.5-27.8 | 3.243-3.209 | 1-12 |
| 28.2 | 3.175 | 0-3 |
| 29.6-29.8 | 3.018-2.998 | 0-sh |
| 29.7-30.5* | 3.008-2.931 | 4-15 |
| 30.5-31.0 | 2.931-2.885 | 16-48 |
| 31.4-31.6 | 2.849-2.831 | sh-1 |
| 32.2-32.5 | 2.780-2.755 | 1-5 |
| 32.7-33.2 | 2.739-2.698 | sh-3 |
| 34.8 | 3.578 | 0-1 |
| 35.3-36.0 | 2.543-2.495 | 3-6 |
| 36.8 | 2.442 | 0-1 |
| 38.4-38.6 | 2.344-2.338 | 0-1 |
| 39.0-39.1 | 2.309-2.304 | 0-1 |
| 39.6-40.0 | 2.276-2.254 | 0-1 |
| 42.0-42.2* | 2.151-2.141 | 0-6 |
| 43.3-43.6 | 2.090-2.076 | 0-2 |
| 46.5 | 1.953 | 0-1 |
| 47.1-47.5 | 1.929-1.914 | 0-5 |
| 48.0-48.2* | 1.895-1.888 | 0-8 |
| 48.5-48.8 | 1.877-1.866 | 0-5 |
| 50.0-50.8 | 1.824-1.797 | 4-10 |
| 51.6-51-8 | 1.771-1.765 | 0-1 |
| 53.0-53.8 | 1.728-1.704 | 4-10 |
| 54.3-54.6 | 1.689-1.681 | 0-2 |

*peak may contain impurity

EXAMPLE 120B (a) The MgAPSO-46, as prepared in example 44B, was subjected to x-ray analysis. MgAPSO-46 was determined to have a characteristic x-ray powder diffraction pattern which contains the d-spacings set forth below:

| 2θ | d, (Å) | 100 × I/Io |
|---|---|---|
| 6.6 | 13.44 | 3 |
| 7.7 | 11.48 | 100 |
| 10.1 | 8.76 | <1 |

-continued

| 2θ | d, (Å) | 100 × I/Io |
|---|---|---|
| 12.4 | 7.15 | 2 |
| 13.2 | 6.71 | 2 |
| 13.75 | 6.44 | 3 |
| 14.9 | 5.95 | 1 |
| 15.3 | 5.79 | 2 |
| 16.6 | 5.33 | 3 |
| 17.4 | 5.10 | <1 |
| 19.8 | 4.48 | 1 |
| 20.45 | 4.34 | 4 |
| 20.7 | 4.29 | sh |
| 21.5 | 4.13 | 12 |
| 22.75 | 3.906 | 6 |
| 24.2 | 3.682 | 3 |
| 25.2 | 3.534 | <1 |
| 26.85 | 3.320 | 4 |
| 27.7 | 3.219 | 3 |
| 28.2 | 3.163 | 2 |
| 28.7 | 3.109 | 4 |
| 29.8 | 3.000 | 1 |
| 31.1 | 2.873 | 2 |
| 31.7 | 2.823 | <1 |
| 32.9 | 2.722 | <1 |
| 34.2 | 2.622 | 1 |
| 35.85 | 2.505 | 2 |
| 36.5 | 2.462 | <1 |
| 37.2 | 2.417 | <1 |
| 38.4 | 2.344 | <1 |
| 39.6 | 2.276 | <1 |
| 41.0 | 2.201 | <1 |
| 42.2 | 2.141 | <1 |
| 43.9 | 2.062 | 1 |
| 45.9 | 1.977 | <1 |
| 47.5 | 1.914 | <1 |
| 49.4 | 1.845 | <1 |
| 50.1 | 1.821 | <1 |
| 51.4 | 1.778 | <1 |
| 52.2 | 1.752 | <1 |

(b) A portion of the as-synthesized MgAPSO-46 of part (a) was calcined in nitrogen at 500° C. for about 1.75 hours. The calcined product was characterized by the x-ray powder diffraction pattern below:

| 2θ | d, (Å) | 100 × I/Io |
|---|---|---|
| 6.8 | 13.0 | 8 |
| 7.8 | 11.33 | 100 |
| 13.5 | 6.56 | 8 |
| 14.0 | 6.33 | 3 |
| 15.2 | 5.83 | 9 |
| 15.6 | 5.68 | sh |
| 16.95 | 5.23 | 11 |
| 20.2 | 4.40 | sh |
| 20.7 | 4.29 | 6 |
| 21.7 | 4.10 | 10 |
| 23.0 | 3.867 | 6 |
| 24.4 | 3.648 | 3 |
| 27.2 | 3.278 | 4 |
| 27.9 | 3.198 | 3 |
| 28.4 | 3.143 | sh |
| 28.9 | 3.089 | 6 |
| 30.2 | 2.959 | 2 |
| 31.4 | 2.849 | 3 |
| 32.0 | 2.797 | 1 |
| 33.4 | 2.683 | 2 |
| 34.2 | 2.622 | 2 |
| 36.2 | 2.481 | 2 |
| 37.0 | 2.430 | <1 |
| 40.2 | 2.243 | <1 |
| 41.3 | 2.186 | 1 |
| 44.2 | 2.049 | 1 |
| 46.3 | 1.961 | <1 |
| 47.9 | 1.899 | <1 |
| 50.5 | 1.807 | 1 |
| 51.9 | 1.762 | <1 |
| 52.6 | 1.740 | <1 |

(c) The MgAPSO-46 compositions are generally characterized by the data of Table XXIX-B below:

TABLE XXIX-B

| 2θ | d, (Å) | Relative Intensity |
|---|---|---|
| 7.2–8.1 | 12.28–10.92 | vs |
| 21.2–21.8 | 4.19–4.08 | v–m |
| 22.5–23.0 | 3.952–3.867 | vw–m |
| 26.6–27.2 | 3.351–3.278 | vw–w |
| 28.5–29.0 | 3.132–3.079 | vw–w |

(d) The MgAPSO-46 compositions for which x-ray powder diffraction data have been obtained to date have patterns which are characterized by the x-ray powder diffraction pattern shown in Table XXX-B below:

TABLE XXX-B

| 2θ | d, (Å) | 100 × I/Io |
|---|---|---|
| 6.5–6.9 | 13.60–12.81 | 3–10 |
| 7.2–8.1 | 12.28–10.92 | 100 |
| 9.8–10.3 | 9.03–8.59 | 0–1 |
| 12.4 | 7.14 | 0–4 |
| 12.9–13.5 | 6.86–6.56 | 2–8 |
| 13.5–14.0 | 6.56–6.33 | 3–8 |
| 14.8–15.2 | 5.99–5.83 | 1–9 |
| 15.2–15.8 | 5.83–5.61 | (sh)–5 |
| 16.5–17.6 | 5.37–5.04 | 3–11 |
| 17.3–17.4 | 5.13–5.10 | 0–1 |
| 19.7–20.2 | 4.51–4.40 | (sh)–5 |
| 20.3–20.7 | 4.37–4.29 | 4–9 |
| 21.2–21.8 | 4.19–4.08 | 10–36 |
| 22.5–23.0 | 3.952–3.867 | 6–20 |
| 23.7–24.4 | 3.754–3.648 | 3–11 |
| 25.0–25.5 | 3.562–3.648 | 0–1 |
| 26.6–27.2 | 3.351–3.278 | 4–17 |
| 27.5–27.9 | 3.243–3.198 | 3–12 |
| 28.0–28.4 | 3.255–3.143 | sh–2 |
| 28.5–29.0 | 3.132–3.079 | 4–15 |
| 29.6–30.2 | 3.018–2.959 | 1–4 |
| 30.9–31.4 | 2.894–2.849 | 2–6 |
| 31.6–32.0 | 2.831–2.797 | 1–3 |
| 32.6–33.4 | 2.747–2.683 | 1–2 |
| 33.95–34.4 | 2.640–2.607 | 1–4 |
| 35.7–36.2 | 2.515–2.481 | 2–6 |
| 36.3–37.0 | 2.475–2.430 | 0–2 |
| 37.0–37.6 | 2.430–2.392 | 0–1 |
| 37.9–38.4 | 2.374–2.344 | 0–1 |
| 39.5–40.2 | 2.281–2.243 | 0–1 |
| 40.7–41.3 | 2.217–2.186 | 0–1 |
| 43.7–44.3 | 2.071–2.045 | 0–1 |
| 45.8–46.4 | 1.981–1.957 | 0–1 |
| 47.3–47.9 | 1.922–1.899 | 0–1 |
| 49.2–49.3 | 1.852–1.848 | 0–1 |
| 49.9–50.5 | 1.828–1.807 | 0–1 |
| 51.2–51.9 | 1.784–1.762 | 0–1 |
| 52.1–52.6 | 1.755–1.740 | 0–1 |

EXAMPLE 121-B (a) MgAPSO-47, as prepared in example 104B, was subjected to x-ray analysis. MgAPSO-47 was determined to have a characteristic x-ray powder diffraction pattern which contains the d-spacings set forth below:

| 2θ | d, (Å) | 100 × I/Io |
|---|---|---|
| 9.5 | 9.29 | 100 |
| 12.95 | 6.84 | 9 |
| 13.9 | 6.36 | 5 |
| 16.05 | 5.52 | 22 |
| 17.65 | 5.03 | 9 |
| 19.05 | 4.66 | 2 |
| 20.65 | 4.30 | 53 |
| 21.9 | 4.06 | 7 |
| 22.45* | 3.961 | 2 |
| 23.05 | 3.859 | 7 |

-continued

| 2θ | d, (Å) | 100 × I/Io |
|---|---|---|
| 24.75 | 3.598 | 21 |
| 25.95 | 3.432 | 12 |
| 27.7 | 3.222 | 5 |
| 27.95 | 3.190 | 3 |
| 28.55* | 3.126 | 1 |
| 29.55 | 3.022 | 3 |
| 30.6 | 2.919 | 21 |
| 30.9 | 2.893 | sh |
| 31.5 | 2.837 | 2 |
| 32.4 | 2.763 | 1 |
| 33.25 | 2.695 | 2 |
| 34.55 | 2.597 | 4 |
| 34.95 | 2.567 | 1 |
| 35.8 | 2.510 | 3 |
| 38.5 | 2.338 | 2 |
| 39.1 | 2.305 | 1 |
| 39.7 | 2.270 | 2 |
| 42.5 | 2.126 | 2 |
| 43.4 | 1.085 | 1 |
| 47.7 | 1.907 | 2 |
| 48.7 | 1.870 | 4 |
| 50.4 | 1.810 | 3 |
| 51.7 | 1.768 | 1 |
| 52.45 | 1.745 | 1 |
| 53.3 | 1.719 | 2 |
| 54.1 | 1.695 | 1 |
| 54.6 | 1.681 | 1 |
| 55.9 | 1.645 | 2 |

(b) A portion of the as-synthesized MgAPSO-47 of part (a) was calcined in air at 500° C. for about 1.75 hours. The calcined product was characterized by the x-ray powder diffraction pattern below:

| 2θ | d, (Å) | 100 × I/Io |
|---|---|---|
| 9.65 | 9.17 | 100 |
| 13.05 | 6.79 | 20 |
| 14.2 | 6.25 | 4 |
| 16.2 | 5.46 | 14 |
| 18.0 | 4.92 | 11 |
| 19.3 | 4.60 | 3 |
| 20.85 | 4.26 | 33 |
| 22.3 | 3.980 | 2 |
| 22.6* | 3.933 | 3 |
| 23.3 | 3.819 | 4 |
| 23.6* | 3.771 | 1 |
| 24.55* | 3.626 | 2 |
| 25.25 | 3.556 | 12 |
| 26.2 | 3.400 | 10 |
| 28.0 | 3.188 | 2 |
| 28.5 | 3.132 | 4 |
| 29.95 | 2.983 | 2 |
| 30.95 | 2.889 | 15 |
| 31.4 | 2.849 | sh |
| 34.8 | 2.575 | 3 |
| 36.5 | 2.459 | 2 |

*Impurity peak (c) The MgAPSO-47 compositions are generally characterized by the date of Table XXXI-B below:

TABLE XXXI-B

| 2θ | d, (Å) | Relative Intensity |
|---|---|---|
| 9.5–9.65 | 9.33–9.17 | vs |
| 12.85–13.05 | 6.89–6.79 | vw-m |
| 16.0–16.2 | 5.54–5.46 | w-m |
| 20.6–20.85 | 4.32–4.26 | m-s |
| 24.75–25.3 | 3.598–3.526 | vw-m |
| 130.55–30.95 | 2.925–2.889 | w-m |

(d) The MgAPSO-47 compositions for which x-ray powder diffraction data have been obtained to date have patterns which are characterized by the x-ray powder diffraction pattern shown in Table XXXII-B below.

TABLE XXXII-B

| 2θ | d, (Å) | 100 × I/Io |
|---|---|---|
| 9.5–9.65 | 9.33–9.17 | 100 |
| 12.85–13.05 | 6.89–6.79 | 7–20 |
| 13.9–14.2 | 6.36–6.25 | 3–7 |
| 16.0–16.2 | 5.54–5.46 | 14–41 |
| 17.65–18.0 | 5.03–4.92 | 4–11 |
| 19.0–19.3 | 4.67–4.60 | 2–3 |
| 20.6–20.85 | 4.32–4.26 | 33–89 |
| 21.9–22.3 | 4.06–3.98 | 2–7 |
| 23.0–23.3 | 3 866–3.819 | 3–11 |
| 24.75–25.3 | 3.598–3.526 | 8–22 |
| 25.85–26.2 | 3.444–3.400 | 7–18 |
| 27.6–28.0 | 3.229–3.188 | 2–7 |
| 27.95–28.5 | 3.190–3.132 | 1–4 |
| 29.5–29.95 | 3.030–3.983 | 2–5 |
| 30.55–30.95 | 2.925–2.889 | 13–36 |
| 30.9–31.4 | 2.891–2.849 | sh |
| 31.4–31.5 | 2 849–2.837 | 0–3 |
| 32.4 | 2.763 | 0–1 |
| 33.25 | 2.695 | 0–3 |
| 34.4–34.8 | 2.606–2.575 | 3–7 |
| 34.95 | 2.567 | 0–1 |
| 35.8–36.55 | 2.510–2.459 | 1–4 |
| 38.5 | 2.338 | 0–2 |
| 39.1–39.65 | 2.305–2.273 | 0–4 |
| 39.6–39.7 | 2.275–2.270 | 0–4 |
| 42.5–42.8 | 2.126–2.115 | 0–3 |
| 43.3–43.8 | 2.091–2.067 | 0–2 |
| 47.6–47.7 | 1.911–1.907 | 0–3 |
| 48.7–49.3 | 1.870–1.848 | 1–7 |
| 50.4–51.1 | 1.810–1.787 | 1–5 |
| 51.7 | 1.768 | 0–1 |
| 52.45 | 1.745 | 0–1 |
| 53.3 | 1.719 | 0–2 |
| 54.1 | 1.695 | 0–1 |
| 54.7 | 1.681 | 0–1 |
| 55.9 | 1.645 | 0–2 |

EXAMPLE 122B

In order to demonstrate the catalytic activity of the MgAPSO compositions, calcined samples of MgAPSO products were tested for catalytic cracking of n-butane using a bench-scale apparatus.

The reactor was a cylindrical quartz tube 254 mm. in length and 10.3 mm. I.D. In each test the reactor was loaded with particles of the test MgAPSO which were 20–40 mesh (U.S. std.) in size and in an amount of from 0.5 to 5 grams, the quantity being selected so that the confession n-butane was at least 5% and not more than 90% under the test conditions. The MgAPSO samples had been previously calcined in air or nitrogen to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed for 10 minutes of on-stream operation.

The pseudo-first-order rate constant ($k_A$) was calculated to determine the relative catalytic activity of the MgAPSO compositions. The $k_A$ value ($cm^3/g$ min) obtained for the MgAPSO compositions are set forth, below, in Table XXX-B:

TABLE XXX-B

| MgAPSO | Prepared in Example No. | Rate Constant ($k_A$)* |
|---|---|---|
| MgAPSO-35 | 80B | 2.6 |

TABLE XXX-B-continued

| MgAPSO | Prepared in Example No. | Rate Constant $(k_A)$* |
|---|---|---|
| MgAPSO-34 | 63B | 4.1 |
| MgAPSO-35 | 82B | 0.9 |
| MgAPSO-36 | 5B | 18.0 |
| MgAPSO-46 | 44B | 7.3 |
| MgAPSO-47 | 104B | 1.7 |

*Prior to activation of the MgAPSO samples of the following examples such were calcined as follows:
(a) Example 80B: calcined in air at 600° for 2.25 hours;
(b) Example 63B: calcined in air at 550° C. for 2 hours;
(c) Example 82B: calcined in nitrogen at 425° C. for 2 hours;
(d) Example 5B: calcined in air at 500° C. for 2 hours and then at 600° C. for 2 hours;
(e) Example 44B: calcined in nitrogen at 500° C. for 1.75 hours; and
(f) Example 104B: calcined in air at 500° C. for 1.75 hours.

C. IRON-ALUMINUM-PHOSPHORUS-SILICON-OXIDE SIEVES

Molecular sieves containing iron, aluminum phosphorus and silicon as framework tetrahedral oxide units are prepared as follows:

Preparative Reagents

In the following examples the FeAPSO compositions were prepared using numerous reagents. The reagents employed and abbreviations employed herein, if any, for such reagents are as follows:

(a) Alipro: aluminum isopropoxide, Al-(OCH(CH$_3$)$_2$)$_3$;

(b) LUDOX-LS: LUDOX-LS is the trademark of Du Pont for an aqueous solution of 30 weight percent SiO$_2$ and 0.1 weight percent Na$_2$O;

(c) CATAPAL: trademark for hydrated aluminum oxide containing about 75 Wt. % Al$_2$O$_3$ (pseudo-boehmite phase) and about 25 wt. percent water.

(c) Fe(Ac)$_2$: Iron (II) acetate;

(d) FeSO$_4$: Iron (II) sulfate hexahydrate;

(e) H$_3$PO$_4$: 85 weight percent phosphoric acid in water;

(f) TEAOH: 40 weight percent aqueous solution of tetraethylammonium hydroxide;

(g) TBAOH: 40 weight percent aqueous solution of tetrabutylammonium hydroxide;

(h) Pr$_2$NH: di-n-propylamine ((C$_3$H$_7$)$_2$NH);

(i) Pr$_3$N: tri-n-propylamine ((C$_3$H$_7$)$_3$N);

(j) Quin: quinclidine (C$_7$H$_{13}$N);

(k) MQuin: Methyl Quinuclidine hydroxide (C$_7$H$_{13}$NCH$_3$OH);

(l) TMAOH: tetramethylammonium hydroxide pentahydrate; and (m) C-hex; cyclohexylamine.

EXAMPLES 1C TO 16C (a) Examples 1C to 8C were carried out to demonstrate the preparation of FEAPSO-34 and FeAPSO-5. The reaction mixtures wer prepared by grinding the aluminum isopropoxide in a blender followed by slowly adding the H$_3$PO$_4$ solution with mixing. A solution/dispersion of iron acetate in water was added and then the LUDOX-LS was added. The organic templating agent was then added to this mixture, or in some cases one-half of this mixture, and the mixture blended to from a homogeneous mixture. The number of moles of each component in the reaction mixture was as follows:

| Component | Moles |
|---|---|
| Al$_2$O$_3$ | 0.9 |
| P$_2$O$_5$ | 0.9 |
| SiO$_2$ | 0.2** |
| FeO* | 0.2 |
| TEAOH | 1.0 |
| H$_2$O | 50 |

*Iron (II) acetate reported as Iron (II) oxide.
**SiO$_2$ was 0.6 in example 5C to 8C Each reaction mixture was sealed in a stainless steel pressure vessel lined with polytetrafluoroethylene and heated in an oven at a temperature (see Table I-C), time (see Table I-C) and at the autogeneous pressure. The solid reaction product was recovered by filtration, washed with water and dried at room temperature. The products were analyzed and th observed FeAPSO products reported in Table I-C.

(c) Examples 9C to 16C were carried out to demonstrate the preparation of FeAPSO-11 and FeAPSO-5. The reaction mixtures were prepared by grinding the aluminum iso-propoxide in a blender followed by addition of a solution/dispersion of Iron (II) acetate. H$_3$PO$_4$ was added to this mixture and the resulting mixture blended to form a homogeneous mixture. LUDOX-LS was added to this mixture except that in examples 13C to 16C the LUDOX-LS were added with H$_3$PO$_4$. The resulting mixtures were blended until a homogeneous mixture was observed. Organic templating agent was added to each mixture and the resulting mixtures placed in a stainless steel pressure vessel lined with polytetrafluoroethylene and heated. Washed and the product recovered as in part (a) of this example. The products were analyzed and the observed FeAPSO products reported in Table I-C. The number of moles of each component in the reaction mixture was as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Template | 1.0 |
| H$_2$O | 50 |

*Iron (II) acetate reported as Iron (II) oxide.

(c) Two reaction mixtures, designated Example AC and BC in Table I-C, did not show FeEAPSO products when analyzed by X-ray. Examples AC and BC followed the same procedure employed for Example 5C and 6C.

TABLE I-C

| Example | Template | Temp (°C.) | Time (hr.) | FeAPSO Product[1] |
|---|---|---|---|---|
| 1C | TEAOH | 150 | 64 | FeAPSO-34; FeAPSO-5 |
| 2C | TEAOH | 150 | 158 | FeAPSO-34; FeAPSO-5 |
| 3C | TEAOH | 200 | 64 | FeAPSO-34; FeAPSO-5 |
| 4C | TEAOH | 200 | 158 | FeAPSO-34; FeAPSO-5 |
| 5C | TEAOH | 150 | 40 | FeAPSO-34; FeAPSO-5 |
| 6C | TEAOH | 150 | 161 | FeAPSO-34; FeAPSO-5 |
| 7C | Pr$_2$NH | 150 | 50 | FeAPSO-11 |
| 8C | Pr$_2$NH | 150 | 168 | FeAPSO-11 |
| 9C | Pr$_2$NH | 200 | 50 | FeAPSO-11 |
| 10C | Pr$_2$NH | 200 | 168 | FeAPSO-11 |
| 11C | Pr$_3$N | 150 | 50 | FeAPSO-5 |
| 12C | Pr$_3$N | 150 | 168 | FeAPSO-5 |
| 13C | Pr$_3$N | 200 | 50 | FeAPSO-5 |
| 14C | Pr$_3$N | 200 | 50 | FeAPSO-5 |
| AC | TEAOH | 100 | 40 | — |

TABLE I-C-continued

| Example | Template | Temp (°C.) | Time (hr.) | FeAPSO Product[1] |
|---|---|---|---|---|
| BC | TEAOH | 100 | 161 | — |

[1]Major species as identified by x-ray powder diffraction pattern of product, except that when two species where identified the first species listed is the major species observed. A "—" indicates no FeAPSO product was present as determined by X-ray analysis.

EXAMPLES 15C TO 19C

Example 15C to 19C were carried out according to the general preparative procedure employed for example 7C to 14C with examples 15C to 18C following the procedure employed for examples 7C to 10C and example 19C following the procedure followed for examples 11C to 14C. The reactive source of iron was Iron (II) sulfate instead of Iron (II) acetate. The temperature and time for the crystallization (digestion) procedure are set forth in Table II-C.

The number of moles of each component in the reaction mixture for examples 15C to 18C was as follows:

| Component | Moles |
|---|---|
| Al$_2$O$_3$ | 0.9 |
| P$_2$O$_5$ | 0.9 |
| SiO$_2$ | 0.6 |
| FeO* | 0.2 |
| Pr$_3$N | 1.5 |
| H$_2$O | 50 |

*Iron (II) sulfate reported as Iron (II) oxide.

the number of moles of each component in the reaction mixture of example 19C was as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Pr$_3$N | 1.0 |
| H$_2$O | 50 |

*Iron (II) sulfate reported as Iron (II) oxide.

The products were subjected to analysis by X-ray and the observed FeAPSO products reported in Table II-C.

TABLE II-C

| Example | Template | Temp (°C.) | Time (hr.) | FeAPSO Product[1] |
|---|---|---|---|---|
| 15C | Pr$_3$N | 150 | 48 | FeAPSO-5 |
| 16C | Pr$_3$N | 150 | 160 | FeAPSO-5 |
| 17C | Pr$_3$N | 200 | 48 | FeAPSO-5 |
| 18C | Pr$_3$N | 200 | 160 | FeAPSO-5 |
| 19C | Pr$_3$N | 200 | 72 | FeAPSO-5 |

[1]Major species as identified by x-ray powder diffraction pattern of product, except that when two species where identified the first species listed is the major species observed.

EXAMPLES 20C–27C

Example 20C–27C were carried out according to the general preparative procedure employed for examples 1C to 8C using the following number of moles of each component in the reaction mixture:

| Component | Moles |
|---|---|
| Al$_2$O$_3$ | 0.9 |
| P$_2$O$_5$ | 0.9 |
| SiO$_2$* | 0.2, 0.6 |
| FeO** | 0.2 |
| Template | 1.0 |
| H$_2$O | 50 |

*0.2 moles in examples 20C to 23C and 0.6 moles in examples 24C to 27C
**Iron (II) acetate reported as Iron (II) oxide.

The temperature and time for the crystallization procedure and the observed FeAPSO products are reported in Table III-C.

TABLE III-C

| Example | Template | Temp (°C.) | Time (hr.) | FeAPSO Product[1] |
|---|---|---|---|---|
| 20C | Quin | 150 | 64 | FeAPSO-16 |
| 21C | Quin | 150 | 158 | FeAPSO-16; FeAPSO-35 |
| 22C | Quin | 200 | 64 | FeAPSO-16; FeAPSO-35 |
| 23C | Quin | 200 | 158 | FeAPSO-16; FeAPSO-35 |
| 24C | MQuin | 100 | 49 | FeAPSO-16 |
| 25C | MQuin | 100 | 161 | FeAPSO-16 |
| 26C | MQuin | 150 | 49 | FeAPSO-16; FeAPSO-35 |
| 27C | MQuin | 150 | 161 | FeAPSO-16; FeAPSO-35 |

[1]Major species as identified by x-ray powder diffraction pattern of product, except that when two species were identified the first species listed is the major species observed.

EXAMPLES 28C AND 29C

Examples 28C and 29C were carried out according to the procedure of examples 13C to 16C. except that Iron (II) sulfate, was employed as the reactive iron source instead of Iron (II) acetate. The number of moles of each component in the reaction mixture for each example was as follows:

| Component | Moles |
|---|---|
| Al$_2$O$_3$ | 0.8 |
| P$_2$O$_5$ | 1.0 |
| SiO$_2$ | 0.4 |
| FeO* | 0.4 |
| Template | 2.0 |
| H$_2$O | 83 |

*Iron (II) sulfate reported here as FeO

Examples CC and DC followed the procedure for examples 28C and 29C. X-ray analysis of the reaction procuts did not show FeAPSO products.

The temperature and time for the crystallization procedure and the observed FeAPSO products are reported in Table IV-C.

TABLE IV-C

| Example | Template | Temp (°C.) | Time (hr.) | FeAPSO Product[1] |
|---|---|---|---|---|
| 28C | TBAOH | 200 | 49 | FeAPSO-5 |
| 29C | TBAOH | 200 | 161 | FeAPSO-5 |
| CC | TBAOH | 150 | 49 | — |
| DC | TBAOH | 150 | 161 | — |

[1]Major species as identified by x-ray powder diffraction pattern of product, except that when two species where identified the first species listed is the major species observed. A "—" indicates no FeAPSO product was present as determined by X-ray analysis.

EXAMPLES 30C TO 43C

Examples 30C to 43C were carried out according to the procedure employed for examples 1C to 8C except that in examples 30C and 31C the aluminum source was CATAPAL and in examples 33C to 36C and 43C a seed crystal of a topologically similar molecular sieve was employed. The number of moles of each component in the reaction mixture in examples 30C to 43C was:

| Component | Moles |
|---|---|
| Al₂O₃ | 0.9 |
| P₂O₅ | 0.9 |
| SiO₂ | 0.2** |
| FeO* | 0.2 |
| Template | 1.0** |
| H₂O | 50 |

*Iron (II) acetate reported as FeO
**SiO₂ was 0.6 in example 32C and was 2.0 moles of template in examples 37C to 40C.

the template, temperature, time for the crystallization procedure and the observed FeAPSO products are reported in Table V-C.

TABLE V-C

| Example | Template | Temp (°C.) | Time (hr.) | FeAPSO Product(s)¹ |
|---|---|---|---|---|
| 30C | TMAOH | 150 | 42 | FeAPSO-20 |
| 31C | TMAOH | 150 | 132 | FeAPSO-20 |
| 32C | C-hex | 220 | 114 | FeAPSO-5; FeAPSO-44 |
| 33C | Pr₂NH | 150 | 47 | FeAPASO-31 |
| 34C | Pr₂NH | 150 | 182 | FeAPASO-31 |
| 35C | Pr₂NH | 200 | 47 | FeAPASO-31 |
| 36C | Pr₂NH | 200 | 158 | FeAPASO-31 |
| 37C | Pr₂NH | 150 | 182 | FeAPASO-46 |
| 38C | Pr₂NH | 150 | 182 | FeAPASO-46 |
| 39C | Pr₂NH | 150 | 47 | FeAPSO-5; FeAPSO-34 |
| 40C | Pr₂NH | 200 | 158 | FeAPSO-11; FeAPSO-31 |
| 41C | Pr₂N | 150 | 42 | FeAPSO-5 |
| 42C | Pr₂N | 150 | 132 | FeAPSO-5 |
| 43C | Pr₂N | 150 | 42 | FeAPSO-5 |
| EC | Pr₂NH | 150 | 47 | FeAPASO-5 |

¹Major species as identified by x-ray powder diffraction pattern of product, except that when two species where identified the first species listed is the major species observed. A "—" indicates no FeAPSO product was present as determined by X-ray analysis.

EXAMPLE 44C (a) Samples of FeAPSP products were calcined at 600° C. in air for 2 hours to remove at least part of the organic templating agent, except that FeAPSO-5 and FeAPSO-11 were calcined for 2.25 hours. The example in which the FeAPSO was prepared is indicated in parenthesis. The adsorption capacities of each calcined sample were measured using a standard McBain-Bakr gravimetric adsorption apparatus. The samples were activated in a vacuum at 350° C. prior to measurement. The McBain-Bakr data for the FeAPSO compositions are set forth hereinafter.

| (b) FeAPSO-5 (example 12C) | | | | |
|---|---|---|---|---|
| Adsorbate | Kinetic Diameter, Å | Pressure (Torr) | Temp (°C.) | Wt. % Adsorbed |
| O₂ | 3.46 | 100 | −183 | 9.7 |
| O₂ | 3.46 | 734 | −183 | 11.6 |
| neopentane | 6.2 | 100 | 24.5 | 3.8 |
| cyclohexane | 6.0 | 59 | 23.7 | 5.7 |
| H₂O | 2.65 | 4.6 | 23.9 | 10.7 |
| H₂O | 2.65 | 20.0 | 23.6 | 19.2 |

The above data demonstrate that the pore size of the calcined product is greater than 6.2 Å.

| (c) FeAPSO-11 (example 10C) | | | | |
|---|---|---|---|---|
| Adsorbate | Kinetic Diameter, Å | Pressure (Torr) | Temp (°C.) | Wt. % Adsorbed |
| O₂ | 3.46 | 100 | −183 | 7.6 |
| O₂ | 3.46 | 734 | −183 | 9.2 |
| neopentane | 6.2 | 100 | 24.5 | 0.2 |
| cyclohexane | 6.0 | 59 | 23.7 | 4.2 |
| H₂O | 2.65 | 4.6 | 23.9 | 10.8 |
| H₂O | 2.65 | 20.0 | 23.6 | 16.7 |

The above data demonstrate that the pore size of the calcined product is about 6.0 Å.

| (d) FeAPSO-20 (example 31C) | | | | |
|---|---|---|---|---|
| Adsorbate | Kinetic Diameter, Å | Pressure (Torr) | Temp (°C.) | Wt. % Adsorbed |
| O₂ | 3.46 | 99 | −183 | 1.5 |
| O₂ | 3.46 | 749 | −183 | 8.5 |
| H₂O | 2.65 | 4.6 | 23.2 | 22.7 |
| H₂O | 2.65 | 16.8 | 23.5 | 30.0 |

The above data demonstrates that the pore size of the calcined product is about 3.0 Å.

| (e) FeAPSO-31 (example 34C) | | | | |
|---|---|---|---|---|
| Adsorbate | Kinetic Diameter, Å | Pressure (Torr) | Temp (°C.) | Wt. % Adsorbed |
| O₂ | 3.46 | 99 | −183 | 6.8 |
| O₂ | 3.46 | 749 | −183 | 11.6 |
| neopentane | 6.2 | 100 | 23.4 | 3.6 |
| cyclohexane | 6.0 | 57 | 23.4 | 6.9 |
| H₂O | 2.65 | 4.6 | 23.2 | 6.5 |
| H₂O | 2.65 | 16.8 | 23.5 | 21.3 |

The above data demonstrates that the pore size of the calcined product is greater than about 6.2 Å.

| (f) FeAPSO-46 (example 38C) | | | | |
|---|---|---|---|---|
| Adsorbate | Kinetic Diameter, Å | Pressure (Torr) | Temp (°C.) | Wt. % Adsorbed |
| O₂ | 3.46 | 100 | −183 | 2.6 |
| O₂ | 3.46 | 749 | −183 | 11.7 |
| neopentane | 6.2 | 100 | 23.4 | 1.1 |
| cyclohexane | 6.0 | 57 | 23.4 | 6.4 |
| H₂O | 2.65 | 4.6 | 23.2 | 7.2 |
| H₂O | 2.65 | 16.8 | 23.5 | 13.0 |

The above data demonstrates that the pore size of the calcined product is greater than about 6.2 Å.

EXAMPLE 45C

Samples of FeAPSO products were subjected to chemical analysis as follows:

(a) The chemical analysis for FeAPSO-5 (example 12C) was:

| Component | Weight Percent |
|---|---|
| Al₂O₃ | 32.2 |
| P₂O₅ | 45.4 |
| FeO | 4.7 |
| SiO₂ | 1.9 |
| Carbon | 4.9 |
| LOI* | 14.6 |

*LOI = Loss on Ignition

The above chemical analysis gives an overall product composition in molar oxide ratios (anhydrous basis) of: 0.4 R;0.21 FeO: 1.0 Al$_2$O$_3$: 1.01 P$_2$O$_5$: 0.10 SiO$_2$: and a formula (anhydrous basis) of:

0.03 R (Fe$_{0.05}$Al$_{0.46}$P$_{0.47}$Si$_{0.02}$)O$_2$ (b) The chemical analysis of FeAPSO-11 (example 10C) was:

| Component | Weight Percent |
|---|---|
| Al$_2$O$_3$ | 33.2 |
| P$_2$O$_5$ | 48.8 |
| FeO | 4.5 |
| SiO$_2$ | 2.4 |
| Carbon | 5.1 |
| LOI* | 9.8 |

*LOI = Loss on Ignition

The above chemical analysis gives an overall product composition in molar oxide ratios (anhydrous basis) of: 0.22 R:0.19 FeO; 1.0 Al$_2$O$_3$: 1.06 P$_2$O$_5$: 0.08 SiO$_2$: and a formula (anhydrous basis) of: 0.05(Fe$_{0.04}$Al$_{0.45}$P$_{0.48}$Si$_{0.03}$)O$_2$ (c) The chemical analysis of FeAPSO-20 (example 31C) was:

| Component | Weight Percent |
|---|---|
| Al$_2$O$_3$ | 29.1 |
| P$_2$O$_5$ | 42.0 |
| FeO | 4.8 |
| SiO$_2$ | 2.5 |
| Carbon | 7.6 |
| LOI* | 19.7 |

*LOI = Loss on Ignition

The above chemical analysis give an overall product composition in molar oxide ratios (anhydrous basis) of: 0.55R:0.23FeO; 1.0Al$_2$O$_3$; 1.04 P$_2$O$_5$; 0.15 SiO$_2$; and a formula (anhydrous basis) of: 0.12(Fe$_{0.05}$Al$_{0.45}$P$_{0.47}$Si$_{0.03}$)O$_2$ (d) The chemical analysis of FeAPSO-31 (example 34C) was:

| Component | Weight Percent |
|---|---|
| Al$_2$O$_3$ | 34.7 |
| P$_2$O$_5$ | 45.3 |
| FeO | 4.2 |
| SiO$_2$ | 1.6 |
| Carbon | 3.4 |
| LOI* | 12.9 |

*LOI = Loss on Ignition

The above chemical analysis gives an overall product composition in molar oxide ratios (anhydrous basis) of: 0.14R:0.17FeO; 1.0 Al$_2$O$_3$; 0.94 P$_2$O$_5$; 0.08 SiO$_2$; and a formula (anhydrous basis) of: 0.03(Fe$_{0.04}$Al$_{0.49}$P$_{0.45}$Si$_{0.02}$)O$_2$

EXAMPLE 46C

EDAX (energy dispersive analysis by X-ray) microprobe analysis in conjunction with SEM (scanning electron microscop) was carried out on clear crystals of FEAPSP products of the hereinafter designated examples. Analysis of crystals having a morphology characteristic of FeAPSO-5, FeAPSO-11, FeAPSO-20, FeAPSO-31, FeAPSO-34 and FeAPSO-46 gave the following analysis based on relative peak heights:

| Average of Spot Probes | |
|---|---|
| (a) FeAPSO-5 (example 12C): | |
| Fe | 0.02 |
| Al | 0.44 |
| P | 0.52 |
| Si | 0.02 |
| (b) FeAPSO-II (example 10C): | |
| Fe | 0.03 |
| Al | 0.42 |
| P | 0.52 |
| Si | 0.03 |
| (c) FeAPSO-20 (example 31C): | |
| Fe | 0.04 |
| Al | 0.42 |
| P | 0.49 |
| Si | 0.05 |
| (d) FeAPSO-31 (example 34C): | |
| Fe | 0.01 |
| Al | 0.44 |
| P | 0.48 |
| Si | 0.06 |
| (e) FeAPSO-34 (example 3C): | |
| Fe | 0.04 |
| Al | 0.43 |
| P | 0.45 |
| Si | 0.07 |
| (f) FeAPSO-46 (example 38C): | |
| Fe | 0.05 |
| Al | 0.40 |
| P | 0.43 |
| Si | 0.12 |

EXAMPLE 47C (a) FeAPSO-5, as prepared in example 12C, was subjected to x-ray analysis. FeAPSO-5 was determined to have a characteristic x-ray powder diffraction pattern which contains the d-spacings set forth below:

| 2Θ | d, (Å) | 100 × I/Io |
|---|---|---|
| 7.4 | 11.95 | 100 |
| 8.0* | 11.05 | 4 |
| 12.6* | 7.03 | 13 |
| 13.0 | 6.81 | 7 |
| 14.95 | 5.93 | 15 |
| 16.0* | 5.54 | <1 |
| 16.5* | 5.37 | 1 |
| 17.1* | 5.19 | 1 |
| 18.4* | 4.82 | <1 |
| 19.8 | 4.48 | 33 |
| 20.3* | 4.37 | 5 |
| 21.1 | 4.21 | 27 |
| 22.0* | 4.04 | sh |
| 22.4 | 3.969 | 38 |
| 22.6* | 3.934 | sh |
| 24.7 | 3.604 | 2 |
| 25.1* | 3.548 | 1 |
| 25.9 | 3.440 | 15 |
| 27.2* | 3.278 | 1 |
| 28.0* | 3.187 | 2 |
| 28.4* | 3.143 | 1 |
| 29.0 | 3.079 | 6 |
| 30.0 | 2.979 | 19 |
| 31.8* | 2.814 | 3 |
| 33.7 | 2.660 | 2 |
| 34.5 | 2.600 | 9 |
| 35.2* | 2.550 | 1 |
| 37.0 | 2.564 | 1 |
| 37.8 | 2.380 | 4 |
| 41.6 | 2.171 | 1 |
| 42.3 | 2.137 | 2 |
| 42.9 | 2.108 | 1 |
| 43.6 | 2.076 | 1 |
| 45.0 | 2.015 | 1 |
| 45.7* | 1.985 | 1 |
| 47.7 | 1.907 | 3 |

-continued

| 2θ | d, (Å) | 100 × I/Io |
|---|---|---|
| 51.5 | 1.774 | 1 |
| 55.6 | 1.653 | 1 |

*peak contains impurity (b) A portion of the as-synthesized FeAPSO-5 of part (a) was calcined in air at a temperature beginning at 500° C. and ending at 600° C. over a period of 2.25 hours. The calcined product was characterized by the x-ray powder diffraction pattern below:

| 2θ | d, (Å) | 100 × I/Io |
|---|---|---|
| 7.4 | 11.95 | 100 |
| 7.9* | 11.19 | sh |
| 8.45* | 10.46 | 35 |
| 12.85 | 6.89 | 18 |
| 14.8 | 5.99 | 8 |
| 15.5* | 5.72 | 13 |
| 16.4* | 5.40 | 2 |
| 17.0* | 5.22 | 5 |
| 19.75 | 4.50 | 31 |
| 20.2* | 4.40 | 14 |
| 21.1 | 4.21 | 33 |
| 21.4* | 4.15 | sh |
| 22.0* | 4.04 | sh |
| 22.45 | 3.960 | 83 |
| 23.8* | 3.739 | 1 |
| 24.8 | 3.59 | 2 |
| 25.1* | 3.548 | 2 |
| 25.95 | 3.434 | 31 |
| 27.0* | 3.302 | 2 |
| 27.9* | 3.198 | 3 |
| 29.05 | 3.074 | 14 |
| 30.05 | 2.974 | 22 |
| 31.5* | 2.840 | 29 |
| 31.65 | 2.827 | 5 |
| 34.55 | 2.596 | 15 |
| 35.0* | 2.564 | 3 |
| 36.1* | 2.488 | 1 |
| 37.0 | 2.430 | 4 |
| 37.8 | 2.380 | 8 |
| 38.2* | 2.356 | 2 |
| 39.2* | 2.298 | 2 |
| 40.2* | 2.151 | 2 |
| 42.3 | 2.137 | 2 |
| 43.0 | 2.103 | 1 |
| 43.8 | 2.067 | 2 |
| 45.2 | 2.006 | 2 |
| 46.6* | 1.949 | 2 |
| 47.7 | 1.907 | 4 |
| 51.6 | 1.771 | 4 |
| 55.6 | 1.653 | 2 |

*Peak contains impurity (c) The FeAPSO-5 compositions are generally characterized by the data of Table VI-C below:

TABLE VI-C

| 2θ | d, (Å) | Relative Intensity |
|---|---|---|
| 7.3–7.5 | 12.11–11.79 | m-vs |
| 14.8–14.95 | 5.99–5.93 | w-m |
| 19.6–19.8 | 4.53–4.48 | m |
| 21.0–21.2 | 4.23–4.19 | m |
| 22.35–22.5 | 3.98–3.95 | m-vs |
| 25.8–25.95 | 3.453–3.434 | w-m |

(d) The FeAPSO-5 compositions for which x-Ray powder diffraction data have been obtained have patterns which are characterized by the x-ray powder diffraction pattern shown in Table VII-C. below:

TABLE VII-C

| 2θ | d, (Å) | 100 × I/Io |
|---|---|---|
| 7.3–7.5 | 12.11–11.79 | 55–100 |
| 12.8–13.0 | 6.92–6.81 | 7–18 |
| 14.8–14.95 | 5.99–5.93 | 17–27 |
| 19.6–19.8 | 4.53–4.48 | 24–60 |
| 21.0–21.2 | 4.23–4.19 | 27–53 |
| 22.35–22.5 | 3.98–3.95 | 38–100 |
| 24.7–24.85 | 3.604–3.583 | 0–6 |
| 25.8–25.95 | 3.453–3.434 | 15–68 |
| 28.85–29.05 | 3.095–3.074 | 6–24 |
| 29.8–30.05 | 2.998–2.974 | 9–27 |
| 33.45–33.7 | 2.679–2.660 | 2–10 |
| 34.4–34.55 | 2.607–2.596 | 8–17 |
| 36.9–37.0 | 2.436–2.564 | 1–7 |
| 37.65–37.9 | 2.389–2.374 | 4–13 |
| 41.4–41.6 | 2.181–2.171 | 0–4 |
| 42.1–42.3 | 2.146–2.137 | 0–4 |
| 42.6–43.1 | 2.122–2.099 | 0–4 |
| 43.5–43.8 | 2.080–2.067 | 0–4 |
| 44.9–45.2 | 2.019–2.006 | 0–7 |
| 47.6–47.7 | 1.910–1.907 | 0–5 |
| 51.3–51.6 | 1.781–1.771 | 0–4 |
| 55.4–55.6 | 1.658–1.653 | 1–6 |

EXAMPLE 48C (a) FeAPSO-11, as prepared in example 10C, was subjected to x-ray analysis. FeAPSO-11 was determined to have a characteristic x-ray powder diffraction pattern which contains the d-spacings set forth below:

| 2θ | d, (Å) | 100 × I/Io |
|---|---|---|
| 8.1 | 10.92 | 31 |
| 9.45 | 9.36 | 47 |
| 13.15 | 6.73 | 15 |
| 15.7 | 5.64 | 34 |
| 16.2 | 5.47 | 5 |
| 19.0 | 4.67 | 6 |
| 20.3 | 4.37 | 43 |
| 21.0 | 4.23 | 100 |
| 22.1 | 4.022 | 62 |
| 22.5* | 3.952 | sh |
| 22.65 | 3.926 | 61 |
| 23.1 | 3.850 | 86 |
| 24.7 | 3.604 | 10 |
| 26.4 | 3.376 | 25 |
| 28.2** | 3.164 | sh |
| 28.6 | 3.121 | 17 |
| 29.0 | 3.079 | sh |
| 29.5 | 3.028 | 7 |
| 31.5 | 2.840 | 9 |
| 32.7 | 2.755 | 19 |
| 33.6** | 2.667 | 2 |
| 34.1 | 2.629 | 9 |
| 36.3 | 2.415 | 6 |
| 37.7 | 2.386 | 14 |
| 39.2 | 2.298 | 5 |
| 42.9 | 2.108 | 5 |
| 44.7 | 2.027 | 6 |
| 50.6 | 1.804 | 5 |
| 54.7 | 1.678 | 5 |
| 55.5 | 1.656 | 3 |

*peak may contain impurity
**impurity peak (b) A portion of the as-synthesized FeAPSO-11 of part (a) was calcined in air at 600° C. for about 2.25 hours. The calcined product was characterized by the x-ray powder diffraction pattern below:

| 2θ | d, (Å) | 100 × I/Io |
|---|---|---|
| 8.05 | 10.98 | 60 |
| 9.5 | 9.31 | 72 |
| 12.9** | 6.86 | sh |
| 13.1 | 6.76 | 20 |

-continued

| 2θ | d, (Å) | 100 × I/Io |
|---|---|---|
| 13.7** | 6.46 | 3 |
| 14.7** | 6.03 | 3 |
| 15.9 | 5.57 | 55 |
| 16.1 | 5.51 | sh |
| 17.6** | 5.04 | 3 |
| 19.9** | 4.46 | sh |
| 20.3 | 4.37 | 28 |
| 21.3 | 4.17 | 100 |
| 21.9* | 4.06 | sh |
| 22.4 | 3.969 | 88 |
| 23.0* | 3.867 | sh |
| 23.4 | 3.802 | 70 |
| 24.0** | 3.708 | 3 |
| 24.4** | 3.648 | 5 |
| 25.0* | 3.562 | 4 |
| 25.8* | 3.453 | 6 |
| 26.5 | 3.363 | 20 |
| 27.7** | 3.220 | 5 |
| 29.0 | 3.079 | sh |
| 29.6 | 3.018 | 20 |
| 30.4* | 2.940 | 7 |
| 31.8 | 2.814 | 10 |
| 32.7 | 2.739 | 18 |
| 34.1 | 2.629 | 5 |
| 34.5** | 2.600 | 4 |
| 35.6* | 2.522 | 4 |
| 36.2 | 2.481 | 4 |
| 38.0 | 2.368 | 10 |
| 43.3 | 2.090 | 3 |
| 44.8 | 2.023 | 5 |
| 49.0* | 1.859 | 3 |
| 49.6* | 1.838 | 3 |
| 54.6 | 1.681 | 3 |
| 55.7* | 1.650 | 3 |

*peak may contain impurity
**impurity peak (c) The FeAPS)-11 compositions are generally characterized by the data of Table VIII-C below:

TABLE VIII-C

| 2θ | d, (Å) | Relative Intensity |
|---|---|---|
| 8.05–8.1 | 10.98–10.92 | m–s |
| 9.4–9.5 | 9.41–9.31 | m |
| 21.0–21.3 | 4.23–4.17 | vs |
| 22.1–22.4 | 4.022–3.969 | m–s |
| 22.65–23.1 | 3.926–3.850 | vw–m |
| 23.1–23.4 | 3.850–3.802 | m–s |

(d) The FeAPSO-11 compositions for which x-ray powder diffraction data have been obtained have patterns which are characterized by the x-ray powder diffraction pattern shown in Table IX-C. below:

TABLE IX-C

| 2θ | d, (Å) | 100 × I/Io |
|---|---|---|
| 8.05–8.1 | 10.98–10.92 | 30–80 |
| 9.4–9.5 | 9.41–9.31 | 47–78 |
| 13.05–13.2 | 6.78–6.71 | 13–24 |
| 15.7–15.9 | 5.64–5.57 | 33–54 |
| 16.15–16.3 | 5.49–5.44 | 0–6 |
| 18.9–19.05 | 4.70–4.66 | 0–6 |
| 20.2–20.4 | 4.40–4.35 | 30–43 |
| 21.0–21.3 | 4.23–4.17 | 100 |
| 21.9 | 4.06 | sh |
| 22.1–22.4 | 4.022–3.969 | 54–86 |
| 22.5–22.6 | 3.952–3.934 | sh |
| 22.65–23.1 | 3.926–3.850 | sh–61 |
| 23.1–23.4 | 3.850–3.802 | 48–86 |
| 24.4–24.5 | 3.648–3.633 | sh–6 |
| 24.7–24.9 | 3.604–3.576 | 0–10 |
| 26.4–26.5 | 3.376–3.363 | 15–25 |
| 28.6–28.8 | 3.121–3.100 | 17–19 |
| 28.9–29.0 | 3.079–3.089 | sh |
| 29.5–29.6 | 3.028–3.018 | 7–21 |
| 31.5–31.8 | 2.840–2.814 | 8–12 |

TABLE IX-C-continued

| 2θ | d, (Å) | 100 × I/Io |
|---|---|---|
| 32.7–32.85 | 2.755–2.726 | 13–19 |
| 34.1–34.25 | 2.629–2.618 | 5–9 |
| 36.2–36.5 | 2.481–2.462 | 5–7 |
| 37.6–38.0 | 2.392–2.368 | 7–14 |
| 39.2–39.4 | 2.298–2.287 | 2–5 |
| 42.9–43.2 | 2.108–2.094 | 3–5 |
| 44.7–44.9 | 2.027–2.019 | 3–6 |
| 48.3–48.4 | 1.884–1.881 | 0–2 |
| 50.5–50.9 | 1.807–1.794 | 0–5 |
| 54.5–54.8 | 1.684–1.675 | 0–5 |
| 55.4–55.6 | 1.658–1.653 | 0–3 |

EXAMPLE 49C (a) FeAPSO-16, as prepared in example 21C, was subjected to x-ray analysis. FeAPSO-16 was determined to have a characteristic x-ray powder diffraction pattern which contains the d-spacings set forth below:

| 2θ | d, (Å) | 100 × I/Io |
|---|---|---|
| 8.6** | 10.28 | 7 |
| 10.9** | 8.12 | sh |
| 11.3 | 7.83 | 58 |
| 13.2** | 6.71 | 8 |
| 15.8** | 5.61 | 2 |
| 17.25** | 5.14 | 21 |
| 17.7** | 5.01 | 2 |
| 18.65 | 4.76 | 40 |
| 20.3** | 4.37 | sh |
| 20.7** | 4.29 | sh |
| 21.1** | 4.21 | sh |
| 21.85 | 4.07 | 100 |
| 22.9 | 3.883 | 10 |
| 23.6** | 3.770 | 2 |
| 25.0** | 3.562 | 1 |
| 25.8** | 3.453 | 1 |
| 26.5 | 3.363 | 22 |
| 27.1** | 3.290 | sh |
| 28.6** | 3.121 | sh |
| 28.9 | 3.089 | 9 |
| 29.7 | 3.008 | 24 |
| 32.0** | 2.797 | 10 |
| 32.6 | 2.747 | 4 |
| 34.6* | 2.592 | 8 |
| 35.6** | 2.522 | 1 |
| 37.85 | 2.377 | 8 |
| 39.7 | 2.270 | 3 |
| 44.3 | 2.045 | 2 |
| 48.45* | 1.879 | 7 |
| 49.4** | 1.845 | 2 |
| 51.4** | 1.778 | 1 |
| 52.4 | 1.746 | 1 |
| 54.8* | 1.675 | 2 |

*peak may contain impurity
*impurity peak (b) The FeAPSO-16 compositions are generally characterized by the data of Table X-C below:

TABLE X-C

| 2θ | d, (Å) | Relative Intensity |
|---|---|---|
| 11.3–11.4 | 7.83–7.76 | m |
| 18.55–18.75 | 4.78–4.73 | m |
| 21.85–22.0 | 4.07–4.04 | vs |
| 26.45–26.6 | 3.370–3.351 | w–m |
| 29.6–29.8 | 3.018–2.998 | w–m |

(c) The FeAPSO-16 compositions for which x-ray powder diffraction data have been obtained powder diffraction pattern shown in Table XI-C, below:

TABLE XI-C

| 2θ | d, (Å) | 100 × I/Io |
|---|---|---|
| 11.3–11.4 | 7.83–7.76 | 38–63 |
| 18.55–18.75 | 4.78–4.73 | 31–63 |
| 21.85–22.0 | 4.07–4.04 | 100 |
| 22.9 | 3.883 | sh–10 |
| 26.45–26.6 | 3.370–3.351 | 18–26 |
| 28.9–29.0 | 3.089–3.079 | 0–13 |
| 29.6–29.8 | 3.018–2.998 | 17–30 |
| 32.4–32.8 | 2.763–2.730 | 0–13 |
| 34.5–34.6 | 2.600–2.592 | 0–10 |
| 37.65–37.9 | 2.389–2.374 | 0–10 |
| 39.5–39.7 | 2.281–2.270 | 0–6 |
| 44.1–44.5 | 2.054–2.036 | 0–6 |
| 48.2–48.5 | 1.888–1.877 | 0–8 |
| 52.0–52.4 | 1.759–1.746 | 0–3 |
| 54.4–54.8 | 1.687–1.675 | 0–3 |

EXAMPLE 50C (a) FeAPSO20, as prepared to in example 31C, was subjected to x-ray analysis. FeAPSO-20 was determined to have a characteristic x-ray powder diffraction pattern which contains the d-spacings set forth below:

| 2θ | d, (Å) | 100 × I/Io |
|---|---|---|
| 14.0 | 6.32 | 59 |
| 19.85 | 4.47 | 47 |
| 22.25 | 3.998 | 4 |
| 24.35 | 3.654 | 100 |
| 28.2 | 3.164 | 16 |
| 31.6 | 2.831 | 12 |
| 34.7 | 2.584 | 16 |
| 37.6 | 2.394 | 2 |
| 40.3 | 2.240 | 4 |
| 42.85 | 2.110 | 5 |
| 47.65 | 1.909 | 4 |
| 52.0 | 1.758 | 8 |

(b) A portion of the as-synthesized FeAPSO-20 of part (a) was calcined in air heating the sample from 500° C. to 600° C. over a period of 2 hours. The calcined product was characterized by the x-ray powder diffraction pattern below:

| 2θ | d, (Å) | 100 × I/Io |
|---|---|---|
| 7.05* | 12.56 | 6 |
| 7.5* | 11.82 | 6 |
| 14.05 | 6.31 | 100 |
| 20.05 | 4.43 | 28 |
| 22.6 | 3.935 | 6 |
| 23.85* | 3.733 | 5 |
| 24.5 | 3.635 | 45 |
| 28.4 | 3.143 | 11 |
| 31.7 | 2.823 | 11 |
| 34.8 | 2.578 | 9 |

*impurity peak (c) The FeAPSO20 compositions are generally characterized by the data of Table XII-C below:

TABLE XII-C

| 2θ | d, (Å) | Relative Intensity |
|---|---|---|
| 13.95–14.0 | 6.34–6.33 | m-vs |
| 19.8–20.0 | 4.48–4.44 | m |
| 24.3–24.5 | 3.663–3.633 | m-vs |
| 28.15–28.4 | 3.169–3.143 | w |
| 31.6–31.7 | 2.831–2.823 | w |
| 34.7–34.8 | 2.585–2.578 | w |

(d) The FeAPSO-20 compositions for which x-ray powder diffraction data have been obtained have patterns which are characterized by the x-ray powder diffraction pattern shown in Table XIII-C, below:

TABLE XIII-C

| 2θ | d, (Å) | 100 × I/Io |
|---|---|---|
| 13.95–14.0 | 6.34–6.33 | 57–100 |
| 19.8–20.0 | 4.48–4.44 | 28–47 |
| 22.25–22.6 | 3.998–3.935 | 3–6 |
| 24.3–24.5 | 3.663–3.633 | 45–100 |
| 28.15–28.4 | 3.169–3.143 | 11–16 |
| 31.6–31.7 | 2.831–2.823 | 11–12 |
| 34.7–34.8 | 2.585–2.578 | 9–16 |
| 37.6 | 2.392 | 2–3 |
| 40.2–40.3 | 2.242–2.240 | 4 |
| 42.7–42.85 | 2.114–2.110 | 5 |
| 47.5–47.6 | 1.914–1.909 | 3–4 |
| 52.0 | 1.759 | 8 |

EXAMPLE 51C (a) FeAPSO-31, as prepared in example 34C, was subjected to x-ray analysis. FeAPSO-31 was determined to have a characteristic x-ray powder diffraction pattern which contains the d-spacings set forth below:

| 2θ | d, (Å) | 100 × I/Io |
|---|---|---|
| 8.5 | 10.41 | 64 |
| 9.45* | 9.35 | 5 |
| 13.0 | 6.81 | 1 |
| 14.6 | 6.07 | 1 |
| 15.7 | 5.64 | 3 |
| 17.05 | 5.20 | 6 |
| 18.3 | 4.85 | 3 |
| 20.25 | 4.39 | 49 |
| 21.05* | 4.22 | 9 |
| 21.95 | 4.05 | 32 |
| 22.6 | 3.936 | 100 |
| 23.2 | 3.833 | 6 |
| 25.1 | 3.546 | 4 |
| 25.65 | 3.474 | 4 |
| 26.45 | 3.372 | 2 |
| 27.9 | 3.195 | 13 |
| 28.7 | 3.110 | 1 |
| 29.7 | 3.008 | 7 |
| 31.7 | 2.821 | 20 |
| 32.7 | 2.739 | 1 |
| 35.15 | 2.555 | 9 |
| 36.1 | 2.489 | 2 |
| 37.2 | 2.418 | 2 |
| 37.65 | 2.390 | 2 |
| 38.15 | 2.358 | 3 |
| 39.3 | 2.293 | 4 |
| 39.6 | 2.275 | 3 |
| 40.2 | 2.244 | 2 |
| 45.2 | 2.006 | 2 |
| 46.65 | 1.947 | 3 |
| 48.65 | 1.871 | 2 |
| 50.75 | 1.799 | 2 |
| 51.65 | 1.770 | 4 |
| 55.5 | 1.650 | 2 |

*Peak may contain impurity (b) A portion of the as-synthesized FeAPSO-31 of part (a) was calcined in air at 600° C. for about 2 hours. The calcined product was characterized by the x-ray powder diffraction pattern below:

| 2θ | d, (Å) | 100 × I/Io |
|---|---|---|
| 8.6 | 10.26 | 73 |
| 9.8* | 9.04 | 3 |
| 12.95 | 6.83 | 1 |
| 14.9 | 5.95 | 5 |
| 16.2 | 5.46 | 4 |
| 17.2 | 5.16 | 11 |
| 18.45 | 4.80 | 4 |
| 20.4 | 4.35 | 50 |

-continued

| 2Θ | d, (Å) | 100 × I/Io |
|---|---|---|
| 22.15 | 4.016 | 44 |
| 22.75 | 3.909 | 100 |
| 23.45 | 3.795 | 3 |
| 25.3 | 3.521 | 5 |
| 25.8 | 3.449 | 9 |
| 28.1 | 3.174 | 13 |
| 29.9 | 2.990 | 12 |
| 31.1** | 2.876 | 2 |
| 31.9 | 2.806 | 30 |
| 32.7 | 2.739 | 2 |
| 35.3 | 2.542 | 10 |
| 36.3 | 2.475 | 5 |
| 37.35 | 2.407 | 3 |
| 37.85 | 2.378 | 2 |
| 38.35 | 2.346 | 3 |
| 39.5 | 2.282 | 4 |
| 40.35 | 2.234 | 3 |
| 44.15 | 2.052 | 2 |
| 45.05* | 2.013 | 2 |
| 45.4 | 1.997 | 2 |
| 46.85 | 1.940 | 5 |
| 47.65 | 1.909 | 2 |
| 48.9 | 1.863 | 3 |
| 49.3 | 1.848 | 2 |
| 50.95 | 1.793 | 2 |
| 51.8 | 1.765 | 6 |
| 55.6 | 1.653 | 3 |

*peak may contain impurity
**impurity peak (c) The FeAPSO-31 compositions are generally characterized by the data of Table XIV-C below:

TABLE XIV-C

| 2Θ | d, (Å) | Relative Intensity |
|---|---|---|
| 8.5–8.6 | 10.40–10.28 | w-s |
| 20.2–20.4 | 4.40–4.35 | m |
| 21.1–21.2 | 4.21–4.19 | w |
| 22.0–22.1 | 4.040–4.022 | m |
| 22.6–22.7 | 3.934–3.917 | vs |
| 31.7–31.9 | 2.822–2.805 | w-m |

(d) The FeAPSO-31 compositions for which x-ray powder diffraction data have been obtained have patterns which are characterized by the x-ray powder diffraction pattern shown in Table XV-C below:

TABLE XV-C

| 2Θ | d, (Å) | 100 × I/Io |
|---|---|---|
| 8.5–8.6 | 10.40–10.28 | 10–88 |
| 9.5–9.8 | 9.35–9.04 | 3–11 |
| 9.9 | 8.92 | 0–3 |
| 13.0–13.3 | 6.81–6.67 | 1–4 |
| 14.6–14.9 | 6.07–5.95 | 0–5 |
| 15.7–16.2 | 5.64–5.46 | 3–7 |
| 17.0–17.2 | 5.20–5.17 | 5–11 |
| 18.3–18.5 | 4.84–4.80 | 2–4 |
| 20.2–20.4 | 4.40–4.35 | 36–50 |
| 21.1–21.2 | 4.21–4.19 | 9–18 |
| 22.0–22.1 | 4.040–4.022 | 26–44 |
| 22.6–22.7 | 3.934–3.919 | 100 |
| 23.2–23.4 | 3.833–3.795 | 3–12 |
| 25.1–25.3 | 3.546–3.521 | 4–5 |
| 25.6–25.8 | 3.474–3.449 | 3–9 |
| 26.4–26.6 | 3.372–3.352 | 0–5 |
| 27.4–27.5 | 3.258–3.248 | 2–4 |
| 27.9–28.1 | 3.195–3.174 | 12–14 |
| 28.3 | 3.152 | 0–3 |
| 28.7–28.8 | 3.111–3.103 | 0–3 |
| 29.7–29.9 | 3.008–2.990 | 6–12 |
| 31.1 | 2.876 | 0–2 |
| 31.7–31.9 | 2.822–2.805 | 19–30 |
| 32.7–33.0 | 2.739–2.718 | 0–3 |
| 35.1–35.3 | 2.555–2.542 | 9–10 |
| 36.1–36.3 | 2.489–2.475 | 2–5 |
| 37.3–37.4 | 2.418–2.407 | 0–3 |
| 37.6–37.8 | 2.390–2.378 | 2–3 |
| 38.1–38.4 | 2.365–2.346 | 2–3 |
| 39.3–39.5 | 2.293–2.282 | 3–4 |
| 39.6–39.7 | 2.275–2.271 | 0–3 |
| 40.2–40.3 | 2.244–2.239 | 0–3 |
| 44.1 | 2.052 | 0–2 |
| 44.9 | 2.020 | 0–2 |
| 45.0–45.1 | 2.015–2.012 | 0–2 |
| 45.2–45.4 | 2.006–1.997 | 2–3 |
| 46.6–46.8 | 1.947–1.940 | 3–5 |
| 47.5–47.6 | 1.914–1.909 | 0–2 |
| 48.6–48.9 | 1.872–1.863 | 2–3 |
| 49.1–49.3 | 1.854–1.848 | 0–3 |
| 50.8–50.9 | 1.799–1.793 | 0–2 |
| 51.6–51.8 | 1.771–1.765 | 0–4 |
| 55.5–55.6 | 1.657–1.653 | 0–3 |

EXAMPLE 52C (a) FeAPSO-34, as prepared in example 3C, was subjected to x-ray analysis. FeAPSO-34 was determined to have a charactristic x-ray powder diffraction pattern which contains the d-spacings set forth below:

| 2Θ | d, (Å) | 100 × I/Io |
|---|---|---|
| 7.3* | 12.1 | 5 |
| 9.35 | 9.5 | 100 |
| 12.7 | 7.0 | 10 |
| 14.0 | 6.3 | 8 |
| 14.8* | 5.99 | 2 |
| 15.9 | 5.57 | 32 |
| 17.9 | 4.96 | 7 |
| 19.6* | 4.53 | 3(sh) |
| 20.4 | 4.35 | 50 |
| 22.3 | 3.99 | 6 |
| 22.9 | 3.88 | 2 |
| 25.1 | 3.548 | 10 |
| 25.7 | 3.466 | 11 |
| 27.5 | 3.243 | 2 |
| 28.2 | 3.164 | 2 |
| 29.4 | 3.038 | 2(sh) |
| 30.4 | 2.940 | 19 |
| 31.1 | 2.876 | 12 |
| 34.4 | 2.607 | 4 |
| 36.2 | 2.481 | 2 |
| 39.5 | 2.281 | 2 |
| 43.3 | 2.090 | 3 |
| 47.5 | 1.914 | 2 |
| 48.9 | 1.863 | 3 |
| 51.0 | 1.791 | 2 |
| 53.0 | 1.728 | 2 |
| 54.5 | 1.684 | 1 |

*Impurity peak (b) A portion of the as-synthesized FeAPSO-34 of part (a) was calcined in air at 600° C. for about 2 hours. The calcined product was characterized by the x-ray powder diffraction pattern below:

| 2Θ | d, (Å) | 100 × I/Io |
|---|---|---|
| 7.5* | 11.79 | 7 |
| 9.6 | 9.21 | 100 |
| 13.0 | 6.81 | 17 |
| 16.2 | 5.47 | 9 |
| 16.9 | 5.25 | 1 |
| 18.0 | 4.93 | 5 |
| 19.3 | 4.60 | 5 |
| 19.9* | 4.46 | 2 |
| 20.9 | 4.25 | 17 |
| 22.55 | 3.943 | 7 |
| 23.4 | 3.802 | 2 |
| 24.2 | 3.678 | 2 |
| 25.1 | 3.548 | 5 |

-continued

| 2θ | d, (Å) | 100 × I/Io |
|---|---|---|
| 26.2 | 3.401 | 7 |
| 27.2* | 3.278 | 1 |
| 28.2 | 3.164 | 2 |
| 29.2 | 3.058 | 2 |
| 31.0 | 2.885 | 16 |

*Impurity peak (c) The FeAPSO-34 compositions are generally characterized by the data of Table XVI-C below:

TABLE XVI-C

| 2θ | d, (Å) | Relative Intensity |
|---|---|---|
| 9.35–9.7 | 9.46–9.12 | vs |
| 12.7–13.0 | 6.97–6.81 | w-m |
| 15.9–16.2 | 5.57–5.47 | w-m |
| 20.4–20.9 | 4.35–4.25 | w-s |
| 22.3–22.5 | 3.99–3.95 | vw-s |
| 25.7–26.2 | 3.466–3.401 | vw-m |

(d) The FeAPSO-34 compositions for which x-ray powder diffraction data have been obtained have patterns which are characterized by the x-ray powder diffraction pattern shown in Table XVII-C below:

TABLE XVII-C

| 2θ | d, (Å) | 100 × I/Io |
|---|---|---|
| 9.35–9.7 | 9.46–9.12 | 100 |
| 12.7–13.0 | 6.97–6.81 | 10–25 |
| 13.9–14.1 | 6.37–6.28 | 2–11 |
| 15.9–16.2 | 5.57–5.47 | 9–47 |
| 17.6–18.0 | 5.04–4.93 | 5–16 |
| 18.9–19.3 | 4.70–4.60 | 0–5 |
| 20.4–20.9 | 4.35–4.25 | 17–89 |
| 22.3–22.5 | 3.99–3.95 | 4–88 |
| 22.9–23.4 | 3.88–3.80 | 2–8 |
| 24.8–25.3 | 3.59–3.52 | 5–18 |
| 25.7–26.2 | 3.466–3.401 | 7–32 |
| 27.5–27.6 | 3.243–3.232 | 0–5 |
| 28.0–28.4 | 3.187–3.134 | 1–3 |
| 29.4–29.6 | 3.038–3.018 | 0–4(sh) |
| 30.4–30.6 | 2.940–2.922 | 0–28 |
| 31.0–31.2 | 2.885–2.867 | 2(sh)–17 |
| 32.4 | 2.763 | 0–1 |
| 34.4–34.6 | 2.607–2.592 | 0–13 |
| 35.9–36.3 | 2.501–2.475 | 0–3 |
| 39.5–39.6 | 2.281–2.276 | 0–3 |
| 43.3–43.4 | 2.090–2.085 | 0–4 |
| 47.5–47.6 | 1.914–1.910 | 0–5 |
| 48.6–49.1 | 1.873–1.855 | 0–7 |
| 50.6–51.1 | 1.804–1.787 | 0–3 |
| 53.0–53.2 | 1.728–1.722 | 0–3 |
| 54.5–54.6 | 1.684–1.681 | 0–1 |

EXAMPLE 53C (a) FeAPSO-35, as prepared in example 27C, C was subjected to x-ray analysis. FeAPSO-35 was determined to have a characteristic x-ray powder diffraction pattern which contains the d-spacings set forth below:

| 2θ | d, (Å) | 100 × I/Io |
|---|---|---|
| 8.7 | 10.19 | 5 |
| 11.0 | 8.03 | sh |
| 11.4** | 7.77 | 51 |
| 13.5 | 6.57 | 9 |
| 16.0 | 5.55 | 3 |
| 17.4 | 5.09 | 28 |
| 17.9 | 4.95 | 5 |
| 18.65** | 4.76 | 50 |
| 21.0 | 4.22 | 15 |
| 21.9 | 4.06 | 100 |
| 22.9** | 3.885 | 9 |

-continued

| 2θ | d, (Å) | 100 × I/Io |
|---|---|---|
| 23.45 | 3.793 | 8 |
| 25.1 | 3.548 | 3 |
| 26.5** | 3.365 | 25 |
| 27.15 | 3.285 | 7 |
| 28.6 | 3.118 | 16 |
| 28.9* | 3.091 | (sh) |
| 29.7** | 3.010 | 27 |
| 32.2 | 2.780 | (sh) |
| 32.5** | 2.754 | 13 |
| 34.6 | 2.591 | 7 |
| 37.8* | 2.381 | 10 |
| 44.1** | 2.053 | 3 |
| 48.25* | 1.886 | 8 |
| 51.6 | 1.774 | 1 |
| 52.15** | 1.754 | 2 |
| 54.5** | 1.684 | 3 |

*peak may contain impurity
**impurity peak (b) The FeAPSO-35 compositions are generally characterized by the data of Table XVIII-C below:

TABLE XVIII-C

| 2θ | d, (Å) | Relative Intensity |
|---|---|---|
| 10.9–11.1 | 8.12–7.97 | vw-m |
| 13.2–13.5 | 6.71–6.56 | vw-w |
| 17.2–17.4 | 5.16–5.10 | w-m |
| 21.85–22.0 | 4.07–4.04 | vs |
| 23.2–23.8 | 3.834–3.739 | vw-m |
| 32.0–32.25 | 2.797–2.776 | vw-m |

(c) The FeAPSO-325 compositions are generally characterized by the x-ray powder diffraction pattern shown in Table XIX-C, below:

TABLE XIX-C

| 2θ | d, (Å) | 100 × I/Io |
|---|---|---|
| 8.6–8.7 | 10.28–10.19 | 0–14 |
| 10.9–11.1 | 8.12–7.97 | sh-38 |
| 13.2–13.5 | 6.71–6.56 | 7–19 |
| 15.8–16.2 | 5.61–5.47 | 1–6 |
| 17.2–17.4 | 5.16–5.10 | 11–41 |
| 17.75–17.9 | 5.00–4.95 | sh-8 |
| 20.8–21.25 | 4.27–4.18 | sh-15 |
| 21.85–22.0 | 4.07–4.040 | 100 |
| 23.2–23.8 | 3.834–3.739 | 0–20 |
| 24.9–25.1 | 3.576–3.548 | 0–3 |
| 26.9–27.15 | 3.314–3.285 | 0–15 |
| 28.5–28.65 | 3.132–3.114 | sh-16 |
| 28.8–29.0 | 3.100–3.082 | 0-sh |
| 32.0–32.25 | 2.797–2.776 | sh-24 |
| 34.5–34.9 | 2.600–2.571 | 3–8 |
| 37.7–38.1 | 2.386–2.362 | 6–10 |

EXAMPLE 54C (a) FeAPSO-44, as prepared in example 32C, was subjected to x-ray analysis. FeAPSO-44 was determined to have a characteristic x-ray powder diffraction pattern which contains at least the d-spacings set forth below:

| 2θ | d, (Å) | 100 × I/Io |
|---|---|---|
| 7.5** | 11.80 | 670 |
| 9.5 | 9.29 | 94 |
| 12.95* | 6.83 | 70 |
| 14.95** | 5.92 | 132 |
| 16.15 | 5.48 | 30 |
| 17.4 | 5.10 | 7 |
| 19.0 | 4.67 | 7 |
| 19.8** | 4.48 | 326 |
| 21.0* | 4.23 | 332 |

-continued

| 2θ | d, (Å) | 100 × I/Io |
|---|---|---|
| 21.8 | 4.07 | 34 |
| 22.45** | 3.963 | 631 |
| 23.1 | 3.850 | 7 |
| 24.5 | 3.635 | 100 |
| 24.7** | 3.604 | 40 |
| 26.0* | 3.425 | 193 |
| 27.15** | 3.283 | 30 |
| 28.05* | 3.180 | 19 |
| 29.05** | 3.075 | 110 |
| 30.1* | 2.966 | 137 |
| 30.9 | 2.894 | 40 |
| 33.0 | 2.714 | 7 |
| 33.65** | 2.664 | 37 |
| 34.6** | 2.591 | 105 |
| 35.55 | 2.525 | 128 |
| 37.0** | 2.430 | 28 |
| 37.65** | 2.389 | 82 |
| 42.3* | 2.137 | 23 |
| 42.55* | 2.125 | 17 |
| 43.7* | 2.072 | 15 |
| 45.1** | 2.011 | 14 |
| 47.75* | 1.904 | 36 |
| 51.6** | 1.77 | 17 |
| 52.0** | 1.758 | 16 |
| 55.8** | 1.647 | 19 |

*peak might contain impurity
**impurity peak (b) The FeAPSO-44 compositions are generally characterized by the data of Table XX-C below:

TABLE XX-C

| 2θ | d, (Å) | Relative Intensity* |
|---|---|---|
| 9.5 | 9.31 | m |
| 12.95 | 6.83 | m |
| 16.15 | 5.49 | vw |
| 21.0 | 4.23 | vs |
| 24.5 | 3.631 | m |
| 30.9 | 2.894 | w |

*peak intensities were low and may affect accuracy (c) The FeAPSO-44 compositions for which x-ray powder diffraction data have been obtained have patterns which are characterized by the x-ray powder diffraction pattern shown in Table XXI-C below:

TABLE XXI-C

| 2θ | d, (Å) | 100 × I/Io* |
|---|---|---|
| 9.5 | 9.31 | 28 |
| 12.95 | 6.83 | 21 |
| 16.15 | 5.49 | 9 |
| 17.4 | 5.10 | 2 |
| 19.0 | 4.67 | 2 |
| 21.0 | 4.23 | 100 |
| 21.8 | 4.07 | 10 |
| 23.1 | 3.850 | 2 |
| 24.5 | 3.636 | 30 |
| 26.0 | 3.427 | 58 |
| 28.05 | 3.180 | 6 |
| 30.1 | 2.966 | 11 |
| 30.9 | 2.894 | 12 |
| 33.0 | 2.714 | 2 |
| 35.55 | 2.525 | 39 |
| 42.3 | 2.137 | 7 |
| 42.55 | 2.125 | 5 |
| 43.7 | 2.072 | 5 |
| 47.75 | 1.904 | 11 |

*peak intensities were low and may effect accuracy

EXAMPLE 55C (a) FeAPSO-46, as prepared in example 38C was subjected to x-ray analysis. FeAPSO-46 was determined to have a characteristic x-ray powder diffraction pattern which contains the d-spacings set forth below:

| 2θ | d, (Å) | 100 × I/Io |
|---|---|---|
| 6.6 | 13.42 | 3 |
| 7.75 | 11.38 | 100 |
| 12.45 | 7.11 | 2 |
| 13.2 | 6.70 | 2 |
| 13.8 | 6.41 | 1 |
| 15.0 | 5.91 | 1 |
| 15.35 | 5.77 | 1 |
| 16.7 | 5.31 | 2 |
| 17.3 | 5.13 | <1 |
| 19.9 | 4.47 | 1 |
| 20.6 | 4.31 | 3 |
| 21.65 | 4.11 | 7 |
| 22.9 | 3.885 | 4 |
| 24.3 | 3.660 | 3 |
| 25.2 | 3.534 | <1 |
| 26.95 | 3.307 | 3 |
| 27.85 | 3.206 | 2 |
| 28.35 | 3.147 | 1 |
| 28.85 | 3.093 | 3 |
| 29.95 | 2.985 | 1 |
| 30.2 | 2.959 | <1 |
| 30.95 | 2.889 | <1 |
| 31.35 | 2.855 | 2 |
| 31.8 | 2.814 | <1 |
| 33.05 | 2.711 | 1 |
| 34.4 | 2.606 | 1 |
| 36.05 | 2.490 | 3 |
| 36.7 | 2.448 | <1 |
| 39.9 | 2.259 | <1 |
| 41.25 | 2.188 | <1 |
| 44.2 | 2.049 | 1 |
| 47.85 | 1.902 | 1 |
| 50.4 | 1.811 | <1 |
| 51.7 | 1.768 | <1 |
| 52.5 | 1.743 | <1 |

(b) A portion of the as-synthesized FeAPSO-46 of part a) was calcined in air at 500° C. for about 2 hours. The calcined product was characterized by the x-ray powder diffraction pattern below:

| 2θ | d, (Å) | 100 × I/Io |
|---|---|---|
| 6.85 | 12.92 | 9 |
| 8.0 | 11.04 | 100 |
| 13.6 | 6.51 | 4 |
| 15.35 | 5.76 | 3 |
| 16.0 | 5.55 | 3 |
| 17.15 | 5.17 | 3 |
| 21.3 | 4.17 | 2 |
| 22.2 | 4.006 | 2 |
| 23.45 | 3.793 | 2 |
| 24.9 | 3.575 | 2 |
| 27.6 | 3.232 | 2 |
| 32.0 | 2.797 | 2 |

(c) The FeAPSO-46 compositions are generally characterized by the data of Table XXII-C below.

TABLE XXII-C

| 2θ | d, (Å) | Relative Intensity |
|---|---|---|
| 6.6–6.8 | 13.39–13.00 | vw |
| 7.8–8.0 | 11.33–11.05 | vs |
| 13.2–13.6 | 6.71–6.51 | vw |
| 21.65–22.2 | 4.10–4.00 | vw |
| 22.9–23.45 | 3.883–3.793 | vw |
| 26.95–27.6 | 3.308–3.232 | vw |

(d) The FeAPSO-46 compositions for which x-ray powder diffraction data have been obtained to data have patterns which are characterized by the x-ray powder diffraction pattern shown in Table XXIII-C below:

TABLE XXIII-C

| 2θ | d, (Å) | 100 × I/Io |
|---|---|---|
| 6.6–6.8 | 13.39–13.00 | 3–9 |
| 7.8–8.0 | 11.33–11.05 | 100 |
| 12.45–12.6 | 7.11–7.03 | 0–3 |
| 13.2–13.6 | 6.71–6.51 | 2–4 |
| 13.8–14.0 | 6.41–6.33 | 1–2 |
| 15.0–15.35 | 5.91–5.76 | 1–3 |
| 15.35–16.0 | 5.77–5.55 | 1–3 |
| 16.7–17.15 | 5.31–5.17 | 2–3 |
| 17.3 | 5.13 | 0–1 |
| 19.9–20.5 | 4.47–4.43 | 1–2 |
| 20.6–21.3 | 4.31–4.17 | 2–3 |
| 21.65–22.2 | 4.10–4.00 | 2–8 |
| 22.9–23.45 | 3.883–3.793 | 2–4 |
| 24.3–24.9 | 3.659–3.575 | 2–3 |
| 25.2 | 3.534 | 0–1 |
| 26.95–27.6 | 3.308–3.232 | 2–4 |
| 27.85–27.95 | 3.206–3.190 | 0–3 |
| 28.35–28.55 | 3.147–3.125 | 0–2 |
| 28.85–29.05 | 3.093–3.076 | 0–3 |
| 29.95–30.1 | 2.985–2.968 | 0–1 |
| 30.2 | 2.959 | 0–1 |
| 30.95 | 2.889 | 0–1 |
| 31.3–32.0 | 2.855–2.797 | 2 |
| 31.8–32.05 | 2.814–2.792 | 0–1 |
| 33.05 | 2.711 | 0–1 |
| 34.4 | 2.608 | 0–1 |
| 36.05–36.2 | 2.490–2.481 | 0–3 |
| 36.7 | 2.448 | 0–1 |
| 39.9 | 2.259 | 0–1 |
| 41.25 | 2.188 | 0–1 |
| 44.2–44.35 | 2.049–2.043 | 0–1 |
| 47.8–48.0 | 1.902–1.895 | 0–1 |
| 50.4 | 1.811 | 0–1 |
| 51.7 | 1.768 | 0–1 |
| 52.5 | 1.743 | 0–1 |

EXAMPLE 56C

In order to demonstrate the catalytic activity of the FeAPSO compositions, calcined samples of FeAPSO products were tested for the catalytic cracking of n-butane using a bench-scale apparatus.

The reactor was a cylindrical quartz tube 254 mm. in length and 10.3 mm I.D. In each test the reactor was loaded with particles of the selected FeAPSO which were 20–40 mesh (U.S. std.) in size and in an amount of from 0.5 to 5 grams, the quantity being selected so that the conversion of n-butane was at least 5% and not more than 90% under the test conditions. The samples had been previously calcined in air or nitrogen to remove organic materials from the pore system, and were activated in situ in the reactor in a flowing stream of helium at 500° C. for one hour. The feedstock was a helium and n-butane mixture containing 2 mole percent n-butane and was passes through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the FeAPSO compositions. The $k_A$ value (cm$^3$/g min) obtained for the FeAPSO compositions are set forth, below, in Table XXIV-C:

TABLE XXIV-C

| FeAPSO of Example No.:[1] | Rate Constant ($k_A$) |
|---|---|
| FeAPSO-5 (Ex. 12C) | 0.5 |
| FeAPSO-11 (Ex. 10C) | 0.7 |
| FeAPSO-31 (Ex. 34C) | 1.3 |
| FeAPSO-46 (Ex. 37C) | 0.9 |

[1]FeAPSO were calcined as follows prior to being activated.
(a) FeAPSO-5 at 600° C. in air for 2 hours,
(b) FeAPSO-11: at 600° C. in air for 2.25 hours,
(c) FeAPSO-31: at 500° C. to 600° C. in air for 2 hours; and
(d) FeAPSO-46: heated from 100° C. to 600° C. in nitrogen over a 2-hour period.

D. MANGANESE-ALUMINUM-PHOSPHORUS-SILICON-OXIDE MOLECULAR SIEVES

Molecular sieves containing manganese, aluminum, phosphorus and silicon as framework tetrahedral oxide units are prepared as follows:

Preparative Reagents

In the following examples the MnAPSO compositions were prepared using numerous reagents. The reagents employed and abbreviations employed herein, if any, for such reagents are as follows:

(a) Alipro: aluminum isopropoxide;
(b) CATAPAL: Trademark of Condea Corporation for hydrated pseudoboehmite:
(c) LUDOX-LS: LUDOX-LS is the tradename of DuPont for an aqueous solution of 30 weight percent SiO$_2$ and 0.1 weight percent Na$_2$O:
(d) H$_3$PO$_4$: 85 weight percent aqueous phosphoric acid:
(e) MnAc: Manganese acetate, Mn(C$_2$H$_3$O$_2$)$_2$·4H$_2$O;
(f) TEAOH: 40 weight percent aqueous solution of tetraethylammonium hydroxide;
(g) TBAOH: 40 weight percent aqueous solution of tetrabutylammonium hydroxide;
(h) Pr$_2$NH: di-n-propylamine, (C$_3$H$_7$)$_2$NH;
(i) Pr$_3$N: tri-n-propylamine (C$_3$H$_7$)$_3$N;
(j) Quin: Quinuclidine, (C$_7$H$_{13}$N);
(k) MQuin: Methyl Quinuclidine hydroxide, (C$_7$H$_{13}$NCH$_3$OH);
(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

Preparative Procedures

The following preparative examples were carried out by forming a starting reaction mixture by adding the H$_3$PO$_4$ to one half of the quantity of water. This mixture was mixed and to this mixture the aluminum isopropoxide or CATAPAL was added. This mixture was then blended until a homogeneous mixture was observed. To this mixture the LUDOX LS was added and the resulting mixture blended (about 2 minutes) until a homogeneous mixture was observed. A second mixture was prepared using the manganese acetate and the remainder (about 50%) of the water. The two mixtures were admixed and the resulting mixture blended until a homogeneous mixture was observed. The organic templating agent was then added to the resulting mixture and the resulting mixture blended until a homogeneous mixture was observed, i.e., about 2 to 4 minutes. (The pH of the mixture was measured and adjusted for temperature). The mixture was then placed in a lined (polytetrafluoroethylene) stainless steel pressure vessel and digested at a temperature (150° C. or 200° C.) for a time or placed in lined screw top bottles for digestion at 100° C. All digestions were carried out at the autogeneous pressure.

The molar composition for each preparation will be given by the relative moles of the components of the reaction mixture with H₃PO₄ and MnAc are given respectively in terms of $P_2O_5$ and MnO content of the reaction mixture.

The following examples are provided to further illustrate the invention and are not intended to be limiting thereof;

EXAMPLES 1D TO 64D

MnAPSO molecular sieves were prepared according to the above identified procedure and the MnAPSO products determined by X-ray analysis. The results of examples 1D to 64D are set forth in Tables I-D to IV-D.

TABLE I-D

| Example[1] | Template | Temp (°C.) | Time (days) | MnAPSO Product[2] |
|---|---|---|---|---|
| 1D | TEAOH | 150 | 4 | MnAPSO-34; MnAPSO-5 |
| 2D | TEAOH | 150 | 11 | MnAPSO-5; MnAPSO-34 |
| 3D | TEAOH | 200 | 4 | MnAPSO-5; MnAPSO-34 |
| 4D | TEAOH | 200 | 11 | MnAPSO-5; MnAPSO-34 |
| 5D | TEAOH | 100 | 2 | —[3] |
| 6D | TEAOH | 100 | 7 | MnAPSO-34; |
| 7D | TEAOH | 150 | 2 | MnAPSO-34; MnAPSO-5 |
| 8D | TEAOH | 150 | 7 | MnAPSO-34; MnAPSO-5 |
| 9D | TEAOH | 200 | 2 | MnAPSO-5; MnAPSO-34 |
| 10D | TEAOH | 200 | 7 | MnAPSO-5; MnAPSO-34 |
| 11D | TEAOH | 100 | 14 | MnAPSO-34; |
| 12D | TEAOH | 150 | 14 | MnAPSO-34; MnAPSO-5 |
| 13D | TEAOH | 200 | 14 | MnAPSO-5; MnAPSO-34 |

[1]The reaction mixture comprised: 1.0 TEAOH: 0.2 MnO: 0.9 Al₂O₃: 0.9 P₂O₅: rSiO₂: 50 H₂O where "r" was 0.2 for examples 1D to 4D and was 0.6 for examples 5D to 13D.
[2]Major species as identified by x-ray powder diffraction pattern of product, except that when two species where identified the first species listed is the predominant species observed.
[3]No MnAPSO products were observed by x-ray analysis.

TABLE II-D

| Example[1] | Template | Temp (°C.) | Time (days) | MnAPSO Product[2] |
|---|---|---|---|---|
| 14D | Quin | 150 | 4 | MnAPSO-16; MnAPSO-35 |
| 15D | Quin | 150 | 11 | MnAPSO-16; MnAPSO-35 |
| 16D | Quin | 200 | 4 | MnAPSO-16; MnAPSO-35 |
| 17D | Quin | 200 | 11 | MnAPSO-16; MnAPSO-35 |
| 18D | Quin | 100 | 4 | MnAPSO-35 |
| 19D | Quin | 100 | 11 | MnAPSO-35 |
| 20D | MQuin | 150 | 2 | MnAPSO-35; MnAPSO-16 |
| 21D | MQuin | 150 | 7 | MnAPSO-35 |
| 22D | MQuin | 200 | 2 | MnAPSO-35 |
| 23D | MQuin | 200 | 7 | MnAPSO-35 |
| 24D | Pr₂NH | 150 | 4 | MnAPSO-11 |
| 25D | Pr₂NH | 150 | 11 | MnAPSO-11 |
| 26D | Pr₂NH | 200 | 4 | MnAPSO-11; MnAPSO-39 |
| 27D | Pr₂NH | 200 | 11 | MnAPSO-11; MnAPSO-39 |
| 28D | Pr₂NH | 100 | 4 | —[3] |
| 29D | Pr₂NH | 100 | 11 | —[3] |

[1]The reaction mixture comprised: 1.0 R: 0.2 MnO: 0.9 Al₂O₃: 0.9 P₂O₅: 0.2 SiO₂: 50 H₂O where "R" is the template, as identified in Table II-D.
[2]Major species as identified by x-ray powder diffraction pattern of product, except that when two species where identified the first species listed is the predominant species observed.
[3]No MnAPSO products were observed by x-ray analysis.

TABLE III-D

| Example[1] | Template | Temp (°C.) | Time (days) | MnAPSO Product[2] |
|---|---|---|---|---|
| 30D | Pr₃N | 150 | 4 | MnAPSO-5 |
| 31D | Pr₃N | 150 | 11 | MnAPSO-5 |
| 32D | Pr₃N | 200 | 4 | MnAPSO-5 |
| 33D | Pr₃N | 200 | 11 | MnAPSO-5 |
| 34D | Pr₃N | 100 | 4 | —[3] |
| 35D | Pr₃N | 100 | 11 | —[3] |
| 36D | TBAOH | 150 | 4 | —[3] |
| 37D | TBAOH | 150 | 10 | —[3] |
| 38D | TBAOH | 200 | 4 | MnAPSO-5 |
| 39D | TBAOH | 200 | 10 | MnAPSO-5 |
| 40D | C-hex | 150 | 3 | MnAPSO-13 |
| 41D | C-hex | 150 | 9 | MnAPSO-44; MnAPSO-13 |
| 42D | C-hex | 200 | 3 | MnAPSO-5; MnAPSO-44 |
| 43D | C-hex | 200 | 9 | MnAPSO-5; MnAPSO-44 |

[1]The reaction mixture comprised:
(a) Examples 30D to 35D: 1.0 Pr₃N; 0.2 MnO; 0.9 Al₂O₃; 0.9 P₂O₅; 0.2 SiO₂; 50 H₂O
(b) Examples 36D to 39D: 2.0 TBAOH; 0.4 MnO; 0.8 Al₂O₃; 1.0 P₂O₅; 0.4 SiO₂; 50 H₂O
(c) Examples 40D to 43D: 1.0 C-hex; 0.2 MnO; 0.9 Al₂O₃; 0.9 P₂O₅; 0.6 SiO₂; 50 H₂O
[2]Major species as identified by x-ray powder diffraction pattern of product, except that when two species where identified the first species listed is the predominant species observed.
[3]No MnAPSO products were observed by x-ray analysis.

TABLE IV-D

| Example[1] | Template | Temp (°C.) | Time (days) | MnAPSO Product[2] |
|---|---|---|---|---|
| 44D | TPAOH | 150 | 2 | MnAPSO-5 |
| 45D | TPAOH | 200 | 2 | MnAPSO-5 |
| 46D | TMAOH | 150 | 4 | MnAPSO-20 |
| 47D | TMAOH | 200 | 4 | MnAPSO-20 |
| 48D | DEA | 150 | 9 | MnAPSO-47 |
| 49D | DEA | 150 | 18 | MnAPSO-47 |
| 50D[4] | Pr$_2$NH | 150 | 4 | MnAPSO-31 |
| 51D[4] | Pr$_2$NH | 150 | 10 | MnAPSO-31; MnAPSO-46 |
| 52D[4] | Pr$_2$NH | 200 | 4 | MnAPSO-31; MnAPSO-11 |
| 53D[4] | Pr$_2$NH | 200 | 10 | MnAPSO-31; MnAPSO-11 |
| 54D[4] | Pr$_2$NH | 150 | 2 | MnAPSO-31 |
| 55D[4] | Pr$_2$NH | 150 | 2 | MnAPSO-31 |
| 56D[4] | Pr$_2$NH | 200 | 2 | MnAPSO-31; MnAPSO-11 |
| 57D | Pr$_2$NH | 200 | 25 | MnAPSO-11; MnAPSO-5; MnAPSO-39; MnAPSO-46 |
| 58D | Quin | 225 | 5 | MnAPSO-16; MnAPSO-35 |
| 59D[5] | Pr$_3$N | 150 | 2 | MnAPSO-36 |
| 60D[5] | Pr$_3$N | 150 | 7 | MnAPSO-36; MnAPSO-5 |
| 61D[5] | Pr$_3$N | 200 | 2 | MnAPSO-36; MnAPSO-5 |
| 62D[5] | Pr$_3$N | 200 | 7 | MnAPSO-36; MnAPSO-5 |
| 63D | C-hex | 225 | 5 | MnAPSO-5; MnAPSO-44 |
| 64D | C-hex | 200 | 4 | MnAPSO-44 |

[1]The reaction mixture comprised: 1.0 R; 0.2 MnO; 0.9 Al$_2$O$_3$; 0.9 P$_2$O$_5$; 0.6 SiO$_2$; 50 H$_2$O where R is as above identified and except than in examples 48D, 49D, 57D and 64D the moles of "R" was 2.0 and in example 58D the coefficient for P$_2$O$_5$ was 1.0 instead of 0.9.
[2]Major species as identified by x-ray powder diffraction pattern of product, except that when two species where identified the first species listed is the predominant species observed.
[3]No MnAPSO products were observed by x-ray analysis.
[4]Seed crystals of AlPO$_4$-31 were employed (U.S. Pat. No. 4,310,440).
[5]Seed crystals of MnAPO-36 were employed, as disclosed in U.S. Ser. No. 514,334, filed July 15, 1983.

EXAMPLE 65D (a) Samples of the MnAPSO products were calcined in air or nitrogen to remove at least part of the organic templating agent of the product. The example in which a given MnAPSO product was prepared is given in parenthesis. The adsorption capacities of each calcined sample were measured using a standard McBain-Bakr gravimetric adsorption apparatus. The samples were activated in a vacuum (less than 0.04 torr) at 350° C. prior to measurement. The McBain-Bakr data for the aforementioned MnAPSO molecular sieves are set forth hereinafter.

| (a) MnAPSO-5 (Example 31D) | | | | |
|---|---|---|---|---|
| Adsorbate | Kinetic Diameter, Å | Pressure (Torr) | Temp (°C.) | Wt. % Adsorbed* |
| O$_2$ | 3.46 | 102 | −183 | 8.9 |
| O$_2$ | 3.46 | 750 | −183 | 10.8 |
| n-butane | 4.3 | 504 | 23.0 | 4.4 |
| cyclohexane | 6.0 | 65 | 23.4 | 5.4 |
| H$_2$O | 2.65 | 4.6 | 23.0 | 8.1 |
| H$_2$O | 2.65 | 19.5 | 23.0 | 17.1 |

*MnAPSO-5 was calcined at 600° in air for 4 hours.

The above data demonstrate that the pore size of the calcined MnAPSO-5 product is greater than about 6.2 Å.

| (b) MnAPSO-11 (Example 24D) | | | | |
|---|---|---|---|---|
| Adsorbate | Kinetic Diameter, Å | Pressure (Torr) | Temp (°C.) | Wt. % Adsorbed* |
| O$_2$ | 3.46 | 102 | −183 | 7.0 |
| O$_2$ | 3.46 | 744 | −183 | 11.1 |
| neopentane | 6.2 | 741 | 25.3 | 2.5 |
| isobutane | 5.0 | 740 | 24.2 | 3.5 |
| cyclohexane | 6.0 | 82 | 23.9 | 10.7 |
| H$_2$O | 2.65 | 4.6 | 24.9 | 5.1 |
| H$_2$O | 2.65 | 19 | 24.8 | 14.9 |

*MnAPSO was calcined at 600° in air for 2 hours.

The above data demonstrate that the pore size of the calcined MnAPSO-11 product is greater than about 6.0 Å.

| (c) MnAPSO-20 (Example 46D) | | | | |
|---|---|---|---|---|
| Adsorbate | Kinetic Diameter, Å | Pressure (Torr) | Temp (°C.) | Wt. % Adsorbed* |
| O$_2$ | 3.46 | 102 | −183 | 0.7 |
| O$_2$ | 3.46 | 744 | −183 | 1.2 |
| H$_2$O | 2.65 | 4.6 | 23.3 | 9.0 |
| H$_2$O | 2.65 | 19 | 23.2 | 13.7 |

*MnAPSO calcined at 500° C. in air for 1 hour.

The above data demonstrate that the pore size of the calcined MnAPSO-20 product is greater than about 2.65 Å and less than about 3.46 Å.

| (d) MnAPSO-31 (Example 55D) | | | | |
|---|---|---|---|---|
| Adsorbate | Kinetic Diameter, Å | Pressure (Torr) | Temp (°C.) | Wt. % Adsorbed* |
| O$_2$ | 3.46 | 105 | −183 | 5.6 |
| O$_2$ | 3.46 | 741 | −183 | 9.7 |
| Neopentane | 6.2 | 739 | 23.5 | 4.6 |
| H$_2$O | 2.65 | 4.6 | 23.8 | 5.8 |
| H$_2$O | 2.65 | 20 | 24.0 | 15.5 |

*MnAPSO-31 calcined at 500° C. in air for 1.5 hours.

The above data demonstrate that the pore size of the calcined MnAPSO-31 product is greater than about 6.2 Å.

(e) MnAPSO-34 (Example 11D)

| Adsorbate | Kinetic Diameter, Å | Pressure (Torr) | Temp (°C.) | Wt. % Adsorbed* |
|---|---|---|---|---|
| $O_2$ | 3.46 | 103 | −183 | 11.4 |
| $O_2$ | 3.46 | 731 | −183 | 15.6 |
| isobutane | 5.0 | 741 | 24.5 | 0.8 |
| n-hexane | 4.3 | 103 | 24.4 | 4.6 |
| $H_2O$ | 2.65 | 4.6 | 24.4 | 15.2 |
| $H_2O$ | 2.65 | 18.5 | 23.9 | 24.4 |

*MnAPSO-34 was calcined at 425° C. in nitrogen for 2 hours.

The above data demonstrate that the pore size of the calcined MnAPSO-34 product is about 4.3 Å.

(f) MnAPSO-35 (Example 21D)

| Adsorbate | Kinetic Diameter, Å | Pressure (Torr) | Temp (°C.) | Wt. % Adsorbed* |
|---|---|---|---|---|
| $O_2$ | 3.46 | 103 | −183 | 1.8 |
| $O_2$ | 3.46 | 731 | −183 | 2.6 |
| n-hexane | 4.3 | 103 | 24.4 | 0.8 |
| $H_2O$ | 2.65 | 4.6 | 24.4 | 9.9 |
| $H_2O$ | 2.65 | 18.5 | 23.9 | 15.9 |

*MnAPSO-35 was calcined at 500° C. in nitrogen for 2 hours.

The above data demonstrate that the pore size of the calcined MnAPSO-35 product is about 4.3 Å.

(g) MnAPSO-44 (Example 64D)

| Adsorbate | Kinetic Diameter, Å | Pressure (Torr) | Temp (°C.) | Wt. % Adsorbed* |
|---|---|---|---|---|
| $O_2$ | 3.46 | 102 | −183 | 18.2 |
| $O_2$ | 3.46 | 744 | −183 | 20.1 |
| n-hexane | 4.3 | 95 | 23.6 | 1.3 |
| isobutane | 5.0 | 746 | 24.1 | 0.5 |
| $H_2O$ | 2.65 | 4.6 | 24.8 | 22.7 |
| $H_2O$ | 2.65 | 19 | 29.8 | 27.7 |

*MnAPSO-44 was calcined at 500° C. in air for 1.0 hour.

The above data demonstrate that the pore size of the calcined MnAPSO-44 product about 4.3 Å.

EXAMPLE 66D

Samples of the as-synthesized products of certain examples were subjected to chemical analysis. The example in which a given MnAPSO was prepared is noted in parenthesis. The chemical analysis for these MnAPSO was as follows:

(a) The chemical analysis of MnAPSO-5 (Example 31D) was:

| Component | Weight Percent |
|---|---|
| $Al_2O_3$ | 31.8 |
| $P_2O_5$ | 46.4 |
| MnO | 4.1 |
| $SiO_2$ | 3.0 |
| Carbon | 5.2 |
| LOI* | 14.5 |

*LOI = Loss on Ignition

The above chemical analysis gives an overall product composition in molar oxide ratios (anhydrous basis) of: 0.058 MnO; 0.312 $Al_2O_3$: 0.327 $P_2O_5$: 0.050 $SiO_2$; and a formula (anhydrous basis) of:

0.05 R $(Mn_{0.04}Al_{0.45}P_{0.47}Si_{0.04})O_2$ (b) The chemical analysis of MnAPSO-11 (Example 24D) was:

| Component | Weight Percent |
|---|---|
| $Al_2O_3$ | 32.5 |
| $P_2O_5$ | 46.7 |
| MnO | 4.3 |
| $SiO_2$ | 2.1 |
| Carbon | 4.1 |
| LOI* | 14.0 |

*LOI = Loss on Ignition

The above chemical analysis gives an overall product composition in molar oxide ratios (anhydrous basis) of: 0.061 MnO; 0.319 $Al_2O_3$: 0.329 $P_2O_5$; 0.035 $SiO_2$; and a formula (anhydrous basis) of:

0.06 R $(Mn_{0.04}Al_{0.46}P_{0.47}Si_{0.03})O_2$ (c) The chemical analysis of MnAPSO-20 (Example 46D) was:

| Component | Weight Percent |
|---|---|
| $Al_2O_3$ | 27.3 |
| $P_2O_5$ | 39.6 |
| MnO | 4.6 |
| $SiO_2$ | 8.0 |
| Carbon | 8.4 |
| LOI* | 19.4 |

*LOI = Loss on Ignition

The above chemical analysis gives an overall product composition in molar oxide ratios (anhydrous basis) of: 0.065 MnO; 0.268 $Al_2O_3$: 0.279 $P_2O_5$: 0.133 $SiO_2$; and a formula (anhydrous basis) of:

0.18 R $(Mn_{0.05}Al_{0.41}P_{0.43}Si_{0.10})O_2$ (d) The chemical analysis of MnAPSO-31 was:

| Component | Weight Percent |
|---|---|
| $Al_2O_3$ | 31.8 |
| $P_2O_5$ | 43.8 |
| MnO | 3.2 |
| $SiO_2$ | 2.6 |
| Carbon | 2.9 |
| LOI* | 16.7 |

*LOI = Loss on Ignition

The above chemical analysis gives an overall product composition in molar oxide ratios (anhydrous basis) of: 0.058 MnO: 0.312 $Al_2O_3$; 0.309 $P_2O_5$; 0.043 $SiO_2$; and a formula (anhydrous basis) of:

0.04 R $(Mn_{0.04}Al_{0.47}P_{0.46}Si_{0.03})O_2$ (e) The chemical analysis of MnAPSO-34 (Example 6D) was:

| Component | Weight Percent |
|---|---|
| $Al_2O_3$ | 25.0 |
| $P_2O_5$ | 35.8 |
| MnO | 7.9 |
| $SiO_2$ | 11.6 |
| Carbon | 3.3 |
| LOI* | 19.7 |

*LOI = Loss on Ignition

The above chemical analysis gives an overall product composition in molar oxide ratios (anhydrous basis) of: 0.11 MnO; 0.25 $Al_2O_3$; 0.19 $P_2O_5$; 0.19 $SiO_2$; and a formula (anhydrous basis) of:

0.04 R $(Mn_{0.09}Al_{0.38}P_{0.39}Si_{0.15})O_2$ (f) The chemical analysis of MnAPSO-35 (Example 23D) was:

| Component | Weight Percent |
|---|---|
| $Al_2O_3$ | 25.2 |
| $P_2O_5$ | 41.3 |
| MnO | 7.1 |
| $SiO_2$ | 4.2 |
| Carbon | 12.8 |
| LOI* | 21.3 |

*LOI = Loss on Ignition

The above chemical analysis gives an overall product composition in molar oxide ratios (anhydrous basis) of: 0.100 MnO; 0.247 $Al_2O_3$; 0.291 $P_2O_5$; 0.07 $SiO_2$; and a formula (anhydrous basis) of:

0.13 R $(Mn_{0.08}Al_{0.40}P_{0.47}Si_{0.06})O_2$ (g) The chemical analysis of MnAPSO-36 (Example 59D) was:

| Component | Weight Percent |
|---|---|
| $Al_2O_3$ | 27.7 |
| $P_2O_5$ | 37.2 |
| MnO | 4.6 |
| $SiO_2$ | 9.5 |
| Carbon | 3.0 |
| LOI* | 19.6 |

*LOI = Loss on Ignition

The above chemical analysis gives an overall product composition in molar oxide ratios anhydrous basis) of: 0.065 MnO; 0.272 $Al_2O_3$; 0.262 $P_2O_5$; 0.158 $SiO_2$; and a formula (anhydrous basis) of:

0.03 R $(Mn_{0.05}Al_{0.42}P_{0.41}Si_{0.12})O_2$ (h) The chemical analysis of MnAPSO-44 (Example 64D) was:

| Component | Weight Percent |
|---|---|
| $Al_2O_3$ | 25.8 |
| $P_2O_5$ | 36.6 |
| MnO | 4.4 |
| $SiO_2$ | 9.7 |
| Carbon | 2.5 |
| LOI* | 23.1 |

*LOI = Loss on Ignition

The above chemical analysis gives an overall product composition in molar oxide ratios (anhydrous basis) of: 0.062 MnO; 0.253 $Al_2O_3$; 0.258 $P_2O_5$; 0.161 $SiO_2$; and a formula (anhydrous basis) of:

0.04 R $(Mn_{0.05}Al_{0.41}P_{0.41}Si_{0.13})O_2$ (i) The chemical analysis of MnAPSO-47 (Example 49D) was:

| Component | Weight Percent |
|---|---|
| $Al_2O_3$ | 27.6 |
| $P_2O_5$ | 36.2 |
| MnO | 5.0 |
| $SiO_2$ | 5.7 |
| Carbon | 9.9 |
| LOI* | 25.1 |

*LOI = Loss on Ignition

The above chemical analysis gives an overall product composition in molar oxide ratios (anhydrous basis) of: 0.071 MnO; 0.271 $Al_2O_3$; 0.255 $P_2O_5$; 0.095 $SiO_2$; and a formula (anhydrous basis) of:

0.17 R $(Mn_{0.06}Al_{0.44}P_{0.42}Si_{0.08})O_2$

EXAMPLE 67D

EDAX (energy dispersive analysis by x-ray) microprobe analysis in conjunction with SEM (scanning electron microscope) was carried out on clear crystals from the products of certain examples, as identified in parenthesis hereinafter. Analysis of crystals having a morphology characteristic of each MnAPSO product gave the following analysis based on relative peak heights:

| | Average of Spot Probes |
|---|---|
| (a) MnAPSO-5 (Example 4D) | |
| Mn | 0.5 |
| Al | 8.0 |
| P | 9.5 |
| Si | 0.7 |
| (b) MnAPSO-11 (Example 24D) | |
| Mn | 1.0 |
| Al | 8.0 |
| P | 9.5 |
| Si | 1.5 |
| (c) MnAPSO-20 (Example 46D) | |
| Mn | 0.8 |
| Al | 8.2 |
| P | 9.4 |
| Si | 1.7 |
| (d) MnAPSO-34 (Example 6D) | |
| Mn | 1.3 |
| Al | 7.0 |
| P | 9.0 |
| Si | 1.5 |
| (e) MnAPSO-35 (Example 23D) | |
| Mn | 1.0 |
| Al | 7.0 |
| P | 10.0 |
| Si | 1.2 |
| (f) MnAPSO-36 (Example 59D) | |
| Mn | 0.8 |
| Al | 9.3 |
| P | 9.9 |
| Si | 1.6 |
| (g) MnAPSO-44 (Example 42D) | |
| Mn | 0.7 |
| Al | 9.0 |
| P | 10.0 |
| Si | 1.7 |
| (h) MnAPSO-44 (Example 64D) | |
| Mn | 1.1 |
| Al | 8.7 |
| P | 10.0 |
| SI | 5.6 |
| (i) MnAPSO-47 (Example 49D) | |
| Mn | 1.0 |
| Al | 9.0 |
| P | 9.5 |
| Si | 1.9 |

EXAMPLE 68D (a) The MnAPSO-5, prepared in Example 31D, was subjected to x-ray analysis. The MnAPSO-5 was impure but the major phase was determined to have an x-ray powder diffraction pattern characterized by the following data:

| $2\theta$ | d, (Å) | $I/I_o \times 100$ |
|---|---|---|
| 6.9* | 12.81 | 13 |
| 7.5 | 11.79 | 100 |
| 8.0* | 11.05 | 5 |
| 9.1* | 9.72 | 4 |
| 9.3* | 9.51 | 4 |
| 13.0 | 6.81 | 14 |
| 13.7* | 6.46 | 3 |
| 15.0 | 5.91 | 27 |

-continued

| 2θ | d, (Å) | I/Io × 100 |
|---|---|---|
| 16.5* | 5.37 | 3 |
| 18.5* | 4.80 | 7 |
| 19.8 | 4.48 | 43 |
| 21.0 | 4.23 | 58 |
| 22.3 | 3.99 | 75 |
| 24.7 | 3.60 | 6 |
| 25.9 | 3.440 | 42 |
| 29.0 | 3.079 | 18 |
| 30.0 | 2.979 | 34 |
| 33.6 | 2.667 | 8 |
| 34.5 | 2.600 | 21 |
| 36.9 | 2.436 | 4 |
| 37.7 | 2.386 | 10 |
| 41.5 | 2.176 | 5 |
| 42.1 | 2.146 | 5 |
| 42.2 | 2.141 | 5 |
| 42.6 | 2.122 | 5 |
| 43.5 | 2.080 | 3 |
| 44.9 | 2.019 | 3 |
| 47.5 | 1.914 | 7 |
| 51.4 | 1.778 | 5 |
| 51.9 | 1.762 | 3 |
| 55.5 | 1.656 | 5 |

*Peak may contain an impurity (b) A portion of the as-synthesized MnAPSO-5 of part (a) was calcined in air at 500° C. for about two (2) hours. The calcined product was characterized by the following x-ray powder diffraction pattern:

| 2θ | d, (Å) | I/Io × 100 |
|---|---|---|
| 7.4 | 11.95 | 100 |
| *7.8 | 11.33 | 4 |
| 12.9 | 6.86 | 25 |
| 15.0 | 5.91 | 21 |
| *16.5 | 5.37 | 3 |
| *16.7 | 5.31 | 3 |
| *17.5 | 5.07 | 5 |
| 19.8 | 4.48 | 40 |
| 21.2 | 4.19 | 40 |
| 22.5 | 3.95 | 43 |
| 26.0 | 3.427 | 30 |
| 29.1 | 3.069 | 11 |
| 30.1 | 2.969 | 35 |
| 33.7 | 2.660 | 5 |
| 34.6 | 2.592 | 19 |
| 37.1 | 2.423 | 4 |
| 37.9 | 2.374 | 6 |
| 42.5 | 2.127 | 4 |
| 43.1 | 2.099 | 3 |
| 46.0 | 1.973 | 3 |
| 47.9 | 1.899 | 5 |
| 55.8 | 1.647 | 4 |

*Peak may contain an impurity (c) The species denominated herein as MnAPSO-5 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

mR:$(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-5 having a characteristic x-ray powder diffraction pattern which contains at least the d-spacings set forth in Table V-D as follows:

TABLE V-D

| 2θ | d, (Å) | Relative Intensity |
|---|---|---|
| 7.3–7.7 | 12.11–11.48 | vs |
| 14.7–15.1 | 6.03–5.87 | m |
| 19.6–19.9 | 4.53–4.46 | m |
| 20.8–21.3 | 4.27–4.17 | m |
| 22.1–22.6 | 4.02–3.93 | m |
| 29.8–30.2 | 2.998–2.959 | m |

(d) All of the MnAPSO-5 compositions, both as-synthesized and calcined, for which x-ray power diffraction data have presently been obtain have patterns which are within the generalized pattern of Table VI-D below:

TABLE VI-D

| 2θ | d, (Å) | I/Io × 100 |
|---|---|---|
| 7.3–7.7 | 12.11–11.48 | 100 |
| 12.7–13.0 | 6.97–6.81 | 14–27 |
| 14.7–15.1 | 6.03–5.87 | 20–60 |
| 19.6–19.9 | 4.53–4.46 | 36–51 |
| 20.8–21.3 | 4.27–4.17 | 29–58 |
| 22.1–22.6 | 4.02–3.93 | 30–75 |
| 24.5–24.7 | 3.63–3.60 | 4–6 |
| 25.7–26.1 | 3.466–3.414 | 25–42 |
| 28.8–29.2 | 3.100–3.058 | 10–30 |
| 29.8–30.2 | 2.998–2.959 | 34–50 |
| 33.4–33.8 | 2.683–2.652 | 4–10 |
| 34.3–34.7 | 2.614–2.585 | 19–44 |
| 36.7–37.2 | 2.449–2.417 | 3–4 |
| 37.5–38.0 | 2.398–2.368 | 5–20 |
| 41.3–41.5 | 2.186–2.176 | 3–5 |
| 41.9–42.1 | 2.156–2.146 | 4–5 |
| 42.0–42.2 | 2.151–2.141 | 3–5 |
| 42.4–42.6 | 2.132–2.122 | 3–5 |
| 43.1–43.5 | 2.099–2.080 | 3–5 |
| 44.7–44.9 | 2.027–2.019 | 3–5 |
| 46.0–46.1 | 1.973–1.969 | 3–4 |
| 47.3–47.6 | 1.922–1.910 | 5–7 |
| 47.9–48.0 | 1.899–1.895 | 4–5 |
| 51.2–51.4 | 1.784–1.778 | 5–7 |
| 51.7–51.9 | 1.768–1.762 | 3–5 |
| 55.3–55.9 | 1.661–1.645 | 2–7 |

EXAMPLE 69D (a) MnAPSO-11, as prepared in example 24D, was subjected to x-ray analysis. The MnAPSO-11 was determined to have an x-ray powder diffraction pattern characterized by the following data:

| 2θ | d, (Å) | I/Io × 100 |
|---|---|---|
| 8.1 | 10.92 | 36 |
| 9.5 | 9.31 | 61 |
| 13.1 | 6.76 | 19 |
| 15.7 | 5.64 | 36 |
| 16.2 | 5.47 | 10 |
| 19.1 | 4.65 | 13 |
| 20.5 | 4.33 | 45 |
| 21.1 | 4.21 | 100 |
| 22.2 | 4.00 | 55 |
| 22.5 | 3.95 | 52 |
| 22.7 | 3.92 | 61 |
| 23.2 | 3.83 | 71 |
| 24.5 | 3.63 | 13 |
| 24.8 | 3.59 | 16 |
| 25.0 | 3.562 | 13 |
| 26.4 | 3.38 | 26 |
| 28.3 | 3.153 | 13 |
| 28.6 | 3.121 | 23 |
| 29.5 | 3.028 | 13 |
| 31.5 | 2.84 | 16 |
| 32.8 | 2.730 | 23 |

-continued

| 2θ | d, (Å) | I/Io × 100 |
|---|---|---|
| 34.2 | 2.622 | 16 |
| 35.4 | 2.54 | 10 |
| 35.8 | 2.508 | 10 |
| 36.3 | 2.475 | 10 |
| 37.5 | 2.398 | 13 |
| 37.8 | 2.370 | 16 |
| 39.4 | 2.287 | 10 |
| 42.9 | 2.108 | 10 |
| 44.8 | 2.023 | 10 |
| 48.8 | 1.866 | 3 |
| 50.6 | 1.804 | 10 |
| 54.6 | 1.681 | 10 |

(b) A portion of the as-synthesized MnAPSO-11 of part (a) was calcined in air at 600° C. for about two (2) hours. The calcined product was characterized by the following x-ray powder diffraction pattern:

| 2θ | d, (Å) | I/Io × 100 |
|---|---|---|
| 8.1 | 10.92 | 33 |
| 9.8 | 9.03 | 60 |
| 11.8 | 7.50 | 13 |
| 12.8 | 6.92 | 27 |
| 13.5 | 6.56 | 13 |
| 14.8 | 5.99 | sh |
| 16.1 | 5.51 | 67 |
| 19.5 | 4.55 | 27 |
| 19.9 | 4.46 | 40 |
| 20.4 | 4.35 | 33 |
| 21.5 | 4.13 | 73 |
| 21.8 | 4.08 | 100 |
| 22.2 | 4.00 | 73 |
| 22.4 | 3.97 | 80 |
| 23.5 | 3.79 | 73 |
| 24.3 | 3.66 | 27 |
| 25.8 | 3.453 | 33 |
| 26.7 | 3.339 | 27 |
| 27.3 | 3.267 | 33 |
| 27.8 | 3.209 | 33 |
| 28.5 | 3.132 | 27 |
| 29.5 | 3.028 | 33 |
| 29.8 | 2.998 | 40 |
| 30.4 | 2.940 | 27 |
| 31.8 | 2.814 | 20 |
| 32.6 | 2.747 | 33 |
| 34.0 | 2.637 | 20 |
| 35.5 | 2.529 | 27 |
| 37.1 | 2.423 | 20 |
| 37.4 | 2.404 | 20 |
| 38.2 | 2.356 | 20 |
| 38.6 | 2.332 | 27 |
| 41.0 | 2.201 | 20 |

(c) The species denominated herein as MnAPSO-11 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-11 having a characteristic x-ray powder diffraction pattern which contains at least the d-spacings set forth in Table VII-D as follows:

TABLE VII-D

| 2θ | d, (Å) | Relative Intensity |
|---|---|---|
| 9.4–9.8 | 9.41–9.03 | m |
| 16.1–16.2 | 5.50–5.47 | vw–m |
| 21.0–21.5 | 4.23–4.13 | m–vs |
| 22.1–22.2 | 4.02–4.00 | m |
| 22.4–22.5 | 3.97–3.95 | m–s |
| 23.1–23.5 | 3.85–3.79 | m |

(d) All of the MnAPSO-11 compositions, both as-synthesized and calcined, for which x-ray power diffraction data have presently been obtained have patterns which are within the generalized pattern of Table VIII-D below:

TABLE VIII-D

| 2θ | d, (Å) | I/Io × 100 |
|---|---|---|
| 8.0–8.1 | 11.05–10.92 | 31–36 |
| 9.4–9.8 | 9.41–9.03 | 56–61 |
| 11.8 | 7.50 | 13 |
| 12.8–13.1 | 6.92–6.76 | 17–27 |
| 13.5 | 6.56 | 13 |
| 14.8 | 5.99 | sh |
| 15.6–15.7 | 5.68–5.64 | 33–36 |
| 16.1–16.2 | 5.50–5.47 | 8–67 |
| 19.0–19.5 | 4.68–4.55 | 8–27 |
| 19.9 | 4.46 | 40 |
| 20.4–20.5 | 4.35–4.33 | 33–45 |
| 21.0–21.5 | 4.23–4.13 | 73–100 |
| 21.8 | 4.08 | 100 |
| 22.1–22.2 | 4.02–4.00 | 55–73 |
| 22.4–22.5 | 3.97–3.95 | 52–80 |
| 22.6–22.7 | 3.93–3.92 | 61 |
| 23.1–23.5 | 3.85–3.79 | 69–73 |
| 24.3–24.5 | 3.66–3.63 | 11–27 |
| 24.7–24.8 | 3.60–3.59 | 14–16 |
| 24.9–25.0 | 3.58–3.562 | sh–13 |
| 25.8 | 3.453 | 33 |
| 26.3–26.7 | 3.389–3.339 | 25–27 |
| 27.3 | 3.267 | 33 |
| 27.8 | 3.209 | 33 |
| 28.2–28.3 | 3.164–3.153 | 11–13 |
| 28.5–28.6 | 3.132–3.121 | 22–27 |
| 29.4–29.5 | 3.038–3.028 | 11–33 |
| 29.8 | 2.998 | 40 |
| 30.4 | 2.940 | 27 |
| 31.4–31.8 | 2.849–2.814 | 14–20 |
| 32.6–32.8 | 2.747–2.730 | 19–33 |
| 34.0–34.2 | 2.637–2.622 | 14–20 |
| 35.3–35.5 | 2.543–2.529 | sh–27 |
| 35.7–35.8 | 2.515–2.508 | 8–10 |
| 36.2–26.3 | 2.481–2.475 | 8–10 |
| 37.1 | 2.423 | 20 |
| 37.4–37.5 | 2.404–2.398 | 11–20 |
| 37.7–37.8 | 2.386–2.380 | 16–17 |
| 38.2 | 2.356 | 20 |
| 38.6 | 2.332 | 27 |
| 39.3–39.4 | 2.292–2.287 | 8–10 |
| 41.0 | 2.201 | 20 |
| 42.8–42.9 | 2.113–2.108 | 8–10 |
| 44.7–44.8 | 2.027–2.023 | 8–10 |
| 48.7–48.8 | 1.870–1.866 | 3–5 |
| 50.5–50.6 | 1.807–1.804 | 8–10 |
| 54.5–54.6 | 1.684–1.681 | 8–10 |

EXAMPLE 70D (a) MnAPSO-16, as prepared in example 14D was subjected to x-ray analysis. The MnAPSO-16 was determined to have an x-ray powder diffraction pattern characterized by the following data:

| 2θ | d, (Å) | I/Io × 100 |
|---|---|---|
| 8.6* | 10.28 | 8 |
| 11.0* | 8.04 | 23 |
| 11.4 | 7.76 | 48 |
| 13.3* | 6.66 | 11 |
| 15.9* | 5.57 | 5 |
| 17.3* | 5.13 | 24 |
| 17.7* | 5.01 | 8 |
| 18.7 | 4.75 | 40 |
| 21.1* | 4.21 | 19 |
| 21.9** | 4.06 | 100 |
| 23.0 | 3.87 | 13 |
| 23.2* | 3.83 | 10 |
| 23.7* | 3.75 | 5 |
| 25.1 | 3.548 | 5 |
| 26.6** | 3.351 | 26 |
| 26.7* | 3.339 | (sh) |
| 27.8 | 3.209 | 5 |
| 28.8* | 3.100 | 15 |
| 29.0 | 3.079 | 15 |
| 29.8 | 2.998 | 24 |
| 32.0* | 2.797 | 16 |
| 32.6 | 2.747 | 7 |
| 34.7** | 2.585 | 10 |
| 35.7* | 2.515 | 5 |
| 37.8 | 2.380 | 11 |
| 39.7 | 2.270 | 5 |
| 42.0* | 2.151 | 5 |
| 44.2 | 2.049 | 5 |
| 48.5** | 1.877 | 10 |
| 49.4* | 1.845 | 5 |
| 52.4 | 1.746 | 5 |
| 54.7 | 1.678 | 5 |

*Impurity Peak
**Peak may contain impurity (b) A portion of the as-synthesized MnAPSO-16 of part (a) was calcined in nitrogen at 600° C. for about 2 hours. The calcined product was characterized by the following x-ray powder diffraction pattern:

| 2θ | d, (Å) | I/Io × 100 |
|---|---|---|
| 11.5 | 7.69 | 100 |
| 13.3* | 6.66 | 9 |
| 18.6 | 4.77 | 25 |
| 20.3* | 4.37 | 44 |
| 20.5* | 4.33 | 41 |
| 21.5* | 4.13 | 66 |
| 21.9** | 4.06 | 72 |
| 22.9 | 3.88 | 31 |
| 23.5* | 3.79 | 13 |
| 26.5** | 3.363 | 31 |
| 27.9 | 3.198 | 13 |
| 29.0 | 3.079 | 19 |
| 29.7 | 3.008 | 34 |
| 32.6 | 2.747 | 13 |
| 34.7** | 2.585 | 13 |
| 35.6* | 2.522 | 16 |
| 37.8 | 2.380 | 13 |
| 48.2** | 1.888 | 9 |

*Impurity Peak
**Peak may contain impurity (c) The species denominated herein as MnAPSO-16 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points, a, b, c and d of FIG. 2, said MnAPSO-16 having a characterized x-ray powder diffraction pattern which contains at least the d-spacings set forth in Table IX-D as follows:

TABLE IX-D

| 2θ | d, (Å) | Relative Intensity |
|---|---|---|
| 11.4–11.5 | 7.76–7.69 | m–vs |
| 18.6–18.7 | 4.77–4.75 | m |
| 21.9 | 4.06 | m–vs |
| 22.9–23.0 | 3.88–3.87 | w–m |
| 26.5–26.6 | 3.363–3.351 | m |
| 29.7–29.8 | 3.008–2.998 | m |

(d) All of the MnAPSO-16 compositions, both as-synthesized and calcined, for which x-ray power diffraction data have presently been obtain have patterns which are within the generalized pattern of Table X-D below:

TABLE X-D

| 2θ | d, (Å) | I/Io × 100 |
|---|---|---|
| 11.4–11.5 | 7.76–7.69 | 48–100 |
| 18.6–18.7 | 4.77–4.75 | 25–40 |
| 21.9* | 4.06 | 72–80 |
| 22.9–23.0 | 3.88–3.87 | 13–31 |
| 26.5–26.6* | 3.363–3.351 | 26–31 |
| 27.8–27.9 | 3.209–2.198 | 5–13 |
| 29.0 | 3.079 | 15–19 |
| 29.7–29.8 | 3.008–2.998 | 24–34 |
| 32.6 | 2.747 | 7–14 |
| 34.7* | 2.585 | 9–14 |
| 37.8 | 2.380 | 11–15 |
| 39.7 | 2.270 | 5–6 |
| 44.2 | 2.049 | 5–6 |
| 48.2–48.5* | 1.888–1.877 | 9–12 |
| 49.4 | 1.845 | 4–5 |
| 52.4 | 1.746 | 4–5 |
| 54.7 | 1.678 | 4–5 |

*Peak might contain an impurity

EXAMPLE 71D (a) MnAPSO-20, as prepared in example 46D was subjected to x-ray analysis. The MnAPSO-20 was determined to have an x-ray powder diffraction pattern characterized by the following data:

| 2θ | d, (Å) | I/Io × 100 |
|---|---|---|
| 14.0 | 6.35 | 49 |
| 19.8 | 4.49 | 43 |
| 22.1 | 4.02 | 3 |
| 23.7* | 3.75 | 1 |
| 24.3 | 3.67 | 100 |
| 28.1 | 3.177 | 13 |
| 31.5 | 2.842 | 11 |
| 34.6 | 2.595 | 16 |
| 37.5 | 2.400 | 2 |
| 40.1 | 2.247 | 4 |
| 42.7 | 2.118 | 4 |
| 47.4 | 1.917 | 4 |
| 51.8 | 1.764 | 7 |

*Peak may contain an impurity (b) A portion of the as-synthesized MnAPSO-20 of part (a) was calcined in air at 500° C. for about 1 hour. The calcined product was characterized by the following x-ray powder diffraction pattern:

| 2θ | d, (Å) | Relative Intensity |
|---|---|---|
| 7.1 | 12.51 | 2 |
| 14.0 | 6.33 | 100 |
| 19.8 | 4.48 | 40 |
| 22.2 | 4.00 | 4 |
| 24.3 | 3.66 | 99 |
| 28.2 | 3.168 | 17 |
| 31.6 | 2.835 | 15 |
| 34.7 | 2.589 | 17 |
| 40.2 | 2.243 | 3 |
| 42.7 | 2.116 | 4 |
| 47.5 | 1.913 | 4 |

(c) The species denominated herein as MnAPSO-20 is a molecular sieve having a three dimensional microporous sieve having a three structure of $MnO_2^{-2}$, $AlO_2^{-}$, $PO_2^{+}$ and $SiO_2$ tetrahedral oxide units and have an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-20 having a characteristic x-ray powder diffraction pattern which contains at least the d-spacings set forth in Table XI-D as follows:

TABLE XI-D

| 2θ | d, (Å) | Relative Intensity |
|---|---|---|
| 13.904–13.998 | 6.3692–6.3263 | m–vs |
| 19.723–19.818 | 4.5011–4.4918 | m |
| 24.223–24.329 | 3.6742–3.6584 | vs |
| 28.039–28.163 | 3.1822–3.1684 | w |
| 31.434–31.560 | 2.8458–2.8348 | w |
| 34.527–34.652 | 2.5976–2.5866 | w |

(d) All of the MnAPSO-20 compositions, both as-synthesized and calcined for which x-ray power diffraction data have presently been obtain have patterns which are within the generalized pattern of Table XII-D below:

TABLE XII-D

| 2θ | d, (Å) | I/Io × 100 |
|---|---|---|
| 13.904–13.998 | 6.3692–6.3263 | 49–100 |
| 19.723–19.818 | 4.5011–4.4918 | 40–43 |
| 22.091–22.200 | 4.0236–4.0041 | 3–4 |
| 24.223–24.329 | 3.6742–3.6584 | 99–100 |
| 28.039–28.163 | 3.1822–3.1684 | 13–17 |
| 31.434–31.560 | 2.8458–2.8348 | 11–15 |
| 34.527–34.652 | 2.5976–2.5886 | 15–17 |
| 34.413–27.465 | 2.2501–2.4004 | 2 |
| 40.071–40.207 | 2.2501–2.2428 | 3–4 |
| 42.627–42.730 | 2.1209–2.1160 | 3–4 |
| 47.383–47.519 | 1.9185–1.9134 | 3–4 |
| 51.790–51.840 | 1.7652–1.7636 | 7 |

EXAMPLE 72D (a) MnAPSO-31, as prepared in example 54D was subjected to x-ray analysis. MnAPSO-31 was determined to have an x-ray powder diffraction pattern characterized by the following data:

| 2θ | d, (Å) | I/Io × 100 |
|---|---|---|
| 7.9 | 11.22 | 4 |
| 8.6 | 10.27 | 61 |
| 17.2 | 5.17 | 5 |
| 18.5 | 4.81 | 4 |
| 20.4 | 4.36 | 49 |
| 21.2 | 4.19 | 4 |
| 22.0 | 4.04 | 30 |
| 22.1 | 4.02 | 32 |
| 22.7 | 3.92 | 100 |
| 25.3 | 3.526 | 5 |
| 25.8 | 3.459 | 3 |
| 28.1 | 3.181 | 12 |
| 29.8 | 2.995 | 6 |
| 31.8 | 2.812 | 22 |
| 35.2 | 2.548 | 9 |
| 36.2 | 2.482 | 3 |
| 37.3 | 2.411 | 3 |
| 37.8 | 2.382 | 3 |
| 38.3 | 2.353 | 3 |
| 38.4 | 2.346 | 3 |
| 39.4 | 2.285 | 3 |
| 39.8 | 2.266 | 3 |
| 40.3 | 2.241 | 3 |
| 46.8 | 1.942 | 3 |
| 48.8 | 1.866 | 2 |
| 51.8 | 1.766 | 5 |
| 55.6 | 1.654 | 2 |

(b) A portion of the as-synthesized MnAPSO-31 of part (a) was calcined in air at 500° C. for about 1.5 hours. The calcined product was characterized by the following x-ray powder diffraction pattern:

| 2θ | d, (Å) | I/Io × 100 |
|---|---|---|
| 8.6 | 10.31 | 58 |
| 14.8 | 5.98 | 4 |
| 17.1 | 5.18 | 9 |
| 18.5 | 4.81 | 4 |
| 20.4 | 4.36 | 52 |
| 22.1 | 4.03 | 44 |
| 22.7 | 3.92 | 100 |
| 25.3 | 3.526 | 7 |
| 25.8 | 3.460 | 8 |
| 28.1 | 3.181 | 15 |
| 29.8 | 2.998 | 11 |
| 31.1 | 2.879 | 3 |
| 31.8 | 2.811 | 33 |
| 35.3 | 2.546 | 11 |
| 36.3 | 2.477 | 6 |
| 37.3 | 2.409 | 3 |
| 37.8 | 2.383 | 3 |
| 38.3 | 2.348 | 3 |
| 39.4 | 2.289 | 4 |
| 40.3 | 2.236 | 3 |
| 45.4 | 2.000 | 3 |
| 46.8 | 1.942 | 5 |
| 47.6 | 1.909 | 4 |
| 48.9 | 1.864 | 3 |
| 51.7 | 1.767 | 6 |

(c) The species denominated herein as MnAPSO-31 is a molecular sieve having a three dimensional microporous crystalline framework structure of $MnO_2^{-2}$, $AlO_2^{-}$, $PO_2^{+}$ and $SiO_2$ tetrahedral oxide units and have an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present an tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-31 having a characteristic x-ray powder diffraction pattern which contains at least the d-spacings set forth in Table XIII-D as follows:

TABLE XIII-D

| 2θ | d, (Å) | Relative Intensity |
|---|---|---|
| 8.482–9.501 | 10.4240–9.3084 | m |
| 20.222–20.353 | 4.3913–4.3632 | m |
| 21.879–21.993 | 4.0622–4.0415 | m |
| 22.071–22.088 | 4.0272–4.0242 | m |
| 22.587–22.698 | 3.9364–3.9174 | vs |
| 31.724–31.836 | 2.8546–2.8108 | m |

(d) All of the MnAPSO-31 compositions, both as-synthesized and calcined for which x-ray power diffraction data have presently been obtain have patterns which are within the generalized pattern of Table XIV-D below:

TABLE XIV-D

| 2θ | d, (Å) | I/Io × 100 |
|---|---|---|
| 7.694–7.383 | 11.4904–11.2145 | 2–4 |
| 8.482–9.501 | 10.4240–9.3084 | 58–66 |
| 14.756–14.822 | 6.0034–5.9767 | 2–4 |
| 17.016–17.158 | 5.2105–5.1679 | 5–9 |
| 18.310–18.466 | 4.8451–4.8046 | 3–4 |
| 20.222–20.353 | 4.3913–4.3632 | 45–52 |
| 21.032–21.221 | 4.2238–4.1867 | 4–5 |
| 21.879–21.993 | 4.0622–4.0415 | 30–51 |
| 22.071–22.088 | 4.0272–4.0242 | 32–44 |
| 22.587–22.698 | 3.9364–3.9174 | 100 |
| 23.164–23.190 | 3.8398–3.8355 | 2–3 |
| 25.115–25.260 | 3.5457–3.5256 | 4–7 |
| 25.663–25.757 | 3.4712–3.4588 | 3–8 |
| 27.922–28.050 | 3.1953–3.1809 | 12–15 |
| 29.701–29.831 | 3.0078–2.9950 | 6–11 |
| 31.068–31.315 | 2.8785–2.8564 | 2–3 |
| 31.724–31.836 | 2.8564–2.8108 | 21–33 |
| 35.117–35.251 | 2.5553–2.5460 | 9–11 |
| 35.871 | 2.5033 | 1 |
| 36.070–36.261 | 2.4900–2.4730 | 2–6 |
| 37.123–37.325 | 2.4217–2.4091 | 2–3 |
| 37.628–27.763 | 2.3904–2.3822 | 2–3 |
| 38.163–38.254 | 2.3581–2.3527 | 2–3 |
| 38.334–38.367 | 2.3480–2.3461 | 3 |
| 39.285–39.442 | 2.2933–2.2845 | 3–4 |
| 39.654–39.772 | 2.2728–2.2663 | 2–4 |
| 40.111–40.337 | 2.2480–2.2359 | 2–3 |
| 45.179–45.354 | 2.0069–1.9996 | 2–3 |
| 46.617–46.786 | 1.9483–1.9416 | 3–5 |
| 47.454–47.631 | 1.9158–1.9091 | 2–4 |
| 48.610–48.846 | 1.8729–1.8644 | 2–3 |
| 50.679–50.750 | 1.8012–1.7989 | 2 |
| 51.588–51.766 | 1.7716–1.7659 | 4–6 |
| 55.410–55.557 | 1.6581–1.6541 | 2 |

EXAMPLE 73D (a) MnAPSO-34, as prepared in example 11D was subjected to x-ray analysis. MnAPSO-34 was determined to have an x-ray powder diffraction pattern characterized by the following data:

| 2θ | d, (Å) | I/Io × 100 |
|---|---|---|
| 9.6 | 9.21 | 100 |
| 12.9 | 6.86 | 17 |
| 14.2 | 6.24 | 15 |
| 16.1 | 5.51 | 33 |
| 18.1 | 4.90 | 23 |
| 20.6 | 4.31 | 69 |
| 22.3 | 3.99 | 10 |
| 23.1 | 3.85 | 8 |
| 25.2 | 3.534 | 25 |
| 25.8 | 3.43 | 19 |
| 27.5 | 3.243 | 10 |
| 28.4 | 3.143 | 10 |
| 29.5 | 3.028 | 10 |
| 30.5 | 2.931 | 27 |
| 31.2 | 2.867 | 23 |
| 33.8 | 2.652 | 8 |
| 34.3 | 2.614 | 12 |
| 36.3 | 2.475 | 8 |
| 43.0 | 2.103 | 6 |
| 43.5 | 2.080 | 6 |
| 47.5 | 1.914 | 6 |
| 48.9 | 1.863 | 8 |
| 50.9 | 1.794 | 6 |
| 53.0 | 1.728 | 6 |
| 55.7 | 1.650 | 6 |

(b) A portion of the as-synthesized MnAPSO-34 of part (a) was calcined in nitrogen at 425° C. for about 2 hours. The calcined product was characterized by the following x-ray powder diffraction pattern:

| 2θ | d, (Å) | I/Io × 100 |
|---|---|---|
| 9.6 | 9.21 | 100 |
| 13.0 | 6.86 | 25 |
| 14.1 | 6.28 | 5 |
| 16.2 | 5.47 | 15 |
| 17.9 | 4.96 | 15 |
| 19.1 | 4.65 | 5 |
| 20.8 | 4.27 | 37 |
| 22.2 | 4.00 | 5 |
| 22.4 | 3.97 | 5 |
| 23.2 | 3.83 | 7 |
| 25.2 | 3.534 | 15 |
| 26.0 | 3.427 | 12 |
| 27.7 | 3.220 | 4 |
| 28.3 | 3.153 | 5 |
| 29.7 | 3.008 | 4 |
| 30.7 | 2.912 | 17 |
| 31.3 | 2.849 | 11 |
| 32.4 | 2.763 | 3 |
| 34.6 | 2.592 | 5 |
| 36.2 | 2.481 | 4 |
| 38.8 | 2.321 | 3 |
| 39.8 | 2.265 | 3 |
| 43.1 | 2.099 | 3 |
| 43.6 | 2.076 | 3 |
| 47.8 | 1.903 | 1 |
| 49.0 | 1.859 | 3 |
| 51.0 | 1.791 | 3 |
| 53.3 | 1.719 | 4 |
| 54.6 | 1.681 | 3 |

(c) The species denominated herein as MnAPSO-34 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

mR: $(Mn_wAl_xP_ySi_z)O_2$ wherein "R" represent at least one organic templating agent present in the intracrystalline pore system; "m" represent the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-34 having a characteristic x-ray powder diffraction pattern which contains at least the d-spacings set forth in Table XV-D as follows:

TABLE XV-D

| 2θ | d, (Å) | Relative Intensity |
|---|---|---|
| 9.4–9.6 | 9.41–9.21 | vs |
| 15.9–16.2 | 5.57–5.47 | m |
| 20.4–20.8 | 4.35–4.27 | m–vs |
| 25.0–25.3 | 3.562–3.520 | w–m |
| 31.0–31.3 | 2.885–2.858 | w–m |
| 33.6–33.9 | 2.667–2.644 | m |

(d) All of the MnAPSO-34 compositions, both as-synthesized and calcined for which x-ray power diffraction data have presently been obtain have patterns which are within the generalized pattern of Table XIV-D below:

TABLE XIV-D

| 2θ | d, (Å) | I/Io × 100 |
|---|---|---|
| 9.4–9.6 | 9.41–9.21 | 100 |
| 12.7–13.0 | 6.97–6.86 | 17–25 |
| 14.0–14.2 | 6.33–6.24 | 5–17 |
| 15.9–16.2 | 5.57–5.47 | 15–44 |
| 17.9–18.1 | 4.96–4.90 | 15–32 |
| 19.1 | 4.65 | 5 |
| 20.4–20.8 | 4.35–4.27 | 37–92 |
| 22.1–22.3 | 4.02–3.99 | 5–16 |
| 22.4 | 3.97 | 5 |
| 22.9–23.2 | 3.88–3.83 | 7–16 |
| 25.0–25.3 | 3.562–3.520 | 15–36 |
| 25.8–26.0 | 3.453–3.427 | 12–19 |
| 27.3–27.7 | 3.267–3.220 | 4–28 |
| 28.2–28.5 | 3.164–3.132 | 5–16 |
| 29.3–29.7 | 3.048–3.008 | 4–16 |
| 30.3–30.7 | 2.950–2.912 | 10–17 |
| 31.0–31.3 | 2.885–2.849 | 11–40 |
| 32.4 | 2.763 | 3 |
| 33.6–33.9 | 2.667–2.644 | 23–32 |
| 34.3–34.6 | 2.614–2.592 | 5–12 |
| 36.2–36.4 | 2.481–2.468 | 4–16 |
| 38.8 | 2.321 | 3 |
| 39.8 | 2.265 | 3 |
| 33.0–43.1 | 2.103–2.099 | 3–12 |
| 43.5–43.6 | 2.080–2.076 | 3–12 |
| 47.4–47.8 | 1.918–1.903 | 1–12 |
| 48.8–49.0 | 1.866–1.859 | 3–12 |
| 50.8–51.0 | 1.797–1.791 | 3–12 |
| 52.9–53.3 | 1.731–1.719 | 4–12 |
| 54.6 | 1.681 | 3 |
| 55.6–55.8 | 1.653–1.647 | 6–12 |

EXAMPLE 74D (a) MnAPSO-35, as prepared in example 22D was subjected to x-ray analysis. MnAPSO-35 was determined to have an x-ray powder diffraction pattern characterized by the following data:

| 2θ | d, (Å) | I/Io × 100 |
|---|---|---|
| 8.6 | 10.28 | 14 |
| 10.9 | 8.12 | 45 |
| 13.4 | 6.61 | 23 |
| 15.9 | 5.57 | 11 |
| 17.4 | 5.10 | 80 |
| 17.8 | 4.98 | 16 |
| 20.9 | 4.25 | 57 |
| 21.9 | 4.06 | 100 |
| 23.2 | 3.83 | 34 |
| 24.8 | 3.59 | 9 |
| 25.7 | 3.466 | 7 |
| 26.9 | 3.314 | 21 |
| 28.3 | 3.153 | 50 |
| 29.1 | 3.069 | 11 |
| 31.4 | 2.849 | 9 |
| 32.1 | 2.788 | 41 |
| 34.3 | 2.614 | 14 |
| 34.9 | 2.571 | 7 |
| 35.3 | 2.543 | 5 |
| 35.8 | 2.508 | 7 |
| 37.7 | 2.386 | 5 |
| 39.5 | 2.281 | 5 |
| 41.9 | 2.156 | 7 |
| 42.7 | 2.118 | 7 |
| 44.6 | 2.032 | 5 |
| 47.6 | 1.910 | 7 |
| 48.3 | 1.884 | 7 |
| 49.5 | 1.841 | 7 |
| 51.0 | 1.791 | 9 |
| 55.0 | 1.670 | 5 |
| 55.4 | 1.658 | 7 |

(b) A portion of the as-synthesized MnAPSO-35 of part (a) was calcined in nitrogen at 500° C. for about 2 hours. The calcined product was characterized by the following x-ray powder diffraction pattern:

| 2θ | d, (Å) | I/Io × 100 |
|---|---|---|
| 8.6 | 10.28 | 27 |
| 10.9 | 8.12 | 96 |
| 11.4 | 7.76 | 14 |
| 13.4 | 6.61 | 41 |
| 15.8 | 5.61 | 14 |
| 17.3 | 5.13 | 68 |
| 17.7 | 5.01 | sh |
| 20.8 | 4.27 | 64 |
| 21.9 | 4.06 | 100 |
| 23.3 | 3.82 | 32 |
| 24.8 | 3.59 | 23 |
| 25.7 | 3.466 | 18 |
| 26.9 | 3.314 | 27 |
| 28.3 | 3.153 | 59 |
| 29.1 | 3.069 | 23 |
| 31.4 | 2.849 | 18 |
| 32.2 | 2.780 | 46 |
| 34.2 | 2.622 | 18 |
| 34.8 | 2.578 | 14 |
| 35.8 | 2.508 | 9 |
| 41.9 | 2.156 | 9 |
| 42.5 | 2.127 | 9 |
| 44.6 | 2.032 | 9 |
| 47.4 | 1.918 | 9 |
| 48.2 | 1.888 | 9 |
| 49.4 | 1.845 | 9 |
| 51.0 | 1.791 | 14 |
| 55.2 | 1.664 | 9 |
| 55.7 | 1.650 | 9 |

(c) The species denominated herein as MnAPSO-35 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-35 having a characteristic x-ray powder diffraction pattern

MISSING PAGE TEMPORARY NOTICE

PATENT # 4973785  FOR ISSUE DATE 11-27-90

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 125, 126 n/a at Bayers
10/6/92

MISSING PAGE TEMPORARY NOTICE

PATENT # 4973785     FOR ISSUE DATE 11-27-90

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 127, 128 n/a at Bayers
10/6/92

TABLE XXII-D-continued

| 2θ | d, (Å) | I/Io × 100 |
|---|---|---|
| 24.396–24.424 | 3.6485–3.6444 | 58 |
| 26.143–26.184 | 3.4085–3.4032 | 22 |
| 27.837–27.881 | 3.2049–3.1999 | 10 |
| 29.661 | 3.0117 | 5 |
| 30.002–30.096 | 2.9783–2.9692 | 16 |
| 30.833–20.853 | 2.8999–2.8981 | 50 |
| 32.520–32.562 | 2.7532–2.7498 | 4 |
| 32.900–32.918 | 2.7223–2.7208 | 6 |
| 34.812 | 2.5770 | 3 |
| 35.516–35.534 | 2.5275–2.5263 | 9 |
| 38.536 | 2.3361 | 2 |
| 38.185 | 2.2989 | 2 |
| 39.991 | 2.2545 | 2 |
| 42.162–42.177 | 2.1432–2.1425 | 3 |
| 42.533–42.541 | 2.1254–2.1250 | 3 |
| 43.607–73.621 | 2.0755–2.0749 | 2 |
| 47.283 | 1.9224 | 2 |
| 48.157–48.177 | 1.8895–1.8888 | 7 |
| 48.640–48.697 | 1.8719–1.8698 | 4 |
| 50.303–50.307 | 1.8138–1.8137 | 7 |
| 53.885–53.887 | 1.7014–1.7013 | 6 |

EXAMPLE 77D (a) MnAPSO-47, as prepared in example 49D was subjected to x-ray analysis. The MnAPSO-47 was determined to have an x-ray powder diffraction pattern characterized by the following data:

| 2θ | d, (Å) | I/Io × 100 |
|---|---|---|
| 4.8 | 18.44 | 1 |
| 9.4 | 9.38 | 100 |
| 12.9 | 6.89 | 5 |
| 13.9 | 6.40 | 3 |
| 16.0 | 5.56 | 9 |
| 17.5 | 5.06 | 4 |
| 18.9 | 4.69 | 3 |
| 20.5 | 4.32 | 30 |
| 21.8 | 4.08 | 4 |
| 22.4 | 3.98 | 1 |
| 22.9 | 3.88 | 3 |
| 24.6 | 3.61 | 11 |
| 25.9 | 3.445 | 7 |
| 27.6 | 3.234 | 2 |
| 27.9 | 3.199 | 1 |
| 29.5 | 3.033 | 2 |
| 30.5 | 2.930 | 10 |
| 30.8 | 2.901 | 7 |
| 31.5 | 2.845 | 1 |
| 33.2 | 2.700 | 1 |
| 34.4 | 2.604 | 2 |
| 34.8 | 2.576 | 1 |
| 35.7 | 2.516 | 2 |
| 38.4 | 2.343 | 1 |
| 39.2 | 2.297 | 1 |
| 39.6 | 2.277 | 1 |
| 42.4 | 2.132 | 1 |
| 43.3 | 2.091 | 1 |
| 47.6 | 1.911 | 1 |
| 48.6 | 1.874 | 5 |
| 50.3 | 1.813 | 2 |
| 53.2 | 1.722 | 1 |
| 54.0 | 1.698 | 1 |

(b) A portion of the as-synthesized MnAPSO-47 of part (a) was calcined in air at 500° C. for about one (1) hour. The calcined product was characterized by the following x-ray powder diffraction pattern:

| 2θ | d, (Å) | I/Io × 100 |
|---|---|---|
| 5.0 | 17.80 | 1 |
| 9.7 | 9.12 | 100 |
| 10.0 | 8.85 | 1 |
| 13.1 | 6.75 | 5 |
| 14.2 | 6.23 | 1 |
| 16.3 | 5.45 | 2 |
| 18.0 | 4.92 | 2 |
| 19.4 | 4.58 | 3 |
| 20.9 | 4.24 | 7 |
| 22.4 | 3.99 | 1 |
| 23.4 | 3.80 | 1 |
| 25.3 | 3.521 | 2 |
| 26.3 | 3.385 | 2 |
| 28.1 | 3.176 | 1 |
| 28.6 | 3.125 | 1 |
| 30.0 | 2.977 | 1 |
| 31.1 | 2.876 | 3 |
| 31.5 | 2.837 | 2 |
| 33.9 | 2.645 | 1 |
| 35.0 | 2.562 | 1 |
| 49.6 | 1.838 | 1 |

(c) The species denominated herein as MnAPSO-47 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_wAl_xP_ySi_z)O_2$$

wherein "R" represents at least one organic templating agent present in the intracrystalline pore system: "m" represents the molar amount of "R" present per mole of $(Mn_wAl_xP_ySi_z)O_2$ and has a value of from zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-47 having a characteristic x-ray powder diffraction pattern which contains at least the d-spacings set forth in Table XXIII-D as follows:

TABLE XXIII-D

| 2θ | d, (Å) | Relative Intensity |
|---|---|---|
| 9.434–9.696 | 9.3746–9.1214 | vs |
| 15.946–16.276 | 5.5579–5.4457 | vw |
| 20.539–20.940 | 4.3242–4.2423 | vw-m |
| 24.643 | 3.6125 | w |
| 30.511 | 2.9297 | w |
| 30.820–31.096 | 2.9011–2.8759 | vw |

(d) All of the MnAPSO-47 compositions, both as-synthesized and calcined for which x-ray power diffraction data have presently been obtain have patterns which are within the generalized pattern of Table XXIV-D below:

TABLE XXIV-D

| 2θ | d, (Å) | I/Io × 100 |
|---|---|---|
| 4.793–4.964 | 18.4368–17.8028 | 1 |
| 9.434–9.696 | 9.3746–9.1214 | 100 |
| 12.847–13.107 | 6.8907–6.7543 | 5 |
| 13.840–14.211 | 6.3983–6.2321 | 1–3 |
| 15.946–16.276 | 5.5579–5.4457 | 2–9 |
| 17.544–18.032 | 5.0550–4.9191 | 2–4 |
| 18.941–19.365 | 4.6851–4.5836 | 3 |
| 20.539–20.940 | 4.3242–4.2423 | 6–30 |
| 21.811 | 4.0747 | 4 |
| 22.351–22.352 | 3.9775–3.9774 | 1 |
| 22.936 | 3.8773 | 3 |

TABLE XXIV-D-continued

| 2θ | d, (Å) | I/Io × 100 |
|---|---|---|
| 23.401 | 3.8013 | 1 |
| 24.643 | 3.6125 | 11 |
| 25.294–25.864 | 3.5210 | 2–7 |
| 26.327–27.577 | 3.3851–3.2344 | 2 |
| 27.881–28.093 | 3.1992–3.1762 | 1 |
| 28.560 | 3.1253 | 1 |
| 29.448–30.019 | 3.0331–2.9767 | 1–2 |
| 30.511 | 2.9297 | 10 |
| 30.820–31.096 | 2.9011–2.8759 | 3–7 |
| 31.448–31.532 | 2.8446–2.8372 | 1–2 |
| 33.186–33.894 | 2.6995–2.6447 | 1 |
| 34.444 | 2.6037 | 2 |
| 34.834–35.026 | 2.5755–2.5618 | 1 |
| 35.685 | 2.5159 | 2 |
| 38.412 | 2.3434 | 1 |
| 39.223 | 2.2968 | 1 |
| 39.582 | 2.2768 | 1 |
| 42.403 | 2.1316 | 1 |
| 43.278 | 2.0905 | 1 |
| 47.595 | 1.9105 | 1 |
| 48.584–49.595 | 1.8739–1.8380 | 1–5 |
| 50.327 | 1.8130 | 2 |
| 53.205 | 1.7215 | 1 |
| 54.006 | 1.6979 | 1 |

EXAMPLE 78D

The catalytic activity of MnAPSO compositions, calcined samples of the MnAPSO products of Examples 11D, 21D, 25D, 31D, 49D, 55D, 59D and 64D were tested for catalytic cracking.

The catalytic activity was determined using a reactor comprising a cylindrical quartz tube 254 mm. in length and 10.3 mm. I.D. In each test MnAPSO which were 20–40 mesh (U.S. std.) in size and in an amount of from 0.5 to 5 grams, the quantity being selected so that the conversion of n-butane was at least 5% and not more than 90% under the test conditions. Most of the MnAPSO samples had been previously calcined in air or nitrogen to remove organic materials from the pore system, and were activated in situ in the reactor in a flowing stream of helium at 500° C. for one hour. The feedstock was a helium- n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the MnAPSO compositions. The $k_A$ value (cm³/g min) obtained for the MnAPSO compositions are set forth, below, in Table XXV-D:

TABLE XXV-D

| MnAPSO | Prepared in Example No. | Rate Constant ($k_A$)* |
|---|---|---|
| MnAPSO-5 | 31D | 0.2 |
| MnAPSO-11 | 25D | 0.6 |
| MnAPSO-20 | 46D | 0.2 |
| MnAPSO-31 | 55D | 1.0; 0.5 |
| MnAPSO-34 | 11D | 3.1 |
| MnAPSO-35 | 21D | 0.1** |
| MnAPSO-36 | 59D | 0.3 |
| MnAPSO-44 | 64D | 1.5 |

TABLE XXV-D-continued

| MnAPSO | Prepared in Example No. | Rate Constant ($k_A$)* |
|---|---|---|
| MnAPSO-47 | 49D | 1.7 |

*Prior to determination of the catalytic activity of a given MnAPSO, each was calcined as follows:
a) MnAPSO-5 was calcined at 500° C. in air for 2 hours;
b) MnAPSO-11, MnAPSO-34 and MnAPSO-36 were calcined in situ;
c) MnAPSO-31 was calcined in air at 500° C. for 1.5 hours and then at 600° C. for 1 hour;
d) MnAPSO-35 was calcined at 500° C. in nitrogen for 1 hour; and
e) MnAPSO-20, MnAPSO-44 and MnAPSO-47 were calcined at 500° C. in air for 1 hour.
**Less than 0.1

E. TITANIUM-ALUMINUM-PHOSPHORUS-SILICON-OXIDE SIEVES

Molecular sieves containing titanium, aluminum, phosphorus and silicon as framework tetrahedral oxides are prepared as follows:

PREPARATIVE REAGENTS

In the following examples the TiAPSO compositions were prepared using numerous regents. The reagents employed and abbreviations employed herein, if any, for such reagents are as follows:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent aqueous phosphoric acid;
(d) Tiipro: titanium isopropoxide;
(e) TEAOH: 40 weight percent aqueous solution of tetraethylammonium hydroxide;
(f) $Pr_2NH$: di-n-propylamine, $(C_3H_7)_2NH$.
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

PREPARATIVE PROCEDURES

The following preparative examples were carried out by forming a starting reaction mixture by adding the $H_3PO_4$ and the water. This mixture was mixed and to this mixture the aluminum isopropoxide was added. This mixture was then blended until a homogeneous mixture was observed. To this mixture the LUDOX-LS was added and the resulting mixture blended (about 2 minutes) until a homogeneous mixture was observed.

The titanium isopropoxide was added to the above mixture and the resulting mixture blended until a homogeneous mixture was observed. The organic templating agent was then added to the resulting mixture and the resulting mixture blended until a homogeneous mixture was observed, i.e., about 2 to 4 minutes. When the organic templating agent was quinuclidine the procedure was modified such that the quinuclidine was dissolved in about one half the water and accordingly the $H_3PO_4$ was mixed with about one half the water. (The pH of the mixture was measured and adjusted for temperature). The mixture was then placed in a lined (polytetrafluoroethylene) stainless steel pressure vessel and digested at a temperature (150° C. or 200° C.) for a time or placed in lined screw top bottles for digestion at 100° C. All digestions were carried out at the autogeneous pressure.

The molar composition for each preparation will be given by the relative moles of the components of the reaction mixture. H$_3$PO$_4$ and titanium isopropoxide are given respectively in terms of the P$_2$O$_5$ and TiO$_2$ content of the reaction mixture.

All digestions were carried out at the autogeneous pressure. The products were removed from the reaction vessel cooled and evaluated as set forth hereinafter.

EXAMPLES 1E to 30E

TiAPSO molecular sieves were prepared according to the above described preparative procedure and the TiAPSO products determined by x-ray analysis. The results of examples 1E to 30E are set forth in Tables I-E and II-E.

TABLE I-E

| Example | Template[1] | Temp (°C.) | Time (days) | TiAPSO Product(s)[2] |
|---------|-------------|------------|-------------|----------------------|
| 1E | Quin | 150 | 28 | TiAPSO-16 |
| 2E | Quin | 200 | 10 | TiAPSO-35; TiAPSO-16 |
| 3E | Quin | 200 | 28 | TiAPSO-35; TiAPSO-16 |
| 4E | Quin | 225 | 5 | TiAPSO-16 |
| 5E | Pr$_3$N | 150 | 3 | TiAPSO-5 |
| 6E | Pr$_3$N | 150 | 11 | TiAPSO-5 |
| 7E | Pr$_3$N | 200 | 3 | TiAPSO-5 |
| 8E | Pr$_3$N | 200 | 11 | TiAPSO-5 |
| 9E | Pr$_3$N | 100 | 3 | — |
| 10E | Pr$_3$N | 100 | 11 | — |

[1]Reaction mixture comprised:
1.0 R:0.2 TiO$_2$:0.9 Al$_2$O$_3$:0.9 P$_2$O$_5$:0.2 SiO$_2$:50 H$_2$O where "R" is the organic template.
[2]Major species as identified by x-ray powder diffraction pattern of product, except that when two or more species were identified the species are listed in the order of their predominance in the product. The "—" denotes that TiAPSO products were not identified by X-ray analysis.

TABLE II-E

| Example | Template[1] | Temp (°C.) | Time (days) | TiAPSO Product(s)[2] |
|---------|-------------|------------|-------------|----------------------|
| 11E | C-hex | 225 | 5 | TiAPSO-44; TiAPSO-35 |
| 12E | Pr$_2$NH | 150 | 4 | TiAPSO-11; TiAPSO-41 |
| 13E | Pr$_2$NH | 150 | 11 | TiAPSO-11 |
| 14E | Pr$_2$NH | 200 | 4 | TiAPSO-11 |
| 15E | Pr$_2$NH | 200 | 11 | TiAPSO-11 |
| 16E | Pr$_2$NH | 100 | 4 | — |
| 17E | Pr$_2$NH | 100 | 11 | — |
| 18E | TEAOH | 150 | 4 | TiAPSO-34; TiAPSO-5 |
| 19E | TEAOH | 150 | 10 | TiAPSO-34; TiAPSO-5 |
| 20E | TEAOH | 200 | 4 | TiAPSO-5; TiAPSO-34 |
| 21E | TEAOH | 200 | 10 | TiAPSO-5; TiAPSO-34 |
| 22E | TEAOH | 100 | 17 | — |
| 23E | TEAOH | 150 | 2 | TiAPSO-34; TiAPSO-5 |
| 24E | TEAOH | 150 | 13 | TiAPSO-34 |
| 25E | TEAOH | 200 | 2 | TiAPSO-34; TiAPSO-5 |
| 26E | TEAOH | 200 | 13 | TiAPSO-34 |
| 27E | MQuin | 150 | 21 | — |
| 28E | MQuin | 200 | 21 | TiAPSO-35 |
| 29E | MQuin | 150 | 45 | TiAPSO-35 |
| 30E | MQuin | 200 | 45 | TiAPSO-35 |

[1]The reaction mixture generally comprised:
kR:0.2 TiO$_2$:0.9 Al$_2$O$_3$:p P$_2$O$_5$:q SiO$_2$:50 H$_2$O where R is the organic template; "k" is 1.0 for examples 11E to 22E and 27E to 30E and is 1.5 for examples 23E to 26E; "p" is 0.9 for examples 12E–30E and is 1.0 for example 11E; and "q" is 0.6 for examples 11E and 23E–26E and is 0.2 for examples 12E–22E and 27E–30E.
[2]Major species as identified by x-ray powder diffraction pattern of product, except that when two or more species were identified the species are listed in the order of their predominance in the product. The "—" denotes that TiAPSO products were not identified by X-ray analysis.

EXAMPLE 31E

Samples of the products of examples 4E, 6E, 15E, 24E and 30E were subjected to chemical analysis. The chemical analysis for each product is given hereinafter with the example in which the TiAPSO was prepared being given in parenthesis after the designation of the TiAPSO species.

(a) The chemical analysis for TiAPSO-16 (Example 4E) was:

| Component | Weight Percent |
|-----------|----------------|
| Al$_2$O$_3$ | 27.1 |
| P$_2$O$_5$ | 36.1 |
| TiO$_2$ | 6.8 |
| SiO$_2$ | 6.7 |
| Carbon | 12.0 |
| Nitrogen | 1.9 |
| LOI* | 22.9 |

*LOI = Loss on Ignition

The above chemical analysis gives an overall product composition in molar oxide ratios (anhydrous basis) of: 0.085 TiO$_2$:0.266 Al$_2$O$_3$:0.254 P$_2$O$_5$:0.112 SiO$_2$; and a formula (anhydrous basis) of:

0.14R(Ti$_{0.07}$Al$_{0.43}$P$_{0.41}$Si$_{0.09}$)O$_2$ (b) The chemical analysis for TiAPSO-35 (Example 30E) was:

| Component | Weight Percent |
|-----------|----------------|
| Al$_2$O$_3$ | 23.4 |
| P$_2$O$_5$ | 28.3 |
| TiO$_2$ | 17.6 |
| SiO$_2$ | 4.37 |
| Carbon | 11.3 |
| Nitrogen | 1.6 |

| Component | Weight Percent |
|---|---|
| LOI* | 26.3 |

*LOI = Loss on Ignition

The above chemical analysis gives an overall product composition in molar oxide ratios (anhydrous basis) of: 0.220 $TiO_2$:0.230 $Al_2O_3$:0.199 $P_2O_5$:0.073 $SiO_2$; and a formula (anhydrous basis) of:

0.12 R($Ti_{0.19}Al_{0.40}P_{0.35}Si_{0.06}$)$O_2$ (c) The chemical analysis for TiAPSO-5 (Example 6E) was:

| Component | Weight Percent |
|---|---|
| $Al_2O_3$ | 34.0 |
| $P_2O_5$ | 46.9 |
| $TiO_2$ | 3.0 |
| $SiO_2$ | 1.2 |
| Carbon | 5.8 |
| Nitrogen | 0.74 |
| LOI* | 14.4 |

*LOI = Loss on Ignition

The above chemical analysis gives an overall product composition in molar oxide ratios (anhydrous basis) of: 0.038 $TiO_2$:0.334 $Al_2O_3$:0.330 $P_2O_5$:0.020 $SiO_2$; and a formula (anhydrous basis) of:

0.54R($Ti_{0.03}Al_{0.48}P_{0.48}Si_{0.01}$)$O_2$ (d) The chemical analysis of TiAPSO-11 (Example 15E) was:

| Component | Weight Percent |
|---|---|
| $Al_2O_3$ | 35.8 |
| $P_2O_5$ | 49.0 |
| $TiO_2$ | 1.08 |
| $SiO_2$ | 3.3 |
| Carbon | 5.0 |
| Nitrogen | 1.0 |
| LOI* | 10.5 |

*LOI = Loss on Ignition

The above chemical analysis gives an overall product composition in molar oxide ratios (anhydrous basis) of: 0.014 $TiO_2$:0.351 $Al_2O_3$:0.345 $P_2O_5$:0.055 $SiO_2$; and a formula (anhydrous basis) of:

0.07R($Ti_{0.01}Al_{0.48}P_{0.47}Si_{0.04}$)$O_2$ (e) The chemical analysis for TiAPSO-34 (example 24E) was:

| Component | Weight Percent |
|---|---|
| $Al_2O_3$ | 32.3 |
| $P_2O_5$ | 37.9 |
| $TiO_2$ | 0.4 |
| $SiO_2$ | 8.2 |
| Carbon | 9.8 |
| Nitrogen | 1.6 |
| LOI* | 20.5 |

*LOI = Loss on Ignition

The above chemical analysis gives an overall product composition in molar oxide ratios (anhydrous basis) of: 0.01 $TiO_2$:0.32 $Al_2O_3$:0.27 $P_2O_5$:0.14 $SiO_2$; and a formula (anhydrous basis) of:

0.103R($Ti_{0.01}Al_{0.48}P_{0.41}Si_{0.11}$)$O_2$

EXAMPLE 32E

EDAX (energy dispersive analysis by x-ray) microprobe analysis in conjunction with SEM (scanning electron microscope was carried out on clear crystals from the products of example 4E, 11E, 12E, and 21E. Analysis of crystals having a morphology characteristic of TiAPSO compositions gave the following analysis based on relative peak heights:

| | Average of Spot Probes |
|---|---|
| (a) TiAPSO-44/35 (Example 11E): | |
| Ti | 0.02 |
| Al | 0.97 |
| P | 0.94 |
| Si | 0.25 |
| (b) TiAPSO-16 (Example 4E): | |
| Ti | 0.38 |
| Al | 0.79 |
| P | 0.84 |
| Si | 0.33 |
| (c) TiAPSO-34/5 (Example 21E): | |
| Ti | 0.005 |
| Al | 0.85 |
| P | 1.00 |
| Si | 0.08 |
| (d) TiAPSO-11 (Example 12E): | |
| Ti | 0.12 |
| Al | 0.88 |
| P | 0.84 |
| Si | 0.07 |

EXAMPLE 33E

Samples of the TiAPSO products of examples 4E, 13E, and 6E were evaluated for adsorption capacities in the calcined form by calcination in air to remove at least part of the organic templating agent, as hereinafter set forth. The adsorption capacities of each calcined sample were measured using a standard McBain-Bakr gravimetric adsorption apparatus. The samples were activated in a vacuum at 350° C. prior to measurement. The McBain-Bakr data for the aforementioned calcined TiAPSO products were:

| Adsorbate | Kinetic Diameter, Å | Pressure (Torr) | Temp (°C.) | Wt. %* Adsorbed |
|---|---|---|---|---|
| (a) TiAPSO-16 (Example 4E): | | | | |
| $O_2$ | 3.46 | 102 | −183 | 3.3 |
| $O_2$ | 3.46 | 744 | −183 | 12.8** |
| n-hexane | 4.3 | 95 | 23.6 | 7.0 |
| $H_2O$ | 2.65 | 4.6 | 23.3 | 13.4 |
| $H_2O$ | 2.65 | 19 | 23.2 | 25.4 |

*TiAPSO-16 was calcined at 500° C. in air for 1.5 hours prior to being activated.
**Sample may not have been fully equilibrated.

The above data demonstrate that the pore size of the calcined product is about 4.3 Å.

| Adsorbate | Kinetic Diameter, Å | Pressure (Torr) | Temp (°C.) | Wt. %* Adsorbed |
|---|---|---|---|---|
| (b) TiAPSO-11 (Example 13E): | | | | |
| $O_2$ | 3.46 | 101 | −183 | 9.3 |
| $O_2$ | 3.46 | 736 | −183 | 10.3 |
| neopentane | 5.0 | 742 | 23.0 | 1.1 |
| cyclohexane | 6.0 | 67 | 22.9 | 5.2 |
| $H_2O$ | 2.65 | 4.6 | 22.4 | 12.4 |
| $H_2O$ | 2.65 | 19 | 22.5 | 23.4 |

*TiAPSO-11 was calcined at 600° C. in air for 1.5 hours prior to being activated.

The above data demonstrate that the pore size of the calcined product is about 6.0 Å.

| Adsorbate | Kinetic Diameter, Å | Pressure (Torr) | Temp (°C.) | Wt. %* Adsorbed |
|---|---|---|---|---|
| (c) TiAPSO-5 (Example 6E): | | | | |
| O₂ | 3.46 | 101 | −183 | 13.0 |
| O₂ | 3.46 | 736 | −183 | 14.5 |
| neopentane | 6.2 | 742 | 23.0 | 4.9 |
| cyclohexane | 6.0 | 67 | 22.9 | 7.1 |
| H₂O | 2.65 | 4.6 | 22.4 | 14.7 |
| H₂O | 2.65 | 19 | 22.5 | 23.4 |

*TiAPSO was calcined at 600° C. in air for 2.5 hours prior to being activated.

The above data demonstrate that the pore size of the calcined product is greater than 6.2 Å.

EXAMPLE 34E (a) TiAPSO-5 compositions, as referred to herein in both the as-synthesized and calcined forms, have a characteristic x-ray powder diffraction pattern which contains at least the d-spacings set forth in Table III below:

TABLE III-E

| 2θ | d, (Å) | Relative Intensity |
|---|---|---|
| 7.3–7.5 | 12.11–11.79 | s–vs |
| 19.7–19.9 | 4.51–4.46 | m |
| 20.9–21.0 | 4.25–4.23 | m–s |
| 22.3–22.5 | 3.99–3.95 | m–vs |
| 25.8–26.1 | 3.453–3.411 | m |
| 28.9–29.1 | 3.089–3.069 | w–m |

(b) TiAPSO-5 compositions for which x-ray powder diffraction data have been obtained to date have patterns which are X-ray powder diffraction patterns characterized by Table IV-E below.

TABLE IV-E

| 2θ | d, (Å) | 100 × I/Io |
|---|---|---|
| 7.3–7.5 | 12.11–11.79 | 94–100 |
| 12.9–13.0 | 6.86–6.81 | 19–22 |
| 14.9–15.0 | 5.95–5.91 | 9–21 |
| 19.7–19.9 | 4.51–4.46 | 26–50 |
| 20.9–21.0 | 4.25–4.23 | 43–82 |
| 22.3–22.5 | 3.99–3.95 | 60–100 |
| 24.6–24.8 | 3.62–3.59 | 7–9 |
| 25.8–26.1 | 3.453–3.414 | 25–40 |
| 28.9–29.1 | 3.089–3.069 | 17–27 |
| 30.0–30.2 | 2.979–2.959 | 18–25 |
| 33.5–33.7 | 2.675–2.660 | 6–9 |
| 34.5–34.7 | 2.600–2.585 | 17–19 |
| 36.8–37.1 | 2.442–2.423 | 6 |
| 37.5–37.8 | 2.398–2.380 | 10–13 |
| 41.4–41.5 | 2.181–2.176 | 5–6 |
| 41.7–42.0 | 2.166–2.151 | 3–4 |
| 42.5–42.9 | 2.127–2.108 | 3–6 |
| 43.6–43.7 | 2.076–2.071 | 3–4 |
| 44.9–45.0 | 2.019–2.014 | 3–4 |
| 47.4–47.6 | 1.918–1.910 | 5–7 |
| 47.8–47.9 | 1.903–1.900 | 6–7 |
| 51.4–51.5 | 1.778–1.774 | 4–5 |
| 51.8–51.9 | 1.765–1.762 | 3–4 |
| 55.6 | 1.653 | 6 |

(c) A portion of the as-synthesized TiAPSO-5 of Example 6E was subjected to X-ray analysis. The TiAPSO-5 product was characterized by the x-ray powder diffraction pattern of Table V-E, below:

TABLE V-E

| 2θ | d, (Å) | 100 × I/Io |
|---|---|---|
| 7.3 | 12.11 | 94 |
| 9.1* | 9.72 | 3 |
| 12.9 | 6.86 | 19 |
| 13.6* | 6.51 | 6 |
| 14.9 | 5.95 | 21 |
| 18.2* | 4.87 | 6 |
| 19.7 | 4.51 | 50 |
| 20.9 | 4.25 | 82 |
| 22.3 | 3.99 | 100 |
| 24.6 | 3.62 | 9 |
| 25.8 | 3.453 | 40 |
| 28.9 | 3.089 | 27 |
| 30.0 | 2.979 | 25 |
| 33.5 | 2.675 | 9 |
| 34.5 | 2.600 | 19 |
| 36.8 | 2.442 | 6 |
| 37.5 | 2.398 | 13 |
| 41.4 | 2.181 | 6 |
| 42.0 | 2.151 | 4 |
| 42.5 | 2.127 | 6 |
| 43.6 | 2.076 | 4 |
| 44.9 | 2.019 | 3 |
| 47.6 | 1.910 | 7 |
| 51.4 | 1.778 | 4 |
| 51.8 | 1.765 | 4 |
| 55.6 | 1.653 | 6 |

*peak may contain an impurity.

(d) The TiAPSO-5 compositions of Example 6E was calcined at 600° C. in air for 2.5 hours. The calcined product was characterized by the x-ray powder diffraction pattern shown in Table VI-E below:

TABLE VI-E

| 2θ | d, (Å) | 100 × I/Io |
|---|---|---|
| 7.5 | 11.79 | 100 |
| 12.5* | 7.08 | 8 |
| 13.0 | 6.81 | 22 |
| 15.0 | 5.91 | 9 |
| 19.9 | 4.46 | 26 |
| 21.0 | 4.23 | 43 |
| 22.5 | 3.95 | 60 |
| 24.8 | 3.59 | 7 |
| 26.1 | 3.414 | 25 |
| 29.1 | 3.069 | 17 |
| 30.2 | 2.959 | 18 |
| 33.7 | 2.660 | 6 |
| 34.7 | 2.585 | 17 |
| 37.1 | 2.423 | 6 |
| 37.8 | 2.380 | 10 |
| 41.7 | 2.166 | 3 |
| 42.9 | 2.108 | 3 |
| 47.4 | 1.918 | 5 |
| 47.9 | 1.900 | 6 |
| 51.4 | 1.778 | 3 |
| 51.8 | 1.765 | 3 |

*peak may contain an impurity.

EXAMPLE 35-E (a) TiAPSO-11, as referred to herein in both the as-synthesized and calcined forms, have a characteristic x-ray powder diffraction pattern which contains at least the d-spacings set forth in Table VII-E below:

TABLE VII-E

| 2θ | d, (Å) | Relative Intensity |
|---|---|---|
| 9.4–9.6 | 9.41–9.21 | vw–m |
| 19.9–20.5 | 4.46–4.33 | m |
| 21.0–21.8 | 4.23–4.08 | vs |
| 22.0–22.1 | 4.04–4.02 | m–vs |
| 22.4–22.6 | 3.97–3.93 | m–s |
| 22.7 | 3.92 | m |
| 23.1–23.4 | 3.85–3.80 | m–vs |

(b) The TiAPSo-11 compositions for which x-ray powder diffraction data have been obtained to date have patterns which are

TABLE VIII-E

| 2θ | d, (Å) | 100 × I/Io |
|---|---|---|
| 8.0–8.1 | 11.05–10.92 | 23–59 |
| 9.4–9.6 | 9.41–9.21 | sh–73 |
| 9.8 | 9.03 | 51 |
| 12.8–13.2 | 6.92–6.71 | 26–27 |
| 13.5–13.7 | 6.56–6.46 | 9–11 |
| 14.7–15.0 | 6.03–5.91 | 9–18 |
| 15.6–16.1 | 5.68–5.51 | 32–63 |
| 16.2–16.3 | 5.47–5.44 | 7–18 |
| 19.0–19.5 | 4.67–4.55 | 20–23 |
| 19.9–20.5 | 4.46–4.33 | 31–68 |
| 21.0–21.8 | 4.23–4.08 | 100 |
| 22.0–22.1 | 4.04–4.02 | 57–100 |
| 22.4–22.6 | 3.97–3.93 | 54–82 |
| 22.7 | 3.92 | 73 |
| 23.1–23.4 | 3.85–3.80 | 63–91 |
| 23.9–24.4 | 3.72–3.65 | 23 |
| 24.7 | 3.60 | 27 |
| 26.5–26.6 | 3.363–3.351 | 17–36 |
| 27.2–27.3 | 3.278–3.267 | 16–20 |
| 27.6–27.7 | 3.232–3.220 | 20–23 |
| 27.8–27.9 | 3.209–3.200 | 20–21 |
| 28.5–28.6 | 3.132–3.121 | 14–27 |
| 28.7 | 3.110 | 11–32 |
| 29.0–29.5 | 3.079–3.028 | 27–31 |
| 29.6–29.7 | 3.018–3.008 | 23–34 |
| 30.3–30.4 | 2.950–2.940 | 20–22 |
| 31.4–31.6 | 2.849–2.831 | 14–23 |
| 32.5–32.9 | 2.755–2.722 | 26–32 |
| 33.9–34.2 | 2.644–2.622 | 11–23 |
| 35.5–35.6 | 2.529–2.522 | 17–19 |
| 36.5 | 2.462 | 18 |
| 37.2–37.5 | 2.417–2.398 | 14–23 |
| 38.7–39.4 | 2.327–2.287 | 14–17 |
| 41.0 | 2.201 | 11 |
| 42.8 | 2.113 | 14 |
| 43.6 | 2.076 | 9 |
| 44.5–44.6 | 2.036–2.032 | 9–14 |
| 45.0 | 2.014 | 14 |
| 48.7–49.2 | 1.870–18.52 | 14 |
| 49.4 | 1.845 | 11 |
| 49.6 | 1.838 | 11 |
| 50.6 | 1.804 | 7–18 |
| 53.4 | 1.716 | 11 |
| 53.6 | 1.707 | 9 |
| 54.6–54.7 | 1.681–1.678 | 9–14 |
| 55.4–55.8 | 1.658–1.647 | 11–14 |

(c) A portion of the as-synthesized TiAPSO-11 of Example 13E was subjected to x-ray analysis. The TiAPSO-11 product was characterized by the x-ray powder diffraction pattern of Table IX-E, below:

TABLE IX-E

| 2θ | d, (Å) | 100 × I/Io |
|---|---|---|
| 8.1 | 10.92 | 59 |
| 9.4 | 9.41 | 73 |
| 13.2 | 6.71 | 27 |
| 15.0 | 5.91 | 18 |
| 15.7 | 5.64 | 50 |
| 16.3 | 5.44 | 18 |
| 19.0 | 4.67 | 23 |
| 20.5 | 4.33 | 68 |
| 21.0 | 4.23 | 100 |
| 22.1 | 4.02 | 73 |
| 22.6 | 3.93 | 82 |
| 22.7 | 3.92 | 73 |
| 23.2 | 3.83 | 91 |
| 24.4 | 3.65 | 23 |
| 24.7 | 3.60 | 27 |
| 26.5 | 3.363 | 36 |
| 28.5 | 3.132 | 27 |
| 28.7 | 3.110 | 32 |
| 29.0 | 3.079 | 27 |
| 29.5 | 3.028 | 23 |
| 31.4 | 2.849 | 23 |
| 32.9 | 2.722 | 32 |
| 34.2 | 2.622 | 23 |
| 36.5 | 2.462 | 18 |
| 37.5 | 2.398 | 23 |
| 39.4 | 2.287 | 14 |
| 42.8 | 2.113 | 14 |
| 44.6 | 2.032 | 14 |
| 45.0 | 2.014 | 14 |
| 48.7 | 1.870 | 14 |
| 50.6 | 1.804 | 18 |
| 54.7 | 1.678 | 14 |
| 55.4 | 1.658 | 14 |

(d) The TiAPSO-11 composition of Example 13E was calcined at 500° C. in air for 2 hours. The calcined product was characterized by the x-ray powder diffraction pattern shown in Table X-E, below:

TABLE X-E

| 2θ | d, (Å) | 100 × I/Io |
|---|---|---|
| 8.1 | 10.92 | 23 |
| 9.6 | 9.21 | sh |
| 9.8 | 9.03 | 51 |
| 12.8 | 6.92 | 26 |
| 13.5 | 6.56 | 11 |
| 13.7 | 6.46 | 9 |
| 14.7 | 6.03 | 9 |
| 16.1 | 5.51 | 63 |
| 19.5 | 4.55 | 20 |
| 19.9 | 4.46 | 31 |
| 21.8 | 4.08 | 100 |
| 22.1 | 4.02 | 57 |
| 22.4 | 3.97 | 54 |
| 23.4 | 3.80 | 63 |
| 23.9 | 3.72 | 23 |
| 24.2 | 3.68 | 17 |
| 26.6 | 3.351 | 17 |
| 27.2 | 3.278 | 20 |
| 27.6 | 3.232 | 23 |
| 27.8 | 3.209 | 20 |
| 28.5 | 3.132 | 14 |
| 28.7 | 3.110 | 11 |
| 29.5 | 3.028 | 31 |
| 29.7 | 3.008 | 34 |
| 30.3 | 2.950 | 20 |
| 31.6 | 2.831 | 14 |
| 32.5 | 2.755 | 26 |
| 33.9 | 2.644 | 11 |
| 35.5 | 2.529 | 17 |
| 37.2 | 2.417 | 14 |
| 38.7 | 2.327 | 17 |
| 41.0 | 2.201 | 11 |
| 43.6 | 2.076 | 9 |
| 44.5 | 2.036 | 9 |
| 49.2 | 1.852 | 14 |
| 49.4 | 1.845 | 11 |
| 49.6 | 1.838 | 11 |
| 53.4 | 1.716 | 9 |
| 53.6 | 1.707 | 9 |
| 55.8 | 1.647 | 11 |

EXAMPLE 36E (a) TiAPSO-16, as referred to herein in both the as-synthesized and calcined form, have a characteristic x-ray powder diffraction pattern which contains at least the d-spacings set forth in Table XI-E below:

TABLE XI-E

| 2θ | d, (Å) | Relative Intensity |
|---|---|---|
| 11.4 | 7.75 | m–vs |
| 18.7 | 4.75 | m |
| 21.9–22.1 | 4.05–4.02 | m–vs |
| 26.4–26.5 | 3.370–3.363 | m |
| 29.6–29.8 | 3.018–3.002 | m |
| 29.9 | 2.984 | m |
| 30.1 | 2.971 | m |

(b) The TiAPSO-16 compositions for which x-ray powder diffraction data have been obtained to date have patterns which are characterized by the X-ray powder diffraction pattern of Table XII-E below:

TABLE XII-E

| 2θ | d, (Å) | 100 × I/Io |
|---|---|---|
| 10.5 | 8.41 | 5 |
| 11.4 | 7.75 | 72–100 |
| 18.7 | 4.75 | 25–59 |
| 21.1 | 4.21 | 3 |
| 21.9–22.1 | 4.05–4.02 | 56–100 |
| 22.8–22.9 | 3.90–3.89 | 10–15 |
| 23.3 | 3.818 | 3 |
| 25.0 | 3.561 | 6 |
| 25.4–25.5 | 3.506–3.489 | 13–17 |
| 26.4–26.5 | 3.370–3.363 | 20–23 |
| 26.6 | 3.346 | 16 |
| 26.9–27.1 | 3.314–3.290 | 4–15 |
| 28.9–29.1 | 3.088–3.073 | 12–13 |
| 29.6–29.8 | 3.018–3.002 | 22–27 |
| 29.9 | 2.984 | 24 |
| 30.1 | 2.971 | 23 |
| 32.5–32.7 | 2.755–2.739 | 3–4 |
| 34.4–34.8 | 2.607–2.581 | 3–5 |
| 37.3–37.6 | 2.411–2.394 | 4–5 |
| 37.8–37.9 | 2.380–2.373 | 8–14 |
| 38.2–38.4 | 2.356–2.343 | 5 |
| 39.5 | 2.282 | 3–4 |
| 39.7–39.8 | 2.270–2.265 | 3–5 |
| 40.1 | 2.247 | 7 |
| 40.5 | 2.227 | 4 |
| 44.4 | 2.040 | 3 |
| 47.8–47.9 | 1.904–1.899 | 5 |
| 48.0–48.1 | 1.897–1.893 | 6–8 |
| 48.2–48.3 | 1.887–1.885 | 7–8 |
| 48.4–48.5 | 1.881–1.876 | 7–8 |
| 48.8 | 1.865 | 5–6 |
| 49.0 | 1.858 | 5 |
| 49.2 | 1.853 | 4 |
| 54.2 | 1.692 | 3 |
| 54.3 | 1.689 | 3 |

(c) A portion of the as-synthesized TiAPSO-16 of example 4E was subjected to x-ray analysis. The TiAPSO-16 product was characterized by the x-ray powder diffraction pattern of Table XIII-E, below:

TABLE XIII-E

| 2θ | d, (Å) | 100 × I/Io |
|---|---|---|
| 11.4 | 7.75 | 72 |
| 18.7 | 4.74 | 59 |
| 22.1 | 4.02 | 100 |
| 22.9 | 3.89 | 11 |
| 25.3 | 3.521 | 15 |
| 26.4 | 3.376 | 13 |
| 26.6 | 3.346 | 16 |
| 26.9 | 3.314 | 15 |
| 29.1 | 3.073 | 13 |
| 29.8 | 3.002 | 22 |
| 29.9 | 2.984 | 24 |
| 30.1 | 2.971 | 23 |
| 34.8 | 2.581 | 3 |
| 37.6 | 2.395 | 5 |
| 37.9 | 2.371 | 14 |
| 38.4 | 2.343 | 5 |
| 39.5 | 2.282 | 4 |
| 39.7 | 2.270 | 5 |
| 40.1 | 2.247 | 7 |
| 40.5 | 2.227 | 4 |
| 47.8 | 1.904 | 5 |
| 48.1 | 1.893 | 8 |
| 48.2 | 1.887 | 8 |
| 48.5 | 1.876 | 8 |
| 48.8 | 1.865 | 6 |
| 49.0 | 1.858 | 5 |
| 49.2 | 1.853 | 4 |

*peak may contain impurity (d) The TiAPSO-16 composition of part (c) was calcined at 500° C. in air for 1.5 hours. The calcined product was characterized by the x-ray powder diffraction pattern shown in Table XIV-E, below:

TABLE XIV-E

| 2θ | d, (Å) | 100 × I/Io |
|---|---|---|
| 10.5 | 8.41 | 5 |
| 11.4 | 7.75 | 100 |
| 18.7 | 4.75 | 25 |
| 21.1 | 4.27 | 3 |
| 21.9 | 4.05 | 56 |
| 22.8 | 3.90 | 10 |
| 25.0 | 3.561 | 6 |
| 25.4* | 3.506 | 14 |
| 25.5 | 3.489 | 13 * |
| 26.4 | 3.370 | 20 |
| 28.9 | 3.088 | 12 |
| 29.7 | 3.007 | 27 |
| 34.6 | 2.594 | 5 |
| 37.6 | 2.391 | 5 |
| 37.9 | 2.373 | 9 |
| 38.2 | 2.356 | 5 |
| 48.0 | 1.897 | 6 |
| 48.3 | 1.885 | 7 |

*peak may contain impurity

EXAMPLE 37E (a) TiAPSO-34, as referred to herein in both the as-synthesized and calcined forms, have a characteristic x-ray powder diffraction pattern which contains at least the d-spacings set forth in Table XV-E below:

TABLE XV-E

| 2θ | d, (Å) | Relative Intensity |
|---|---|---|
| 9.4–9.5 | 9.41–9.31 | vs |
| 12.9–13.0 | 6.86–6.81 | w–m |
| 16.0–16.2 | 5.54–5.47 | w–m |
| 20.5–20.8 | 4.33–4.27 | m–vs |
| 30.5–30.9 | 2.931–2.894 | m |
| 31.5–31.6 | 2.840–2.831 | vw–m |

(b) The TiAPSO-34 compositions for which x-ray powder diffraction data have been obtained to date have patterns which are characterized by the x-ray powder diffraction pattern of Table XVI-E below:

TABLE XVI-E

| 2θ | d, (Å) | 100 × I/Io |
|---|---|---|
| 9.4–9.5 | 9.41–9.31 | 100 |
| 12.9–13.0 | 6.86–6.81 | 16–31 |
| 14.0–14.1 | 6.33–6.28 | 7–16 |
| 16.0–16.2 | 5.54–5.47 | 19–50 |
| 17.8–17.9 | 4.98–4.96 | 16–23 |
| 19.2 | 4.62 | 10 |
| 20.5–20.8 | 4.33–4.27 | 38–97 |
| 22.1–22.2 | 4.02–4.00 | 8–9 |
| 23.1–23.3 | 3.85–3.82 | 8–14 |
| 25.0–25.1 | 3.562–3.548 | 17–27 |
| 25.8–26.2 | 3.453–3.401 | 19–21 |
| 27.5–27.9 | 3.243–3.198 | 7–10 |
| 28.2–28.3 | 3.164–3.153 | 7–12 |
| 29.5–29.8 | 3.028–2.998 | 8–12 |
| 30.5–30.9 | 2.931–2.894 | 31–39 |
| 31.1–31.3 | 2.876–2.858 | Sh–29 |
| 31.5–31.6 | 2.840–2.831 | 8–32 |
| 32.3–32.4 | 2.772–2.763 | 6–7 |
| 33.2 | 2.698 | 5 |
| 33.8 | 2.652 | 5 |
| 34.4–34.9 | 2.607–2.571 | 8–9 |
| 35.0 | 2.564 | 3 |
| 36.1–36.2 | 2.488–2.481 | 6–7 |
| 38.8 | 2.321 | 3 |
| 39.6–39.8 | 2.276–2.265 | 5–7 |
| 40.2 | 2.243 | 5 |
| 43.0 | 2.103 | 5 |

TABLE XVI-E-continued

| 2θ | d, (Å) | 100 × I/Io |
|---|---|---|
| 43.4 | 2.085 | 7 |
| 47.5 | 1.914 | 5 |
| 48.9–49.2 | 1.863–1.852 | 5–8 |
| 49.8 | 1.831 | 5 |
| 50.9–51.0 | 1.794–1.791 | 7–8 |
| 51.5–51.6 | 1.774–1.771 | 3–5 |
| 53.1–53.2 | 1.725–1.722 | 7–8 |
| 54.4–54.5 | 1.687–1.684 | 5–6 |
| 55.8–55.9 | 1.647–1.645 | 6–7 |

(c) A portion of the as-synthesized TiAPSO-34 of example 24E was subjected to x-ray analysis. The TiAPSO-34 product was characterized by the x-ray powder diffraction pattern of Table XVII-E below:

TABLE XVII-E

| 2θ | d, (Å) | 100 × I/Io |
|---|---|---|
| 9.4 | 9.41 | 100 |
| 12.9 | 6.86 | 16 |
| 14.0 | 6.33 | 16 |
| 16.0 | 5.54 | 50 |
| 17.9 | 4.96 | 23 |
| 20.5 | 4.33 | 97 |
| 22.1 | 4.02 | 8 |
| 23.1 | 3.85 | 8 |
| 25.1 | 3.548 | 27 |
| 25.8 | 3.453 | 21 |
| 27.5 | 3.243 | 7 |
| 28.3 | 3.153 | 7 |
| 29.5 | 3.028 | 8 |
| 30.5 | 2.931 | 39 |
| 31.1 | 2.876 | 29 |
| 31.6 | 2.831 | 8 |
| 32.4 | 2.763 | 7 |
| 33.2 | 2.698 | 5 |
| 33.8 | 2.652 | 5 |
| 34.4 | 2.607 | 8 |
| 35.0 | 2.564 | 3 |
| 36.2 | 2.481 | 7 |
| 38.8 | 2.321 | 3 |
| 39.6 | 2.276 | 7 |
| 43.0 | 2.103 | 5 |
| 43.4 | 2.085 | 7 |
| 47.5 | 1.914 | 5 |
| 48.9 | 1.863 | 8 |
| 49.8 | 1.831 | 5 |
| 50.9 | 1.794 | 7 |
| 51.6 | 1.771 | 3 |
| 53.1 | 1.725 | 7 |
| 54.4 | 1.687 | 5 |
| 55.8 | 1.647 | 7 |

(d) The TiAPSO-34 compositions of example 24E was calcined at 500° C. in air for 2 hours. The calcined product was characterized by the x-ray powder diffraction pattern shown in Table XVIII-E, below:

TABLE XVIII-E

| 2θ | d, (Å) | 100 × I/Io |
|---|---|---|
| 9.5 | 9.31 | 100 |
| 13.0 | 6.81 | 31 |
| 14.1 | 6.28 | 7 |
| 16.2 | 5.47 | 19 |
| 17.9 | 4.96 | 16 |
| 19.2 | 4.62 | 10 |
| 20.8 | 4.27 | 38 |
| 22.2 | 4.00 | 9 |
| 23.3 | 3.82 | 14 |
| 25.0 | 3.562 | 17 |
| 26.2 | 3.401 | 19 |
| 27.9 | 3.198 | 10 |
| 28.2 | 3.164 | 12 |
| 29.8 | 2.998 | 12 |
| 30.9 | 2.894 | 31 |
| 31.3 | 2.858 | sh |
| 32.4 | 2.763 | 9 |

TABLE XVIII-E-continued

| 2θ | d, (Å) | 100 × I/Io |
|---|---|---|
| 34.9 | 2.571 | 9 |
| 36.2 | 2.481 | 7 |
| 39.8 | 2.265 | 5 |
| 40.2 | 2.243 | 5 |
| 49.2 | 1.852 | 5 |
| 51.0 | 1.791 | 7 |

EXAMPLE 38E (a) TiAPSO-35, as referred to herein in both the as-synthesized and calcined forms, have a characteristic x-ray powder diffraction pattern which contains at least the d-spacings set forth in Table XIX-E below:

TABLE XIX-E

| 2θ | d, (Å) | Relative Intensity |
|---|---|---|
| 10.9–11.1 | 8.12–7.97 | m |
| 13.3–13.7 | 6.66–6.46 | m |
| 17.3–17.4 | 5.13–5.10 | w–m |
| 20.8–21.1 | 4.27–4.21 | m |
| 21.9–22.2 | 4.06–4.00 | m–vs |
| 28.3–28.7 | 3.153–3.110 | m |

(b) The TiAPSO-35 compositions for which x-ray powder diffraction data have been obtained to date have patterns which are characterized by the x-ray powder diffraction pattern of Table XX-E below:

TABLE XX-E

| 2θ | d, (Å) | 100 × I/Io |
|---|---|---|
| 8.6–8.8 | 10.28–10.05 | 13–14 |
| 10.9–11.1 | 8.12–7.97 | 36–74 |
| 13.3–13.7 | 6.66–6.46 | 20–39 |
| 15.9–16.1 | 5.57–5.51 | 11–15 |
| 17.3–17.4 | 5.13–5.10 | 17–75 |
| 17.6–17.7 | 5.04–5.01 | 13–17 |
| 20.8–21.1 | 4.27–4.21 | 25–49 |
| 21.9–22.2 | 4.06–4.00 | 65–100 |
| 23.2–23.7 | 3.83–3.75 | 22–32 |
| 24.9–25.2 | 3.58–3.534 | 19–30 |
| 26.6–26.9 | 3.363–3.314 | 19–35 |
| 28.3–28.7 | 3.153–3.110 | 30–48 |
| 29.1–29.2 | 3.069–3.058 | 11–15 |
| 29.6–29.7 | 3.018–3.008 | 6–39 |
| 31.5–31.7 | 2.840–2.823 | 9–11 |
| 32.1–32.7 | 2.788–2.739 | 30–41 |
| 34.3–34.6 | 2.614–2.592 | 11–17 |
| 35.0–35.1 | 2.564–2.557 | 4–5 |
| 35.8–35.9 | 2.508–2.501 | 5–6 |
| 37.8–38.0 | 2.380–2.368 | 9–13 |
| 39.5 | 2.281 | 4–5 |
| 40.9 | 2.206 | 3–4 |
| 41.9 | 2.156 | 6 |
| 42.1–42.6 | 2.146–2.122 | 5–6 |
| 42.7 | 2.118 | 4–6 |
| 48.4–48.5 | 1.881–1.877 | 9–13 |
| 49.0 | 1.859 | 5–6 |
| 50.1 | 1.821 | 10–11 |
| 55.0–55.1 | 1.670–1.667 | 9–13 |
| 55.4–55.5 | 1.658–1.656 | 9–10 |

(c) A portion of the as-synthesized TiAPSO-35 of example 30E was subjected to x-ray analysis. The TiAPSO-35 product was characterized by the x-ray powder diffraction pattern of Table XXI-E below:

TABLE XXI-E

| 2θ | d, (Å) | 100 × I/Io |
|---|---|---|
| 8.6 | 10.28 | 13 |
| 10.9 | 8.12 | 36 |
| 11.4* | 7.76 | 6 |
| 13.3 | 6.66 | 21 |
| 15.9 | 5.57 | 11 |

TABLE XXI-E-continued

| 2θ | d, (Å) | 100 × I/Io |
|---|---|---|
| 17.3 | 5.13 | 75 |
| 17.7 | 5.01 | 13 |
| 18.6* | 4.77 | 6 |
| 20.8 | 4.27 | 49 |
| 21.9 | 4.06 | 100 |
| 22.6* | 3.93 | 9 |
| 23.2 | 3.83 | 32 |
| 24.9 | 3.58 | 19 |
| 25.2* | 3.534 | 28 |
| 26.9 | 3.314 | 19 |
| 28.3 | 3.153 | 47 |
| 29.1 | 3.069 | 11 |
| 29.7 | 3.008 | 6 |
| 31.5 | 2.840 | 9 |
| 32.1 | 2.788 | 38 |
| 34.3 | 2.614 | 11 |
| 35.0 | 2.564 | 4 |
| 35.9 | 2.501 | 6 |
| 37.8 | 2.380 | 9 |
| 39.5 | 2.281 | 4 |
| 40.9 | 2.206 | 4 |
| 41.9 | 2.156 | 6 |
| 42.6 | 2.122 | 6 |
| 42.7 | 2.118 | 6 |
| 44.7* | 2.027 | 6 |
| 47.6* | 1.910 | 11 |
| 48.4 | 1.881 | 9 |
| 49.0 | 1.859 | 6 |
| 49.6* | 1.838 | 7 |
| 50.1 | 1.821 | 11 |
| 54.0* | 1.698 | 6 |
| 55.0 | 1.670 | 9 |
| 55.4 | 1.658 | 9 |

*peak may contain an impurity (d) The calcined TiAPSO-35 compositions of example 2E was calcined at 600° C. in air for 2 hours. The calcined product was characterized by the x-ray powder diffraction pattern shown in Table XXII-E, below.

TABLE XXII-E

| 2θ | d, (Å) | 100 × I/Io |
|---|---|---|
| 8.8 | 10.05 | 13 |
| 11.1 | 7.97 | 74 |
| 11.5* | 7.69 | 100 |
| 13.7 | 6.46 | 39 |
| 17.6 | 5.04 | 17 |
| 18.9* | 4.70 | 26 |
| 21.1 | 4.21 | 26 |
| 22.2 | 4.00 | 65 |
| 23.1* | 3.85 | 26 |
| 23.7 | 3.75 | 22 |
| 25.2 | 3.534 | 30 |
| 26.6 | 3.363 | 35 |
| 27.4* | 3.255 | 26 |
| 28.7 | 3.110 | 35 |
| 29.6* | 3.018 | 39 |
| 29.8* | 2.998 | 44 |
| 32.7 | 2.739 | 30 |
| 34.6 | 2.592 | 17 |
| 38.0 | 2.368 | 13 |
| 48.5 | 1.877 | 13 |
| 55.1 | 1.667 | 13 |

*peak may contain an impurity

EXAMPLE 39E (a) TiAPSO-44, as referred to herein in both the as-synthesized and calcined forms, have a characteristic x-ray powder diffraction pattern which contains at least the d-spacings set forth in Table XXIII-E below:

TABLE XIX-E

| 2θ | d, (Å) | Relative Intensity |
|---|---|---|
| 9.5 | 9.30 | s |
| 16.1 | 5.49 | m |
| 20.8 | 4.27 | vs |
| 22.0 | 4.05 | m |
| 24.5 | 3.63 | m |
| 30.9 | 2.893 | m |

(b) The TiAPSO-44 compositions for which x-ray powder diffraction data have been obtained to date have patterns which are characterized by the x-ray powder diffraction pattern of Table XXIV-E below:

TABLE XXIV-E

| 2θ | d, (Å) | 100 × I/Io |
|---|---|---|
| 9.5 | 9.30 | 83 |
| 11.0 | 8.06 | 45 |
| 13.0 | 6.79 | 24 |
| 13.4 | 6.62 | 30 |
| 13.9 | 6.40 | 3 |
| 16.1 | 5.49 | 51 |
| 17.4 | 5.11 | 48 |
| 19.0 | 4.66 | 5 |
| 20.8 | 4.27 | 100 |
| 21.1 | 4.22 | 36 |
| 22.0 | 4.05 | 77 |
| 22.7 | 3.92 | 7 |
| 23.2 | 3.83 | 19 |
| 24.5 | 3.63 | 52 |
| 26.2 | 3.400 | 20 |
| 27.0 | 3.307 | 11 |
| 27.9 | 3.195 | 10 |
| 28.6 | 3.123 | 28 |
| 29.8 | 3.000 | 6 |
| 30.3 | 2.954 | 14 |
| 30.9 | 2.893 | 57 |
| 31.7 | 2.820 | 6 |
| 32.2 | 2.777 | 30 |
| 32.6 | 2.745 | 5 |
| 33.1 | 2.708 | 4 |
| 35.0 | 2.567 | 4 |
| 35.7 | 2.519 | 11 |
| 38.7 | 2.328 | 3 |
| 42.1 | 2.145 | 4 |
| 42.6 | 2.122 | 5 |
| 43.7 | 2.073 | 4 |
| 47.4 | 1.920 | 3 |
| 48.2 | 1.888 | 12 |
| 48.8 | 1.867 | 8 |
| 51.5 | 1.775 | 6 |
| 54.1 | 1.696 | 7 |

(c) A portion of the as-synthesized TiAPSO-44 of Example 11E was subjected to X-ray analysis. The TiAPSO-44 product was characterized by the x-ray powder diffraction pattern of Table XXV-E, below:

TABLE XXV-E

| 2θ | d, (Å) | 100 × I/Io |
|---|---|---|
| 8.7* | 10.21 | 14 |
| 9.5 | 9.30 | 83 |
| 11.0 | 8.06 | 45 |
| 11.7* | 7.57 | 3 |
| 13.0 | 6.79 | 24 |
| 13.4 | 6.62 | 30 |
| 13.9 | 6.40 | 3 |
| 16.1 | 5.49 | 51 |
| 17.4 | 5.11 | 48 |
| 17.8* | 4.98 | 7 |
| 19.0 | 4.66 | 5 |
| 20.8 | 4.27 | 100 |
| 21.1 | 4.22 | 36 |
| 21.5* | 4.13 | 19 |
| 22.0 | 4.05 | 77 |
| 22.7 | 3.92 | 7 |
| 23.2 | 3.83 | 19 |
| 23.6* | 3.78 | 3 |

TABLE XXV-E-continued

| 2θ | d, (Å) | 100 × I/Io |
|---|---|---|
| 24.5 | 3.63 | 52 |
| 25.1* | 3.554 | 8 |
| 25.4* | 3.501 | 4 |
| 25.6* | 3.481 | 3 |
| 26.2 | 3.400 | 20 |
| 27.0 | 3.307 | 11 |
| 27.9 | 3.195 | 10 |
| 28.6 | 3.123 | 28 |
| 29.2* | 3.062 | 5 |
| 29.8 | 3.000 | 6 |
| 30.3 | 2.954 | 14 |
| 30.9 | 2.893 | 57 |
| 31.7 | 2.820 | 6 |
| 32.2 | 2.777 | 30 |
| 32.6 | 2.745 | 5 |
| 33.1 | 2.708 | 4 |
| 34.6* | 2.595 | 7 |
| 35.0 | 2.567 | 4 |
| 35.1* | 2.559 | 3 |
| 35.7 | 2.519 | 11 |
| 37.9* | 2.372 | 3 |
| 38.7 | 2.328 | 3 |
| 42.1 | 2.145 | 4 |
| 42.4* | 2.134 | 5 |
| 42.6 | 2.122 | 5 |
| 43.0* | 2.103 | 6 |
| 43.7 | 2.073 | 4 |
| 47.4 | 1.920 | 3 |
| 48.2 | 1.888 | 12 |
| 48.7* | 1.871 | 8 |
| 48.8 | 1.867 | 8 |
| 49.7* | 1.836 | 4 |
| 50.4* | 1.809 | 9 |
| 51.5 | 1.775 | 6 |
| 54.1 | 1.696 | 7 |

*peak may contain an impurity

EXAMPLE 40E

In order to demonstrate the catalytic activity of the TiAPSO compositions, calcined samples of the TiAPSO products of Examples 6E, 13E, and 24E were tested for catalytic cracking of n-butane.

The reactor was a cylindrical quartz tube 254 mm. in length and 10.3 mm. I.D. In each test the reactor was loaded with particles of the test TiAPSO which were 20–40 mesh (U.S. std.) in size and in an amount of from 0.5 to 5 grams, the quantity being selected so that the conversion of n-butane was at least 5% and not more than 90% under the test conditions. The TiAPSO samples were calcined in air (TiAPSO-5 at 600° C. for 2.5 hours; TiAPSO-11 at 600° C. for 1.5 hours; and TiAPSO-34 at 500° C. for 2 hours) to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation. The pseudo-first-order rate constant ($k_A$) was calculated to determine the relative catalytic activity of the TiAPSO compositions. The $k_A$ value (cm³/g min) obtained for the TiAPSO compositions are set forth, below, in Table XXVI-E:

TABLE XXVI-E

| TiAPSO | $k_A$ |
|---|---|
| TiAPSO-5 | 0.6 |
| TiAPSO-11 | 0.5 |
| TiAPSO-34 | 1.3 |

F. ZINC-ALUMINUM-PHOSPHORUS-SILICON-OXIDE SIEVES

Molecular sieves containing zinc, aluminum, phosphorus and silicon as framework tetrahedral oxide units are prepared as follows:

Preparatiive Reagents

In the following examples the ZnAPSO compositions were prepared using numerous reagents. The reagents employed and abbreviations employed herein, if any, for such reagents are as follows:

(a) Alipro: aluminum isopropoxide;
(b) LUDOX-LS: LUDOX-LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite;
(d) $H_3PO_4$: 85 weight percent aqueous phosphoric acid:
(e) ZnAc: Zinc Acetate, $Zn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH.5H_2O$;
(i) TPAOH: 40 weight percent aqueous solution of tetraphrpylammonium hydroxide, $(C_3H_7)_4NOH$;
(j) $Pr_2NH$: di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

Preparative Reagents

The ZnAPSO compositions were prepared by preparing reaction mixtures having a molar composition expressed as:

$eR:fZnO:gAl_2O_3:hP_2O_5:iSiO_2:jH_2O$ wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively. The values for e, f, g, h, i and j were as set forth in the hereinafter discussed preparative examples where "j" was 50 in each example, and "e" was 1.0.

The reaction mixtures were prepared by forming a starting reaction mixture comprising the $H_3PO_4$ and a portion of the water. This mixture was stirred and the aluminum source added. The resulting mixture was blended until a homogeneous mixture was observed. The LUDOX LS was then added to the resulting mixture and the new mixture blended until a homogeneous mixture was observed. The zinc source (zinc acetate) was dissolved in the remaining water and combined with the first mixture. The combined mixture was blended until a homogenous mixture was observed. The organic templating agent was added to this mixture and blended for about two to four minutes until a homogenous mixture was observed. The resulting mixture (final reaction mixture) was placed in a liner (polytetrafluoroethylene) stainless steel pressure vessel and digested at an effective temperature for an effective time. All digestions were carried out at the autogeneous pressure. The products were removed from the reaction vessel cooled and evaluated as set forth hereinafter.

EXAMPLES 1F to 41F

ZnAPSO molecular sieves were prepared according to the above described procedure and the ZnAPSO products determined by x-ray analysis. The results of preparative examples 1F to 41F are set forth in Tables I-F and II-F. The reactive zinc source was zinc acetate. The reactive aluminum source was Alipro. The reactive phosphorus source was $H_3PO_4$, the reactive silicon source was LUDOX-LS. The organic templating agents are set forth in Tables I-F and II-F.

The chemical analysis for each product is given hereinafter with the example in which the ZnAPSO was prepared being given in parenthesis after the designation of the ZnAPSO species.

(a) the chemical analysis for ZnAPSO-5 (Example 4F) was:

| Component | Weight Percent |
|---|---|
| $Al_2O_3$ | 31.3 |
| $P_2O_5$ | 45.7 |
| ZnO | 2.8 |
| $SiO_2$ | 5.7 |
| Carbon | 5.5 |
| LOI* | 12.8 |

*LOI = Loss on Ignition

TABLE I-F

| Example[2] | Template | f | g | h | i | Temp (°C.) | Time (hrs) | ZnAPSO Product(s)[1] |
|---|---|---|---|---|---|---|---|---|
| 1F | Pr₃N | 0.1 | 1.0 | 1.0 | 0.6 | 150 | 42 | ZnAPSO-36; ZnAPSO-5 |
| 2F | Pr₃N | 0.1 | 1.0 | 1.0 | 0.6 | 150 | 183 | ZnAPSO-36; ZnAPSO-5 |
| 3F | Pr₃N | 0.1 | 1.0 | 1.0 | 0.6 | 200 | 42 | ZnAPSO-5; ZnAPSO-36 |
| 4F | Pr₃N | 0.1 | 1.0 | 1.0 | 0.6 | 200 | 183 | ZnAPSO-5; ZnAPSO-36 |
| 5F | Pr₃N | 0.2 | 0.9 | 0.9 | 0.2 | 150 | 48 | ZnAPSO-5; ZnAPSO-36 |
| 6F | TPAOH | 0.2 | 0.9 | 0.7 | 0.6 | 200 | 165 | ZnAPSO-5; |
| 7F | TPAOH | 0.2 | 0.9 | 0.7 | 0.6 | 200 | 165 | ZnAPSO-5 |
| 8F | Pr₂N | 0.1 | 1.0 | 1.0 | 0.6 | 150 | 42 | ZnAPSO-46; ZnAPSO-39; ZnAPSO-11 |
| 9F | Pr₂NH | 0.1 | 1.0 | 1.0 | 0.6 | 150 | 183 | ZnAPSO-39; ZnAPSO-11; ZnAPSO-46 |
| 10F | Pr₂NH | 0.1 | 1.0 | 1.0 | 0.6 | 200 | 42 | ZnAPSO-11; ZnAPSO-46; ZnAPSO-39 |
| 11F | Pr₂NH | 0.1 | 1.0 | 1.0 | 0.6 | 200 | 183 | ZnAPSO-11; ZnAPSO-39; ZnAPSO-46 |
| 12F | Pr₂NH | 0.2 | 0.9 | 0.7 | 0.6 | 150 | 41 | ZnAPSO-46; ZnAPSO-31; |
| 13F | Pr₂NH | 0.2 | 0.9 | 0.7 | 0.6 | 150 | 145 | ZnAPSO-31; ZnAPSO-46 |
| 14F | Pr₂NH | 0.2 | 0.9 | 0.7 | 0.6 | 200 | 41 | ZnAPSO-31 |
| 15F | Pr₂NH | 0.2 | 0.9 | 0.7 | 0.6 | 200 | 145 | ZnAPSO-31 |

[1] Major species as identified by x-ray powder diffraction pattern of product, except that when two or more species were identified the species are listed in the order of their predominance in the product.
[2] AlPO₄-31 (as described in U.S. Pat. No. 4,310,440) employed as seed crystals in examples 12F to 15F.

TABLE II-F

| Example | Template | f | g | h | i | Temp (°C.) | Time (hrs) | ZnAPSO Product(s)[1] |
|---|---|---|---|---|---|---|---|---|
| 16F | TEAOH | 0.1 | 1.0 | 1.0 | 0.6 | 100 | 134 | ZnAPSO-34 |
| 17F | TEAOH | 0.1 | 1.0 | 1.0 | 0.6 | 100 | 251 | ZnAPSO-34 |
| 18F | TEAOH | 0.1 | 1.0 | 1.0 | 0.6 | 150 | 134 | ZnAPSO-5; ZnAPSO-34 |
| 19F | TEAOH | 0.1 | 1.0 | 1.0 | 0.6 | 150 | 251 | ZnAPSO-34; ZnAPSO-5 |
| 20F | TEAOH | 0.1 | 1.0 | 1.0 | 0.6 | 200 | 134 | ZnAPSO-5; ZnAPSO-34 |
| 21F | TEAOH | 0.1 | 1.0 | 1.0 | 0.6 | 200 | 251 | ZnAPSO-34; ZnAPSO-5 |
| 22F | TEAOH | 0.1 | 0.95 | 0.7 | 0.6 | 100 | 17 | ZnAPSO-34 |
| 23F | TEAOH | 0.1 | 0.95 | 0.7 | 0.6 | 100 | 66 | ZnAPSO-34 |
| 24F | TEAOH | 0.1 | 0.95 | 0.7 | 0.6 | 100 | 166 | ZnAPSO-34 |
| 25F | TEAOH | 0.1 | 0.95 | 0.7 | 0.6 | 100 | 66 | ZnAPSO-34 |
| 26F | TMAOH | 0.2 | 0.9 | 0.7 | 0.6 | 150 | 46 | ZnAPSO-20; ZnAPSO-43 |
| 27F | TMAOH | 0.2 | 0.9 | 0.7 | 0.6 | 150 | 165 | ZnAPSO-20; ZnAPSO-43 |
| 28F | TMAOH | 0.2 | 0.9 | 0.7 | 0.6 | 200 | 46 | ZnAPSO-20; ZnAPSO-43 |
| 29F | TMAOH | 0.2 | 0.9 | 0.7 | 0.6 | 200 | 165 | ZnAPSO-20; ZnAPSO-43 |
| 30F | QUIN | 0.2 | 0.9 | 0.7 | 0.6 | 150 | 40 | ZnAPSO-35 |
| 31F | Quin | 0.2 | 0.9 | 0.7 | 0.6 | 150 | 158 | ZnAPSO-35 |
| 32F | Quin | 0.2 | 0.9 | 0.7 | 0.6 | 200 | 40 | ZnAPSO-35 |
| 33F | Quin | 0.2 | 0.9 | 0.7 | 0.6 | 200 | 158 | ZnAPSO-35 |
| 34F | C-hex | 0.2 | 0.9 | 0.7 | 0.6 | 150 | 40 | ZnAPSO-44 |
| 35F | C-hex | 0.2 | 0.9 | 0.7 | 0.6 | 150 | 158 | ZnAPSO-44 |
| 36F | C-hex | 0.2 | 0.9 | 0.7 | 0.6 | 200 | 40 | ZnAPSO-44; ZnAPSO-5 |
| 37F | C-hex | 0.2 | 0.9 | 0.7 | 0.6 | 200 | 158 | ZnAPSO-44; ZnAPSO-5 |
| 38F | DEEA | 0.2 | 0.9 | 0.7 | 0.6 | 150 | 40 | ZnAPSO-47; ZnAPSO-5 |
| 39F | DEEA | 0.2 | 0.9 | 0.7 | 0.6 | 150 | 158 | ZnAPSO-47; ZnAPSO-5 |
| 40F | DEEA | 0.2 | 0.9 | 0.7 | 0.6 | 200 | 40 | ZnAPSO-47; ZnAPSO-5 |
| 41F | DEEA | 0.2 | 0.9 | 0.7 | 0.6 | 200 | 158 | ZnAPSO-47 |

[1] Major species as identified by x-ray powder diffraction pattern of product, except that when two or more species were identified the species are listed in the order of their predomenance in the product.

EXAMPLE 42F

Samples of the products of examples 4F, 17F, 24F, 33F, 35F and 39F were subjected to chemical analysis.

The above chemical analysis gives an overall product composition in molar oxide ratios (anhydrous basis) of:

0.17R; 0.11 ZnO; 1.0 Al$_2$O$_3$; 1.05 P$_2$O$_5$; 0.31 SiO$_2$; and a formula (anhydrous basis) of:

0.04R (Zn$_{0.03}$Al$_{0.44}$P$_{0.47}$Si$_{0.07}$)O$_2$ (b) The chemical analysis for ZnAPSO-34 (Example 17F) was:

| Component | Weight Percent |
|---|---|
| Al$_2$O$_3$ | 32.3 |
| P$_2$O$_5$ | 35.3 |
| ZnO | 2.8 |
| SiO$_2$ | 1.6 |
| Carbon | 5.0 |
| LOI* | 26.7 |

*LOI = Loss on Ignition

The above chemical analysis gives an overall product composition in molar oxide ratios (anhydrous basis) of: 0.16 R; 0.11 ZnO; 1.0 Al$_2$O$_3$; 0.79 P$_2$O$_5$: 0.08 SiO$_2$; and a formula (anhydrous basis) of:

0.04R (Zn$_{0.03}$Al$_{0.54}$P$_{0.41}$Si$_{0.02}$)O$_2$ (c) The chemical analysis for ZnAPSO-34 (Example 24F) was:

| Component | Weight Percent |
|---|---|
| Al$_2$O$_3$ | 36.2 |
| P$_2$O$_5$ | 30.3 |
| ZnO | 3.8 |
| SiO$_2$ | 3.7 |
| Carbon | 5.2 |
| LOI* | 24.0 |

*LOI = Loss on Ignition

The above chemical analysis gives an overall product composition in molar oxide ratios of: 0.15 R; 0.13 ZnO; 1.0 Al$_2$O$_3$; 0.60 P$_2$O$_5$: 0.07 SiO$_2$; and a formula (anhydrous basis) of:

0.04R (Zn$_{0.04}$Al$_{0.57}$P$_{0.34}$Si$_{0.05}$)O$_2$ (d) The chemical analysis of ZnAPSO-35 (Example 33F) was:

| Component | Weight Percent |
|---|---|
| Al$_2$O$_3$ | 30.4 |
| P$_2$O$_5$ | 33.2 |
| ZnO | 5.6 |
| SiO$_2$ | 7.6 |
| Carbon | 10.1 |
| LOI* | 22.1 |

*LOI = Loss on Ignition

The above chemical analysis gives an overall product composition in molar oxide ratios of: 0.4OR; 0.23 ZnO; 1.0 Al$_2$O$_3$: 0.78 P$_2$O$_5$: 0.42 SiO$_2$; and a formula (anhydrous basis) of:

0.12R (Zn$_{0.06}$Al$_{0.47}$P$_{0.37}$Si$_{0.10}$)O$_2$ (e) The chemical analysis for ZnAPSO-44 (Example 35F) was:

| Component | Weight Percent |
|---|---|
| Al$_2$O$_3$ | 27.5 |
| P$_2$O$_5$ | 31.1 |
| ZnO | 4.8 |
| SiO$_2$ | 10.6 |
| Carbon | 11.7 |
| LOI* | 25.1 |

*LOI = Loss on Ignition

The above chemical analysis gives an overall product composition in molar oxide ratios of: 0.60 R; 0.22 ZnO; 1.0 Al$_2$O$_3$; 0.81 P$_2$O$_5$; 0.65 SiO$_2$; and a formula (anhydrous basis) of:

0.13R (Zn$_{0.05}$Al$_{0.44}$P$_{0.36}$Si$_{0.15}$)O$_2$ (f) The chemical analysis of ZnAPSO-47 (Example 39F) was:

| Component | Weight Percent |
|---|---|
| Al$_2$O$_3$ | 30.4 |
| P$_2$O$_5$ | 32.6 |
| ZnO | 5.3 |
| SiO$_2$ | 6.5 |
| Carbon | 7.7 |
| LOI* | 23.4 |

*LOI = Loss on Ignition

The above chemical analysis gives an overall product composition in molar oxide ratios of: 0.35 R; 0.22 ZnO; 1.0 Al$_2$O$_3$: 0.77 P$_2$O$_5$; 0.36 SiO$_2$; and a formula (anhydrous basis) of:

0.09R (Zn$_{0.05}$Al$_{0.49}$P$_{0.37}$Si$_{0.09}$)O$_2$

EXAMPLE 43F

EDAX (energy dispersive analysis by x-ray microprobe analysis in conjunction with SEM (scanning electron microscope was carried out on clear crystals from the products of examples 4F, 24F, 33F, 35F and 39F. Analysis of crystals having a morphology characteristic of the ZnAPSO products gave the following analysis based on relative peak heights:

| | Average of Spot Probes |
|---|---|
| (a) ZnAPSO-5 (Example 4F): | |
| Zn | 1 |
| Al | 44 |
| P | 50 |
| Si | 5 |
| (b) ZnAPSO-34 (Example 24F): | |
| Zn | 3 |
| Al | 45 |
| P | 46 |
| Si | 6 |
| (c) ZnAPSO-35 (Example 33F): | |
| Zn | 5 |
| Al | 43 |
| P | 46 |
| Si | 6 |
| (d) ZnAPSO-36 (Example 4F): | |
| Zn | 4 |
| Al | 42 |
| P | 50 |
| Si | 4 |
| (e) ZnAPSO-44 (Example 35F): | |
| Zn | 2 |
| Al | 43 |
| P | 39 |
| Si | 16 |
| (f) ZnAPSO-47 (Example 39F): | |
| Zn | 5 |
| Al | 42 |
| P | 44 |
| Si | 9 |

EXAMPLE 44F

Samples of the ZnAPSO products of examples 4F, 27F, 33F, 35F and 39F were for adsorption capacities evaluated in the as-synthesized form or were calcined in air or nitrogen, to remove at least part of the organic templating agent, as hereinafter set forth. The adsorption capacities of each calcined sample were measured using a standard McBain-Bakr gravimetric adsorption apparatus. The samples were activated in a vacuum at 350° C. prior to measurement. The McBain-Bakr data for the aforementioned calcined ZnAPSO products were:

(a) ZnAPSO-5 (Example 4F):

| Adsorbate | Kinetic Diameter, Å | Pressure (Torr) | Temp (°C.) | Wt. % Adsorbed* |
|---|---|---|---|---|
| O₂ | 3.46 | 99 | −183 | 11.0 |
| O₂ | 3.46 | 749 | −183 | 14.9 |
| neopentane | 6.2 | 100 | 23.4 | 3.5 |
| cyclohexane | 6.0 | 57 | 23.4 | 7.4 |
| H₂O | 2.65 | 4.6 | 23.2 | 13.5 |
| H₂O | 2.65 | 16.8 | 23.5 | 17.5 |

*calcined in air at 500° C. for 0.75 hours and at 600° C. for 1.25 hours prior to activation.

The above data demonstrate that the pore size of the calcined product is greater than 6.2 Å.

(b) ZnAPSO-34 (Example 27F):

| Adsorbate | Kinetic Diameter, Å | Pressure (Torr) | Temp (°C.) | Wt. % Adsorbed* |
|---|---|---|---|---|
| O₂ | 3.46 | 99 | −183 | 14.5 |
| O₂ | 3.46 | 725 | −183 | 25.8 |
| isobutane | 5.0 | 100 | 22.8 | 0.8 |
| n-hexane | 4.3 | 98 | 23.3 | 13.3 |
| H₂O | 2.65 | 4.6 | 23.1 | 19.9 |
| H₂O | 2.65 | 17.8 | 23.1 | 30.1 |

*calcined in air at 500° C. for 2 hours prior to activation

The above data demonstrate that the pore size of the calcined product is about 4.3 Å.

(c) ZnAPSO-35 (Example 33F):

| Adsorbate | Kinetic Diameter, Å | Pressure (Torr) | Temp (°C.) | Wt. % Adsorbed* |
|---|---|---|---|---|
| O₂ | 3.46 | 99 | −183 | 10.2 |
| O₂ | 3.46 | 725 | −183 | 19.1 |
| n-hexane | 4.3 | 98 | 23.3 | 8.6 |
| isobutane | 5.0 | 100 | 22.8 | 0.8 |
| H₂O | 2.65 | 4.6 | 23.1 | 17.2 |
| H₂O | 2.65 | 17.8 | 23.1 | 26.3 |

*calcined in air at 500° C. for 1.75 hours prior to activation

The above data demonstrate that the pore size of the calcined product is about 4.3 Å.

(d) ZnAPSO-44 (Example 35F):

| Adsorbate | Kinetic Diameter, Å | Pressure (Torr) | Temp (°C.) | Wt. % Adsorbed* |
|---|---|---|---|---|
| O₂ | 3.46 | 99 | −183 | 10.3 |
| O₂ | 3.46 | 745 | −183 | 19.8 |
| n-hexane | 4.3 | 98 | 23.3 | 9.7 |
| isobutane | 5.0 | 100 | 22.8 | 0.8 |
| H₂O | 2.65 | 4.6 | 23.1 | 14.0 |
| H₂O | 2.65 | 17.8 | 23.1 | 24.0 |

*calcined in air at 500° C. for 67 hours prior to activation

The above data demonstrate that the pore size of the calcined product is about 4.3 Å.

(e) ZnAPSO-47 (Example 39F):

| Adsorbate | Kinetic Diameter, Å | Pressure (Torr) | Temp (°C.) | Wt. % Adsorbed* |
|---|---|---|---|---|
| O₂ | 3.46 | 99 | −183 | 13.9 |
| O₂ | 3.46 | 725 | −183 | 23.0 |
| isobutane | 4.3 | 100 | 23.8 | 0.7 |
| n-hexane | 5.0 | 98 | 23.3 | 7.8 |
| H₂O | 2.65 | 4.6 | 23.1 | 18.8 |
| H₂O | 2.65 | 17.8 | 23.1 | 27.0 |

*calcined in air at 500° C. for 1.75 hours prior to activation

The above data demonstrate that the pore size of the calcined product is about 4.3 Å.

EXAMPLE 45F (a) ZnAPSO-5, as prepared in example 4F, was subjected to x-ray analysis. ZnAPSO-5 was determined to have a characteristic x-ray powder diffraction pattern which contains at least the d-spacings set forth below:

| 2θ | d, (Å) | 100 × I/Io |
|---|---|---|
| 7.4 | 11.91 | 100 |
| 7.9** | 11.17 | 29 |
| 12.85 | 6.88 | 10 |
| 13.5* | 6.56 | 1 |
| 14.85 | 5.96 | 19 |
| 15.85** | 5.60 | 3 |
| 16.45** | 5.39 | 8 |
| 19.1** | 4.65 | 9 |
| 19.7 | 4.51 | 38 |
| 20.3** | 4.38 | 4 |
| 20.8** | 4.27 | 10 |
| 21.05 | 4.22 | 30 |
| 21.5** | 4.14 | 5 |
| 21.65** | 4.10 | 5 |
| 22.4 | 3.973 | 73 |
| 22.95** | 3.876 | 3 |
| 23.85** | 3.730 | 1 |
| 24.75 | 3.596 | 2 |
| 25.9 | 3.442 | 25 |
| 27.2** | 3.279 | 4 |
| 27.75** | 3.212 | 1 |
| 28.3** | 3.154 | 2 |
| 29.0 | 3.078 | 15 |
| 29.95 | 2.981 | 15 |
| 30.35** | 2.947 | 2 |
| 32.0** | 2.798 | 3 |
| 33.6 | 2.666 | 4 |
| 34.45 | 2.602 | 12 |
| 34.8** | 2.577 | 4 |
| 35.45** | 2.532 | 2 |
| 35.9 | 2.501 | 1 |
| 36.95 | 2.434 | 3 |
| 37.7 | 2.386 | 7 |
| 41.45* | 2.177 | 2 |
| 42.2 | 2.141 | 3 |
| 42.8 | 2.112 | 1 |
| 43.4 | 2.085 | 1 |
| 45.0 | 2.013 | 1 |
| 47.6 | 1.910 | 4 |
| 51.4 | 1.778 | 2 |
| 51.95 | 1.760 | 1 |
| 55.6* | 1.654 | 2 |

*peak may contain impurity
**impurity peak (b) A portion of the as-synthesized ZnAPSO-5 of part (a) was calcined in air at 500° C. for about 0.75 hours and then in air at 600° C. for about 1.5 hours. The calcined product was characterized by the x-ray powder diffraction pattern below:

| 2θ | d, (Å) | 100 × I/Io |
|---|---|---|
| 7.45 | 11.91 | 100 |
| 7.85* | 11.23 | 21 |
| 8.2* | 10.79 | 7 |
| 12.9 | 6.87 | 20 |
| 13.45* | 6.57 | 3 |

-continued

| 2θ | d, (Å) | 100 × I/Io |
|---|---|---|
| 14.9 | 5.95 | 6 |
| 16.5* | 5.37 | 5 |
| 19.35* | 4.58 | 5 |
| 19.75 | 4.49 | 24 |
| 20.3 | 4.38 | 10 |
| 20.7 | 4.29 | 4 |
| 21.1 | 4.21 | 28 |
| 21.4 | 4.14 | 11 |
| 22.4 | 3.962 | 69 |
| 22.75* | 3.907 | 5 |
| 24.85 | 3.584 | 2 |
| 26.0 | 3.430 | 24 |
| 27.25* | 3.275 | 4 |
| 27.45* | 3.252 | 2 |
| 27.8* | 3.207 | 2 |
| 28.15* | 3.168 | 3 |
| 28.35* | 3.146 | 2 |
| 29.1 | 3.068 | 16 |
| 30.1 | 2.970 | 14 |
| 33.7 | 2.658 | 3 |
| 34.6 | 2.592 | 13 |
| 35.45* | 2.532 | 4 |
| 37.05 | 2.427 | 3 |
| 37.85 | 2.378 | 6 |
| 42.4 | 2.132 | 2 |
| 47.8 | 1.903 | 2 |
| 51.5 | 1.774 | 3 |
| 55.8 | 1.647 | 1 |

*Impurity Peak (c) The ZnAPSO-5 compositions are generally characterized by the data of Table III-F below.

TABLE III-F

| 2θ | d (Å) | Relative Intensity |
|---|---|---|
| 7.2–7.4 | 12.28–11.91 | vs |
| 19.4–19.8 | 4.58–4.48 | m |
| 21.0–21.2 | 4.23–4.19 | m |
| 22.3–22.5 | 3.971–3.952 | m–s |
| 25.7–26.0 | 3.466–3.427 | w–m |

(d) The ZnAPSO-5 compositions for which x-ray powder diffraction data have been obtained to date have patterns which are characterized by the x-ray powder diffraction pattern shown in Table IV-F, below.

TABLE IV-F

| 2θ | d, (Å) | 100 × I/Io |
|---|---|---|
| 7.2–7.4 | 12.28–11.91 | 100 |
| 12.6–13.0 | 7.03–6.81 | 8–21 |
| 14.6–14.9 | 6.07–5.95 | 9–20 |
| 19.4–19.8 | 4.58–4.48 | 24–38 |
| 21.0–21.2 | 4.23–4.19 | 20–35 |
| 22.3–22.5 | 3.971–3.952 | 47–82 |
| 24.7–24.9 | 3.604–3.576 | 1–2 |
| 25.7–26.0 | 3.466–3.427 | 18–27 |
| 28.9–29.1 | 3.089–3.069 | 10–20 |
| 29.9–30.1 | 2.988–2.969 | 12–17 |
| 33.6–33.8 | 2.667–2.652 | 3–4 |
| 34.4–34.6 | 2.607–2.592 | 10–14 |
| 36.9–37.0 | 2.436–2.430 | 2–3 |
| 37.6–37.9 | 2.392–2.374 | 5–8 |
| 41.45 | 2.177 | 0–2 |
| 42.2–42.4 | 2.141–2.132 | 2–3 |
| 42.8 | 2.113 | 0–1 |
| 43.4 | 2.090 | 0–1 |
| 45.0 | 2.014 | 0–1 |
| 47.5–47.8 | 1.914–1.903 | 2–4 |
| 51.3–51.6 | 1.781 | 2–3 |
| 51.95 | 1.760 | 0–1 |
| 55.5–55.8 | 1.656–1.647 | 0–2 |

EXAMPLE 46F (a) ZnAPSO-11, as prepared in example 10F was subjected to x-ray analysis. ZnAPSO-11 was determined to have a characteristic x-ray powder diffraction pattern which contains at least the d-spacings set forth below:

| 2θ | d, (Å) | 100 × I/Io |
|---|---|---|
| 6.6** | 13.44 | 10 |
| 7.7** | 11.46 | 97 |
| 8.1 | 10.89 | 26 |
| 8.45** | 10.44 | 6 |
| 9.45* | 9.35 | 60 |
| 13.3* | 6.66 | 22 |
| 13.8** | 6.43 | 4 |
| 14.9** | 5.94 | 5 |
| 15.3** | 5.80 | 8 |
| 15.7 | 5.64 | 24 |
| 16.2 | 5.47 | 3 |
| 16.65** | 5.33 | 7 |
| 18.35** | 4.83 | 16 |
| 19.0 | 4.66 | 4 |
| 19.8** | 4.49 | 4 |
| 20.45* | 4.35 | 29 |
| 21.1* | 4.20 | 100 |
| 21.55** | 4.123 | 24 |
| 22.2* | 4.008 | 32 |
| 22.75 | 3.905 | 85 |
| 23.2 | 3.830 | 45 |
| 24.2** | 3.674 | 5 |
| 24.45** | 3.643 | 3 |
| 24.8 | 3.590 | 5 |
| 26.55 | 3.355 | 14 |
| 26.8* | 3.327 | 12 |
| 27.8** | 3.212 | 4 |
| 28.7* | 3.109 | 20 |
| 29.05* | 3.075 | 5 |
| 29.8* | 3.000 | 11 |
| 30.15* | 2.966 | 11 |
| 30.75** | 2.909 | 3 |
| 31.1** | 2.874 | 5 |
| 31.6 | 2.832 | 6 |
| 32.85* | 2.725 | 11 |
| 34.3* | 2.615 | 7 |
| 34.5** | 2.598 | 5 |
| 35.9* | 2.501 | 6 |
| 36.55* | 2.459 | 5 |
| 37.85* | 2.377 | 10 |
| 39.7* | 2.270 | 1 |
| 43.0* | 2.103 | 4 |
| 44.85 | 2.022 | 3 |
| 48.85* | 1.864 | 3 |
| 50.8 | 1.797 | 1 |
| 54.8 | 1.675 | 1 |

*Peak may contain impurity
**Impurity Peak (b) The ZnAPSO-11 compositions are generally characterized by the data of Table V-F below.

TABLE V-F

| 2θ | d (Å) | Relative Intensity |
|---|---|---|
| 9.35–9.45 | 9.44–9.35 | m |
| 13.15–13.35 | 6.67–6.63 | m |
| 21.1–21.25 | 4.21–4.19 | s–vs |
| 22.75–22.85 | 3.911–3.896 | s–vs |
| 23.15–23.3 | 3.839–3.819 | w–m |
| 26.8–26.9 | 3.327–3.313 | w–m |

(c) The ZnAPSO-11 compositions for which x-ray powder diffraction data have been obtained to date have patterns which are characterized by the x-ray powder diffraction pattern shown in Table VI-F, below:

TABLE VI-F

| 2θ | d, (Å) | 100 × I/Io |
|---|---|---|
| 8.05–8.1 | 10.98–10.92 | 8–26 |
| 9.35–9.45 | 9.44–9.35 | 54–72 |
| 13.15–13.35 | 6.67–6.63 | 22–40 |
| 15.65–15.75 | 5.66–5.62 | 10–27 |
| 16.05–16.2 | 5.53–5.47 | 0–3 |
| 19.0 | 4.66 | 0–4 |
| 19.85 | 4.49–4.46 | 4–14 |
| 20.4–20.5 | 4.35–4.33 | 19–38 |
| 21.1–21.25 | 4.21–4.19 | 83–100 |
| 22.1–22.25 | 4.018–3.998 | 12–32 |
| 22.75–22.85 | 3.911–3.896 | 85–100 |
| 23.15–23.3 | 3.839–3.819 | 12–45 |
| 26.45–26.55 | 3.369–3.354 | 8–14 |
| 26.8–26.9 | 3.327–3.313 | 12–40 |
| 28.7–28.8 | 3.111–3.100 | 20–36 |
| 29.75–29.85 | 3.005–2.993 | 11–23 |
| 31.6–31.8 | 2.832–2.813 | 0–10 |
| 32.8–32.95 | 2.731–2.719 | 7–15 |
| 34.2–34.3 | 2.620–2.615 | 6–9 |
| 35.85–36.0 | 2.503–2.495 | 6–12 |
| 36.45–36.55 | 2.464–2.459 | 4–8 |
| 37.65–37.7 | 2.389–2.387 | 0–7 |
| 37.85 | 2.377 | 0–10 |
| 39.7 | 2.271 | 0–1 |
| 43.0–43.05 | 2.103–2.100 | 0–4 |
| 44.85–44.9 | 2.022–2.018 | 0–3 |
| 48.75–48.85 | 1.867–1.864 | 0–3 |
| 50.8–50.9 | 1.797–1.794 | 0–3 |
| 54.8 | 1.675 | 0–1 |

EXAMPLE 47F (a) ZnAPSO-20, as prepared in example 29F, was subjected to x-ray analysis. ZnAPSO-20 was determined to have a characteristic x-ray powder diffraction pattern which contains at least the d-spacings set forth below:

| 2θ | d, (Å) | 100 × I/Io |
|---|---|---|
| 12.35* | 7.17 | 6 |
| 13.9 | 6.37 | 47 |
| 14.35* | 6.16 | 2 |
| 14.5* | 6.10 | 1 |
| 14.65* | 6.04 | 1 |
| 14.85* | 5.96 | 1 |
| 19.75 | 4.50 | 40 |
| 20.8* | 4.27 | 1 |
| 21.05* | 4.22 | 1 |
| 21.7* | 4.09 | 3 |
| 22.1 | 4.024 | 2 |
| 24.25 | 3.672 | 100 |
| 24.85* | 3.582 | 1 |
| 27.0* | 3.302 | 5 |
| 28.05 | 3.181 | 12 |
| 28.65* | 3.116 | 1 |
| 31.45 | 2.845 | 12 |
| 32.45* | 2.758 | 1 |
| 34.55 | 2.596 | 20 |
| 37.45 | 2.402 | 2 |
| 38.4* | 2.248 | 1 |
| 40.1 | 2.344 | 4 |
| 42.65 | 2.121 | 4 |
| 45.13* | 2.009 | 1 |
| 47.4 | 1.917 | 5 |
| 49.35* | 1.846 | 1 |
| 51.8 | 1.765 | 9 |

*Impurity peak (b) The ZnAPSO-20 compositions are generally characterized by the data of Table VII-F below:

TABLE VII-F

| 2θ | d, (Å) | Relative Intensity |
|---|---|---|
| 13.85–14.0 | 6.39–6.33 | m |
| 19.65–19.8 | 4.52–4.48 | m |
| 24.15–24.3 | 3.685–3.663 | vs |
| 28.0–28.15 | 3.187–3.170 | w |
| 31.35–31.5 | 2.853–2.840 | w |
| 34.5–34.65 | 2.600–2.589 | w–m |

(c) The ZnAPSO-20 compositions for which x-ray powder diffraction data have been obtained to date have patterns which are characterized by the x-ray powder diffraction pattern shown in Table VIII-F, below:

TABLE VIII-F

| 2θ | d, (Å) | 100 × I/Io |
|---|---|---|
| 13.85–14.0 | 6.39–6.33 | 45–47 |
| 19.65–19.8 | 4.52–4.48 | 40–41 |
| 22.0–22.15 | 4.040–4.013 | 2–3 |
| 24.15–24.3 | 3.685–3.663 | 100 |
| 28.0–28.15 | 3.187–3.170 | 12–13 |
| 31.35–31.5 | 2.853–2.840 | 11–12 |
| 34.5–34.65 | 2.600–2.589 | 16–20 |
| 37.35–37.5 | 2.408–2.398 | 2 |
| 40.0–40.2 | 2.254–2.243 | 4 |
| 42.55–42.7 | 2.125–2.118 | 4 |
| 47.35–47.5 | 1.920–1.914 | 5 |
| 51.75–51.9 | 1.767–1.762 | 8–9 |

EXAMPLE 48F (a) ZnAPSO-31, as prepared in example 14F, was subjected to x-ray analysis. ZnAPSO-31 was determined to have a characteristic x-ray powder diffraction pattern which contains at least the d-spacings set forth below:

| 2θ | d, (Å) | 100 × I/Io |
|---|---|---|
| 6.6** | 13.40 | 14 |
| 7.7** | 11.45 | 10 |
| 8.1** | 10.94 | 11 |
| 8.5 | 10.40 | 50 |
| 9.5* | 9.32 | 8 |
| 9.85* | 8.96 | 2 |
| 12.45** | 7.12 | 25 |
| 13.4 | 6.60 | 10 |
| 17.05 | 5.21 | 5 |
| 17.4** | 5.10 | 3 |
| 18.25 | 4.86 | 8 |
| 20.3 | 4.38 | 52 |
| 21.3* | 4.17 | 16 |
| 21.6** | 4.11 | 10 |
| 22.0 | 4.036 | 30 |
| 22.6 | 3.394 | 100 |
| 23.55* | 3.779 | 2 |
| 24.25** | 3.668 | 4 |
| 25.15* | 3.543 | 4 |
| 27.0** | 3.302 | 3 |
| 27.75* | 3.213 | 12 |
| 27.95 | 3.192 | 13 |
| 28.2* | 3.162 | 4 |
| 28.7** | 3.109 | 3 |
| 29.75 | 3.004 | 10 |
| 30.3 | 2.950 | 4 |
| 31.75 | 2.810 | 20 |
| 32.95 | 2.718 | 4 |
| 34.2** | 2.623 | 3 |
| 35.15 | 2.554 | 12 |
| 35.7* | 2.515 | 3 |
| 35.9* | 2.500 | 3 |
| 36.2 | 2.481 | 4 |
| 37.25* | 2.413 | 3 |
| 37.65* | 2.390 | 2 |
| 38.25 | 2.353 | 3 |
| 39.3 | 2.291 | 2 |
| 40.3 | 2.238 | 2 |
| 45.0* | 2.014 | 2 |

-continued

| 2θ | d, (Å) | 100 × I/Io |
|---|---|---|
| 46.6 | 1.949 | 4 |
| 47.4** | 1.918 | 2 |
| 48.6 | 1.873 | 2 |
| 51.5 | 1.774 | 7 |

*peak may contain impurity
**impurity peak (b) The ZnAPSO-31 compositions are generally characterized by the data of Table IX-F below:

TABLE IX-F

| 2θ | d, (Å) | Relative Intensity |
|---|---|---|
| 8.4–8.5 | 10.53–10.40 | m |
| 20.2–20.3 | 4.40–4.37 | m |
| 21.3 | 4.171 | w |
| 22.0 | 4.036 | m |
| 22.5–22.6 | 3.952–3.934 | vs |
| 31.6–31.75 | 2.831–2.820 | w–m |

(c) The ZnAPSO-31 compositions for which x-ray powder diffraction data have been obtained to date have patterns which are characterized by the x-ray powder diffraction pattern shown in Table X-F, below:

TABLE X-F

| 2θ | d, (Å) | 100 × I/Io |
|---|---|---|
| 8.4–8.5 | 10.53–10.40 | 50–53 |
| 9.45–9.5 | 9.35–9.32 | 7–8 |
| 13.2–13.4 | 6.76–6.60 | 10–11 |
| 18.2–18.25 | 4.87–4.86 | 5–8 |
| 20.2–20.3 | 4.39–4.37 | 49–52 |
| 21.3 | 4.171 | 16–18 |
| 22.0 | 4.036 | 30 |
| 22.5–22.6 | 3.952–3.934 | 100 |
| 26.9–27.0 | 3.314–3.302 | 3–7 |
| 27.95–28.25 | 3.192–3.529 | 13–17 |
| 29.6–29.7 | 3.018–3.008 | 8–10 |
| 30.2–30.3 | 2.959–2.950 | 0–4 |
| 31.6–31.75 | 2.831–2.820 | 18–20 |
| 32.95 | 2.718 | 4–9 |
| 35.15–35.2 | 2.554–2.550 | 12 |
| 36.1–36.2 | 2.489–2.481 | 4–7 |
| 37.25–37.35 | 2.413–2.409 | 2–3 |
| 38.25 | 2.353 | 3 |
| 39.3 | 2.291 | 2 |
| 40.3 | 2.238 | 2 |
| 46.6–46.65 | 1.949–1.948 | 4–6 |
| 47.4–47.45 | 1.918–1.916 | 2–4 |
| 51.5 | 1.774 | 7 |

EXAMPLE 49F (a) ZnAPSO-34, as prepared in example 24F, was subjected to x-ray analysis. ZnAPSO-34 was determined to have a characteristic x-ray powder diffraction pattern which contains at least the d-spacings set forth below:

TABLE XIII-F

| 2θ | d, (Å) | 100 × I/Io |
|---|---|---|
| 9.6 | 9.19 | 100 |
| 12.95 | 6.84 | 16 |
| 14.2 | 6.25 | 14 |
| 16.1 | 5.50 | 42 |
| 18.1 | 4.90 | 22 |
| 20.65 | 4.30 | 91 |
| 22.4 | 3.978 | 5 |
| 23.15 | 3.842 | 5 |
| 25.3 | 3.521 | 25 |
| 25.9 | 3.437 | 18 |
| 27.7 | 3.218 | 5 |
| 28.45 | 3.135 | 6 |

TABLE XIII-F-continued

| 2θ | d, (Å) | 100 × I/Io |
|---|---|---|
| 29.65 | 3.015 | 5 |
| 30.6 | 2.920 | 33 |
| 31.3 | 2.856 | 23 |
| 32.5 | 2.755 | 2 |
| 34.45 | 2.602 | 7 |
| 36.4 | 2.468 | 5 |
| 38.8 | 2.320 | 4 |
| 39.75 | 2.267 | 5 |
| 43.15 | 2.097 | 4 |
| 43.55* | 2.077 | 4 |
| 47.65 | 1.908 | 5 |
| 49.10 | 1.856 | 8 |
| 49.9 | 1.827 | 4 |
| 51.0 | 1.791 | 4 |
| 53.15 | 1.723 | 3 |
| 54.65 | 1.679 | 3 |
| 55.9 | 1.645 | 3 |

*impurity peak (b) A portion of the as-synthesized ZnAPSO-34 of part (a) was calcined in air at 500° C. for about 2 hours. The calcined product was characterized by the x-ray powder diffraction pattern below:

| 2θ | d, (Å) | 100 × I/Io |
|---|---|---|
| 9.55 | 9.27 | 100 |
| 12.95 | 6.85 | 24 |
| 16.15 | 5.49 | 13 |
| 17.95 | 4.94 | 10 |
| 20.75 | 4.28 | 30 |
| 22.2 | 4.004 | 2 |
| 23.25 | 3.828 | 5 |
| 25.2 | 3.533 | 9 |
| 26.15 | 3.411 | 12 |
| 28.45 | 3.138 | 4 |
| 30.9 | 2.896 | 16 |
| 31.35 | 2.852 | 9 |

(c) The ZnAPSO-34 compositions are generally characterized by the data of Table XI-F below.

TABLE XI-F

| 2θ | d, (Å) | Relative Intensity |
|---|---|---|
| 9.4–9.8 | 9.41–9.03 | m–vs |
| 12.7–13.2 | 6.97–6.71 | w–m |
| 15.8–16.2 | 5.61–5.47 | w–m |
| 20.5–20.9 | 4.33–4.25 | m–vs |
| 25.0–25.3 | 3.562–3.520 | vw–m |
| 30.5–30.9 | 2.931–2.894 | w–m |

(d) The ZnAPSO-34 compositions for which x-ray powder diffraction data have been obtained to date have patterns which are characterized by the x-ray powder diffraction pattern shown in Table XII-F, below:

TABLE XII-F

| 2θ | d, (Å) | 100 × I/Io |
|---|---|---|
| 9.4–9.8 | 9.41–9.03 | 77–100 |
| 12.7–13.2 | 6.97–6.71 | 16–31 |
| 14.0–14.3 | 6.33–6.19 | 0–22 |
| 15.8–16.2 | 5.61–5.47 | 16–47 |
| 17.8–18.2 | 4.98–4.87 | 13–29 |
| 20.5–20.9 | 4.33–4.25 | 36–100 |
| 22.2–22.5 | 4.004–3.952 | 5.8 |
| 23.0–23.3 | 3.867–3.818 | 5–6 |
| 25.0–25.3 | 3.562–3.520 | 9–32 |
| 25.7–26.25 | 3.466–3.395 | 12–20 |
| 27.45–27.7 | 3.249–3.220 | 5–8 |
| 28.1–28.45 | 3.175–3.137 | 4–8 |
| 29.4–29.8 | 3.038–2.998 | 0–5 |
| 30.5–30.9 | 2.931–2.894 | 16–35 |
| 31.0–31.65 | 2.885–2.827 | 9–25 |

TABLE XII-F-continued

| 2θ | d, (Å) | 100 × I/Io |
|---|---|---|
| 32.2–32.5 | 2.780–2.755 | 0–2 |
| 34.3–34.8 | 2.614–2.578 | 5–8 |
| 36.1–36.4 | 2.488–2.468 | 0–5 |
| 38.65–38.8 | 2.330–2.321 | 0–4 |
| 39.5–39.8 | 2.281–2.265 | 4–7 |
| 43.0–43.4 | 2.103–2.085 | 4 |
| 47.5–48.0 | 1.914–1.895 | 3–6 |
| 48.8–49.1 | 1.866–1.855 | 8–10 |
| 49.9 | 1.859 | 0–4 |
| 50.8–51.0 | 1.797–1.791 | 0–4 |
| 53.1–53.15 | 1.725–1.723 | 0–3 |
| 54.5–54.8 | 1.684–1.675 | 0–3 |
| 55.8–55.9 | 1.647–1.645 | 0–4 |

EXAMPLE 50F (a) ZnAPSO-35, as prepared in example 33F, was subjected to x-ray analysis. ZnAPSO-35 was determined to have a characteristic x-ray powder diffraction pattern which contains at least the d-spacings set forth below:

| 2θ | d, (Å) | 100 × I/Io |
|---|---|---|
| 8.6 | 10.27 | 20 |
| 10.5* | 8.44 | sh |
| 10.95 | 8.08 | 47 |
| 11.35 | 7.80 | 4 |
| 13.30 | 6.66 | 39 |
| 15.9 | 5.57 | 10 |
| 17.3 | 5.13 | 72 |
| 17.8 | 4.98 | sh |
| 21.15 | 4.20 | 48 |
| 21.9 | 4.06 | 100 |
| 23.15 | 3.841 | 19 |
| 23.65 | 3.762 | 3 |
| 25.05 | 3.552 | 4 |
| 26.8 | 3.325 | 22 |
| 28.7 | 3.107 | 30 |
| 29.1 | 3.069 | sh |
| 32.1 | 2.788 | 43 |
| 34.75 | 2.582 | 9 |
| 35.5 | 2.530 | 3 |
| 35.8 | 2.507 | 5 |
| 37.75 | 2.382 | 5 |
| 39.35 | 2.889 | 4 |
| 42.35 | 2.134 | 6 |
| 43.15 | 2.096 | 4 |
| 48.6 | 1.873 | 11 |
| 49.4 | 1.845 | 8 |
| 51.55 | 1.773 | 6 |
| 55.3 | 1.661 | 6 |

*impurity peak (b) A portion of the as-synthesized ZnAPSO-35 of part (a) was calcined in air at 500° C. for about 1.75 hours. The calcined product was characterized by the x-ray powder diffraction pattern below:

| 2θ | d, (Å) | 100 × I/Io |
|---|---|---|
| 7.45* | 11.85 | 10 |
| 8.7 | 10.15 | 22 |
| 11.0 | 8.04 | 91 |
| 13.5 | 6.55 | 100 |
| 17.45 | 5.08 | 35 |
| 21.0 | 4.23 | 21 |
| 22.15 | 4.011 | 60 |
| 23.5 | 3.782 | 19 |
| 25.15 | 3.542 | 13 |
| 27.2 | 3.278 | 20 |
| 28.6 | 3.122 | 28 |
| 29.35 | 3.041 | 14 |
| 32.45 | 2.759 | 28 |

*impurity peak (c) The ZnAPSO-35 compositions obtained to date have patterns which are generally characterized by the data of Table XIII-F below.

TABLE XIII-F

| 2θ | d, (Å) | Relative Intensity |
|---|---|---|
| 10.8–11.0 | 8.19–8.04 | m–vs |
| 13.30–13.5 | 6.66–6.56 | m–vs |
| 17.2–17.45 | 5.16–5.08 | m |
| 20.95–21.2 | 4.24–4.19 | m |
| 21.9–22.15 | 4.06–4.01 | m–vs |
| 32.0–32.5 | 2.797–2.755 | m |

(d) The ZnAPSO-35 compositions for which x-ray powder diffraction data have been obtained to date have patterns which are characterized by the x-ray powder diffraction pattern shown in Table XIV-F below:

| 2θ | d, (Å) | 100 × I/Io |
|---|---|---|
| 8.6–8.7 | 10.27–10.16 | 18–22 |
| 10.8–11.0 | 8.19–8.04 | 43–91 |
| 11.35 | 7.80 | 0–4 |
| 13.30–13.5 | 6.66–6.56 | 39–100 |
| 15.8–15.9 | 5.61–5.57 | 0–10 |
| 17.2–17.45 | 5.16–5.08 | 35–75 |
| 17.8–17.9 | 4.98–4.96 | 0–sh |
| 20.95–21.2 | 4.24–4.19 | 21–49 |
| 21.9–22.15 | 4.06–4.01 | 60–100 |
| 23.0–23.5 | 3.867–3.786 | 0–19 |
| 23.65 | 3.762 | 0–3 |
| 24.85–25.15 | 3.583–3.541 | 4–13 |
| 26.6–27.2 | 3.351–3.278 | 20–22 |
| 28.5–28.8 | 3.132–3.100 | 26–30 |
| 29.1–29.35 | 3.069–3.043 | sh–14 |
| 32.0–32.5 | 2.797–2.755 | 28–43 |
| 34.55–34.9 | 2.596–2.571 | 0–9 |
| 35.7–35.8 | 2.515–2.507 | 0–5 |
| 37.75 | 2.382 | 0–5 |
| 39.35 | 2.889 | 0–4 |
| 42.1–42.35 | 2.146–2.134 | 0–6 |
| 43.0–43.2 | 2.103–2.094 | 0–4 |
| 48.5–48.7 | 1.877–1.870 | 0–11 |
| 49.35–49.4 | 1.847–1.845 | 0–8 |
| 51.4–51.6 | 1.778–1.771 | 0–7 |
| 55.3–55.4 | 1.661–1.658 | 0–6 |

EXAMPLE 51F (a) ZnAPSO-36, as prepared in example 1F, was subjected to x-ray analysis. ZnAPSO-36 was determined to have a characteristic x-ray powder diffraction pattern which contains at least the d-spacings set forth below:

| 2θ | d, (Å) | 100 × I/Io |
|---|---|---|
| 7.45** | 11.85 | 76 |
| 7.95 | 11.13 | 100 |
| 8.2 | 10.76 | sh |
| 12.9** | 6.87 | 3 |
| 13.6 | 6.52 | 4 |
| 14.9** | 5.95 | 10 |
| 15.9 | 5.58 | 10 |
| 16.45 | 5.38 | 25 |
| 19.1 | 4.64 | 16 |
| 19.75** | 4.50 | 15 |
| 20.8* | 4.27 | 32 |
| 21.05** | 4.22 | sh |

-continued

| 2θ | d, (Å) | 100 × I/Io |
|---|---|---|
| 21.75 | 4.09 | 14 |
| 22.1 | 4.025 | 14 |
| 22.4* | 3.966 | 24 |
| 23.0 | 3.863 | 3 |
| 23.95 | 3.716 | 5 |
| 25.9** | 3.440 | 9 |
| 27.3 | 3.269 | 11 |
| 28.35 | 3.147 | 7 |
| 29.05* | 3.074 | 9 |
| 30.0** | 2.978 | 8 |
| 30.35 | 2.944 | 4 |
| 32.0 | 2.796 | 8 |
| 33.2 | 2.698 | 1 |
| 33.65** | 2.663 | 1 |
| 34.5** | 2.599 | 6 |
| 34.8 | 2.575 | 7 |
| 35.9 | 2.500 | 2 |
| 37.75 | 2.383 | 2 |
| 40.3 | 2.237 | 2 |
| 41.45 | 2.178 | 2 |
| 42.2 | 2.142 | 1 |
| 47.6* | 1.910 | 2 |
| 51.35 | 1.779 | 2 |
| 54.0 | 1.697 | 1 |
| 55.65 | 1.652 | 2 |

*peak may contain impurity
**impurity peak (b) The ZnAPSO-36 compositions obtained to date have patterns which are generally characterized by the data of Table XV-F below.

TABLE XV-F

| 2θ | d, (Å) | Relative Intensity |
|---|---|---|
| 7.45–8.0 | 11.14–11.04 | vs |
| 16.45–16.5 | 5.38–5.36 | w–m |
| 19.1–19.2 | 4.65–4.62 | w–m |
| 20.8–20.9 | 4.28–4.25 | w–m |
| 21.75–21.8 | 4.09–4.08 | w |
| 22.05–22.15 | 4.027–4.017 | w |

(c) The ZnAPSO-36 compositions for which x-ray powder diffraction data have been obtained to date have patterns which are characterized by the x-ray powder diffraction pattern shown in Table XVI-F below:

TABLE XVI-F

| 2θ | d, (Å) | 100 × I/Io |
|---|---|---|
| 7.45–8.0 | 11.14–11.04 | 100 |
| 8.2–8.3 | 10.76–10.68 | 0–sh |
| 13.55–13.6 | 6.53–6.50 | 3–4 |
| 15.85–15.95 | 5.60–5.56 | 10–12 |
| 16.45–16.5 | 5.38–5.36 | 18–31 |
| 19.1–19.2 | 4.65–4.62 | 19–22 |
| 20.8–20.9 | 4.28–4.25 | 17–39 |
| 21.75–21.8 | 4.09–4.08 | 10–17 |
| 22.05–22.15 | 4.027–4.017 | 14–17 |
| 23.0–23.05 | 3.865–3.859 | 3–4 |
| 23.85–24.0 | 3.728–3.707 | 3–6 |
| 27.25–27.35 | 3.273–3.260 | 9–15 |
| 28.3–28.4 | 3.152–3.142 | 6–9 |
| 30.1–30.4 | 2.970–2.940 | 4–6 |
| 31.95–32.1 | 2.803–2.788 | 6–11 |
| 33.2–33.6 | 2.698–2.665 | 1–2 |
| 34.75–34.9 | 2.580–2.572 | 7–10 |
| 35.85–35.95 | 2.504–2.497 | 2–6 |
| 37.75–37.8 | 2.384–2.380 | 2 |
| 40.15–40.4 | 2.246–2.232 | 1–3 |
| 41.45–41.5 | 2.180–2.176 | 1–2 |
| 42.2–42.3 | 2.142–2.137 | 0–2 |
| 51.4–51.45 | 1.779–1.776 | 2 |
| 54.0 | 1.697 | 0–1 |
| 55.4–55.8 | 1.658–1.648 | 1–2 |

EXAMPLE 52F (a) ZnAPSO-39, as referred to in example 9F, was subjected to x-ray analysis. ZnAPSO-39 was determined to have a characteristic x-ray powder diffraction pattern which contains at least the d-spacings set forth below:

| 2θ | d, (Å) | 100 × I/Io |
|---|---|---|
| 6.5** | 13.59 | 17 |
| 7.65** | 11.56 | 173 |
| 8.05** | 10.99 | 12 |
| 8.35** | 10.58 | 4 |
| 9.35* | 9.44 | 72 |
| 13.25* | 6.67 | 35 |
| 13.7** | 6.46 | 8 |
| 14.9** | 5.95 | 8 |
| 15.2** | 5.82 | 12 |
| 15.65** | 5.66 | 12 |
| 16.6** | 5.34 | 13 |
| 18.3 | 4.85 | 36 |
| 19.8** | 4.48 | 4 |
| 20.4** | 4.35 | 19 |
| 21.1* | 4.21 | 83 |
| 21.5** | 4.13 | 36 |
| 22.1** | 4.018 | 12 |
| 22.75* | 3.911 | 100 |
| 23.15** | 3.839 | 19 |
| 23.95** | 3.716 | 4 |
| 24.2** | 3.681 | 9 |
| 24.8** | 3.593 | 3 |
| 26.45** | 3.369 | 8 |
| 26.8* | 3.324 | 21 |
| 27.75** | 3.215 | 6 |
| 28.2** | 3.162 | 5 |
| 28.7** | 3.111 | 19 |
| 29.7* | 3.005 | 15 |
| 30.1* | 2.970 | 22 |
| 30.6** | 2.922 | 4 |
| 31.05** | 2.881 | 7 |
| 32.8* | 2.731 | 8 |
| 34.3* | 2.615 | 6 |
| 34.55** | 2.597 | 10 |
| 35.9** | 2.502 | 8 |
| 36.45* | 2.464 | 4 |
| 38.05* | 2.365 | 5 |
| 40.7* | 2.217 | 4 |

*peak may contain impurity
**impurity peak (b) The ZnAPSO-39 compositions are generally characterized by the data of Table XVII-F below.

TABLE XVII-F

| 2θ | d, (Å) | Relative Intensity |
|---|---|---|
| 9.35–9.45 | 9.46–9.36 | m |
| 13.15–13.35 | 6.73–6.63 | m |
| 18.3–18.4 | 4.85–4.82 | w–m |
| 21.1–21.2 | 4.21–4.19 | s–vs |
| 22.75–22.85 | 3.909–3.892 | s–vs |
| 26.8–26.9 | 3.389–3.314 | w–m |

(c) The ZnAPSO-39 compositions for which x-ray powder diffraction data have been obtained to date have patterns which are characterized by the x-ray powder diffraction pattern shown in Table XVIII-F below:

| 2θ | d, (Å) | 100 × I/Io |
|---|---|---|
| 9.35–9.45 | 9.46–9.36 | 60–72 |
| 13.15–13.35 | 6.73–6.63 | 22–40 |
| 18.3–18.4 | 4.85–4.82 | 16–40 |
| 21.1–21.2 | 4.21–4.19 | 83–100 |
| 22.75–22.85 | 3.909–3.892 | 85–100 |
| 26.8–26.9 | 3.389–3.314 | 12–40 |

-continued

| 2θ | d, (Å) | 100 × I/Io |
|---|---|---|
| 28.2–28.3 | 3.164–3.153 | 5–8 |
| 28.7–28.8 | 3.110–3.100 | 19–20 |
| 29.7–29.8 | 3.008–2.998 | 11–32 |
| 30.1–30.2 | 2.979–2.959 | 11–25 |
| 32.8–32.95 | 2.730–2.718 | 8–12 |
| 34.5–34.65 | 2.600–2.589 | 5–6 |
| 36.45–36.5 | 2.465–2.462 | 4–12 |
| 37.85–38.1 | 2.377–2.362 | 3–10 |
| 40.6–40.95 | 2.222–2.204 | 0–4 |

EXAMPLE 53F (a) ZnAPSO-43, as referred to in example 28F, was subjected to x-ray analysis. ZnAPSO-43 was determined to have a characteristic x-ray powder diffraction pattern which contains at least the d-spacings set forth below:

| 2θ | d, (Å) | 100 × I/Io |
|---|---|---|
| 12.45 | 7.11 | 76 |
| 14.0* | 6.32 | 194 |
| 16.95 | 5.24 | 8 |
| 19.8* | 4.48 | 160 |
| 20.95 | 4.24 | 13 |
| 21.15* | 4.20 | 13 |
| 21.85 | 4.07 | 48 |
| 22.15* | 4.010 | 8 |
| 24.3* | 3.659 | 400 |
| 27.1 | 3.291 | 100 |
| 28.15* | 3.171 | 52 |
| 28.75 | 3.104 | 4 |
| 31.55* | 2.837 | 49 |
| 32.55 | 2.751 | 20 |
| 32.75* | 2.733 | 9 |
| 34.25* | 2.620 | 8 |
| 34.65* | 2.590 | 68 |
| 37.5* | 2.399 | 8 |
| 38.5* | 2.340 | 6 |
| 40.2* | 2.244 | 16 |
| 41.2 | 2.190 | 4 |
| 42.7* | 2.117 | 16 |
| 45.1 | 2.010 | 8 |
| 47.5* | 1.914 | 18 |
| 49.45* | 1.843 | 7 |
| 51.15 | 1.787 | 7 |
| 51.9* | 1.761 | 36 |
| 53.8 | 1.704 | 7 |

*Impurity peak (b) ZnAPSO-43 compositions are generally characterized by the data of Table XIX-F below:

TABLE XIX-F

| 2θ | d, (Å) | Relative Intensity |
|---|---|---|
| 12.3–12.45 | 7.20–7.11 | m–vs |
| 16.8–16.95 | 5.28–5.23 | vw–w |
| 21.7–21.85 | 4.095–4.068 | vw–m |
| 26.95–27.1 | 3.308–3.291 | s–vs |
| 32.4–33.55 | 2.763–2.751 | w–m |

(c) The ZnAPSO-43 compositions for which x-ray powder diffraction data have been obtained to date have patterns which are characterized by the x-ray powder diffraction pattern shown in Table XX-F below:

TABLE XX-F

| 2θ | d, (Å) | 100 × I/Io |
|---|---|---|
| 12.3–12.45 | 7.20–7.11 | 66–100 |
| 16.8–16.95 | 5.28–5.23 | 0–10 |
| 20.8–20.95 | 4.27–4.24 | 10–13 |
| 21.7–21.85 | 4.095–4.068 | 0–48 |
| 26.95–27.1 | 3.308–3.290 | 82–100 |
| 28.65–28.75 | 3.116–3.105 | 11–23 |
| 32.4–32.55 | 2.763–2.751 | 18–20 |
| 41.2 | 2.191 | 0–4 |
| 44.95–45.1 | 2.017–2.010 | 8–15 |
| 50.95–51.15 | 1.792–1.786 | 0–7 |
| 53.7–53.8 | 1.710–1.707 | 0–8 |

EXAMPLE 54F (a) ZnAPSO-44 as prepared in example 34F, was subjected to x-ray analysis. ZnAPSO-44 was determined to have a characteristic x-ray powder diffraction pattern which contains at least the d-spacings set forth below:

| 2θ | d, (Å) | 100 × I/Io |
|---|---|---|
| 4.95* | 17.93 | 11 |
| 8.75* | 10.09 | sh |
| 9.25* | 9.56 | sh |
| 9.55 | 9.25 | 100 |
| 13.05 | 6.77 | 13 |
| 13.8 | 6.41 | 3 |
| 16.15 | 5.49 | 21 |
| 17.4 | 5.10 | 3 |
| 19.05 | 4.65 | 7 |
| 19.6* | 4.53 | 2 |
| 20.8 | 4.27 | 46 |
| 21.8 | 4.08 | 18 |
| 22.65 | 3.923 | 4 |
| 23.15 | 3.845 | 5 |
| 24.45 | 3.638 | 47 |
| 26.25 | 3.395 | 14 |
| 27.3* | 3.266 | 1 |
| 27.9 | 3.197 | 7 |
| 29.8 | 2.999 | 3 |
| 30.15 | 2.962 | 13 |
| 30.9 | 2.895 | 31 |
| 32.65 | 2.745 | 2 |
| 33.0 | 2.716 | 6 |
| 34.9 | 2.571 | 2 |
| 35.15 | 2.553 | 2 |
| 35.6 | 2.523 | 9 |
| 38.7 | 2.329 | 2 |
| 39.25 | 2.295 | 2 |
| 40.1 | 2.247 | 1 |
| 42.25 | 2.139 | 3 |
| 42.55 | 2.124 | 2 |
| 43.7 | 2.072 | 1 |
| 48.2 | 1.887 | 3 |
| 48.8 | 1.866 | 4 |
| 50.4 | 1.811 | 5 |
| 52.0 | 1.759 | 1 |
| 54.0 | 1.698 | 7 |

*Impurity peak (b) A portion of the as-synthesized ZnAPSO-44 of part (a) was calcined in air at 500° C. for about 67 hours. The calcined product was characterized by the x-ray powder diffraction pattern below:

| 2θ | d, (Å) | 100 × I/Io |
|---|---|---|
| 9.6 | 9.23 | 100 |
| 13.0 | 6.81 | 34 |
| 14.05 | 6.29 | 5 |
| 16.2 | 5.48 | 16 |
| 17.95 | 4.95 | 30 |
| 20.3** | 4.37 | 22 |
| 20.8 | 4.27 | 52 |
| 21.4 | 4.15 | 32 |
| 22.3 | 3.987 | 7 |
| 22.75* | 3.906 | 7 |
| 23.25 | 3.826 | 10 |

-continued

| 2θ | d, (Å) | 100 × I/Io |
|---|---|---|
| 24.75** | 3.599 | 5 |
| 25.15 | 3.538 | 22 |
| 26.15 | 3.406 | 11 |
| 28.4 | 3.142 | 9 |
| 28.75** | 3.107 | 7 |
| 30.95 | 2.888 | 23 |
| 31.35* | 2.852 | 15 |
| 35.3* | 2.542 | 9 |

*Peak may contain impurity
**Impurity peak (c) The ZnAPSO-44 compositions are generally characterized by the data of Table XXI-F below:

TABLE XXI-F

| 2θ | d, (Å) | Relative Intensity |
|---|---|---|
| 9.4–9.55 | 9.41–9.26 | vs |
| 12.9–13.05 | 6.86–6.78 | vw-m |
| 20.65–20.8 | 4.30–4.27 | m |
| 21.4–21.8 | 4.15–4.08 | w-m |
| 24.3–25.15 | 3.663–3.541 | m |
| 30.75–30.95 | 2.908–2.889 | m |

(d) The ZnAPSO-44 compositions for which x-ray powder diffraction data have been obtained to date have patterns which are characterized by the x-ray powder diffraction pattern shown in Table XXII-F below:

TABLE XXII-F

| 2θ | d, (Å) | 100 × I/Io |
|---|---|---|
| 9.4–9.55 | 9.41–9.25 | 100 |
| 12.9–13.05 | 6.86–6.78 | 8–34 |
| 13.6–14.05 | 6.51–6.30 | 3–5 |
| 16.0–16.2 | 5.54–5.47 | 14–21 |
| 17.25–17.95 | 5.14–4.94 | 0–6 |
| 18.95–19.05 | 4.68–4.66 | 0–5 |
| 20.65–20.8 | 4.30–4.27 | 35–52 |
| 21.4–21.8 | 4.15–4.08 | 18–32 |
| 22.55–22.65 | 3.943–3.926 | 4 |
| 23.15–23.25 | 3.842–3.826 | 5–10 |
| 24.3–25.15 | 3.663–3.541 | 22–47 |
| 26.1–26.25 | 3.414–3.395 | 8–14 |
| 27.7–28.4 | 3.220–3.143 | 7–9 |
| 29.8 | 2.998– | 0–3 |
| 30.05–30.15 | 2.974 | 0–13 |
| 30.75–30.95 | 2.908–2.889 | 23–31 |
| 32.65–32.8 | 2.743–2.730 | 0–3 |
| 33.0 | 2.714 | 0–6 |
| 34.9 | 2.571 | 0–2 |
| 35.15 | 2.553 | 0–2 |
| 35.3–35.6 | 2.543–2.522 | 9–10 |
| 38.7 | 2.327–2.327 | 0–2 |
| 39.3–40.2 | 2.292–2.243 | 0–2 |
| 40.1 | 2.249 | 0–1 |
| 42.1–42.3 | 2.146–2.137 | 0–3 |
| 42.55 | 2.127 | 0–2 |
| 43.7 | 2.071 | 0–1 |
| 48.2 | 1.888 | 0–3 |
| 48.65–48.8 | 1.872–1.866 | 0–5 |
| 50.2–50.4 | 1.817–1.811 | 0–5 |
| 52.0 | 1.759 | 0–1 |
| 53.8–54.0 | 1.704–1.698 | 0–7 |

EXAMPLE 55F (a) ZnAPSO-46, as referred to in example 8F was subjected to x-ray analysis. ZnAPSO-46 was determined to have a characteristic x-ray powder diffraction pattern which contains at least the d-spacings set forth below:

| 2θ | d, (Å) | 100 × I/Io |
|---|---|---|
| 6.6 | 13.39 | 8 |
| 7.75 | 11.42 | 100 |
| 8.1** | 10.90 | 3 |
| 9.45** | 9.34 | 18 |
| 10.2 | 8.67 | 1 |
| 13.35* | 6.63 | 10 |
| 13.8 | 6.41 | 4 |
| 14.95 | 5.92 | 4 |
| 15.75** | 5.62 | 3 |
| 16.7 | 5.31 | 7 |
| 17.5 | 5.07 | 1 |
| 18.4** | 4.83 | 10 |
| 19.85 | 4.47 | 3 |
| 20.5* | 4.33 | 6 |
| 21.25** | 4.19 | 25 |
| 21.6 | 4.12 | 18 |
| 22.25** | 3.998 | 3 |
| 22.8 | 3.896 | 32 |
| 23.3** | 3.818 | 4 |
| 24.05 | 3.700 | 3 |
| 24.25* | 3.669 | 5 |
| 25.3* | 3.523 | 1 |
| 26.55** | 3.354 | 3 |
| 26.9 | 3.313 | 10 |
| 27.8 | 3.207 | 3 |
| 28.3 | 3.152 | 2 |
| 28.8* | 3.100 | 8 |
| 29.85* | 2.993 | 6 |
| 30.2** | 2.961 | 7 |
| 31.15 | 2.870 | 3 |
| 31.8* | 2.813 | 1 |
| 32.95* | 2.719 | 3 |
| 34.3* | 2.612 | 2 |
| 34.65** | 2.590 | 3 |
| 36.0* | 2.495 | 3 |
| 36.55 | 2.459 | 2 |
| 36.8* | 2.442 | 1 |
| 37.3 | 2.410 | 1 |
| 38.1** | 2.361 | 1 |
| 39.7* | 2.271 | 1 |
| 40.95* | 2.204 | 1 |
| 43.2** | 2.093 | 1 |
| 44.1* | 2.054 | 1 |
| 46.1* | 1.969 | 1 |
| 47.65* | 1.908 | 1 |
| 49.45** | 1.844 | 1 |
| 49.65* | 1.836 | 1 |
| 51.55 | 1.772 | 1 |
| 52.45* | 1.745 | 1 |

*Peak may contain impurity
**Impurity peak (b) The ZnAPSO-46 compositions are characterized by the data of Table XXIII-F below:

TABLE XXIII-F

| 2θ | d, (Å) | Relative Intensity |
|---|---|---|
| 7.6–7.75 | 11.63–11.42 | vs |
| 13.1–13.35 | 6.76–6.63 | w-m |
| 21.5–21.6 | 4.13–4.12 | w-m |
| 22.6–22.85 | 3.934–3.896 | m |
| 26.75–27.0 | 3.333–3.302 | w |

(c) The ZnAPSO-46 compositions for which x-ray powder diffraction data have been obtained to date have patterns which are characterized by the x-ray powder diffraction pattern shown in Table XXIV-F below:

TABLE XXIV-F

| 2θ | d, (Å) | 100 × I/Io |
|---|---|---|
| 6.5–6.7 | 13.60–13.19 | 7–10 |
| 7.6–7.75 | 11.63–11.42 | 100 |
| 10.2 | 8.67 | 0–1 |
| 13.1–13.35 | 6.76–6.63 | 10–20 |
| 13.7–13.8 | 6.46–6.41 | 4–5 |

TABLE XXIV-F-continued

| 2θ | d, (Å) | 100 × I/Io |
|---|---|---|
| 14.9–15.0 | 5.95–5.91 | 4–5 |
| 15.2–15.35 | 5.83–5.77 | 5–7 |
| 16.6–16.8 | 5.34–5.28 | 7 |
| 17.35–17.5 | 5.11–5.07 | 0–1 |
| 19.7–20.0 | 4.51–4.44 | 2–3 |
| 20.3–20.5 | 4.37–4.33 | 6–11 |
| 21.5–21.6 | 4.13–4.12 | 18–21 |
| 22.6–22.85 | 3.934–3.896 | 32–58 |
| 23.9–24.05 | 3.723–3.700 | 2–3 |
| 25.1–25.3 | 3.548–3.520 | 0–1 |
| 26.75–27.0 | 3.333–3.302 | 10–12 |
| 27.7–28.0 | 3.220–3.187 | 3–4 |
| 28.2–28.3 | 3.175–3.152 | 2–3 |
| 28.6–28.9 | 3.121–3.089 | 8–11 |
| 29.7–29.9 | 3.008–2.988 | 6–9 |
| 31.0–31.15 | 2.885–2.870 | 3–4 |
| 31.6–31.8 | 2.831–2.813 | 0–1 |
| 32.8–33.2 | 2.730–2.706 | 3–4 |
| 34.15–34.4 | 2.626–2.607 | 2–4 |
| 35.8–36.0 | 2.508–2.495 | 3–4 |
| 36.45–36.55 | 2.464–2.459 | 2–3 |
| 37.3–37.7 | 2.410–2.386 | 0–2 |
| 39.7 | 2.271 | 0–1 |
| 40.9–41.1 | 2.206–2.196 | 0–1 |
| 43.85–44.1 | 2.065–2.054 | 0–1 |
| 46.1 | 1.969 | 0–1 |
| 47.4–47.7 | 1.918–1.908 | 0–1 |
| 49.7–49.8 | 1.834–1.831 | 0–1 |
| 51.4–51.7 | 1.778–1.768 | 0–1 |
| 52.2–52.45 | 1.752–1.745 | 0–1 |

EXAMPLE 56F (a) ZnAPSO-47, as referred to in example 38F, was subjected to x-ray analysis. ZnAPSO-47 was determined to have a characteristic x-ray powder diffraction pattern which contains at least the d-spacings set forth below:

| 2θ | d, (Å) | 100 × I/Io |
|---|---|---|
| 7.45* | 11.88 | 2 |
| 9.45 | 9.35 | 93 |
| 12.9 | 6.87 | 17 |
| 13.9 | 6.38 | 7 |
| 16.0* | 5.54 | 42 |
| 17.65 | 5.03 | 11 |
| 19.0* | 4.67 | 3 |
| 20.6 | 4.31 | 100 |
| 21.85 | 4.07 | 7 |
| 22.4* | 3.97 | 6 |
| 23.0 | 3.867 | 11 |
| 24.75 | 3.600 | 21 |
| 25.9 | 3.439 | 23 |
| 27.65 | 3.228 | 10 |
| 28.0 | 3.188 | 3 |
| 29.5 | 3.029 | 5 |
| 30.6 | 2.922 | 49 |
| 30.9 | 2.894 | sh |
| 31.5 | 2.839 | 3 |
| 32.3 | 2.772 | 2 |
| 33.3 | 2.689 | 3 |
| 34.5 | 2.600 | 10 |
| 34.9 | 2.573 | 2 |
| 35.7 | 2.516 | 4 |
| 38.4 | 2.344 | 3 |
| 39.65 | 2.273 | 4 |
| 42.5 | 2.126 | 3 |
| 43.3 | 2.089 | 2 |
| 44.9 | 2.019 | 2 |
| 47.6 | 1.909 | 4 |
| 48.6 | 1.873 | 5 |
| 50.5 | 1.807 | 5 |
| 53.25 | 1.721 | 5 |
| 54.5 | 1.684 | 2 |

-continued

| 2θ | d, (Å) | 100 × I/Io |
|---|---|---|
| 56.0 | 1.642 | 5 |

*Impurity peak (b) A portion of the as-synthesized ZnAPSO-47 of part (a) was calcined in air at 500° C. for about 1.75 hours. The calcined product was characterized by the x-ray powder diffraction pattern below:

| 2θ | d, (Å) | 100 × I/Io |
|---|---|---|
| 7.5* | 11.78 | 11 |
| 9.65 | 9.17 | 100 |
| 13.05 | 6.78 | 25 |
| 14.15 | 6.26 | 3 |
| 16.2 | 5.46 | 10 |
| 18.0 | 4.93 | 8 |
| 19.25 | 4.61 | 3 |
| 19.8* | 4.49 | 2 |
| 20.85 | 4.26 | 27 |
| 21.25* | 4.18 | sh |
| 22.5* | 3.950 | 8 |
| 23.3 | 3.816 | 4 |
| 25.2 | 3.533 | 8 |
| 26.2 | 3.399 | 10 |
| 28.0 | 3.187 | 2 |
| 28.55 | 3.126 | 3 |
| 29.8 | 2.998 | 2 |
| 31.0 | 2.885 | 18 |
| 31.4 | 2.849 | sh |
| 34.9 | 2.571 | 2 |

*Impurity peak (c) The ZnAPSO-47 compositions are characterized by the date in Table XXV-F below:

TABLE XXV-F

| 2θ | d, (Å) | Relative Intensity |
|---|---|---|
| 9.45–9.65 | 9.35–9.17 | vs |
| 12.85–13.05 | 6.89–6.78 | w–m |
| 15.95–16.2 | 5.55–5.46 | w–m |
| 20.55–20.85 | 4.31–4.26 | m–vs |
| 25.9–26.2 | 3.439–3.399 | w–m |
| 30.55–31.0 | 2.925–2.885 | w–m |

(d) The ZnAPSO-47 compositions for which x-ray powder diffraction data have been obtained to date have patterns which are characterized by the x-ray powder diffraction pattern shown in Table XXVI-F below:

TABLE XXVI-F

| 2θ | d, (Å) | 100 × I/Io |
|---|---|---|
| 9.45–9.65 | 9.35–9.17 | 93–100 |
| 12.85–13.05 | 6.89–6.78 | 17–25 |
| 13.85–14.15 | 6.39–6.26 | 3–7 |
| 15.95–16.2 | 5.55–5.46 | 10–42 |
| 17.45–18.0 | 5.09–4.93 | 2–11 |
| 20.55–20.85 | 4.31–4.26 | 27–100 |
| 21.85 | 4.07 | 0–7 |
| 22.95–23.3 | 3.867–3.816 | 4–11 |
| 24.75–25.2 | 3.600–3.533 | 8–21 |
| 25.9–26.2 | 3.439–3.399 | 16–29 |
| 27.6–28.55 | 3.231–3.126 | 3–10 |
| 27.9–28.0 | 3.196–3.188 | 0–3 |
| 29.45–29.8 | 3.031–2.998 | 2–5 |
| 30.55–31.0 | 2.925–2.885 | 18–49 |
| 30.9–31.4 | 2.894–2.849 | sh |
| 31.5 | 2.839 | 0–3 |
| 32.3 | 2.772 | 0–2 |
| 33.3 | 2.689 | 0–3 |
| 34.45–34.9 | 2.603–2.600 | 2–19 |
| 34.9 | 2.573 | 0–2 |
| 35.7–35.9 | 2.516–2.503 | 0–5 |
| 38.4–38.55 | 2.344–2.336 | 0–3 |

TABLE XXVI-F-continued

| 2θ | d, (Å) | 100 × I/Io |
|---|---|---|
| 39.6–39.65 | 2.273 | 0–4 |
| 42.25–42.5 | 2.139–2.126 | 0–3 |
| 43.3 | 2.089 | 0–2 |
| 44.9 | 2.019 | 0–2 |
| 47.6 | 1.909 | 0–6 |
| 48.6–48.7 | 1.873–1.870 | 0–5 |
| 50.45–50.5 | 1.807 | 0–5 |
| 53.2–53.25 | 1.722–1.721 | 0–5 |
| 54.5 | 1.684 | 0–2 |
| 56.0 | 1.642 | 0–5 |

EXAMPLE 57F

In order to demonstrate the catalytic activity of calcined ZnAPSO compositions were tested for catalytic cracking of n-butane using a bench-scale apparatus.

The reactor was a cylindrical quartz tube 254 mm. in length and 10.3 mm I.D. In each test the reactor was loaded with particles of the test ZnAPSO which were 20–40 mesh (U.S. std.) in size and in an amount of from 0.5 to 5 grams, the quantity being selected so that the conversion of n-butane was at least 5% and not more than 90% under the test conditions. The ZnAPSO samples had been previously calcined in air to remove organic materials from the pore system, and were activated in situ in the reactor in a flowing stream of helium at 500° C. for one hour. The feedstock was a helium n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the ZnAPSO compositions. The $k_A$ value (cm$^3$/g min) obtained for the ZnAPSO compositions are set forth, below, in Table XXVII-F:

TABLE XXVII-F

| ZnAPSO | Prepared in Example No. | Rate Constant ($k_A$)* |
|---|---|---|
| ZnAPSO-5 | 4F | 1.5 |
| ZnAPSO-34 | 24F | 12.7 |
| ZnAPSO-35 | 33F | 1.0 |
| ZnAPSO-44 | 35F | 5.0 |
| ZnAPSO-47 | 39F | 5.6 |

*ZnAPSO were calcined prior to in situ activation as follows:
(a) ZnAPSO-5: in air at 500° C. for 0.75 and at 600° C. for 1.25 hours;
(b) ZnAPSO-34: in air at 500° C. for 2 hours;
(c) ZnAPSO-35: in air at 500° C. for 1.75 hours;
(d) ZnAPSO-44: in air at 500° C. for 67 hours; and
(e) ZnAPSO-47: in air at 500° C. for 1.75 hours.

G. COBALT-MANGANESE-ALUMINUM-PHOSPHORUS-SILICON-OXIDE SIEVES

Preparative Reagents

In the following examples the CoMnAPSO compositions were prepared using numerous regents. The reagents employed and abbreviations employed herein, if any, for such reagents are as follows:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent phosphoric acid;
(d) MnAc: Manganese acetate, $Mn(C_2H_3O_2)_2 \cdot 4H_2O$;
(e) CoAc: Cobalt Acetate, $Co(C_2H_3O_2)_2 \cdot 4H_2O$;
(f) TEAOH: 40 weight percent aqueous solution of tetraethylammonium hydroxide; and
(g) $Pr_2NH$: di-n-propylamine, $(C_3H_7)_2NH$.

Preparative Procedures

The following preparative examples were carried out by forming a starting reaction mixture by adding the $H_3PO_4$ and one half of the quantity of water. To this mixture the aluminum isopropoxide was added. This mixture was then blended until a homogeneous mixture was observed. To this mixture the LUDOX-LS was added and the resulting mixture blended (about 2 minutes) until a homogeneous mixture was observed. A second mixture was prepared using manganese acetate and one half of the remaining water. A third mixture was prepared using cobalt acetate and one half of the remaining water. The three mixtures were admixed and the resulting mixture blended until a homogeneous mixture was observed. The organic templating agent was then added to the resulting mixture and the resulting mixture blended until a homogeneous mixture was observed, i.e. about 2 to 4 minutes. The pH of the mixture was measured and adjusted for temperature. The mixture was then placed in a lined (polytetrafluoroethylene) stainless steel pressure vessel and digested at a temperature. All digestions were carried out at the autogeneous pressure.

EXAMPLES 1G TO 4G

CoMnAPSO molecular sieves were prepared according to the above identified procedure and the CoMnAPSO products determined by X-ray analysis. The results of examples 1G to 4G are set forth in Table I-G. Examples AG to FG in Table I-G represent reaction mixtures that did not show CoMnAPSO products when determined by X-ray analysis.

TABLE I-G

| Example[1] | Template | Temp (°C.) | Time (days) | CoMnMgAPSO Product(s)[2] |
|---|---|---|---|---|
| 1G | TEAOH | 150 | 2 | CoMnAPSO-34; CoMnAPSO-5 |
| 2G | TEAOH | 150 | 7 | CoMnAPSO-34; CoMnAPSO-5 |
| 3G | Pr$_2$NH | 200 | 2 | CoMnAPSO-5; CoMnAPSO-11 |
| 4G | Pr$_2$NH | 200 | 7 | CoMnAPSO-5; CoMnAPSO-11 |
| AG | TEAOH | 100 | 3 | — |
| BG | TEAOH | 100 | 7 | — |
| CG | Pr$_2$NH | 150 | 2 | — |
| DG[3] | Pr$_2$NH | 150 | 10 | — |
| EG[3] | Pr$_2$NH | 150 | 6 | — |

TABLE I-G-continued

| Example[1] | Template | Temp (°C.) | Time (days) | CoMnMgAPSO Product(s)[2] |
|---|---|---|---|---|
| FG[3] | Pr₂NH | 150 | 15 | — |

[1]The reaction mixture comprised:
1.0R:0.2 MnO:0.2 CoO:0.8 Al₂O₃:0.8 P₂O₅:0.4 SiO₂:50 H₂O where "R" is the template.
[2]Major species as identified by x-ray powder diffraction pattern of product, except that when two species are identified the first species listed is present in an amount equal to or greater than the second species listed. A "—" indicates that crystalline products were not identified by X-ray analysis.
[3]X-ray analysis indicated that crystalline product was beginning to form.

EXAMPLE 5G (a) Samples of the above prepared CoMnAPSO products, as identified in parenthesis, were calcined in air to remove at least part of the organic templating agent of the CoMnAPSO product. The adsorption capacities of each calcined sample were measured using a standard McBain-Bakr gravimetric adsorption apparatus. The samples were activated in a vacuum (less than 0.04 torr) at 350° C. prior to measurement. The McBain-Bakr data were as follows:

(b) CoMnAPSO-34 and CoMnAPSO-5 (Example 2G):

| Adsorbate | Kinetic Diameter, Å | Pressure (Torr) | Temp (°C.) | Wt. % Adsorbed* |
|---|---|---|---|---|
| Oxygen | 3.46 | 105 | −183 | 13.8 |
| Oxygen | 3.46 | 733 | −183 | 18.5 |
| Neopentane | 6.2 | 742 | 23.8 | 2.6 |
| Cyclohexane | 6.0 | 65 | 23.7 | 4.6 |
| n-hexane | 4.3 | 93 | 23.4 | 5.0 |
| H₂O | 2.65 | 4.6 | 23.4 | 15.8 |
| H₂O | 2.65 | 19 | 23.7 | 23.6 |

*calcined in air at 600° C. for one hour prior to activation (c) CoMnAPSO-5 and CoMnAPSO-11 (Example 4G):

| Adsorbate | Kinetic Diameter, Å | Pressure (Torr) | Temp (°C.) | Wt. % Adsorbed* |
|---|---|---|---|---|
| Oxygen | 3.46 | 105 | −183 | 5.5 |
| Oxygen | 3.46 | 733 | −183 | 9.3 |
| Neopentane | 6.2 | 742 | 23.8 | 2.4 |
| Cyclohexane | 6.0 | 65 | 23.7 | 5.9 |
| H₂O | 2.65 | 4.6 | 23.4 | 7.4 |
| H₂O | 2.65 | 19 | 23.7 | 16.2 |

*calcined in air at 600° C. for one hour prior to activation

EXAMPLE 6G

Samples of the as-synthesized products of examples 2G and 4G were subjected to chemical analysis. The chemical analysis for these CoMnAPSOs was:

(a) The chemical analysis for the product of example 2G was:

| Component | Weight Percent |
|---|---|
| Al₂O₃ | 27.5 |
| P₂O₅ | 37.7 |
| SiO₂ | 4.98 |
| CoO | 4.3 |
| MnO | 5.2 |
| Carbon | 5.3 |
| LOI* | 20.5 |

*Loss on Ignition

The above chemical analysis gives an overall product composition in molar oxide ratios (anhydrous basis) of:

0.057 CoO:0.073 MnO:0.270 Al₂O₃:266 P₂O₅:0.083 SiO₂ and a formula (anhydrous basis) of:

0.055R $(Al_{0.420}P_{0.414}Si_{0.065}Co_{0.044}Mn_{0.057})O_2$ (b) The chemical analysis for the product of example 4G was:

| Component | Weight Percent |
|---|---|
| Al₂O₃ | 26.6 |
| P₂O₅ | 37.6 |
| SiO₂ | 7.1 |
| CoO | 5.1 |
| MnO | 6.0 |
| Carbon | 1.91 |
| LOI* | 17.9 |

*Loss on Ignition

The above chemical analysis gives an overall product composition in molar oxide ratios (anhydrous basis) of:

0.068 CoO:0.085 MnO:0.261 Al₂O₃:0.265 P₂O₅:0.118 SiO₂ and a formula (anhydrous basis) of:

0.027R $(Al_{0.40}P_{0.40}Si_{0.089}Co_{0.051}Mn_{0.064})O_2$

EXAMPLE 7G

EDAX (energy dispersive analysis by x-ray) microprobe analysis in conjunction with SEM (scanning electron microscope) was carried out on the products of example 2G and 4G. Analysis of crystals having a morphology characteristic of each CoMnAPSO product gave the following analysis based on relative peak heights:

| Average of Spot Probes | |
|---|---|
| (a) Example 2G (CoMnAPSO-5): | |
| Al | 0.81 |
| P | 0.98 |
| Si | 0.18 |
| Co | 0.10 |
| Mn | 0.17 |
| (b) Example 2G (CoMnAPSO-34): | |
| Al | 0.82 |
| P | 0.93 |
| Si | 0.17 |
| Co | 0.03 |
| Mn | 0.03 |
| (c) Example 4G (CoMnAPSO-5): | |
| Al | 0.93 |
| P | 0.71 |
| Si | 0.15 |
| Co | 0.05 |
| Mn | 0.07 |
| (d) Example 4G (CoMnAPSO-11): | |
| Al | 0.81 |
| P | 0.95 |
| Si | 0.15 |
| Co | 0.03 |
| Mn | 0.05 |

EXAMPLE 8G (a) CoMnAPSO-5, as prepared in example 1G, was subjected to x-ray analysis. The CoMnAPSO-5 was determined to have an x-ray powder diffraction pattern characterized by the following data:

| 2θ | d (Å) | (I/Io) × 100 |
|---|---|---|
| 7.5 | 11.84 | 67 |
| 9.5* | 9.29 | 100 |
| 12.9** | 6.89 | 11 |
| 14.1* | 6.29 | 7 |
| 14.9 | 5.93 | 14 |
| 16.0* | 5.54 | 22 |
| 18.0* | 4.93 | 10 |
| 19.8 | 4.49 | 19 |
| 20.6* | 4.32 | 51 |
| 21.1** | 4.22 | 40 |
| 22.4 | 3.96 | 28 |
| 25.2* | 3.530 | 12 |
| 29.1 | 3.071 | 6 |
| 29.5* | 3.024 | 3 |
| 30.1 | 2.968 | 10 |
| 30.5* | 2.928 | 16 |
| 31.3* | 2.862 | 11 |
| 33.7* | 2.659 | 3 |
| 34.5 | 2.601 | 4 |
| 34.6* | 2.591 | 5 |
| 37.8 | 2.383 | 6 |
| 47.7** | 1.905 | 3 |
| 48.9* | 1.863 | 2 |
| 49.9* | 1.828 | 2 |
| 50.9* | 1.794 | 2 |
| 55.8 | 1.647 | 2 |

*peak may be an impurity
**impurity peak and CoMnMgAPSO-5

(b) A portion of the as-synthesized CoMnAPSO-5 of example 2G was calcined in air at 600° C. for one (1) hour. The calcined product was characterized by the following x-ray powder diffraction pattern:

| 2θ | d (Å) | (I/Io) × 100 |
|---|---|---|
| 7.5 | 11.84 | 32 |
| 9.6* | 9.20 | 100 |
| 13.0** | 6.81 | 20 |
| 14.9 | 5.93 | 4 |
| 16.2* | 5.48 | 8 |
| 18.0* | 4.93 | 6 |
| 19.3* | 4.60 | 3 |
| 19.8 | 4.49 | 8 |
| 20.9** | 4.26 | 22 |
| 21.2** | 4.20 | 26 |
| 21.5* | 4.13 | 3 |
| 22.5 | 3.95 | 32 |
| 23.4* | 3.81 | 3 |
| 25.3* | 3.520 | 7 |
| 26.1 | 3.420 | 11 |
| 26.2* | 3.396 | 7 |
| 28.5* | 3.129 | 3 |
| 29.2 | 3.063 | 6 |
| 30.2 | 2.965 | 6 |
| 31.0* | 2.881 | 11 |
| 31.5* | 2.840 | 7 |
| 34.7 | 2.584 | 4 |
| 34.9 | 2.568 | 3 |
| 38.0* | 2.368 | 2 |

*peak may be an impurity
**impurity peak and CoMnAPSO-5

(c) The species CoMnAPSO-5 is a molecular sieve having a characteristic x-ray powder diffraction pattern which contains at least the d-spacings set forth in Table II-G as follows:

TABLE II-G

| 2θ | d (Å) | Relative Intensity |
|---|---|---|
| 7.4–7.5 | 11.95–11.84 | m |
| 12.9–13.1 | 6.89–6.76 | w–m |
| 14.9 | 5.93 | vw–w |
| 19.7–19.8 | 4.51–4.49 | vw–w |
| 20.9–21.3 | 4.26–4.17 | m |
| 22.4–22.5 | 3.97–3.95 | m |

(d) All of the CoMnAPSO-5 compositions, both as-synthesized and calcined, for which x-ray powder diffraction data have been obtained have patterns which are within the generalized pattern of Table III-G, below:

TABLE III-G

| 2θ | d (Å) | (I/Io) × 100 |
|---|---|---|
| 7.4–7.5 | 11.95–11.84 | 32–67 |
| 12.9–13.1 | 6.89–6.81 | 11–20 |
| 14.9 | 5.93 | 4–14 |
| 19.7–19.8 | 4.51–4.49 | 8–19 |
| 20.9–21.3 | 4.26–4.17 | 22–40 |
| 22.4–22.5 | 3.96–3.95 | 28–32 |
| 24.7–24.8 | 3.60–3.59 | 6 |
| 25.9–26.1 | 3.440–3.420 | 10–11 |
| 29.0–29.2 | 3.079–3.063 | 6 |
| 29.9–30.2 | 2.988–2.965 | 6–10 |
| 34.4–34.7 | 2.607–2.584 | 4 |
| 34.9 | 2.568 | 3 |
| 37.8 | 2.383 | 6 |
| 47.7 | 1.905 | 3 |
| 55.8 | 1.647 | 2 |

EXAMPLE 9G (a) The CoMnAPSO-11, prepared in example 3G, was subjected to X-ray analysis. The CoMnAPSO-11 was impure but the CoMnAPSO-11 was determined to have an X-ray powder diffraction pattern characterized by the following data:

| 2θ | d (Å) | (I/Io) × 100 |
|---|---|---|
| 7.0* | 12.56 | 12 |
| 7.5* | 11.86 | 68 |
| 8.1 | 10.88 | 46 |
| 9.5 | 9.31 | 68 |
| 12.9* | 6.87 | 11 |
| 13.2 | 6.73 | 24 |
| 14.9* | 5.95 | 12 |
| 15.7 | 5.64 | 49 |
| 16.3 | 5.44 | 9 |
| 19.0 | 4.67 | 9 |
| 19.7* | 4.50 | 29 |
| 20.4 | 4.36 | 66 |
| 21.1** | 4.21 | 37 |
| 21.2 | 4.19 | 34 |
| 22.4* | 3.96 | 41 |
| 22.8 | 3.91 | 29 |
| 23.2 | 3.83 | 100 |
| 24.8** | 3.59 | 10 |
| 25.9* | 3.443 | 23 |
| 26.5 | 3.365 | 32 |
| 28.2 | 3.163 | 9 |
| 28.7 | 3.113 | 25 |
| 29.5 | 3.024 | 8 |
| 29.9* | 2.985 | 15 |
| 31.5 | 2.838 | 8 |
| 32.7 | 2.739 | 2 |
| 34.2 | 2.622 | 2 |
| 36.4 | 2.468 | 2 |
| 37.6 | 2.392 | 2 |

*peak may be an impurity
**impurity peak (b) A portion of the as-synthesized CoMnAPSO-11 of example 4G was calcined in air at 600° C. for one (1) hour. The calcined product was characterized by the following X-ray powder diffraction pattern:

| 2θ | d (Å) | (I/Io) × 100 |
|---|---|---|
| 7.5* | 11.86 | 95 |
| 8.2 | 10.85 | 68 |
| 9.6 | 9.19 | 95 |
| 13.1* | 6.77 | 45 |
| 15.9 | 5.58 | 91 |
| 19.8* | 4.48 | 32 |
| 20.3 | 4.37 | 49 |
| 21.3* | 4.17 | 34 |
| 22.5** | 3.96 | 62 |
| 23.4 | 3.80 | 100 |
| 26.0* | 3.423 | 43 |
| 26.4 | 3.376 | 40 |
| 26.6 | 3.346 | 16 |
| 29.1* | 3.073 | 27 |
| 29.2 | 3.061 | 28 |
| 30.2* | 2.962 | 21 |
| 32.8 | 2.732 | 21 |
| 32.9 | 2.719 | 31 |
| 34.7* | 2.586 | 28 |
| 36.2 | 2.481 | 2 |

*peak may contain impurity
**impurity peak (c) The species CoMnAPSO-11 is a molecular sieve having a characteristic x-ray powder diffraction pattern which contains at least the d-spacings set forth in Table IV-G as follows:

TABLE IV-G

| 2θ | d, (Å) | Relative Intensity |
|---|---|---|
| 9.5–9.6 | 9.31–9.21 | m–vs |
| 15.7–15.9 | 5.64–5.57 | m–vs |
| 20.3–20.4 | 4.37–4.36 | m |
| 21.1–21.2 | 4.21–4.19 | m |
| 22.1–22.5 | 4.02–3.95 | m |
| 23.2–23.4 | 3.83–3.80 | vs |

(d) All of the CoMnAPSO-11 compositions both as-synthesized and calcined, for which x-ray powder diffraction data have presently been obtained have patterns which are within the generalized pattern on Table V-G, below:

TABLE V-G

| 2θ | d, (Å) | (I/Io) × 100 |
|---|---|---|
| 8.1–8.2 | 10.88–10.85 | 46–68 |
| 9.5–9.6 | 9.31–9.19 | 68–95 |
| 13.1–13.2 | 6.77–6.73 | 24–45 |
| 15.7–15.9 | 5.64–5.58 | 49–91 |
| 16.3 | 5.44 | 9 |
| 19.0 | 4.67 | 9–10 |
| 20.3–20.4 | 4.37–4.36 | 49–66 |
| 21.1–21.2 | 4.21–4.19 | 30–37 |
| 22.1–22.5 | 4.02–3.96 | 31–62 |
| 22.7–22.8 | 3.92–3.91 | 28–29 |
| 23.2–23.4 | 3.83–3.80 | 100 |
| 24.7–24.8 | 3.60–3.59 | 10–14 |
| 26.4–26.6 | 3.376–3.346 | 16–40 |
| 28.1–28.2 | 3.175–3.163 | 9 |
| 28.7 | 3.113 | 25–26 |
| 29.2–29.5 | 3.061–3.024 | 8–28 |
| 31.5 | 2.838 | 8 |
| 32.7–32.8 | 2.739–2.732 | 2–27 |
| 32.9 | 2.719 | 31 |
| 34.2 | 2.622 | 2–11 |
| 36.2–36.4 | 2.481–2.468 | 2–9 |
| 37.6–37.9 | 2.392–2.374 | 2–3 |

EXAMPLE 10G (a) The CoMnAPSO-34, prepared in example 1G, was subjected to x-ray analysis. The CoMnAPSO-34 was impure but was the major phase and was determined to have an x-ray powder diffraction pattern characterized by the following data:

| 2θ | d (Å) | (I/Io) × 100 |
|---|---|---|
| 7.5* | 11.84 | 67 |
| 9.5 | 9.29 | 100 |
| 12.9** | 6.89 | 11 |
| 14.1 | 6.29 | 7 |
| 14.9* | 5.93 | 14 |
| 16.0 | 5.54 | 22 |
| 18.0 | 4.93 | 10 |
| 19.8* | 4.49 | 19 |
| 20.6 | 4.32 | 51 |
| 21.1** | 4.22 | 40 |
| 22.4* | 3.96 | 28 |
| 25.2 | 3.530 | 12 |
| 29.1* | 3.071 | 6 |
| 29.5 | 3.024 | 3 |
| 30.1* | 2.968 | 10 |
| 30.5 | 2.928 | 16 |
| 31.3 | 2.862 | 11 |
| 33.7 | 2.659 | 3 |
| 34.5* | 2.601 | 4 |
| 34.6 | 2.591 | 5 |
| 37.8* | 2.383 | 6 |
| 47.7** | 1.905 | 3 |
| 48.9 | 1.863 | 2 |
| 49.9 | 1.828 | 2 |
| 50.9 | 1.794 | 2 |
| 55.8* | 1.647 | 2 |

*peak may contain impurity
**impurity peak (b) A portion of the as-synthesized CoMnAPSO-34 of 2G was calcined in air at 600° C. for one (1) hour. The calcined product was characterized by the following x-ray powder diffraction pattern:

| 2θ | d (Å) | (I/Io) × 100 |
|---|---|---|
| 7.5* | 11.84 | 32 |
| 9.6 | 9.20 | 100 |
| 13.0** | 6.81 | 20 |
| 14.9* | 5.93 | 4 |
| 16.2 | 5.48 | 8 |
| 18.0 | 4.93 | 6 |
| 19.3 | 4.60 | 3 |
| 19.8* | 4.49 | 8 |
| 20.9** | 4.26 | 22 |
| 21.2** | 4.20 | 26 |
| 21.5 | 4.13 | 3 |
| 22.5* | 3.96 | 32 |
| 23.4 | 3.81 | 3 |
| 25.3 | 3.520 | 7 |
| 26.1* | 3.420 | 11 |
| 26.2 | 3.396 | 7 |
| 28.5 | 3.129 | 3 |
| 29.2* | 3.063 | 6 |
| 30.2* | 2.965 | 6 |
| 31.0 | 2.881 | 11 |
| 31.5 | 2.840 | 7 |
| 34.7* | 2.584 | 4 |
| 34.9* | 2.568 | 3 |
| 38.0 | 2.368 | 2 |

*peak may contain impurity
**impurity peak (c) The species CoMnAPSO-34 is a molecular sieve having a characteristic x-ray powder diffraction pattern which contains at least the d-spacings set forth in Table VI-G as follows:

TABLE VI-G

| 2θ | d, (Å) | Relative Intensity |
|---|---|---|
| 9.5-9.6 | 9.29-9.20 | vs |
| 12.8-13.0 | 6.92-6.81 | w-m |
| 16.0-16.2 | 5.54-5.48 | vw-m |
| 20.6-20.9 | 4.32-4.26 | m |
| 21.1-21.2 | 4.22-4.20 | m |
| 25.2-25.3 | 3.530-3.520 | vw-w |
| 31.0-31.5 | 2.881-2.840 | w |

(d) All of the CoMnASPO-34 compositions, both as-synthesized and calcined, for which x-ray powder diffraction data have been obtainehave patterns which are within the generalized pattern below:

TABLE VII-G

| 2θ | d (Å) | (I/Io) × 100 |
|---|---|---|
| 9.5-9.6 | 9.29-9.20 | 100 |
| 12.8-13.0 | 6.92-6.81 | 11-20 |
| 14.1 | 6.29 | 7-9 |
| 16.0-16.2 | 5.54-5.48 | 8-23 |
| 18.0 | 4.93 | 6-12 |
| 19.3 | 4.60 | 3 |
| 20.6-20.9 | 4.32-4.26 | 22-57 |
| 21.1-21.2 | 4.22-4.20 | 26-40 |
| 21.5 | 4.13 | 3 |
| 23.0-23.4 | 3.87-3.81 | 2-3 |
| 25.2-25.3 | 3.530-3.520 | 7-14 |
| 25.8-26.2 | 3.453-3.396 | 7-13 |
| 27.5 | 3.243 | 2 |
| 28.3-28.5 | 3.153-3.129 | 3-4 |
| 29.5 | 3.024 | 3 |
| 30.5 | 2.928 | 16-18 |
| 31.0-31.5 | 2.881-2.840 | 11-13 |
| 33.7-33.8 | 2.659-2.652 | 2-7 |
| 34.5-34.6 | 2.601-2.592 | 5 |
| 38.0 | 2.368 | 2 |
| 39.6 | 2.276 | 2 |
| 43.3 | 2.090 | 2 |
| 47.5-47.7 | 1.914-1.905 | 2-3 |
| 48.9-49.0 | 1.863-1.859 | 2-4 |
| 49.9 | 1.828 | 2 |
| 50.8-50.9 | 1.797-1.794 | 2-3 |

EXAMPLE 15G

In order to demonstrate the catalytic activity of the CoMnAPSO compositions, calcined samples of the products of examples 2G and 4G, were tested for catalytic cracking. The CoMnAPSO compositions were evaluated for n-butane cracking using a bench-scale apparatus.

The reactor was cylindrical quartz tube 254 mm. in length and 10.3 mm I.D. In each test the reactor was loaded with particles of the CoMnAPSO which were 20-40 mesh (U.S. std.) in size and in an amount of from 0.5 to 5 grams, the quantity being selected so that the conversion of n-butane was at least 5% and not more than 90% under the test conditions. The CoMnAPSO samples had been previously calcined in air to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of each CoMnAPSO composition. The $k_A$ value (cm$^3$/g min) obtained for the CoMnAPSO are set forth below:

| Product of Example No. | Rate Constant ($k_A$)** |
|---|---|
| 2G* | 6.9 |
| 4G* | 0.8 |

*calcined at 600° C. in air for 1.5 hours prior to activation.
**(cm$^3$/gram minute)

H. COBALT-MANGANESE-MAGNESIUM-ALUMINUM-PHOSPHORUS-SILICONE-OXIDE SIEVES

Molecular sieves containing coblat, manganese, magnesium, aluminum, phosphorus and silicon as framework tetrahedral oxide units are prepared as follows:

Preparative Reagents

In the following examples the CoMnMgAPSO compositions were prepared using numerous reagents. The reagents employed and abbreviations employed herein, if any, for such reagents are as follows:

(a) Alipro: aluminum isopropoxide;
(b) LUDOX-LS: LUDOX-LS is the tradename of Du Pont for an aqueous solution of 30 weight percent SiO$_2$ and 0.1 weight percent Na$_2$O;
(c) H$_3$PO$_4$: aqueous solution which is 85 weight percent phosphoric acid;
(d) MnAc: Manganese acetate, Mn(C$_2$H$_3$O$_2$)$_2$·4H$_2$O;
(e) CoAc: Cobalt Acetate, Co(C$_2$H$_3$O$_2$)$_2$·4H$_2$O;
(f) MgAc: Magnesium Acetate Mg(C$_2$H$_3$O$_2$)·4H$_2$;
(g) TEAOH: 40 weight percent aqueous solution of tetraethylammonium hydroxide; and
(h) Pr$_2$NH: di-n-propylamine, (C$_3$H$_7$)$_2$NH.

Preparative Procedures

The following preparative examples were carried out by forming a starting reaction mixture by adding the H$_3$PO$_4$ and one half of the quantity of water. To this mixture the aluminum isoproxide was added. This mixture was then blended until a homogeneous mixture was observed. To this mixture the LUDOX-LS was added and the resulting mixture blended (about 2 minutes) until a homogeneous mixture was observed.

Three additional mixtures were prepared using cobalt acetate, magnesium acetate and manganese acetate using one third of the remainder of the water for each mixture. The four mixtures were then admixed and the resulting mixture blended until a homogeneous mixture was observed. The organic templating agent was then added to the resulting mixture and the resulting mixture blended until a homogeneous mixture was observed, i.e., about 2 to 4 mixtures. The mixture was then placed in a lined (polytetrafluoroethylene) stainless steel pressure vessel and digested at a temperature for a time. All digestions were carried out at the autogeneous pressure.

The molar composition for each preparation will be given by the relative moles of the components with H$_3$PO$_4$ be given as P$_2$O$_5$.

EXAMPLES 1H TO 4H

CoMnMgAPSO molecular sieves were prepared according to the above identified procedure and the CoMnMgAPSO products determined by X-ray analysis. The results of preparative examples 1H to 4H are set forth in Table I-H. Examples AH, BH and CH of Table I-H did not contain a product identifiable by x-ray analysis.

TABLE I-H

| Example[1] | Template | Temp (°C.) | Time (days) | CoMnMgAPSO Product(s)[2] |
|---|---|---|---|---|
| 1H | TEAOH | 100 | 7 | CoMnMgAPSO-34 |
| 2H | TEAOH | 150 | 2 | CoMnMgAPSO-34; CoMnMgAPSO-5 |
| 3H | TEAOH | 150 | 7 | CoMnMgAPSO-34; CoMnMgAPSO-5 |
| 4H | Pr$_2$NH | 200 | 13 | CoMnMgAPSO-11 |
| AH | TEAOH | 100 | 2 | — |
| BH | Pr$_2$NH | 150 | 3 | — |
| CH | Pr$_2$NH | 150 | 10 | — |

[1]Reaction mixture comprised: 1.0 R:0.2 MnO:0.2 CoO:0.2 MgO:0.7 Al$_2$O$_3$:0.8 P$_2$O$_5$:0.4 SiO$_2$:50H$_2$O where "R" is the template.
[2]Major species as identified by x-ray powder diffraction pattern of product, except that when two species are identified the species are listed in the order of their predominance in the product. A "—" indicated no CoMnMgAPSO product was identified by x-ray analysis.

EXAMPLE 5H

Portions of the products of examples 3H and 4H were calcined in air at 600° C. for 1.5 hour to remove at least part of the organic templating agent. The adsorption capacities of each calcined sample were measured using a standard McBain-Baker gravimetric absorption apparatus. The samples were activated in a vacuum (less than about 0.04 torr) at 350° C. prior to measurement. The McBain-Baker data for the CoMnMgAPSO products were:

| Adsorbate | Kinetic Diameter, Å | Pressure (Torr) | Temp (°C.) | Wt. % Adsorbed |
|---|---|---|---|---|
| (a) Example 3H: (CoMnMgAPSO-34 and CoMnMgAPSO-5): | | | | |
| Oxygen | 3.46 | 105 | −183 | 6.0 |
| Oxygen | 3.46 | 733 | −183 | 8.4 |
| Neopentane | 6.2 | 742 | 23.8 | 1.4 |
| Cyclohexane | 6.0 | 65 | 23.7 | 2.6 |
| n-hexane | 6.0 | 93 | 23.4 | 3.3 |
| H$_2$O | 2.65 | 4.6 | 23.4 | 7.3 |
| H$_2$O | 2.65 | 19 | 23.7 | 12.0 |
| (b) Example 4H: (CoMnMgAPSO-11) | | | | |
| Oxygen | 3.46 | 105 | −183 | 2.9 |
| Oxygen | 3.46 | 733 | −183 | 3.6 |
| Neopentane | 6.2 | 742 | 23.8 | 0.5 |
| Cyclohexane | 6.0 | 65 | 23.7 | 2.1 |
| H$_2$O | 2.65 | 4.6 | 23.4 | 4.1 |
| H$_2$O | 2.65 | 19 | 23.7 | 9.1 |

EXAMPLE 6H

Portions of the products of example 3H and 4H were subjected to chemical analysis. The chemical analyses were as follows:

| (a) Example 3H: | |
|---|---|
| Component | Weight Percent |
| Al$_2$O$_3$ | 21.5 |
| P$_2$O$_5$ | 40.3 |
| SiO$_2$ | 6.5 |
| CoO | 4.58 |
| MnO | 4.41 |
| MgO | 2.43 |
| Carbon | 6.9 |
| LOI* | 18.3 |

*Loss on Ignition

The above chemical analysis gives an overall product composition in molar oxide ratios (anhydrous basis) of:
0.57R: 0.061 CoO: 0.062 MnO: 0.060 MgO: 0.211 Al$_2$O$_3$: 0.284 P$_2$O$_5$: 0.108 SiO$_2$ and a formula (anhydrous basis) of:
0.072R(Co$_{0.048}$Mn$_{0.048}$Mg$_{0.047}$Al$_{0.33}$P$_{0.44}$Si$_{0.084}$)O$_2$

| (b) Example 4H: | |
|---|---|
| Component | Weight Percent |
| Al$_2$O$_3$ | 24.3 |
| P$_2$O$_5$ | 41.8 |
| SiO$_2$ | 8.5 |
| CoO | 6.0 |
| MnO | 6.8 |
| MgO | 2.8 |
| Carbon | 1.54 |
| LOI* | 9.3 |

*Loss on Ignition

The above chemical analysis gives an overall product composition in molar oxide ratios (anhydrous basis) of:
0.128R:0.08CoO:0.096MnO:0.070MgO:0.238Al$_2$O$_3$: 0.294 P$_2$O$_5$:0.141S:O$_2$ and a formula (anhydrous basis) of:
0.0213R(Co$_{0.055}$Mn$_{0.066}$Mg$_{0.048}$Al$_{0.33}$P$_{0.41}$Si$_{0.097}$)O$_2$

EXAMPLE 7H

EDAX (energy dispersive analysis by x-ray) microprobe analysis in conjunction with SEM (scanning electron microscope) was carried out on clean crystals of products from examples 3H and 4H. Analysis of crystals having a morphology characteristic of CoMnMgAPSO-5, CoMnMgAPSO-11, and CoMnMgAPSO-34 gave the following analysis based on relative peak heights:

| | Average of Spot Probes |
|---|---|
| (a) CoMnMgAPSO-5: | |
| Co | 0.11 |
| Mn | 0.16 |
| Mg | 0.08 |
| Al | 0.55 |
| P | 1.0 |
| Si | 0.11 |
| (b) CoMnMgAPSO-11: | |
| Co | 0.09 |
| Mn | 0.06 |
| Mg | 0.11 |
| Al | 0.85 |
| P | 0.99 |
| Si | 0.38 |
| (c) CoMnMgAPSO-34: | |
| Co | 0.05 |
| Mn | 0.03 |
| Mg | 0.05 |
| Al | 0.81 |
| P | 1.0 |
| Si | 0.20 |

EXAMPLE 8H (a) CoMnMgAPSO-5, as prepared to in example 3H, was subjected to x-ray analysis and was determined to have a characteristics x-ray powder diffraction pattern which contains the d-spacings set forth below:

| 2θ | d (Å) | 100 × I/Io |
|---|---|---|
| 7.4 | 11.89 | 15 |
| 9.5* | 9.27 | 100 |
| 12.8** | 6.90 | 19 |
| 14.1* | 6.28 | 14 |
| 14.9 | 5.96 | 6 |

-continued

| 2θ | d (Å) | 100 × I/Io |
|---|---|---|
| 16.0* | 5.54 | 46 |
| 18.1* | 4.90 | 28 |
| 19.2* | 4.63 | 12 |
| 19.7 | 4.50 | 16 |
| 20.6* | 4.32 | 92 |
| 21.1 | 4.20 | 13 |
| 22.4* | 3.97 | 22 |
| 22.6 | 3.94 | 5 |
| 23.1* | 3.85 | 6 |
| 25.2* | 3.529 | 28 |
| 25.8** | 3.454 | 32 |
| 27.6* | 3.237 | 4 |
| 28.4* | 3.142 | 4 |
| 29.0 | 3.079 | 5 |
| 29.5* | 3.025 | 4 |
| 29.9 | 2.987 | 7 |
| 30.5** | 2.930 | 37 |
| 31.3* | 2.863 | 25 |
| 32.4* | 2.767 | 26 |
| 34.4** | 2.608 | 11 |
| 35.4* | 2.537 | 5 |
| 36.3* | 2.473 | 5 |
| 37.8 | 2.382 | 4 |
| 38.7* | 2.329 | 6 |
| 38.8* | 2.323 | 6 |
| 39.6* | 2.276 | 5 |
| 43.3* | 2.088 | 5 |
| 45.1 | 2.010 | 3 |
| 46.1* | 1.971 | 4 |
| 46.3 | 1.962 | 5 |
| 47.2* | 1.924 | 7 |
| 48.7 | 1.870 | 6 |
| 48.9* | 1.863 | 6 |
| 51.0* | 1.791 | 4 |
| 53.0* | 1.728 | 4 |
| 53.1* | 1.726 | 4 |

*peak may be an impurity
**impurity peak and CoMnMgAPSO-5

(b) A portion of the as-sythesized CoMnMgAPSO-5 of part (a) was calcined in air at 600° C. for one (1) hour. The calcined product was characterized by the x-ray powder diffraction pattern below:

| 2θ | d, (Å) | 100 × I/Io |
|---|---|---|
| 7.5 | 11.76 | 100 |
| 9.7* | 9.14 | 86 |
| 13.1** | 6.79 | 18 |
| 15.0 | 5.90 | 30 |
| 16.3* | 5.44 | 8 |
| 18.1* | 4.90 | 7 |
| 19.9 | 4.47 | 19 |
| 21.2** | 4.19 | 35 |
| 21.5* | 4.13 | 44 |
| 22.6 | 3.94 | 37 |
| 23.0* | 3.87 | 6 |
| 26.1 | 3.414 | 21 |
| 26.4* | 3.379 | 9 |
| 29.2 | 3.060 | 8 |
| 30.2 | 2.956 | 59 |
| 31.2* | 2.871 | 12 |
| 31.7* | 2.819 | 7 |
| 34.7 | 2.582 | 13 |
| 35.5* | 2.528 | 16 |

*peak may be an impurity
**impurity peak and CoMnMgAPSO-5

(c) The species CoMnMgAPSO-5 is a molecular sieve having a three-dimensional microporous framework structure of $CoO_2^{-2}$, $MnO_2^{-2}$, $MgO_2^{-2}$, $AlO_2^{-}$, $PO_2^{+}$, and $SiO_2$ tetrahedral oxide units and have an empirical chemical composition on an anhydrous basis expressed by the formula:

mR:$(Co_tMn_uMg_vAl_xP_ySi_z)O_2$ where "R" represents an organic templating agent present in the intracrystalline pore system; "m" represents the molar amount of "R" present per mole of $(Co_tMn_uMg_vAl_xP_ySi_z)O_2$ and has a value of from zero to about 0.3; and "t", "u", "v", "x", "y", and "z", where "w" is the sum of "t+u+v", represent the mole fractions of cobalt, manganese, magnesium, aluminum, phosphorus and silicon, respectively, present as tetrahedral oxides, said mole fractions being within the pentagonal compositional area defined by points A, B, C, D and E of FIG. 1, more preferably by the tetragonal compositional area defined by points a, b, c, and d of FIG. 2, and having a characteristic x-ray powder diffraction pattern which contains at least the d-spacings set forth in Table II-H:

TABLE II-H

| 2θ | d, (Å) | Relative Intensity |
|---|---|---|
| 7.4–7.5 | 11.89–11.76 | w–vs |
| 14.9–15.0 | 5.96–5.90 | vw–m |
| 19.7–19.9 | 4.50–4.47 | w |
| 21.1–21.2 | 4.20–4.19 | w–m |
| 22.6 | 3.94 | vw–m |
| 29.9–30.2 | 2.987–2.956 | vw–m |

(d) The CoMnMgAPSO-5 compositions for which x-ray powder diffraction data have been obtained have patterns which are characterized by the data of Table III-H below:

TABLE III-H

| 2θ | d, (Å) | 100 × I/Io |
|---|---|---|
| 7.4–7.5 | 11.89–11.76 | 15–100.0 |
| 12.8–13.1 | 6.90–6.79 | 16–19 |
| 14.9–15.0 | 5.96–5.90 | 6–30 |
| 19.7–19.9 | 4.50–4.47 | 16–19 |
| 21.1–21.2 | 4.20–4.19 | 10–35 |
| 22.6 | 3.94 | 5–37 |
| 25.8–26.1 | 3.454–3.414 | 18–32 |
| 29.0–29.2 | 3.079–3.060 | 4–8 |
| 29.9–30.2 | 2.987–2.956 | 7–59 |
| 30.5 | 2.930 | 28–37 |
| 34.4–34.7 | 2.608–2.582 | 11–14 |
| 37.8 | 2.382 | 4 |
| 45.1 | 2.010 | 3 |
| 46.3 | 1.962 | 5 |
| 48.7 | 1.870 | 6 |

EXAMPLE 9H (a) CoMnMgAPSO-11, as prepared in example 4H was subjected to x-ray analysis. CoMnMgAPSO-11 was determined to have a characteristic x-ray powder diffraction pattern which contains the d-spacings set forth below:

| 2θ | d, (Å) | 100 × I/Io |
|---|---|---|
| 8.1 | 10.95 | 21 |
| 9.5 | 9.35 | 34 |
| 13.1 | 6.75 | 9 |
| 15.7 | 5.66 | 22 |
| 20.3 | 4.37 | 29 |
| 21.1 | 4.21 | 75 |
| 22.1 | 4.02 | 34 |
| 22.4 | 3.97 | 27 |
| 22.7 | 3.92 | 34 |
| 23.1 | 3.84 | 53 |
| 24.7 | 3.61 | 7 |
| 26.4 | 3.374 | 23 |
| 27.6* | 3.234 | 100 |
| 28.6 | 3.124 | 75 |
| 32.7 | 2.736 | 13 |
| 35.2 | 2.548 | 20 |
| 37.5 | 2.396 | 8 |
| 37.8 | 2.383 | 9 |

-continued

| 2θ | d, (Å) | 100 × I/Io |
|---|---|---|
| 37.9 | 2.373 | 7 |
| 40.1 | 2.247 | 12 |
| 45.0 | 2.013 | 11 |
| 45.2 | 2.006 | 18 |
| 45.3 | 2.001 | 20 |
| 45.8 | 1.983 | 13 |
| 45.9 | 1.977 | 13 |
| 50.4 | 1.812 | 10 |
| 50.6 | 1.803 | 15 |

*peak may contain an impurity (b) A portion of the as-sythesized of part (a) was calcined in air at 600° C. for one (1) hour. The calcined product was characterized by the x-ray powder diffraction pattern of below:

| 2θ | d, (Å) | 100 × I/Io |
|---|---|---|
| 8.1 | 10.95 | 31 |
| 9.6 | 9.23 | 43 |
| 13.0 | 6.80 | 30 |
| 15.8 | 5.60 | 37 |
| 20.2 | 4.40 | 27 |
| 21.3 | 4.18 | 100 |
| 22.3 | 3.99 | 65 |
| 23.0 | 3.87 | 36 |
| 23.4 | 3.80 | 50 |
| 24.4 | 3.65 | 11 |
| 26.3 | 3.392 | 25 |
| 28.3 | 3.157 | 83 |
| 28.9 | 3.090 | 17 |
| 29.1 | 3.067 | 11 |
| 32.8 | 2.734 | 19 |
| 34.3 | 2.614 | 12 |
| 37.9 | 2.373 | 12 |
| 39.0 | 2.309 | 15 |
| 39.3 | 2.294 | 14 |
| 44.8 | 2.025 | 16 |
| 44.9 | 2.021 | 17 |

(c) The species CoMnMgAPSO-11 is a molecular sieve having a three-dimensional microporous framework structure of $CoO_2^{-2}$, $MnO_2^{-2}$, $MgO_2^{-2}$, $AlO_2^{-}$, $PO_2^{+}$, and $SiO_2$ tetrahedral oxide units and have an empirical chemical composition on an anhydrous basis expressed by the formula: $mR:(Co_tMn_uMg_vAl_xP_ySi_z)O_2$ where "R" represents an organic templating agent present in the intracrystalline pore system; "m" represents the molar amount of "R" present per mole of $(Co_tMn_uMg_vAl_xP_ySi_z)O_2$ and has a value of from zero to about 0.3; and "t", "u", "v", "x", "y", and "z", where "w" is the sum of "t+u+v", represent the mole fractions of cobalt, manganese, magnesium, aluminum, phosphorus and silicon, respectively, present as tetrahedral oxides, said mole fractions being within the compositional area defined by points A, B, C, D and E of FIG. 1, more preferably by the compositional area defined by points a, b, c, and d of FIG. 2, and having a characteristic x-ray powder pattern which contains at least the d-spacings set forth in Table IV-H:

TABLE IV-H

| 2θ | d, (Å) | Relative Intensity |
|---|---|---|
| 9.5–9.6 | 9.35–9.23 | m |
| 15.7–15.8 | 5.66–5.60 | m |
| 21.1–21.4 | 4.21–4.15 | m–vs |
| 22.1–22.3 | 4.02–3.99 | m |
| 22.7 | 3.92 | m–vs |
| 23.3–23.4 | 3.82–3.80 | m |
| 28.3–28.7 | 3.157–3.110 | m–s |

(d) The CoMnMgAPSO-11 compositions for which x-ray powder diffraction data have been obtained to date have patterns which are characterized by the data of Table V-H below:

TABLE V-H

| 2θ | d, (Å) | 100 × I/Io |
|---|---|---|
| 8.1–8.2 | 10.95–10.65 | 17–31 |
| 9.5–9.6 | 9.35–9.23 | 34–46 |
| 13.0–13.3 | 6.80–6.66 | 9–30 |
| 15.7–15.8 | 5.66–5.60 | 22–37 |
| 20.2–20.4 | 4.40–4.35 | 27–29 |
| 21.1–21.4 | 4.21–4.15 | 75–100 |
| 22.1–22.3 | 4.02–3.99 | 34–65 |
| 22.4 | 3.97 | 27 |
| 22.7 | 3.92 | 34–100 |
| 23.0–23.2 | 3.87–3.83 | 36–53 |
| 23.3–23.4 | 3.82–3.80 | 50–70 |
| 24.4–24.7 | 3.65–3.61 | 7–11 |
| 26.3–26.5 | 3.392–3.363 | 23–25 |
| 28.3–28.7 | 3.157–3.110 | 75–83 |
| 28.9 | 3.090 | 16 |
| 29.1–30.4 | 3.067–2.940 | 11–14 |
| 32.7–32.8 | 2.739–2.734 | 13–19 |
| 34.3 | 2.614 | 12 |
| 35.2 | 2.548 | 20 |
| 37.5–37.8 | 2.398–2.383 | 8 |
| 37.9 | 2.373 | 7–12 |
| 39.0 | 2.309 | 15 |
| 39.3–40.1 | 2.294–2.247 | 12–16 |
| 44.8–45.0 | 2.025–2.013 | 11–17 |
| 45.2 | 2.006 | 18 |
| 45.3 | 2.001 | 20 |
| 45.8 | 1.983 | 13 |
| 45.9 | 1.977 | 13 |
| 50.4 | 1.812 | 10 |
| 50.6 | 1.803 | 15 |

EXAMPLE 10H (a) CoMnMgAPSO-34, as prepared in example 3H was subjected to x-ray analysis. CoMnMgAPSO-34 was determined to have a characteristic x-ray powder diffraction pattern which contains ao least the d-spacings set forth below:

| 2θ | d, (Å) | 100 × I/Io |
|---|---|---|
| 7.4* | 11.89 | 15 |
| 9.5 | 9.31 | 100 |
| 12.8** | 6.90 | 19 |
| 14.1 | 6.28 | 14 |
| 14.9* | 5.96 | 6 |
| 16.0 | 5.54 | 46 |
| 18.1 | 4.90 | 28 |
| 19.2 | 4.62 | 12 |
| 19.7* | 4.50 | 16 |
| 20.6 | 4.32 | 92 |
| 21.1* | 4.20 | 13 |
| 22.4 | 3.97 | 22 |
| 22.6* | 3.94 | 5 |
| 23.1 | 3.85 | 6 |
| 25.2 | 3.534 | 28 |
| 25.8** | 3.454 | 32 |
| 27.6 | 3.237 | 4 |
| 28.4 | 3.142 | 4 |
| 29.0* | 3.079 | 5 |
| 29.5 | 3.025 | 4 |
| 29.9* | 2.987 | 7 |
| 30.5** | 2.930 | 37 |
| 31.3 | 2.863 | 25 |
| 32.4 | 2.767 | 26 |
| 34.4** | 2.608 | 11 |
| 35.4* | 2.537 | 5 |
| 36.3 | 2.473 | 5 |
| 37.8* | 2.382 | 4 |
| 38.7* | 2.329 | 6 |
| 38.8 | 2.323 | 6 |
| 39.6 | 2.276 | 5 |

-continued

| 2θ | d, (Å) | 100 × I/Io |
|---|---|---|
| 43.3 | 2.088 | 5 |
| 45.1* | 2.010 | 3 |
| 46.1* | 1.971 | 4 |
| 46.3* | 1.962 | 5 |
| 47.2 | 1.924 | 7 |
| 48.7** | 1.870 | 6 |
| 48.9 | 1.863 | 6 |
| 51.0 | 1.791 | 4 |
| 53.0 | 1.728 | 4 |
| 53.1 | 1.726 | 4 |

*peak may contain impurity
**peak contains impurity and CoMnMgAPSO-34

(b) A portion of the as-sythesized CoMnMgAPSO-34 of part (a) was calcined in air at 600° C. for one (1) hour. The calcined product was characterized by the x-ray powder diffraction pattern below:

| 2θ | d, (Å) | 100 × I/Io |
|---|---|---|
| 7.5* | 11.76 | 100 |
| 9.7 | 9.14 | 86 |
| 13.1** | 6.79 | 18 |
| 15.0* | 5.90 | 30 |
| 16.3 | 5.44 | 8 |
| 18.1 | 4.90 | 7 |
| 19.9* | 4.47 | 19 |
| 21.2** | 4.19 | 35 |
| 21.5 | 4.13 | 44 |
| 22.6* | 3.94 | 37 |
| 23.0 | 3.87 | 6 |
| 26.1** | 3.414 | 21 |
| 26.4 | 3.379 | 9 |
| 29.2* | 3.060 | 8 |
| 30.2* | 2.956 | 59 |
| 31.2 | 2.871 | 12 |
| 31.7 | 2.819 | 7 |
| 34.7* | 2.582 | 13 |
| 35.5 | 2.528 | 16 |

*peak may contain impurity
**peak contains impurity and CoMnMgAPSO-34

(c) The species CoMnMgAPSO-34 is a molecular sieve having a three-dimensional microporous framework structure of $CoO_2^{-2}$, $MnO_2^{-2}$, $MgO_2^{-2}$, $AlO_2^{-}$, $PO_2^{+}$, and $SiO_2$ tetrahedral oxide units and have an empirical chemical composition on an anhydrous basis expressed by the formula:

mR:$(Co_tMn_uMg_vAl_xP_ySi_z)O_2$ where "R" represents an organic templating agent present in the intracrystalline pore system; "m" represents the molar amount of "R" present per mole of $(Co_tMn_uMg_vAl_xP_ySi_z)O_2$ and has a value of from zero to about 0.3; and "t", "u", "v", "x", "y", and "z", where "w" is the sum of "t+u+v", represent the mole fractions of cobalt, manganese, magnesium, aluminum, phosphorus and silicon, respectively, present as tetrahedral oxides, said mole fractions being within the compositional area defined by points A, B, C, D and E of FIG. 1, more preferably by the compositional area defined by points a, b, c, and d of FIG. 2, and having a characteristic x-ray powder diffraction pattern which contains at least the d-spacings set forth in Table VI-H:

TABLE VI-H

| 2θ | d, (Å) | Relative Intensity |
|---|---|---|
| 9.5–9.7 | 9.31–9.14 | vs |
| 16.0–16.3 | 5.54–5.44 | m |
| 20.5–21.2 | 4.33–4.19 | m–s |
| 21.5 | 4.13 | m |
| 25.2 | 3.534 | m |

TABLE VI-H-continued

| 2θ | d, (Å) | Relative Intensity |
|---|---|---|
| 30.2–30.5 | 2.960–2.930 | m |

(d) The CoMnMgAPSO-34 compositions for which x-ray powder diffraction data have been obtained to date have patterns which are characterized by the data of Table VII-H below:

TABLE VII-H

| 2θ | d, (Å) | 100 × I/Io |
|---|---|---|
| 9.5–9.7 | 9.31–9.14 | 100 |
| 12.8–13.1 | 6.90–6.79 | 13–19 |
| 14.1 | 6.28 | 12–14 |
| 16.0–16.3 | 5.54–5.44 | 31–46 |
| 18.0–18.1 | 4.93–4.90 | 21–28 |
| 19.2 | 4.62 | 5–12 |
| 20.5–21.2 | 4.33–4.19 | 61–92 |
| 21.5 | 4.13 | 44 |
| 22.4 | 3.97 | 4–25 |
| 23.0–23.1 | 3.87–3.85 | 4–6 |
| 25.2 | 3.534 | 21–28 |
| 25.8–26.1 | 3.453–3.414 | 13–32 |
| 26.4 | 3.379 | 9 |
| 27.6 | 3.237 | 4 |
| 28.4 | 3.142 | 4–5 |
| 29.5 | 3.025 | 4 |
| 30.2–30.5 | 2.960–2.930 | 21–37 |
| 31.2–31.3 | 2.871–2.863 | 14–25 |
| 31.7 | 2.819 | 7 |
| 32.4 | 2.767 | 15–26 |
| 34.4 | 2.608 | 5–11 |
| 35.5 | 2.528 | 16 |
| 36.3 | 2.473 | 4–5 |
| 38.8 | 2.323 | 6 |
| 39.6 | 2.276 | 5 |
| 43.3 | 2.088 | 5 |
| 47.2–47.5 | 1.924–1.916 | 4–7 |
| 48.9 | 1.863 | 4–6 |
| 51.0 | 1.791 | 4 |
| 53.0 | 1.728 | 4 |
| 53.1 | 1.726 | 4 |

EXAMPLE 11H

The catalytic activity of the CoMnMgAPSO compositions of examples 3H and 4H were evaluated in n-butane cracking using a bench-scale apparatus.

The reactor was cylindrical quartz tube 254 mm. in length an 10.3 mm. I.D. In each test the reactor was loaded with particles of the test CoMnMgAPSO's which were 20–40 mesh (U.S. Std.) in size and in an amount of from 0.5 to 5 grams, the quantity being selected so that the conversion of n-butane was at least 5% and not more than 90% under the test conditions. The CoMnMgAPSO samples were calcined in air at 600° C. for 1.5 hours to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation. From the analytical data the pseudo-first-order rate constants ($k_A$) were calculated and are set forth in Table VIII-H below:

TABLE VIII-H

| Product of Ex. No.: | Rate Constant $(k_A)$** |
|---|---|
| 3H* | 8.8 |

TABLE VIII-H-continued

| Product of Ex. No.: | Rate Constant (k$_A$)** |
|---|---|
| 4H* | 0.2 |

*calcined at 600° C. in air for 1.5 hours
**(cm$^3$/gram minute)

PROCESS APPLICATIONS

The ELAPSO compositions of the instant invention exhibit novel surface selectivity characteristics where render them useful as catalysts or catalyst bases in a number of hydrocarbon conversion and oxidative combustion reactions. They can be impregnated or otherwise loaded with catalytically active metals by methods were known in the art and used, for example, in fabricating catalyst compositions having silica or alumina bases. Of the general class, those species having pores larger than about 4 Å are preferred for catalytic applications.

Among the hydrocarbon conversion reactions catalyzed by ELAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using ELAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The ELAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen (H) is supplied to the reactor in admixture with the hydrocarbon (Hc) feedstock in molar proportions (H/Hc) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of C$_7$-C$_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structures of the present ELAPSO catalysts and their availability in a form having very low alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with ELAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the ELAPSO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compound on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening testing with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptane and/or n-octane to isoheptanes, iso-octanes, butane to iso-butane, methylcyclopentane to cyclohexane, meta-xylene and-/or ortho-xylene to paraxylene, 1-butene to 2-butene and/or isobutene, n-hexene to isohexene, cyclohexene to methylcyclopentene etc. The preferred form of the catalyst is a combination of the ELAPSO with polyvalent metal compounds (such as sulfides) of metals of Group II-A, Group II-B and rare earth metals. For alkylation and dealkylation processes the ELAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Process for converting a hydrocarbon which comprises contacting said hydrocarbon under hydrocarbon converting conditions with a molecular sieve, said molecular sieve being a crystalline molecular sieve having three-dimensional microporous framework structures of $ELO_2$, $AlO_2$, $PO_2$, $SiO_2$ oxide units and having an empirical chemical composition on an anhydrous basis expressed by the formula:

$mR:(EL_wAl_xP_ySi_z)O_2$ wherein "R" represents at least one organic templating agent present in the intracrystalline pore system; "m" represents the molar amount of "R" present per mole of $(EL_wAl_xP_ySi_z)O_2$ and has a value of zero to about 0.3; "EL" represents at least one element capable of forming a three dimensional oxide framework, "EL" is characterized as an element having a mean "T—O" distance in tetrahedral oxide structures between about 1.51 Angstroms and about 2.06 Angstroms, "EL" has a cation electronegativity between about 125 kcal/g-atom to about 310 kcal/g-atom and "EL" is capable of forming stable M—O—P, M—O—Al or M—O—M bonds in crystalline three dimensional oxide structures having an "M—O" bond dissociation energy greater than about 59 kcal/mole at 289° C.; and "w", "x", "y" and "z" represent the mole fractions of "EL", aluminum, phosphorus, and silicon, respectively, present as framework oxides, said mole fractions being within the pentagonal compositional area defined by points A, B, C, D and E of FIG. 1, wherein element "EL" and each of aluminum, phosphorus and silicon are present such that "w", "x", "y" and "z" are at least 0.01 and each element "EL" is present as a tetrahedral oxide unit $ELO_2$ in an amount of at least 0.01.

2. Process according to claim 1 wherein the mole fractions "w", "x", "y" and "z" are within the tetragonal compositional area defined by points a, b, c and d of FIG. 2.

3. Process according to claim 1 wherein, before being contacted with said hydrocarbon, said molecular sieve is calcined at a temperature sufficiently high to remove at least some of any organic templating agent present in the intracrystalline pore system.

4. Process according to claim 1 wherein said crystalline molecular sieve has a characteristic X-ray powder diffraction pattern which contains at least the d-spacings set forth in one of Tables A to H and J to W.

TABLE A (ELAPSO-5)

| 2θ | d, (Å) | Relative Intensity |
|---|---|---|
| 7.2 - 7.7 | 12.28 - 11.48 | m - vs |
| 19.4 - 19.9 | 4.58 - 4.46 | w - m |
| 20.85 - 21.3 | 4.26 - 4.17 | w - vs |
| 22.1 - 22.6 | 4.02 - 3.93 | m - vs |
| 25.6 - 26.1 | 3.480 - 3.414 | vw- m |

TABLE B (ELAPSO-11)

| 2θ | d, (Å) | Relative Intensity |
|---|---|---|
| 7.8 - 8.2 | 11.19 - 10.85 | m - s |
| 9.0 - 9.8 | 9.83 - 9.03 | vw- vs |
| 12.8 - 13.6 | 6.92 - 6.51 | vw- m |
| 19.9 - 20.5 | 4.46 - 4.33 | m - s |
| 20.8 - 21.8 | 4.27 - 4.08 | m - vs |
| 22.0 - 22.6 | 4.04 - 3.93 | m - vs |
| 22.6 - 23.1 | 3.93 - 3.85 | vw- vs |
| 23.1 - 23.5 | 3.85 - 3.79 | w - vs |

TABLE C (ELAPSO-14)

| 2θ | d (Å) | Relative Intensity |
|---|---|---|
| 8.6 - 8.9 | 10.3 - 9.93 | vs |
| 13.0 | 6.81 | w |
| 21.9 - 22.2 | 4.06 - 4.00 | w |
| 25.4 | 3.51 | w |
| 27.5 | 3.24 | w |
| 29.7 | 3.01 | w |

TABLE D (ELAPSO-16)

| 2θ | d (Å) | Relative Intensity |
|---|---|---|
| 11.3 - 11.6 | 7.83 - 7.63 | w - vs |
| 18.55 - 18.9 | 4.78 - 4.70 | vw- m |
| 21.85 - 22.2 | 4.07 - 4.00 | m - vs |
| 22.8 - 23.3 | 3.900 - 3.818 | w - m |
| 26.4 - 27.3 | 3.370 - 3.267 | w - m |
| 29.6 - 29.9 | 3.018 - 2.988 | w - m |

TABLE E (ELAPSO-17)

| 2θ | d (Å) | Relative Intensity |
|---|---|---|
| 7.70 – 7.75 | 11.5 – 11.4 | vs |
| 13.4 | 6.61 | s – vs |
| 15.5 – 15.55 | 5.72 – 5.70 | s |
| 19.65 – 19.7 | 4.52 – 4.51 | w – s |
| 20.5 – 20.6 | 4.33 – 4.31 | vs |
| 31.8 – 32.0 | 2.812 – 2.797 | w – s |

TABLE F (ELAPSO-18)

| 2θ | d (Å) | Relative Intensity |
|---|---|---|
| 9.6 – 9.65 | 9.21 – 9.16 | vs |
| 15.5 – 15.55 | 5.72 – 5.70 | m |
| 16.9 – 17.1 | 5.25 – 5.19 | m |
| 20.15 – 20.25 | 4.41 – 4.39 | m |
| 20.95 – 21.05 | 4.24 – 4.22 | m |
| 31.8 – 32.5 | 2.814 – 2.755 | m |

TABLE G (ELAPSO-20)

| 2θ | d (Å) | Relative Intensity |
|---|---|---|
| 13.8 – 14.2 | 6.42 – 6.23 | m – vs |
| 19.6 – 20.15 | 4.53 – 4.41 | m |
| 24.1 – 24.7 | 3.695 – 3.603 | m – vs |
| 27.9 – 28.6 | 3.198 – 3.121 | w |
| 31.3 – 32.05 | 2.861 – 2.791 | w |
| 34.35 – 35.0 | 2.610 – 2.601 | w – m |

TABLE H (ELAPSO-31)

| 2θ | d (Å) | Relative Intensity |
|---|---|---|
| 8.4 – 9.5 | 10.53 – 9.31 | w – s |
| 20.2 – 20.4 | 4.40 – 4.35 | m |
| 22.0 – 22.1 | 4.040 – 4.022 | m |
| 22.5 – 22.7 | 3.952 – 3.92 | vs |
| 31.6 – 31.8 | 2.831 – 2.814 | w – m |

TABLE J* (ELAPSO-33)

| 2θ | d (Å) | Relative Intensity |
|---|---|---|
| 9.25 – 9.55 | 9.56 – 9.26 | w – m |
| 12.5 – 12.9 | 7.08 – 6.86 | vs |
| 16.9 – 17.3 | 5.25 – 5.13 | w – m |
| 20.45 – 20.9 | 4.34 – 4.25 | w – m |
| 23.85 – 24.25 | 3.73 – 3.67 | w – m |
| 26.05 – 26.35 | 3.42 – 3.38 | w – m |
| 27.3 – 27.6 | 3.27 – 3.23 | vs |

* as-synthesized form

TABLE K* (ELAPSO-33)

| 2θ | d (Å) | Relative Intensity |
|---|---|---|
| 13.15 – 13.4 | 6.73 – 6.61 | vs |
| 18.05 – 18.35 | 4.91 – 4.83 | m |
| 18.4 – 18.6 | 4.82 – 4.77 | m |
| 26.55 – 26.7 | 3.36 – 3.34 | m |
| 32.0 – 32.1 | 2.80 – 2.79 | m |

* calcined form

TABLE L (ELAPSO-34)

| 2θ | d (Å) | Relative Intensity |
|---|---|---|
| 9.3 – 9.8 | 9.51 – 9.03 | m – vs |
| 12.6 – 13.2 | 7.03 – 6.71 | w – m |
| 15.8 – 16.3 | 5.61 – 5.44 | vw – m |
| 20.25 – 21.2 | 4.39 – 4.19 | w – vs |
| 24.8 – 25.4 | 3.59 – 3.507 | vw – m |
| 30.0 – 30.9 | 2.979 – 2.894 | vw – m |

TABLE M (ELAPSO-35)

| 2θ | d (Å) | Relative Intensity |
|---|---|---|
| 10.6 – 11.1 | 8.35 – 7.97 | vw – vs |
| 13.1 – 13.7 | 6.76 – 6.46 | vw – vs |
| 17.0 – 17.6 | 5.22 – 5.04 | w – s |
| 20.6 – 21.25 | 4.31 – 4.18 | vw – m |
| 21.6 – 22.3 | 4.11 – 3.99 | m – vs |
| 28.1 – 28.8 | 3.175 – 3.100 | vw – m |

TABLE N (ELAPSO-36)

| 2θ | d (Å) | Relative Intensity |
|---|---|---|
| 7.45 – 8.0 | 11.14 – 11.05 | vs |
| 8.1 – 8.3 | 10.91 – 10.65 | w – m |
| 16.3 – 16.6 | 5.44 – 5.34 | w – m |
| 18.9 – 19.4 | 4.70 – 4.57 | w – m |
| 20.7 – 21.0 | 4.29 – 4.23 | w – m |

TABLE O (ELAPSO-37)

| 2θ | d (Å) | Relative Intensity |
|---|---|---|
| 6.1 – 6.3 | 14.49 – 14.03 | vs |
| 15.5 – 15.7 | 5.72 – 5.64 | w – m |
| 18.5 – 18.8 | 4.80 – 4.72 | w – m |
| 23.5 – 23.7 | 3.79 – 3.75 | w – m |
| 26.9 – 27.1 | 3.31 – 3.29 | w – m |

TABLE P (ELAPSO-39)

| 2θ | d (Å) | Relative Intensity |
|---|---|---|
| 9.2 – 9.6 | 9.61 – 9.21 | m |
| 13.1 – 13.5 | 6.76 – 6.56 | m |
| 17.8 – 18.4 | 4.98 – 4.82 | w – m |
| 20.8 – 21.3 | 4.27 – 4.17 | m – vs |
| 22.2 – 22.85 | 4.00 – 3.892 | m – vs |
| 26.4 – 27.05 | 3.376 – 3.296 | w – m |

TABLE Q (ELAPSO-40)

| 2θ | d (Å) | Relative Intensity |
|---|---|---|
| 7.5 – 7.7 | 11.79 – 11.48 | vw – m |
| 8.0 – 8.1 | 11.05 – 10.94 | s – vs |
| 12.4 – 12.5 | 7.14 – 7.08 | w – vs |
| 13.6 – 13.8 | 6.51 – 6.42 | m – s |
| 14.0 – 14.1 | 6.33 – 6.28 | w – m |
| 27.8 – 28.0 | 3.209 – 3.187 | w – m |

TABLE R (ELAPSO-41)

| 2θ | d (Å) | Relative Intensity |
|---|---|---|
| 13.6 – 13.8 | 6.51 – 6.42 | w – m |
| 20.5 – 20.6 | 4.53 – 4.31 | w – m |
| 21.1 – 21.3 | 4.21 – 4.17 | vs |
| 22.1 – 22.3 | 4.02 – 3.99 | m – s |
| 22.8 – 23.0 | 3.90 – 3.86 | m |
| 23.1 – 23.4 | 3.82 – 3.80 | w – m |
| 25.5 – 25.9 | 3.493 – 3.44 | w – m |

TABLE S (ELAPSO-42)

| 2θ | d (Å) | Relative Intensity |
|---|---|---|
| 7.15 – 7.4 | 12.36 – 11.95 | m – vs |
| 12.5 – 12.7 | 7.08 – 6.97 | m – s |
| 21.75 – 21.9 | 4.09 – 4.06 | m – s |
| 24.1 – 24.25 | 3.69 – 3.67 | vs |
| 27.25 – 27.4 | 3.273 – 3.255 | s |
| 30.05 – 30.25 | 2.974 – 2.955 | m – s |

TABLE T (ELAPSO-43)

| 2θ | d (Å) | Relative Intensity |
|---|---|---|
| 12.3 – 12.95 | 7.20 – 6.83 | m – vs |
| 16.8 – 17.45 | 5.28 – 5.09 | vw – w |
| 21.45 – 21.85 | 4.145 – 4.071 | m – vs |
| 27.1 – 27.85 | 3.291 – 3.232 | w – vs |
| 32.4 – 33.2 | 2.763 – 2.699 | vw – m |

TABLE U (ELAPSO-44)

| 2θ | d (Å) | Relative Intensity |
|---|---|---|
| 9.2 – 9.6 | 9.61 – 9.21 | m – vs |
| 15.9 – 16.3 | 5.57 – 5.44 | vw – m |
| 20.5 – 21.0 | 4.33 – 4.23 | m – vs |
| 24.3 – 25.1 | 3.66 – 3.548 | w – m |
| 30.5 – 31.1 | 2.931 – 2.876 | vw – m |

TABLE V (ELAPSO-46)

| 2θ | d (Å) | Relative Intensity |
|---|---|---|
| 7.2 – 8.1 | 12.28 – 10.92 | vs |
| 12.9 – 13.6 | 6.86 – 6.51 | vw |
| 21.2 – 22.2 | 4.19 – 4.501 | vw – m |
| 22.5 – 23.45 | 3.95 – 3.793 | vw – m |
| 26.6 – 27.9 | 3.351 – 3.198 | vw – m |

TABLE W (ELAPSO-47)

| 2θ | d (Å) | Relative Intensity |
|---|---|---|
| 9.4 – 9.6 | 9.41 – 9.21 | vs |
| 12.8 – 13.1 | 6.92 – 6.76 | vw – m |
| 16.0 – 16.3 | 5.54 – 5.44 | vw – m |
| 20.5 – 21.0 | 4.31 – 4.23 | m – vs |
| 24.6 – 25.3 | 3.613 – 3.526 | vw – m |
| 30.6 – 31.1 | 2.921 – 2.876 | vw – m |

5. Process according to claim 1 wherein the hydrocarbon conversion process is isomerization.

6. Process according to claim 5 wherein the hydrocarbon conversion process is xylene isomerization.

* * * * *